(12) United States Patent
Krieg et al.

(10) Patent No.: US 8,304,396 B2
(45) Date of Patent: Nov. 6, 2012

(54) IMMUNOSTIMULATORY NUCLEIC ACIDS

(75) Inventors: Arthur M. Krieg, Wellesley, MA (US); Ulrike Samulowitz, Langenfeld (DE); Jörg Vollmer, Düsseldorf (DE); Eugen Uhlmann, Glashuetten (DE); Marion Jurk, Dormagen (DE); Grayson B. Lipford, Watertown, MA (US); Robert Rankin, Hemmen (NL)

(73) Assignees: Coley Pharmaceutical Group, Inc., New York, NY (US); Coley Pharmaceutical GmbH, Dusseldorf (DE); Pfizer Inc., New York, NY (US)

( * ) Notice: Subject to any disclaimer, the term of this patent is extended or adjusted under 35 U.S.C. 154(b) by 0 days.

(21) Appl. No.: 11/542,845

(22) Filed: Oct. 4, 2006

(65) Prior Publication Data
US 2007/0224210 A1    Sep. 27, 2007

Related U.S. Application Data

(63) Continuation of application No. 10/644,052, filed on Aug. 19, 2003.

(60) Provisional application No. 60/404,479, filed on Aug. 19, 2002, provisional application No. 60/404,820, filed on Aug. 19, 2002, provisional application No. 60/429,701, filed on Nov. 27, 2002, provisional application No. 60/447,377, filed on Feb. 14, 2003.

(51) Int. Cl.
*C12N 15/11* (2006.01)
*C07H 21/02* (2006.01)
*A61K 39/00* (2006.01)
*A61K 39/38* (2006.01)

(52) U.S. Cl. .................. 514/44 R; 536/23.1; 424/184.1

(58) Field of Classification Search .................. None
See application file for complete search history.

(56) References Cited

U.S. PATENT DOCUMENTS

| | | |
|---|---|---|
| 4,469,863 A | 9/1984 | Ts'o et al. |
| 5,023,243 A | 6/1991 | Tullis |
| 5,527,899 A | 6/1996 | Froehler |
| 5,646,126 A | 7/1997 | Cheng et al. |
| 5,663,153 A | 9/1997 | Hutcherson et al. |
| 5,679,647 A | 10/1997 | Carson et al. |
| 5,696,248 A | 12/1997 | Peyman et al. |
| 5,723,335 A | 3/1998 | Hutcherson et al. |
| 5,929,226 A | 7/1999 | Padmapriya et al. |
| 5,968,909 A | 10/1999 | Agrawal et al. |
| 6,031,086 A | 2/2000 | Switzer |
| 6,090,791 A | 7/2000 | Sato et al. |
| 6,121,434 A | 9/2000 | Peyman et al. |
| 6,194,388 B1 | 2/2001 | Krieg et al. |
| 6,207,646 B1 | 3/2001 | Krieg et al. |
| 6,207,819 B1 | 3/2001 | Manoharan et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,348,312 B1 | 2/2002 | Peyman et al. |
| 6,399,630 B1 | 6/2002 | Macfarlane |
| 6,406,705 B1 | 6/2002 | Davis et al. |
| 6,426,334 B1 | 7/2002 | Agrawal et al. |
| 6,429,199 B1 | 8/2002 | Krieg et al. |
| 6,476,000 B1 | 11/2002 | Agrawal et al. |
| 6,479,504 B1 | 11/2002 | Macfarlane et al. |
| 6,498,148 B1 | 12/2002 | Raz |
| 6,514,948 B1 | 2/2003 | Raz et al. |
| 6,521,637 B2 | 2/2003 | Macfarlane |
| 6,534,062 B2 | 3/2003 | Raz et al. |
| 6,562,798 B1 | 5/2003 | Schwartz |
| 6,589,940 B1 | 7/2003 | Raz et al. |
| 6,605,708 B1 | 8/2003 | Habus et al. |
| 6,653,292 B1 | 11/2003 | Krieg et al. |
| 6,727,230 B1 | 4/2004 | Hutcherson et al. |
| 6,815,429 B2 | 11/2004 | Agrawal |
| 6,821,957 B2 | 11/2004 | Krieg et al. |
| 6,943,240 B2 | 9/2005 | Bauer et al. |
| 6,949,520 B1 | 9/2005 | Hartmann et al. |
| 6,977,245 B2 | 12/2005 | Klinman et al. |
| 7,001,890 B1 | 2/2006 | Wagner et al. |
| 7,105,495 B2 | 9/2006 | Agrawal et al. |
| 7,176,296 B2 | 2/2007 | Agrawal et al. |
| 7,183,111 B2 | 2/2007 | Van Nest et al. |
| 7,223,741 B2 | 5/2007 | Krieg |
| 7,250,403 B2 | 7/2007 | Van Nest et al. |
| 7,255,868 B2 | 8/2007 | Fearon et al. |
| 7,262,286 B2 | 8/2007 | Kandimalla et al. |
| 7,271,156 B2 | 9/2007 | Krieg et al. |
| 7,276,489 B2 | 10/2007 | Agrawal et al. |
| 7,354,711 B2 | 4/2008 | Macfarlane |

(Continued)

FOREIGN PATENT DOCUMENTS

EP    0 092 574 A1    4/1983

(Continued)

OTHER PUBLICATIONS

McCluskie et al, 2001 Vaccine 19: 950-957.*
Yu et al 2001 Biorganic & Medicinal Chemistry vol. 9 Issue 11 pp. 2803-2808.*
Katoaka et al (Jpn. J. Cancer Res. 1992 vol. 83 pp. 244-247.*
Weiner et al 1997 Proc. Natl. Acad. Sci. USA vol. 94 pp. 10833-10837 especially pp. 10835-10836.*
Weigel et al. Clinical Cancer Research vol. 9 2003 pp. 3105-3114.*
Weiner et al 1997 Proc. Natl. Acad. Sci. USA vol. 94 pp. 10833-10837.*
Weiner J (Leukocyte Biology, 68(4):455-463, 2000).*
Krieg et al (Nature, 374:546-549, 1995).*
Agarwal et al (2002) Medicinal chemistry and therapeutic potential of CpG DNA. Trends Mol. Med., 8, 114-121.*
Vollmer J. (Expert Opinion of Biological Therapies, 2005).*
Ballas et al (The Journal of Immunology, 167:4878-4886, 2001).*

(Continued)

*Primary Examiner* — Nita M Minnifield
*Assistant Examiner* — Nina Archie
(74) *Attorney, Agent, or Firm* — Wolf, Greenfield & Sacks, P.C.

(57) ABSTRACT

The invention relates to a class of soft or semi-soft CpG immunostimulatory oligonucleotides that are useful for stimulating an immune response.

9 Claims, 46 Drawing Sheets

U.S. PATENT DOCUMENTS

| | | |
|---|---|---|
| 7,402,572 B2 | 7/2008 | Krieg et al. |
| 7,410,975 B2 | 8/2008 | Lipford et al. |
| 7,488,490 B2 | 2/2009 | Davis et al. |
| 7,517,861 B2 | 4/2009 | Krieg et al. |
| 7,524,828 B2 | 4/2009 | Krieg et al. |
| 7,534,772 B2 | 5/2009 | Weiner et al. |
| 7,566,703 B2 | 7/2009 | Krieg et al. |
| 7,569,553 B2 | 8/2009 | Kreig |
| 7,576,066 B2 | 8/2009 | Krieg |
| 7,585,847 B2 | 9/2009 | Bratzler et al. |
| 7,605,138 B2 | 10/2009 | Krieg |
| 7,615,539 B2 | 11/2009 | Krieg et al. |
| 7,666,674 B2 | 2/2010 | Klinman et al. |
| 7,674,777 B2 | 3/2010 | Krieg |
| 7,713,529 B2 | 5/2010 | Krieg et al. |
| 7,723,022 B2 | 5/2010 | Krieg et al. |
| 7,723,500 B2 | 5/2010 | Krieg et al. |
| 7,741,300 B2 | 6/2010 | Dow et al. |
| 7,776,344 B2 | 8/2010 | Hartmann et al. |
| 7,795,235 B2 | 9/2010 | Krieg et al. |
| 7,807,803 B2 | 10/2010 | Krieg et al. |
| 7,820,379 B2 | 10/2010 | Bauer et al. |
| 7,879,810 B2 | 2/2011 | Krieg et al. |
| 7,888,327 B2 | 2/2011 | Krieg et al. |
| 7,935,351 B2 | 5/2011 | Klinman et al. |
| 7,935,675 B1 | 5/2011 | Krieg et al. |
| 7,956,043 B2 | 6/2011 | Krieg et al. |
| 7,959,934 B2 | 6/2011 | Klinman et al. |
| 7,998,492 B2 | 8/2011 | Ahluwalia et al. |
| 8,008,266 B2 | 8/2011 | Krieg et al. |
| 8,058,249 B2 | 11/2011 | Krieg et al. |
| 8,114,419 B2 | 2/2012 | Krieg |
| 8,114,848 B2 | 2/2012 | Krieg et al. |
| 2001/0044416 A1 | 11/2001 | McCluskie et al. |
| 2002/0064515 A1 | 5/2002 | Krieg et al. |
| 2002/0091097 A1 | 7/2002 | Bratzler et al. |
| 2002/0137714 A1 | 9/2002 | Kandimalla et al. |
| 2002/0151518 A1 | 10/2002 | Agrawal et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 | 2/2003 | Krieg |
| 2003/0026801 A1 | 2/2003 | Weiner et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0060440 A1 | 3/2003 | Klinman et al. |
| 2003/0087848 A1 | 5/2003 | Bratzler et al. |
| 2003/0091599 A1 | 5/2003 | Davis et al. |
| 2003/0100527 A1 | 5/2003 | Krieg et al. |
| 2003/0104523 A1 | 6/2003 | Bauer et al. |
| 2003/0129605 A1 | 7/2003 | Yu et al. |
| 2003/0133988 A1 | 7/2003 | Fearon et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0175731 A1 | 9/2003 | Fearon et al. |
| 2003/0181406 A1 | 9/2003 | Schetter et al. |
| 2003/0186912 A1 | 10/2003 | Agrawal |
| 2003/0191079 A1 | 10/2003 | Krieg et al. |
| 2003/0224010 A1 | 12/2003 | Davis et al. |
| 2003/0232074 A1 | 12/2003 | Lipford et al. |
| 2003/0232856 A1 | 12/2003 | Macfarlane |
| 2004/0006034 A1 | 1/2004 | Raz et al. |
| 2004/0009949 A1 | 1/2004 | Krieg |
| 2004/0030118 A1 | 2/2004 | Wagner et al. |
| 2004/0053880 A1 | 3/2004 | Krieg |
| 2004/0058883 A1 | 3/2004 | Phillips et al. |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092468 A1 | 5/2004 | Schwartz et al. |
| 2004/0092472 A1 | 5/2004 | Krieg |
| 2004/0097719 A1 | 5/2004 | Agrawal et al. |
| 2004/0106568 A1 | 6/2004 | Krieg et al. |
| 2004/0131628 A1 | 7/2004 | Bratzler et al. |
| 2004/0132677 A1 | 7/2004 | Fearon et al. |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009773 A1 | 1/2005 | Kandimalla et al. |
| 2005/0009774 A1 | 1/2005 | Krieg et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0130918 A1 | 6/2005 | Agrawal et al. |
| 2005/0148537 A1 | 7/2005 | Krieg et al. |
| 2005/0169888 A1 | 8/2005 | Hartmann et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0238660 A1 | 10/2005 | Babiuk et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0266015 A1 | 12/2005 | Clerici et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0014713 A1 | 1/2006 | Agrawal et al. |
| 2006/0019909 A1 | 1/2006 | Agrawal et al. |
| 2006/0019916 A1 | 1/2006 | Krieg et al. |
| 2006/0019918 A1 | 1/2006 | Agrawal et al. |

| | | | |
|---|---|---|---|
| 2006/0019923 A1 | 1/2006 | Davis et al. | |
| 2006/0058251 A1 | 3/2006 | Krieg et al. | |
| 2006/0074040 A1 | 4/2006 | Kandimalla et al. | |
| 2006/0089326 A1 | 4/2006 | Krieg et al. | |
| 2006/0094680 A1 | 5/2006 | Agrawal et al. | |
| 2006/0094681 A1 | 5/2006 | Agrawal et al. | |
| 2006/0094683 A1 | 5/2006 | Krieg et al. | |
| 2006/0140875 A1 | 6/2006 | Krieg et al. | |
| 2006/0154890 A1 | 7/2006 | Bratzler et al. | |
| 2006/0172966 A1 | 8/2006 | Lipford et al. | |
| 2006/0188913 A1 | 8/2006 | Krieg et al. | |
| 2006/0211639 A1 | 9/2006 | Bratzler et al. | |
| 2006/0211641 A1 | 9/2006 | Agrawal et al. | |
| 2006/0211644 A1 | 9/2006 | Krieg et al. | |
| 2006/0217328 A1 | 9/2006 | Kandimalla et al. | |
| 2006/0229271 A1 | 10/2006 | Krieg et al. | |
| 2006/0241076 A1 | 10/2006 | Uhlmann et al. | |
| 2006/0246035 A1 | 11/2006 | Ahluwalia et al. | |
| 2006/0286070 A1 | 12/2006 | Hartmann et al. | |
| 2006/0287261 A1 | 12/2006 | Agrawal et al. | |
| 2006/0287262 A1 | 12/2006 | Agrawal et al. | |
| 2006/0287263 A1 | 12/2006 | Davis et al. | |
| 2007/0009482 A9 | 1/2007 | Krieg et al. | |
| 2007/0010470 A9 | 1/2007 | Krieg et al. | |
| 2007/0037767 A1 | 2/2007 | Bratzler et al. | |
| 2007/0065467 A1 | 3/2007 | Krieg et al. | |
| 2007/0066553 A1 | 3/2007 | Krieg et al. | |
| 2007/0066554 A1 | 3/2007 | Krieg et al. | |
| 2007/0078104 A1 | 4/2007 | Krieg et al. | |
| 2007/0105801 A1 | 5/2007 | Agrawal et al. | |
| 2007/0129320 A9 | 6/2007 | Davis et al. | |
| 2007/0142315 A1 | 6/2007 | Forsbach et al. | |
| 2007/0184465 A1 | 8/2007 | Wagner et al. | |
| 2007/0202128 A1 | 8/2007 | Krieg et al. | |
| 2007/0224210 A1 | 9/2007 | Krieg et al. | |
| 2007/0232622 A1 | 10/2007 | Lipford et al. | |
| 2008/0009455 A9 | 1/2008 | Krieg et al. | |
| 2008/0026011 A1 | 1/2008 | Krieg et al. | |
| 2008/0031936 A1 | 2/2008 | Krieg et al. | |
| 2008/0045473 A1 | 2/2008 | Uhlmann et al. | |
| 2008/0113929 A1 | 5/2008 | Lipford et al. | |
| 2008/0152662 A1 | 6/2008 | Agrawal et al. | |
| 2008/0226649 A1 | 9/2008 | Schetter et al. | |
| 2009/0017021 A1 | 1/2009 | Davis et al. | |
| 2009/0060927 A1 | 3/2009 | Wagner et al. | |
| 2009/0117132 A1 | 5/2009 | Readett et al. | |
| 2009/0137519 A1 | 5/2009 | Krieg et al. | |
| 2009/0142362 A1 | 6/2009 | Krieg et al. | |
| 2009/0155212 A1 | 6/2009 | Bratzler et al. | |
| 2009/0155307 A1 | 6/2009 | Davis et al. | |
| 2009/0191188 A1 | 7/2009 | Krieg et al. | |
| 2009/0202575 A1 | 8/2009 | Krieg et al. | |
| 2009/0214578 A1 | 8/2009 | Bauer | |
| 2009/0306177 A1 | 12/2009 | Uhlmann et al. | |
| 2009/0311277 A1 | 12/2009 | Krieg | |
| 2010/0166780 A1 | 7/2010 | Debelak et al. | |
| 2010/0183639 A1 | 7/2010 | Uhlmann et al. | |
| 2010/0285041 A1 | 11/2010 | Uhlmann et al. | |
| 2011/0033421 A1 | 2/2011 | Hartmann et al. | |
| 2011/0081366 A1 | 4/2011 | Krieg | |
| 2011/0098456 A1 | 4/2011 | Uhlmann et al. | |
| 2011/0135605 A1 | 6/2011 | Ahluwalia et al. | |
| 2011/0201672 A1 | 8/2011 | Krieg et al. | |
| 2011/0244025 A1 | 10/2011 | Uhlmann et al. | |

FOREIGN PATENT DOCUMENTS

| | | |
|---|---|---|
| EP | 0 468 520 A2 | 1/1992 |
| WO | WO 92/02258 A1 | 2/1992 |
| WO | WO 98/11211 A2 | 3/1998 |
| WO | WO 98/16247 A1 | 4/1998 |
| WO | WO 98/18810 A1 | 5/1998 |
| WO | WO 98/37919 A1 | 9/1998 |
| WO | WO 98/49288 A1 | 11/1998 |
| WO | WO 99/54459 A2 | 10/1999 |
| WO | WO 99/56755 A1 | 11/1999 |
| WO | WO 00/06588 A1 | 2/2000 |
| WO | WO 00/14217 A2 | 3/2000 |
| WO | WO 00/67023 A1 | 11/2000 |
| WO | WO 01/22972 A2 | 4/2001 |
| WO | WO 01/22990 A2 | 4/2001 |
| WO | WO 01/93905 A1 | 12/2001 |
| WO | WO 01/97843 A2 | 12/2001 |
| WO | WO 02/26757 A2 | 4/2002 |
| WO | WO 03/015711 A2 | 2/2003 |
| WO | WO 03/035836 * | 5/2003 |
| WO | WO 03/035836 A2 * | 5/2003 |
| WO | WO 2004/007743 A2 | 1/2004 |
| WO | WO 2004/026888 A2 | 4/2004 |
| WO | WO 2004/039829 A2 | 5/2004 |
| WO | WO 2004/041183 A2 | 5/2004 |
| WO | WO 2004/053104 A2 | 6/2004 |
| WO | WO 2004/087203 A2 | 10/2004 |
| WO | WO 2004/094671 A2 | 11/2004 |
| WO | WO 2006/080946 A2 | 8/2006 |
| WO | WO 2007/031877 A2 | 3/2007 |
| WO | WO 2007/038720 A2 | 4/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Press Release, Hybridon, Inc. Hybridon shows immonumodulatory activity of synthetic oligonucleotides. Cambrige, MA. May 7, 2001.

Agrawal et al., Medicinal chemistry and therapeutic potential of CpG DNA. Trends Mol Med. Mar. 2002;8(3):114-21.

Agrawal et al., Chapter 19: Pharmacokinetics and bioavailability of antisense oligonucleotides following oral and colorectal administrations in experimental animals. 1998: 525-43.

Crooke et al., Phosphorothioate Oligonucleotides. Therapeut Apps. 1995;ch5:63-84.

Gallichan et al., Intranasal immunization with CpG oligodeoxynucleotides as an adjuvant dramatically increases IgA and protection against herpes simplex virus-2 in the genital tract. J Immunol. Mar. 1, 2001;166(5):3451-7.

Goldberg et al., Beyond danger: unmethylated CpG dinucleotides and the immunopathogenesis of disease. Immunol Lett. Jul. 3, 2000;73(1):13-8.

Hartmann et al., Delineation of a CpG phosphorothioate oligodeoxynucleotide for activating primate immune responses in vitro and in vivo. J Immunol. Feb. 1, 2000;164(3):1617-24.

Hohlweg et al., On the fate of plant or other foreign genes upon the uptake in food or after intramuscular injection in mice. Mol Genet Genomics. Apr. 2001;265(2):225-33.

Jäschke et al., Automated incorporation of polyethylane glycol into synthetic oligonucleotides. Tetrahedron Lett. 1993;34(2):301-4.

Kandimalla et al., Effect of chemical modifications of cytosine and guanine in a CpG-motif of oligonucleotides: structure-immunostimulatory activity relationships. Bioorg Med Chem. Mar. 2001;9(3):807-13.

Kandimalla et al., A dinucleotide motif in oligonucleotides shows potent immunomodulatory activity and overrides species-specific recognition observed with CpG motif. Proc Natl Acad Sci U S A. Nov. 25, 2003;100(24):14303-8. Epub Nov. 10, 2003.

Kandimalla et al., Towards optimal design of second-generation immunomodulatory oligonucleotides. Curr Opin Mol Ther. Apr. 2002;4(2):122-9.

Kandimalla et al., Divergent synthetic nucleotide motif recognition pattern: design and development of potent immunomodulatory oligodeoxyribonucleotide agents with distinct cytokine induction profiles. Nucleic Acids Res. May 1, 2003;31(9):2393-400.

Kandimalla et al., Secondary structures in CpG oligonucleotides affect immunostimulatory activity. Biochem Biophys Res Commun. Jul. 11, 2003;306(4):948-53.

Klinman et al., Immunotherapeutic applications of CpG-containing oligodeoxynucleotides. Drug News Perspect. Jun. 2000;13(5):289-96.

Krieg et al., CpG motifs in bacterial DNA trigger direct B-cell activation. Nature. Apr. 6, 1995;374(6522):546-9.

Krieg et al., P-chirality-dependent immune activation by phosphorothioate CpG oligodeoxynucleotides. Oligonucleotides. 2003;13(6):491-9.

Krieg et al., Enhancing vaccines with immune stimulatory CpG DNA. Curr Opin Mol Ther. Feb. 2001;3(1):15-24.

Krieg, Immune effects and mechanisms of action of CpG motifs. Vaccine. Nov. 8, 2001;19(6):618-22.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Krieg, Now I know my CpGs.Trends Microbiol. Jun. 2001;9(6):249-52.

Krug et al., Identification of CpG oligonucleotide sequences with high induction of IFN-alpha/beta in plasmacytoid dendritic cells. Eur J Immunol. Jul. 2001;31(7):2154-63.

McCluskie et al., CpG DNA is a potent enhancer of systemic and mucosal immune responses against hepatitis B surface antigen with intranasal administration to mice. J Immunol. Nov. 1, 1998;161(9):4463-6.

McCluskie et al., CpG DNA as mucosal adjuvant. Vaccine. 2000;18: 231-7.

McCluskie et al., Oral, intrarectal and intranasal immunizations using CpG and non-CpG oligodeoxynucleotides as adjuvants. Vaccine. Oct. 15, 2000;19(4-5):413-22.

McCluskie et al., Novel strategies using DNA for the induction of mucosal immunity. Crit Rev Immunol. 1999;19(4):303-29.

McCluskie et al., CpG DNA is an effective oral adjuvant to protein antigens in mice. Vaccine. Nov. 22, 2000;19(7-8):950-7.

McCluskie et al., Route and method of delivery of DNA vaccine influence immune responses in mice and non-human primates. Mol Med. May 1999;5(5):287-300.

McCluskie et al., The use of CpG DNA as a mucosal vaccine adjuvant. Curr Opin Investig Drugs. Jan. 2001;2(1):35-9.

McCluskie et al., Intranasal immunization of mice with CpG DNA induces strong systemic and mucosal responses that are influenced by other mucosal adjuvants and antigen distribution. Mol Med. Oct. 2000;6(10):867-77.

Pal et al., Immunization with the Chlamydia trachomatis mouse pneumonitis major outer membrane protein by use of CpG oligodeoxynucleotides as an adjuvant induces a protective immune response against an intranasal chlamydial challenge. Infect Immun. Sep. 2002;70(9):4812-7.

Rankin et al., CpG motif identification for veterinary and laboratory species demonstrates that sequence recognition is highly conserved. Antisense Nucleic Acid Drug Dev. Oct. 2001;11(5):333-40.

Rothenfusser et al., Recent advances in immunostimulatory CpG oligonucleotides. Curr Opin Mol Ther. Apr. 2003;5(2):98-106.

Sajic et al., Parameters of CpG oligodeoxynucleotide-induced protection against intravaginal HSV-2 challenge. J Med Virol. Dec. 2003;71(4):561-8.

Satoh et al., Morphological and immunohistochemical characteristics of the heterogeneous prostate-like glands (paraurethral gland) seen in female Brown-Norway rats. Toxicol Pathol. Mar.-Apr. 2001;29(2):237-41.

Sester et al., Phosphorothioate backbone modification modulates macrophage activation by CpG DNA. J Immunol. Oct. 15, 2000;165(8):4165-73.

Stein et al., Problems in interpretation of data derived from in vitro and in vivo use of antisense oligodeoxynucleotides. Antisense Res Dev. 1994 Summer;4(2):67-9.

Threadgill et al., Mitogenic synthetic polynucleotides suppress the antibody response to a bacterial polysaccharide. Vaccine. Jan. 1998;16(1):76-82.

Uhlmann et al., Recent advances in the development of immunostimulatory oligonucleotides. Curr Opin Drug Discov Devel. Mar. 2003;6(2):204-17.

Van Ojik et al., Phase I/II study with CpG 7909 as adjuvant to vaccination with MAGE-3 protein in patients with MAGE-3 positive tumors. Ann Oncol. 2003;13:157. Abstract 579O.

Vollmer et al., Highly immunostimulatory CpG-free oligodeoxynucleotides for activation of human leukocytes. Antisense Nucleic Acid Drug Dev. Jun. 2002;12(3):165-75.

Vollmer et al., Characterization of three CpG oligodeoxynucleotide classes with distinct immunostimulatory activities. Eur J Immunol. Jan. 2004;34(1):251-62.

Weigel et al., CpG oligodeoxynucleotides potentiate the antitumor effects of chemotherapy or tumor resection in an orthotopic murine model of rhabdomyosarcoma. Clin Cancer Res. Aug. 1, 2003;9(8):3105-14.

Wooldridge et al., CpG DNA and cancer immunotherapy: orchestrating the antitumor immune response. Curr Opin Oncol. Nov. 2003;15(6):440-5.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Synthetic oligonucleotides with certain palindromes stimulate interferon production of human peripheral blood lymphocytes in vitro. Jpn J Cancer Res. Aug. 1994;85(8):775-9.

Yu et al., Accessible 5'-end of CpG-containing phosphorothioate oligodeoxynucleotides is essential for immunostimulatory activity. Bioorg Med Chem Lett. Dec. 4, 2000;10(23):2585-8.

Yu et al., Modulation of immunostimulatory activity of CpG oligonucleotides by site-specific deletion of nucleobases. Bioorg Med Chem Lett. Sep. 3, 2001;11(17):2263-7.

Yu et al., Potent CpG oligonucleotides containing phosphodiester linkages: in vitro and in vivo immunostimulatory properties. Biochem Biophys Res Commun. Sep. 13, 2002;297(1):83-90.

Zhao et al., Effect of different chemically modified oligodeoxynucleotides on immune stimulation. Biochem Pharmacol. Jan. 26, 1996;51(2):173-82.

Zhao et al., Site of chemical modifications in CpG containing phosphorothioate oligodeoxynucleotide modulates its immunostimulatory activity. Bioorg Med Chem Lett. Dec. 20, 1999;9(24):3453-8. Abstract only.

Press Release, Jan. 22, 2007, Coley Pharmaceutical Group Updates Hepatitis C Drug Development Strategy.

Press Release, Jun. 20, 2007, Coley Pharmaceutical Group Announces PFizer's Discontinuation of Clinical Trials for Pf-3512676 Combined with Cytotoxic Chemotherapy in Advanced Non Small Cell Lung Cancer.

[No Author Listed] MSNBC News Services, Mixed results on new cancer drugs. Nov. 9, 2000. 5 pages.

Agrawal et al., Absorption, tissue distribution and in vivo stability in rats of a hybrid antisense oligonucleotide following oral administration. Biochem Pharmacol. Aug. 8, 1995;50(4):571-6.

Agrawal et al., Antisense therapeutics: is it as simple as complementary base recognition? Mol Med Today. Feb. 2000;6(2):72-81.

Agrawal, Importance of nucleotide sequence and chemical modifications of antisense oligonucleotides. Biochim Biophys Acta. Dec. 10, 1999;1489(1):53-68.

Agrawal et al., In vivo pharmacokinetics of phosphorothioate oligonucleotides containing contiguous guanosines. Antisense Nucleic Acid Drug Dev. Jun. 1997;7(3):245-9.

Agrawal et al., Pharmacokinetics of antisense oligonucleotides. Clin Pharmacokinet. Jan. 1995;28(1):7-16.

Agrawal et al., Pharmacokinetics of oligonucleotides. Ciba Found Symp. 1997;209:60-75; discussion 75-8.

Ballas et al., Induction of NK activity in murine and human cells by CpG motifs in oligodeoxynucleotides and bacterial DNA. J Immunol. Sep. 1, 1996;157(5):1840-5.

Ballas et al., Divergent therapeutic and immunologic effects of oligodeoxynucleotides with distinct CpG motifs. J Immunol. Nov. 1, 2001;167(9):4878-86.

Beaucage et al., Deoxynucleoside phosphoramidites—A new class of key intermediates for deoxypolynucleotide synthesis. Tetrahedron Letts. 1981; 22(20):1859-62.

Bhagat et al., CpG penta- and hexadeoxyribonucleotides as potent immunomodulatory agents. Biochem Biophys Res Commun Jan. 24, 2003;300(4):853-61.

Boggs et al., Characterization and modulation of immune stimulation by modified oligonucleotides. Antisense Nucleic Acid Drug Dev. Oct. 1997;7(5):461-71.

Branda et al., Immune stimulation by an antisense oligomer complementary to the rev gene of HIV-1. Biochem Pharmacol. May 25, 1993;45(10):2037-43.

Broide et al., Modulation of asthmatic response by immunostimulatory DNA sequences. Springer Semin Immunopathol. 2000;22(1-2):117-24.

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

Cohen et al., CD4+ T-cells from mice immunized to syngeneic sarcomas recognize distinct, non-shared tumor antigens. Cancer Res. Feb. 15, 1994;54(4):1055-8.

Cohen, Selective anti-gene therapy for cancer: principles and prospects. Tohoku J Exp Med. Oct. 1992;168(2):351-9.

Crooke et al., Progress in antisense oligonucleotide therapeutics. Annu Rev Pharmacol Toxicol. 1996;36:107-29.

Equils et al., Toll-like receptor 2 (TLR2) and TLR9 signaling results in HIV-long terminal repeat trans-activation and HIV replication in HIV-1 transgenic mouse spleen cells: implications of simultaneous activation of TLRs on HIV replication. J Immunol. May 15, 2003;170(10):5159-64.

Fields et al., Fields' Virology. 2001;1:1153.

Filion et al., Development of immunomodulatory six base-length non-CpG motif oligonucleotides for cancer vaccination. Vaccine. Jun. 23, 2004;22(19):2480-8.

Froehler et al., Synthesis of DNA via deoxynucleoside H-phosphonate intermediates. Nucleic Acids Res. Jul. 11, 1986;14(13):5399-407.

Gaffney et al., Large-scale oligonucleotide synthesis by the H-phosphonate method. Tetrahedron Letts. 1988; 29(22):2619-22.

Garegg et al., Nucleoside H-phosphonates. III. Chemical synthesis of oligodeoxyribonucleotides by the hydrogenphosphonate approach. Tetrahedron Letts. 1986; 27(34):4051-4.

Garegg et al., Nucleoside H-phosphonates. IV. Automated solid phase synthesis of oligoribonucleotides by the hydrogenphosphonate approach. Tetrahedron Lett. 1986; 27(34):4055-8.

Ghosh et al., Phosphorothioate-phosphodiester oligonucleotide co-polymers: assessment for antisense application. Anticancer Drug Des. Feb. 1993;8(1):15-32.

Goodchild et al., Conjugates of oligonucleotides and modified oligonucleotides: a review of their synthesis and properties. Bioconjug Chem. May-Jun. 1990;1(3):165-87.

Hacker et al., CpG-DNA-specific activation of antigen-presenting cells requires stress kinase activity and is preceded by non-specific endocytosis and endosomal maturation. EMBO J. Nov. 2, 1998;17(21):6230-40.

Hadden et al., Immunostimulants. Trends Pharmacol Sci. May 1993;14(5):169-74.

Hahm et al., Efficacy of polyadenylic.polyuridylic acid in the treatment of chronic active hepatitis B. Int J Immunopharmacol. Mar. 1994;16(3):217-25.

Hartmann et al., CpG DNA: a potent signal for growth, activation, and maturation of human dendritic cells. Proc Natl Acad Sci U S A. Aug. 3, 1999;96(16):9305-10.

Hartmann et al., Rational design of new CpG oligonucleotides that combine B cell activation with high IFN-alpha induction in plasmacytoid dendritic cells. Eur J Immunol. Jun. 2003;33(6):1633-41.

Hartmann et al., Identification and functional analysis of tumor-infiltrating plasmacytoid dendritic cells in head and neck cancer. Cancer Res. Oct. 1, 2003;63(19):6478-87.

Henry et al., Chemically modified oligonucleotides exhibit decreased immune stimulation in mice. J Pharmacol Exp Ther. Feb. 2000;292(2):468-79.

Hsieh et al., Incorporation of CpG oligodeoxynucleotide fails to enhance the protective efficacy of a subunit vaccine against Mycobacterium tuberculosis. Vaccine. Jan. 26, 2004;22(5-6):655-9.

Jain et al., CpG-oligodeoxynucleotides inhibit airway remodeling in a murine model of chronic asthma. J Allergy Clin Immunol. Dec. 2002;110(6):867-72.

Jain et al., The promise of CpG DNA in the treatment of asthma. Recent Res Develop Resp Crit Care Med. 2002;2:7-18.

Jiang et al., Enhancing immunogenicity by CpG DNA. Curr Opin Mol Ther. Apr. 2003;5(2):180-5.

Jurk et al., C-Class CpG ODN: sequence requirements and characterization of immunostimulatory activities on mRNA level. Immunobiology. 2004;209(1-2):141-54.

Kitagaki et al., Immunomodulatory effects of CpG oligodeoxynucleotides on established th2 responses. Clin Diagn Lab Immunol. Nov. 2002;9(6):1260-9.

Kline et al., DNA therapy for asthma. Curr Opin Allergy Clin Immunol. Feb. 2002;2(1):69-73.

Kline et al., Modulation of airway inflammation by CpG oligodeoxynucleotides in a murine model of asthma. J Immunol. Mar. 15, 1998;160(6):2555-9.

Kline et al., Treatment of established asthma in a murine model using CpG oligodeoxynucleotides. Am J Physiol Lung Cell Mol Physiol. Jul. 2002;283(1):L170-9.

Klinman et al., CpG motifs present in bacteria DNA rapidly induce lymphocytes to secrete interleukin 6, interleukin 12, and interferon gamma Proc Natl Acad Sci U S A. Apr. 2, 1996;93(7):2879-83.

Knipe et al., eds., Fields' Virology. 2001;1:1004-16.

Krieg et al., Causing a commotion in the blood: immunotherapy progresses from bacteria to bacterial DNA. Immunol Today. Oct. 2000;21(10):521-6.

Krieg et al., Chapter 17:Immune stimulation by oligonucleotides. In Antisense Drug Tech. 2001;1394:471-515.

Krieg et al., Lymphocyte activation mediated by oligonucleotides or DNA containing novel un-methylated CpG motifs. American College of Rheumatology 58$^{th}$ National Scientific Meeting. Minneapolis, Minnesota, Oct. 22, 1994. Abstracts. Arthritis Rheum. Sep. 1994;37(9 Suppl).

Krieg et al., Oligodeoxynucleotide modifications determine the magnitude of B cell stimulation by CpG motifs. Antisense Nucleic Acid Drug Dev. 1996 Summer;6(2):133-9.

Krieg et al., Sequence motifs in adenoviral DNA block immune activation by stimulatory CpG motifs. Proc Natl Acad Sci U S A. Oct. 13, 1998;95(21):12631-6.

Krieg, The role of CpG motifs in innate immunity. Curr Opin Immunol. Feb. 2000;12(1):35-43.

Krieg, Therapeutic potential of Toll-like receptor 9 activation. Nat Rev Drug Discov. Jun. 2006;5(6):471-84.

Kuramoto et al., Induction of T-cell-mediated immunity against MethA fibrosarcoma by intratumoral injections of a *bacillus* Calmette-Guerin nucleic acid fraction. Cancer Immunol Immunother. 1992;34(5):283-8.

Lee et al., An oligonucleotide blocks interferon-gamma signal transduction. Transplantation. Nov. 15, 1996;62(9):1297-301.

Lee et al., CpG motif in synthetic ODN primes respiratory burst of olive flounder Paralichthys olivaceus phagocytes and enhances protection against Edwardsiella tarda. Dis Aquat Organ. Aug. 15, 2003;56(1):43-8.

Liang et al., Activation of human B cells by phosphorothioate oligodeoxynucleotides. J Clin Invest. Sep. 1, 1996;98(5):1119-29.

Lipford et al., Bacterial DNA as immune cell activator. Trends Microbiol. Dec. 1998;6(12):496-500.

Lyer et al., Modified oligonucleotides—synthesis, properties and applications. Curr Opin Mol Ther. Jun. 1999;1(3):344-58. Review.

Mackellar et al., Synthesis and physical properties of anti-HIV antisense oligonucleotides bearing terminal lipophilic groups. Nucleic Acids Res. Jul. 11, 1992;20(13):3411-7.

Mannon et al., Stimulation of thymocyte proliferation by phosphorothioate DNA oligonucleotides. Cell Immunol. Apr. 10, 2000;201(1):14-21.

Messina et al., Stimulation of in vitro murine lymphocyte proliferation by bacterial DNA. J Immunol. Sep. 15, 1991;147(6):1759-64.

Mui et al., Immune stimulation by a CpG-containing oligodeoxynucleotide is enhanced when encapsulated and delivered in lipid particles. J Pharmacol Exp Ther. Sep. 2001;298(3):1185-92.

Mutwiri et al., Biological activity of immunostimulatory CpG DNA motifs in domestic animals. Vet Immunol Immunopathol. Jan. 30, 2003;91(2):89-103.

Mutwiri et al., Strategies for enhancing the immunostimulatory effects of CpG oligodeoxynucleotides. J Control Release. May 31, 2004;97(1):1-17.

Parronchi et al., Phosphorothioate oligodeoxynucleotides promote the in vitro development of human allergen-specific CD4+ T cells into Th1 effectors. J Immunol. Dec. 1, 1999;163(11):5946-53.
Paul et al., Technology evaluation: CpG-7909, Coley. Curr Opin Mol Ther. Oct. 2003;5(5):553-9.
Pavlick et al., Novel therapeutic agents under investigation for malignant melanoma. Expert Opin Investig Drugs. Sep. 2003;12(9):1545-58.
Peyman et al., Minimally modified oligonucleotides—combination of end-capping and pyrimidine-protection. Biol Chem Hoppe Seyler. Jan. 1996;377(1):67-70.
Pisetsky et al., Influence of backbone chemistry on immune activation by synthetic oligonucleotides. Biochem Pharmacol. Dec. 15, 1999;58(12):1981-8.
Pisetsky et al., The immunologic properties of DNA. J Immunol. Jan. 15, 1996;156(2):421-3.
Pisetsky, The influence of base sequence on the immunostimulatory properties of DNA. Immunol Res. 1999;19(1):35-46.
Samani et al., Best minimally modified antisense oligonucleotides according to cell nuclease activity. Antisense Nucleic Acid Drug Dev. Jun. 2001;11(3):129-36.
Sato et al., Immunostimulatory DNA sequences necessary for effective intradermal gene immunization. Science. Jul. 19, 1996;273(5273):352-4.
Satoh et al., The study of mechanisms in CpG oligodeoxynucleotides-induced aggravation in murine allergic contact ermatitis to 2,4-dinitrofluorobenzene. Fukushima Igaku Zasshi. 2002;52(3):237-50.
Stein et al., Antisense oligonucleotides as therapeutic agents—is the bullet really magical? Science. Aug. 20, 1993;261(5124):1004-12.
Stein et al., Non-antisense effects of oligodeoxynucleotides. Antisense Technology. 1997; Ch. 11: 241-64.
Stein et al., Physicochemical properties of phosphorothioate oligodeoxynucleotides. Nucleic Acids Res. Apr. 25, 1988;16(8):3209-21.
Tokunaga et al., A synthetic single-stranded DNA, poly(dG,dC), induces interferon-alpha/beta and -gamma, augments natural killer activity, and suppresses tumor growth. Jpn J Cancer Res. Jun. 1998;79(6):682-6.
Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.
Tokunaga et al., Antitumor activity of deoxyribonucleic acid fraction from Mycobacterium bovis BCG. I. Isolation, physicochemical characterization, and antitumor activity. J Natl Cancer Inst. Apr. 1984;72(4):955-62.
Uhlmann, Oligonucleotide technologies: synthesis, production, regulations and applications. Nov. 29-30, 2000, Hamburg, Germany. Expert Opin Biol Ther. Mar. 2001;1(2):319-28.
Uhlmann et al., Antisense oligonucleotides: a new therapeutic principle. Chem Rev. Jun. 1990;90(4):544-84.
Uhlmann et al., Use of minimally modified antisense oligonucleotides for specific inhibition of gene expression. Methods Enzymol. 1999;313:268-84.
Van Uden et al., Immunostimulatory DNA and applications to allergic disease. J Allergy Clin Immunol. Nov. 1999;104(5):902-10.
Vollmer et al., Modulation of CpG oligodeoxynucleotide-mediated immune stimulation by locked nucleic acid (LNA). Oligonucleotides. 2004 Spring;14(1):23-31.
Vollmer, CpG motifs to modulate innate and adaptive immune responses. Int Rev Immunol. May-Aug. 2006;25(3-4):125-34.
Vollmer et al., Identification of a new class of CpG oligonucleotides capable of inducing both B cell proliferation and high IFN-alpha secretion from PBMC of HCV chronic carriers. Antiv Ther. 2002;7:L115.
Wagner et al., Potent and selective inhibition of gene expression by an antisense heptanucleotide. Nat Biotechnol. Jul. 1996;14(7):840-4.
Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.
Yamamoto et al., Oligodeoxyribonucleotides with 5'-ACGT-3' or 5'-TCGA-3' sequence induce production of interferons. Curr Top Microbiol Immunol. 2000;247:23-39.
Yi et al., CpG oligodeoxyribonucleotides rescue mature spleen B cells from spontaneous apoptosis and promote cell cycle entry. J Immunol. Jun. 15, 1998;160(12):5898-906.
Yu et al., 'Immunomers'—novel 3'-3'-linked CpG oligodeoxyribonucleotides as potent immunomodulatory agents. Nucleic Acids Res. Oct. 15, 2002;30(20):4460-9.
Zhao et al., Comparison of cellular binding and uptake of antisense phosphodiester, phosphorothioate, and mixed phosphorothioate and methylphosphonate oligonucleotides. Antisense Res Dev. 1993 Spring;3(1):53-66.
Zhao et al., Immunostimulatory activity of CpG containing phosphorothioate oligodeoxynucleotide is modulated by modification of a single deoxynucleoside. Bioorg Med Chem Lett. May 15, 2000;10(10):1051-4. Abstract Only.
Zhao et al., Pattern and kinetics of cytokine production following administration of phosphorothioate oligonucleotides in mice. Antisense Nucleic Acid Drug Dev. Oct. 1997;7(5):495-502.
Zhu et al., Modulation of ovalbumin-induced Th2 responses by second-generation immunomodulatory oligonucleotides in mice. Int Immunopharmacol. Jul. 2004;4(7):851-62.
Zimmermann et al., Immunostimulatory DNA as adjuvant: efficacy of phosphodiester CpG oligonucleotides is enhanced by 3' sequence modifications. Vaccine. Feb. 14, 2003;21(9-10):990-5.
Hartmann et al., CpG DNA and LPS induce distinct patterns of activation in human monocytes. Gene Ther. May 1999;6(5):893-903.
Kaisho et al., Toll-like receptors as adjuvant receptors. Biochim Biophys Acta. Feb. 13, 2002;1589(1):1-13. Review.
Vollmer, Progress in drug development of immunostimulatory CpG oligodeoxynucleotide ligands for TLR9. Expert Opin Biol Ther. May 2005;5(5):673-82. Review.
Boujrad. et al , Inhibition of hormone-stimulated steroidogenesis in cultured Leydig tumor cells by a cholesterol-linked phosphorothioate oligodeoxynucleotide antisense to diazepam-binding inhibitor. Proc Natl Acad Sci U S A. Jun. 15, 1993;90(12):5728-31.
Ferrer et al., Preparation and properties of oligodeoxynucleotides containing 5-iodouracil and 5-bromo- and 5-iodocytosine. Bioconjug Chem. Sep.-Oct. 1997;8(5):757-61.
Hoheisel et al., Quantitative measurements on the duplex stability of 2,6-diaminopurine and 5-chloro-uracil nucleotides using enzymatically synthesized oligomers. Febs Lett. Nov. 12, 1990;274(1-2):103-6.
Moran et al., A thymidine triphosphate shape analog lacking Watson-Crick pairing ability is replicated with high sequence selectivity. Proc Natl Acad Sci U S A. Sep. 30, 1997;94(20):10506-11.
Schweitzer et al., Hydrophobic, Non-Hydrogen-Bonding Bases and Base Pairs in DNA. J Am Chem Soc. Feb. 22, 1995;117(7):1863-1872.

* cited by examiner

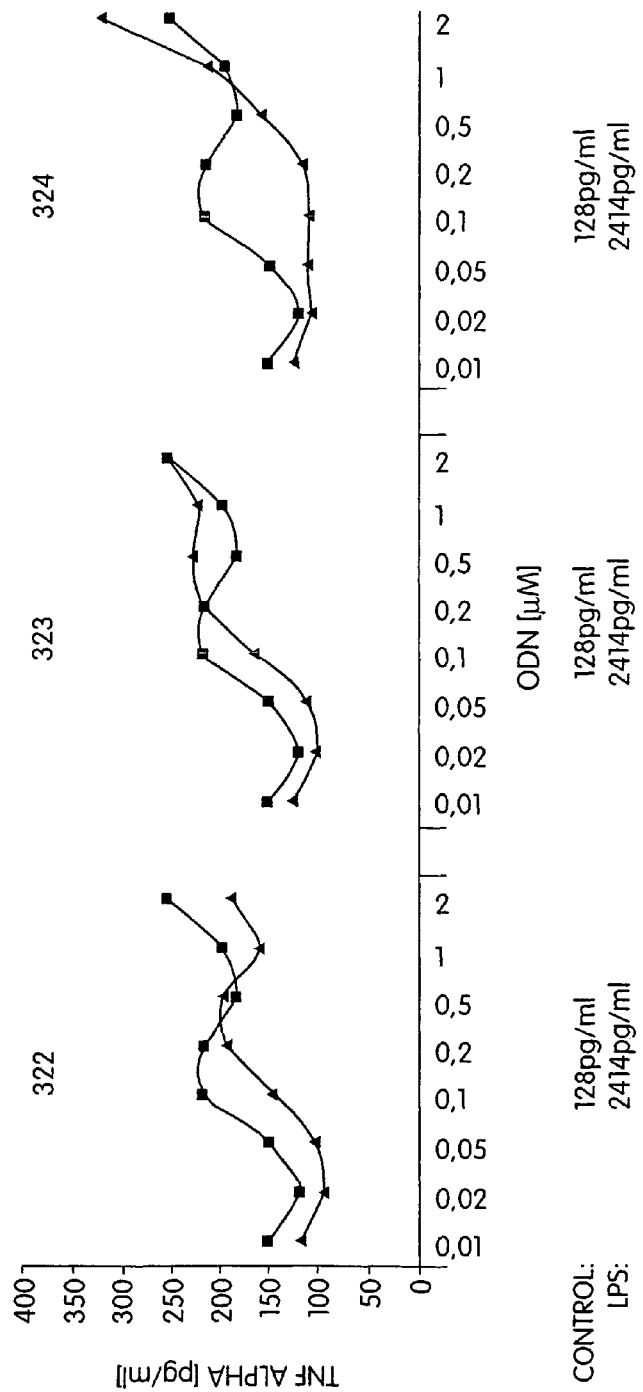

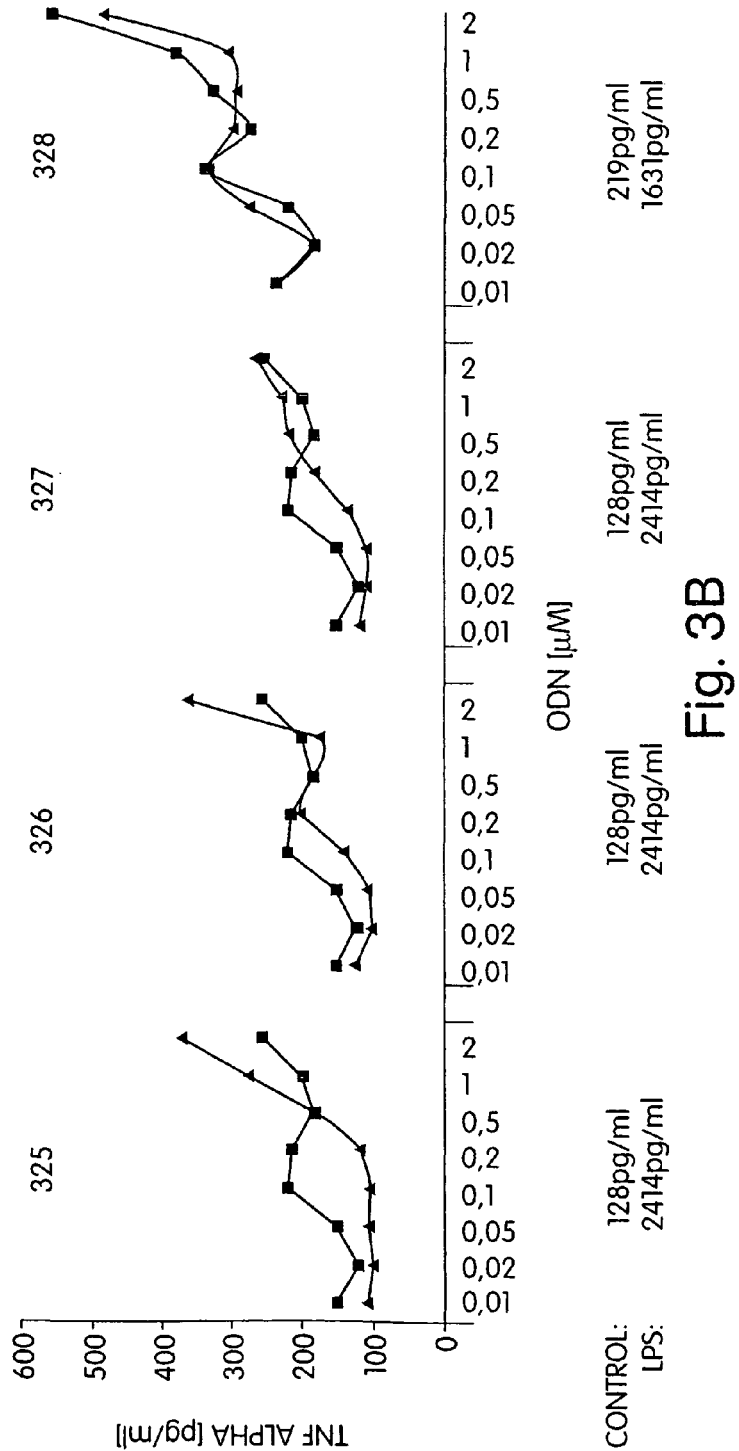

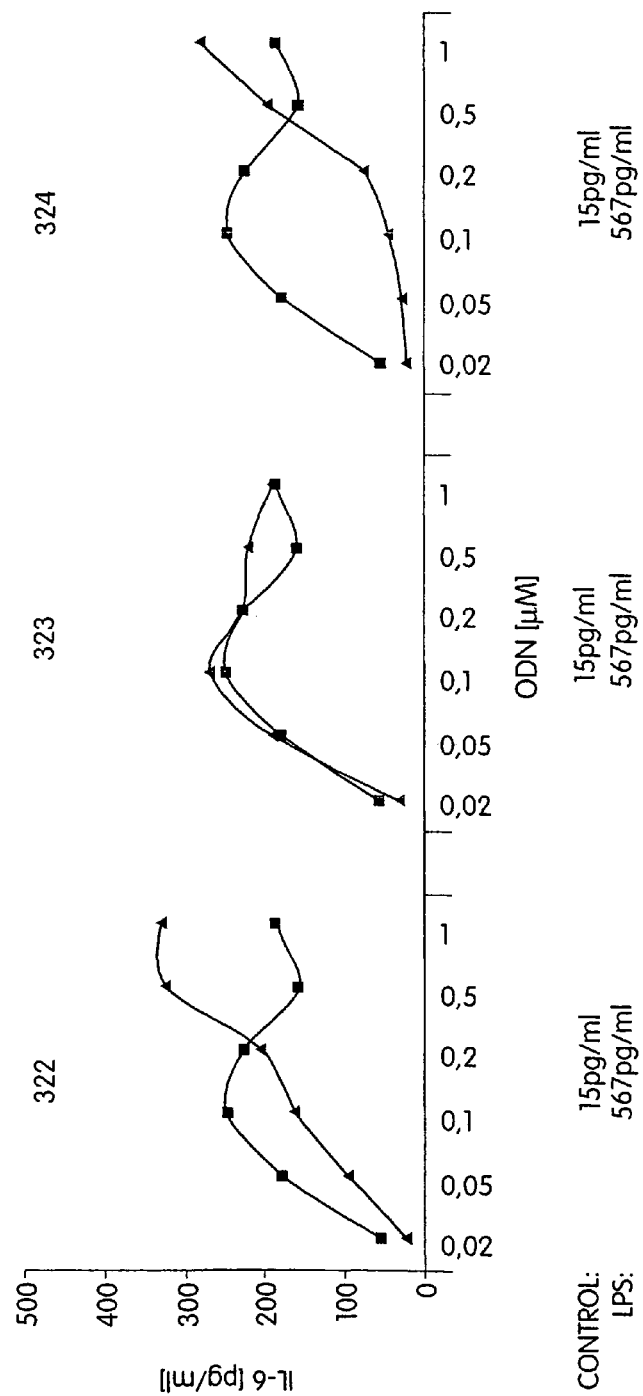

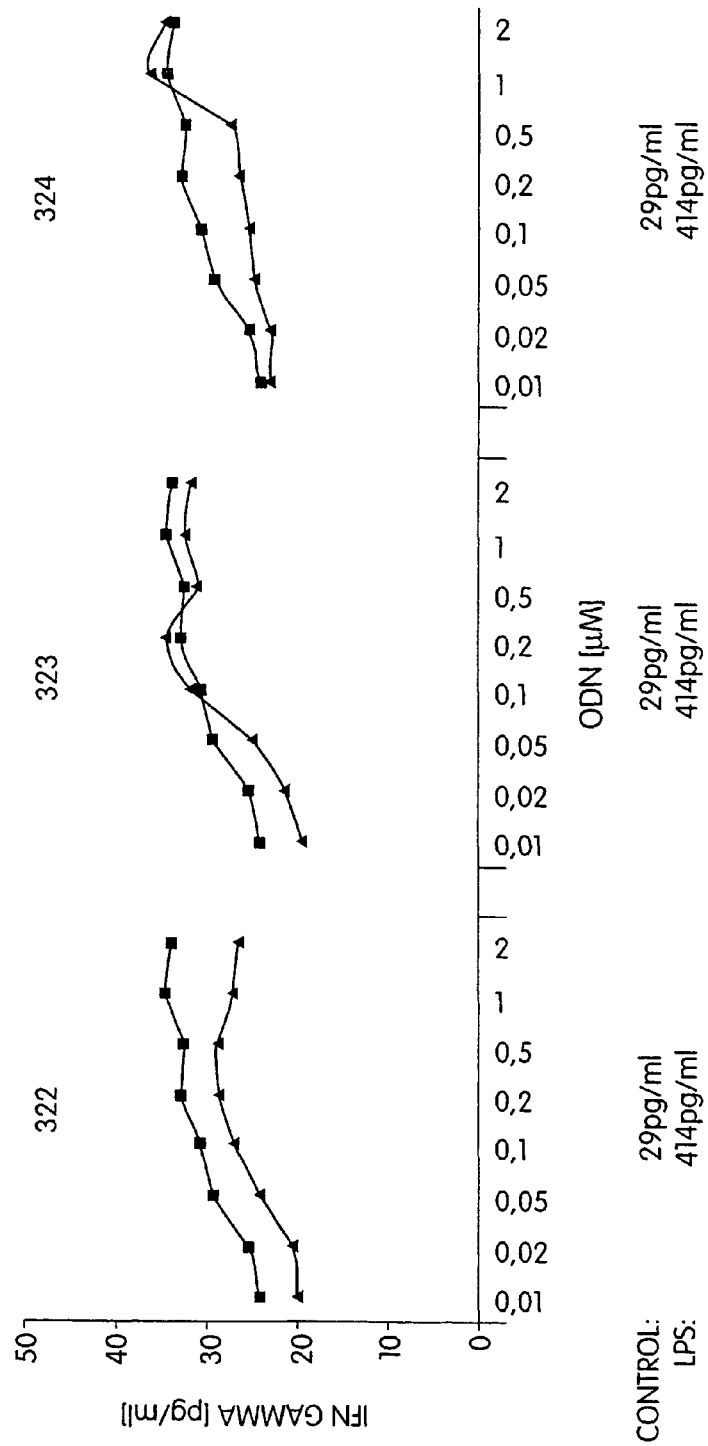

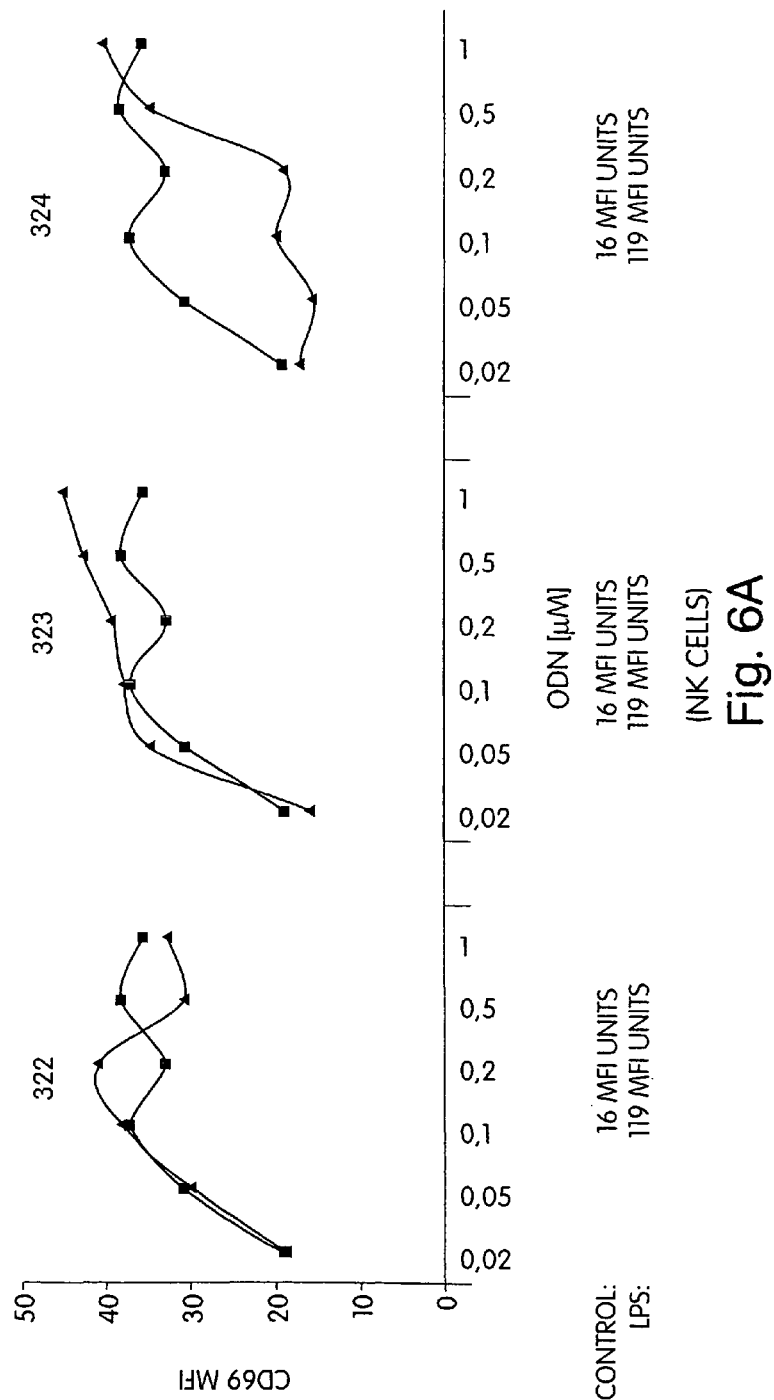

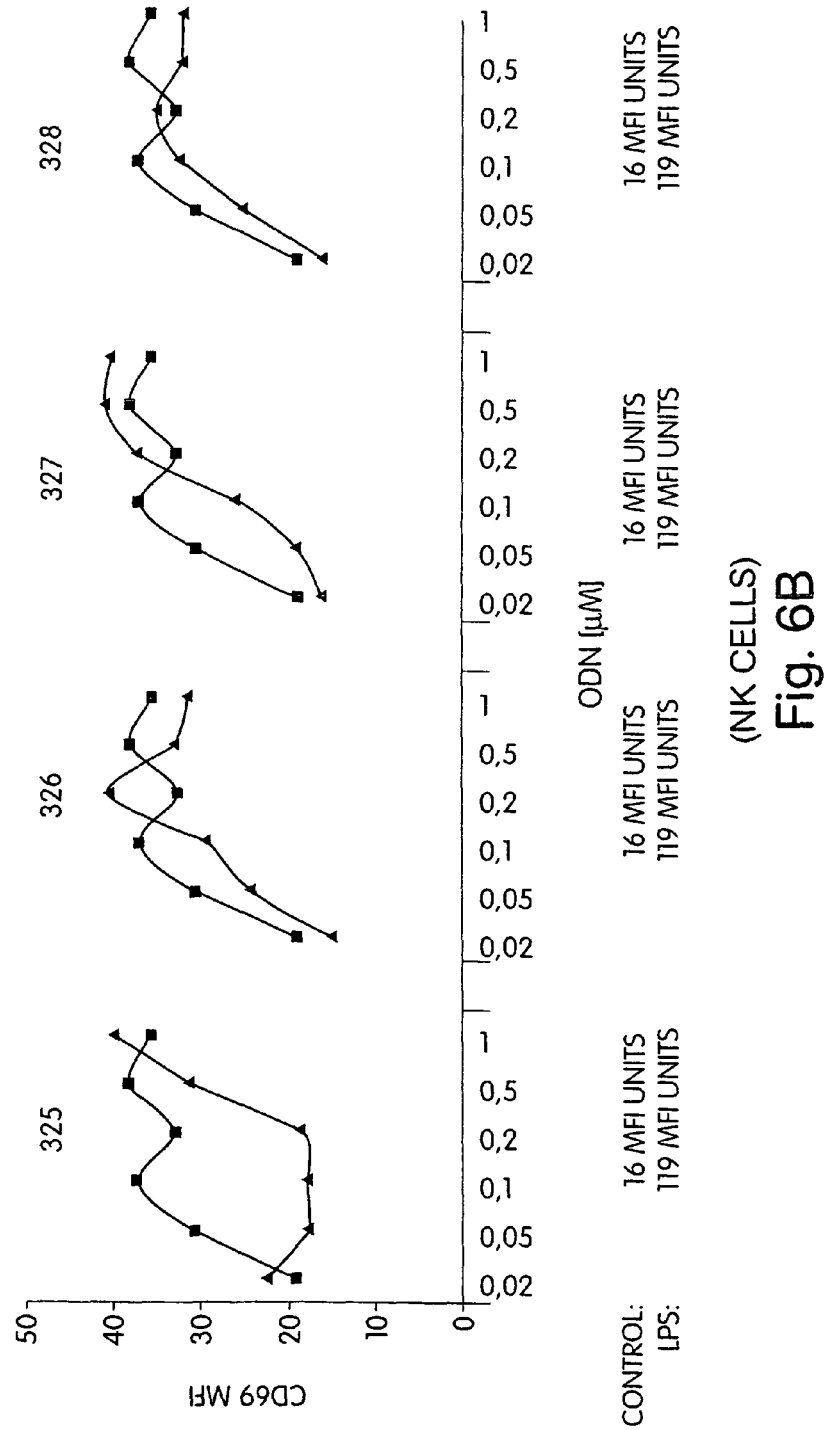

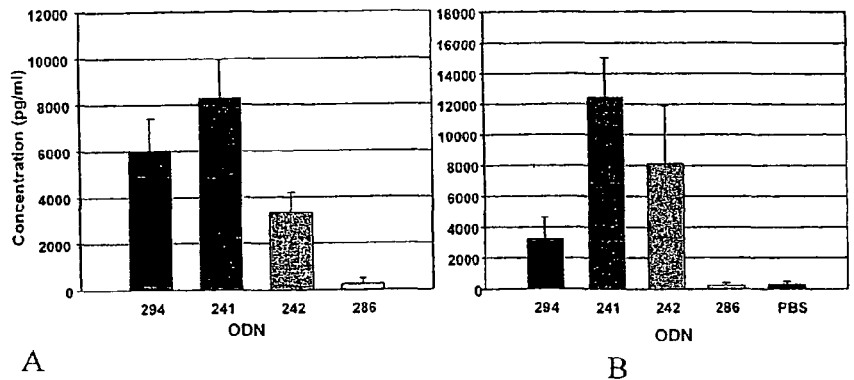
IFN-γ Induction (in plasma)
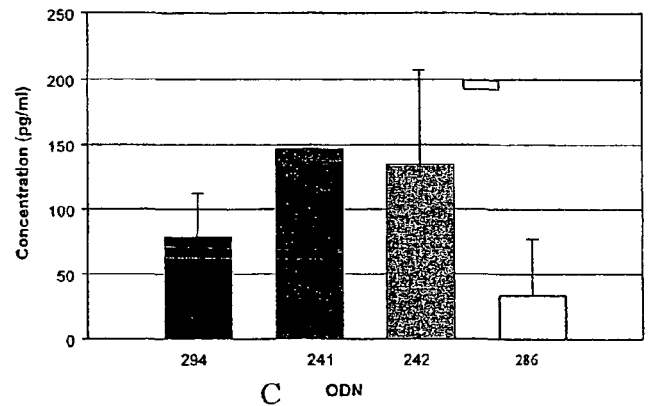
TNF-α Induction (in plasma)
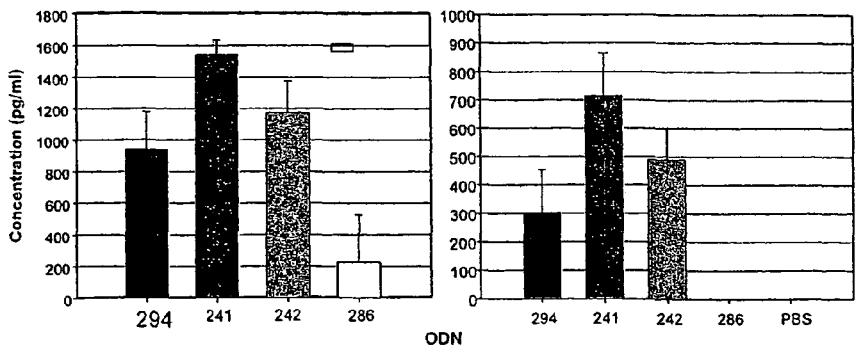
Fig. 41

US 8,304,396 B2

IMMUNOSTIMULATORY NUCLEIC ACIDS

RELATED APPLICATIONS

This application is a continuation of U.S. patent application Ser. No. 10/644,052, filed Aug. 19, 2003, now pending, which claims priority under 35 U.S.C. §119(e) to U.S. Provisional Application Ser. No. 60/404,479, filed Aug. 19, 2002, U.S. Ser. No. 60/404,820 filed Aug. 19, 2002, U.S. Ser. No. 60/429,701 filed Nov. 27, 2002, and U.S. Ser. No. 60/447,377 filed Feb. 14, 2003, each of which are herein incorporated by reference in their entirety.

FIELD OF THE INVENTION

The present invention relates generally to immunostimulatory nucleic acids, as well as immunostimulatory oligonucleotides with reduced renal inflammatory effects, compositions thereof and methods of using the immunostimulatory nucleic acids.

BACKGROUND OF THE INVENTION

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P., et al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci USA 96:9305-10).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci USA 96:9305-10; Liang, 1996 J. Clin. Invest. 98:1119-1129).

Several different classes of CpG nucleic acids has recently been described. One class is potent for activating B cells but is relatively weak in inducing IFN-α and NK cell activation; this class has been termed the B class. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class of CpG nucleic acids activates B cells and NK cells and induces IFN-α; this class has been termed the C-class. The C-class CpG nucleic acids, as first characterized, typically are fully stabilized, include a B class-type sequence and a GC-rich palindrome or near-palindrome. This class has been described in co-pending U.S. provisional patent application 60/313,273, filed Aug. 17, 2001 and US10/224,523 filed on Aug. 19, 2002 and related PCT Patent Application PCT/US02/26468 published under International Publication Number WO 03/015711.

SUMMARY OF THE INVENTION

It has been surprisingly discovered that immunostimulatory properties of the B-class and C-class CpG nucleic acids and other stabilized immunostimulatory nucleic acids can be maintained or even improved by the selective inclusion of one or more non-stabilized linkages between certain nucleotides. The non-stabilized linkages are preferably natural linkages, i.e., phosphodiester linkages or phosphodiester-like linkages. A non-stabilized linkage will typically, but not necessarily, be relatively susceptible to nuclease digestion. The immunostimulatory nucleic acids of the instant invention include at least one non-stabilized linkage situated between a 5' pyrimidine (Y) and an adjacent 3' purine (Z), preferably a guanine (G), wherein both the 5' Y and the 3' Z are internal nucleotides.

Like fully stabilized immunostimulatory nucleic acids, the immunostimulatory nucleic acids of the instant invention are useful for inducing a Th1-like immune response. Accordingly, the immunostimulatory nucleic acids of the instant invention are useful as adjuvants for vaccination, and they are useful for treating diseases including cancer, infectious disease, allergy, and asthma. They are believed to be of particular use in any condition calling for prolonged or repeated administration of immunostimulatory nucleic acid for any purpose.

In addition to being useful for any purpose for which fully stabilized immunostimulatory nucleic acids have utility, the immunostimulatory nucleic acids of the instant invention may in some embodiments have advantages over fully stabilized immunostimulatory nucleic acids, such as, increased potency and decreased toxicity.

The present invention relates in part to immunostimulatory CpG containing oligonucleotides. In one aspect the invention is an oligonucleotide having the formula: 5'T*C*G*T*CGTTTTGAN$_1$CGN$_2$*T*T3' (SEQ ID NO:296). In the oligonucleotide N$_1$ is 0-6 nucleotides and N$_2$ is 0-7 nucleotides. The symbol * refers to the presence of a stabilized internucleotide linkage. Internucleotide linkages not marked with an * may be unstabilized or stabilized, as long as the oligonucleotide includes at least 2 phosphodiester internucleotide linkages. The stabilized internucleotide linkage may be a phosphorothioate linkage. In some embodiments N$_1$ is 0-2 nucleotides. Preferably the oligonucleotide is 16-24 nucleotides in length.

In some embodiment the oligonucleotide has one of the following structures: 5'T*C*G*T*C*G*TTTTGAN$_1$C*G*N$_2$*T*T3' (SEQ ID NO:296), 5'T*C*G*T*C*G*T*T_T_T_GAN$_1$C*G*N$_2$*T*T3' (SEQ ID NO:296) or 5'T*C*G*T*C*G*T*T*T*T*GA_N$_1$C*G*N$_2$*T*T3' (SEQ ID NO:296) The symbol _ refers to the presence of a phosphodiester internucleotide linkage.

Preferably the oligonucleotide is

```
5' T*C*G*T*C*G*T*T*T*T*G*A_C_C_G_    (SEQ ID NO: 297)
G_T*T*C*G*T*G*T*T 3',

5' T*C*G*T*C*G*T*T*T*T*T*G_A_C*G*T*  (SEQ ID NO: 298)
T*T*T*G*T*C*G*T*T 3',

5' T*C*G*T*C*G*T*T_T_T_G*A*C*G*T*    (SEQ ID NO: 299)
T*T*T 3',
or

5' T*C*G*T*C*G*T*T_T_T_G*A*C*G*T*T   (SEQ ID NO: 300)
3'.
```

The invention, in other aspects, relates to an oligonucleotide comprising: 5'T*C*G*(T*/A*)TN₃CGTTTTN₄CGN₅*T*T 3' (SEQ ID NO:301). N₃ is 0-4 nucleotides. N₄ is 1-5 nucleotides. N₅ is 0-7 nucleotides. The symbol * refers to the presence of a stabilized internucleotide linkage. Internucleotide linkages not marked with an * may be unstabilized or stabilized, as long as the oligonucleotide includes at least 2 phosphodiester internucleotide linkages. The stabilized internucleotide linkage may be a phosphorothioate linkage. In some embodiments N₄ is 1-2 nucleotides. Preferably the oligonucleotide is 16-24 nucleotides in length.

In some embodiment the oligonucleotide has one of the following structures: 5' T*C*G*(T*/A*)TN₃CGTTTTN₄C*G*N₅*T*T 3' (SEQ ID NO:301), 5'T*C*G*A*T*N₃C*G*TTTTN₄C_G_*N₅*T*T 3' (SEQ ID NO:302), or 5'T*C*G*T*T*N₃C_G_TTTTN₄CGN₅*T*T 3' (SEQ ID NO:303).

Preferably the oligonucleotide is

```
5' T*C*G*A*T*C*G*T*T*T*T_T_C_G*T*    (SEQ ID NO: 304)
G*C*G*T*T*T*T 3,
or

5' T*C*G*T*T*T*T*G*A_C_G_T*T*T*T*    (SEQ ID NO: 305)
G*T*C*G*T*T 3'.
```

According to other aspects, an oligonucleotide comprising:
5'T*C*G*T*C*GNNNCGNCGNNNC*G*N*C*G*T*T3' (SEQ ID NO:306) is provided. N is any nucleotide. The symbol * refers to the presence of a stabilized internucleotide linkage. Internucleotide linkages not marked with an * may be unstabilized or stabilized, as long as the oligonucleotide includes at least 3 phosphodiester internucleotide linkages. The stabilized internucleotide linkage may be a phosphorothioate linkage. In some embodiments the oligonucleotide includes 5 phosphodiester internucleotide linkages. Preferably the oligonucleotide is 16-24 nucleotides in length.

In some embodiment the oligonucleotide has one of the following structures: 5'T*C*G*T*C*G*N*N*N*C*G_N_C G_N*N*N*C*G*N*C*G*T*T 3' (SEQ ID NO:307), 5'T*C*G*T*C*G*T*T*A*C_G_N_C_G_T*T*A*C*G* N*C*G*T*T 3' (SEQ ID NO:308), or 5'T*C*G*T*C*G*N*N*N*C_G_T_C_G_N*N*N*C*G* T*C*G*T*T 3' (SEQ ID NO:309). In one embodiment the oligonucleotide is 5'T*C*G*T*C*G*T*T*A*C_G_T_ C_G_T*T*A*C*G*T*C*G*T*T 3' (SEQ ID NO:310). The symbol _ refers to the presence of a phosphodiester internucleotide linkage.

In other embodiments the oligonucleotide includes at least one C_G motif with a phosphodiester internucleotide linkage. In yet other embodiments the oligonucleotide does not include any C_G motifs with a phosphodiester internucleotide linkage.

In other aspects an oligonucleotide having the structure 5'T*C_G(N₆C_G N₇)₂₋₃T*C_G*T*T3'(SEQ ID NOS:311-312) is provided. N₆ and N₇ are independently between 1 and 5 nucleotides in length and the oligonucleotide has a length of 16-40 nucleotides.

In some embodiments N₆ is one nucleotide, for instance N₆ may be T or A. N₇ in some embodiments is five nucleotides, for example, N₇ may be five pyrimidines or TTTTG.

In some embodiments the oligonucleotide has the structure:

```
5' T*C_G*T*C_G*T*T*T*T*G*A*C_G*T*   (SEQ ID NO: 313)
T*T*T*G*T*C_G*T*T 3'
or

5' T*C_G*A*C_G*T*T*T*T*G*T*C_G*T*   (SEQ ID NO: 314)
T*T*T*G*T*C_G*T*T 3'.
```

An oligonucleotide having the structure 5'T*CGCGN₈CGCGC*GN₉3' (SEQ ID NO:315) is provided according to other aspects of the invention. N₈ is between 4 and 10 nucleotides in length and includes at least 1 C_G motif. N₉ is between 0 and 3 nucleotides in length. The oligonucleotide has a length of 15-40 nucleotides.

In some embodiments N₈ includes at least 2 or 3 CG motifs. In other embodiments N₈ is PuCGPyPyCG or PuCGPyPyCGCG. Optionally N₈ is ACGTTCG. N₉ may include at least on CG motif, such as, CCG.

In some embodiments the oligonucleotide has the structure:

```
5' T*C_G*C_G*A*C_G*T*T*C_G*G*C*G*   (SEQ ID NO: 316)
C_G*C*G*C*C*G 3'
or

5' T*C*G*C*G*A*C_G*T*T*C*G*C*G*     (SEQ ID NO: 317)
C_G*C*G*C*G 3'.
```

In another aspect an oligonucleotide having the formula 5'T*T*GX₁X₂TG X₃X₄T*T*T*T*N₁₀T*T*T*T*T*T*T3' (SEQ ID NO:318) is provided. N₁₀ is between 4 and 8 nucleotides in length and includes at least 1 C_G motif. X₁, X₂, X₃ and, X₄ are independently C or G. The oligonucleotide has a length of 24-40 nucleotides.

In some embodiments N₁₀ includes at least 2 or 3 CG motifs. In other embodiments the oligonucleotide has one of the following structures:

```
5' T*T*G*C_G*T*G*C_G*T*T*T*T*G*A*   (SEQ ID NO: 319)
C_G*T*T*T*T*T*T 3'
or

5' T*T*G*G_C*T*G*G_C*T*T*T*T*G*A*   (SEQ ID NO: 320)
C_G*T*T*T*T*T*T 3'.
```

In other embodiments, the oligonucleotide has the structure:

```
5' T*C*G*C_G*A*C*G*T*T*C_G*G*C*G*   (SEQ ID NO: 321)
C_G*C*G*C*C*G 3'.
```

In some aspects the ODN is an oligonucleotide having a sequence selected from the group consisting of CGTCGTTTTGACGTTTTGTCGTT (SEQ ID NO: 333), GTCGTTTTGACGTTTTGTCGTT (SEQ ID NO: 334), TCGTTTTGACGTTTTGTCGTT (SEQ ID NO: 335), CGTTTTGACGTTTTGTCGTT (SEQ ID NO: 336), GTTTTGACGTTTTGTCGTT (SEQ ID NO: 337), TTTTGACGTTTTGTCGTT (SEQ ID NO: 338), TTTGACGTTTTGTCGTT (SEQ ID NO: 339), TTGACGTTTTGTCGTT (SEQ ID NO: 340), TGACGTTTTGTCGTT (SEQ ID NO: 341), GACGTTTTGTCGTT (SEQ ID NO: 342), ACGTTTTGTCGTT (SEQ ID NO: 343), GTTTTGTCGTT (SEQ ID NO: 344), GTTTTGTCGTT (SEQ ID NO: 345), TTTTGTCGTT (SEQ ID NO: 346), TTTGTCGTT, TTGTCGTT, TCGTCGTTTTGACGTTTTGTCGT (SEQ ID NO: 347), TCGTCGTTTTGACGTTTTGTCG (SEQ ID NO: 348), TCGTCGTTTTGACGTTTTGTC (SEQ ID NO: 349), TCGTCGTTTTGACGTTTTGT (SEQ ID NO: 350), TCGTCGTTTTGACGTTTTG (SEQ ID NO: 351), TCGTCGTTTTGACGTTTT (SEQ ID NO: 352), TCGTCGTTTTGACGTTT (SEQ ID NO: 353), TCGTCGTTTTGACGTT (SEQ ID NO: 354), TCGTCGTTTTGACGT (SEQ ID NO: 355), TCGTCGTTTTGACG (SEQ ID NO: 356), TCGTCGTTTTGAC (SEQ ID NO: 357), TCGTCGTTTTGA (SEQ ID NO: 358), TCGTCGTTTTG (SEQ ID NO: 359), TCGTCGTTTT (SEQ ID NO: 360), TCGTCGTTT, TCGTCGTT, CGTCGTTTTGACGTTTTGTCGT (SEQ ID NO: 361), GTCGTTTTGACGTTTTGTCG (SEQ ID NO: 362), TCGTTTTGACGTTTTGTC (SEQ ID NO: 363), CGTTTTGACGTTTTGT (SEQ iD NO: 364), GTTTTGACGTTTTG (SEQ ID NO: 365), TTTTGACGTTTT (SEQ ID NO: 366), TTTGACGTTT (SEQ ID NO: 367), and TTGACGTT.

In another aspect the invention is an oligonucleotide comprising an octameric sequence comprising at least one YZ dinucleotide having a phosphodiester or phosphodiester-like internucleotide linkage, and at least 4 T nucleotides, wherein Y is a pyrimidine or modified pyrimidine, wherein Z is a guanosine or modified guanosine, and wherein the oligonucleotide includes at least one stabilized internucleotide linkage.

Y may be an unmethylated C. Z may be a guanosine. In some embodiments Y is cytosine or a modified cystosine bases selected from the group consisting of 5-methyl cytosine, 5-methyl-isocytosine, 5-hydroxy-cytosine, 5-halogeno cytosine, uracil, N4-ethyl-cytosine, 5-fluoro-uracil, and hydrogen. In other embodiments Z is guanine or a modified guanine base selected from the group consisting of 7-deaza-guanine, 7-deaza-7-substituted guanine (such as 7-deaza-7-(C2-C6)alkynylguanine), 7-deaza-8-substituted guanine, hypoxanthine, 2,6-diaminopurine, 2-aminopurine, purine, 8-substituted guanine such as 8-hydroxyguanine, and 6-thioguanine, 2-aminopurine, and hydrogen.

In some embodiments the octameric sequence includes a TTTT motif. In other embodiments the octameric sequence includes two YZ dinucleotides. Optionally both YZ dinucleotides have a phosphodiester or phosphodiester-like internucleotide linkage.

In some embodiments the octameric sequence is selected from the group consisting of T*C-G*T*C-G*T*T, C-G*T*C-G*T*T*T, G*T*C-G*T*T*T*T, T*C-G*T*T*T*T*T*G, C-G*T*T*T*T*T*G*A, T*T*T*T*T*G*A*C-G, T*T*T*T*G*A*C-G*T, T*T*T*G*A*C-G*T*T, T*G*A*C-G*T*T*T*T, G*A*C-G*T*T*T*T*T, A*C-G*T*T*T*T*T*G, C-G*T*T*T*T*T*G*T, T*T*T*T*T*G*T*C-G, T*T*T*T*G*T*C-G*T, G*T*T*T*T*G*T*C, and T*T*G*T*C-G*T*T, wherein * refers to the presence of a stabilized internucleotide linkage, and wherein _ refers to the presence of a phosphodiester internucleotide linkage.

In other embodiments the oligonucleotide has a length of 8-40 nucleotides.

The phosphodiester-like linkage may be boranophosphonate or diastereomerically pure Rp phosphorothioate. Optionally the stabilized internucleotide linkages are phosphorothioate, phosphorodithioate, methylphosphonate, methylphosphorothioate, or any combination thereof.

The oligonucleotide may have a 3'-3' linkage with one or two accessible 5' ends. In some preferred embodiments the oligonucleotide has two accessible 5' ends, each of which are 5'TCG.

In another aspect of the invention an oligonucleotide comprising: 5' TCGTCGTTTTGACGTTTGTCGTT 3' (SEQ ID NO: 368) is provided. At least one CG dinucleotide has a phosphodiester or phosphodiester-like internucleotide linkage, and the oligonucleotide includes at least one stabilized internucleotide linkage.

In other aspects the invention is an oligonucleotide comprising: 5'GNC 3', wherein N is a nucleic aid sequence of 4-10 nucleotides in length and is at least 50% T and does not include a CG dinucleotide, and the oligonucleotide includes at least one stabilized internucleotide linkage. In one embodiment N includes a TTTT motif. In other embodiments the oligonucleotide is selected from the group consisting of G*T*T*T*T*G*T*C and G*T*T*T*T*G*A*C, wherein * refers to the presence of a stabilized internucleotide linkage.

In another aspect the invention provides an immunostimulatory nucleic acid molecule having at least one internal pyrimidine-purine (YZ) dinucleotide and optionally pyrimidine-guansosine (YG) dinucleotide and a chimeric backbone, wherein the at least one internal YZ dinucleotide has a phosphodiester or phosphodiester-like internucleotide linkage, wherein optionally each additional internal YZ dinucleotide has a phosphodiester, phosphodiester-like, or stabilized internucleotide linkage, and wherein all other internucleotide linkages are stabilized. In one embodiment the immunostimulatory nucleic acid comprises a plurality of internal YZ dinucleotides each having a phosphodiester or phosphodiester-like internucleotide linkage. In one embodiment every internal YZ dinucleotide has a phosphodiester or phosphodiester-like internucleotide linkage.

In one embodiment the immunostimulatory nucleic acid molecule is selected from the group consisting of: *A*C_G*T*C_G*T*T*T*T*C_G*T*C_G*T*T (SEQ ID NO:1), G*C_G*T*C_G*A*C_G*T*C_G*A*C_G*C (SEQ ID NO:2), G*C_G*T*C_G*T*T*T*T*C_G*T*C_G*C (SEQ ID NO:3), T*C*C*A*T_G*A*C_G*T*T*C*C*T_G*A*T*G*C (SEQ ID NO:4), T*C*G*T*C*G*T*T*T*T*C*G*T*C_G*T*T (SEQ ID NO:5), T*C*G*T*C*G*T*T*T*T*C_G*G*C_G*G*C*C_G*C*C*G (SEQ ID NO:6), T*C*G*T*C*G*T*T*T*T*C_G*T*C_G*T*T (SEQ ID NO:7), T*C*G*T*C_G*T*T*T*C_G*T*C_G*T*T (SEQ ID NO:8), T*C*G*T*C_G*T*T*T*T*C*G*T*C*G*T*T (SEQ ID NO:9), T*C*G*T*C_G*T*T*T*T*C*G*T*C_G*T*T (SEQ ID NO:10), T*C*G*T*C_G*T*T*T*T*C_G*T*C*G*T*T (SEQ ID NO:11), T*C_7*T*C_7*T*C_G*T*T*T*T_G*T*C_G*T*T*T*T_G*T*C_G*T*T (SEQ ID NO:12), T*C_7*T*C_G*T*T*T*T_G*T*C_G*T*T*T*T_G*T*C_7*T*T (SEQ ID NO:13), T*C_G*C*C_G*T*T*T*T*C_G*G*C_G*G*C*C_G*C*C*G (SEQ ID NO:14), T*C_G*T*C_G*T*T*T*T*A*C*G*A*C*G*T*C*G*C*G (SEQ ID NO:15), T*C_G*T*C_G*T*T*T*T*A*C*G*A*C*G*T*C*G*T*G (SEQ ID NO:16), T*C_G*T*C_G*T*T*T*T*A*C*G*G*C*G*C*C*G*C*G*C*C*G (SEQ ID NO:17), T*C_G*T*C_G*T*T*T*T*C*G*G*C*G*C*G*C*G*C*C*G (SEQ ID NO:21), T*C_G*T*C_G*T*T*T*T*C*G*T*C*G*T*T (SEQ ID NO:22), T*C_G*T*C_G*T*T*T*T*C*G*T*C_G*T*T (SEQ ID NO:23), T*C_G*T*C*G*T*T*T*T*C_G*T*C*G*T*T (SEQ ID NO:24), T*C_G*T*C*G*T*T*T*T*G*C*G*A*C*G*T*C*G*C*G (SEQ ID NO:25), T*C_G*T*C*G*T*T*T*T*T*C*G*A*C*G*T*C*G*A*G (SEQ ID NO:26), T*C_G*T*C*G*T*T*T*T*T*C*G*A*C*G*T*C*G*C*G (SEQ ID NO:27), T*C_G*T*C_7*T*T*T*T_G*T*C_G*T*T*T*T_7*T*C_G*T*T (SEQ ID NO:28), T*C_G*T*C_G*T*T*T*T*C_G*A*C*G*T*T (SEQ ID NO:29), T*C_G*T*C_G*T*T*T*T*C_G*A*C_G*T*T*T*T*G*T*C_G*T*T (SEQ ID NO:30), T*C_G*T*C_G*T*T*T*T*C_G*T*C_G*A*C_G*T*C_G*T*T*T*C_G*T*C*G (SEQ ID NO:31), T*C_G*T*C_G*T*T*T*T*C_G*T*C_G*A*T (SEQ ID NO:32), T*C_G*T*C_G*T*T*T*T*C_G*T*C_G*A*T*T (SEQ ID NO:33), T*C_G*T*C_G*T*T*T*T*C_G*T*C_G*T (SEQ ID NO:34), T*C_G*T*C_G*T*T*T*T*C_G*T*C_G*T*T (SEQ ID NO:35), T*C_G*T*C_G*T*T*T*T*C_G*T*C_G*T*T*T*C_G*T*C_G*T*T (SEQ ID NO:36), T*C_G*T*C_G*T*T*T*T*C_G*T*C_G*T*T*T*T*G*T*C_G*T*T (SEQ ID NO:37), T*C_G*T*C_G*T*T*T*T*G*T*C*G*T*C*G*G*C*G*G*C*C*G*C*C*G (SEQ ID NO:38), T*C_G*T*C_G*T*T*T*T*C*G*G*C*G*C*G*C*C*G*C*C*G (SEQ ID NO:39), T*C_G*T*C_G*T*T*T*T*C*G*G*C*G*G*C*C*G*C*C*G (SEQ ID NO:40), T*C_G*T*C_G*T*T*T*T*C*G*T*C*G*T*T (SEQ ID NO:41), T*C_G*T*C_G*T*T*T*T*T*C_G*G*C_G*C_G*C_G*C*C*G (SEQ ID NO:42), T*C_G*T*C_G*T*T*T*T*T*C_G*G*C_G*G*C*C_G*C*C*G (SEQ ID NO:43), T*C_G*T*C_G*T*T*T*T*T*C_G*T*C_G*T (SEQ ID NO:44), T*C_G*T*C_G*T*T*T*T*T*C_G*T*C_G*T*T (SEQ ID NO:45), T*C_G*T*C_G*T*T*T*T*T*C_G*T*T_G*T*T (SEQ ID NO:46), T*C_G*T*C_G*T*T*T*T*T*G*T*C_G*T*C_G*T*T*T*T (SEQ ID NO:47), T*C_G*T*C_G*T*T*T*T*T*T*T*T*T*C_G*T*C_G*T*T*T (SEQ ID NO:48), T*C_G*T*C_G*T*T*T*T*T*T_G*T*C_G*T*T (SEQ ID NO:49), T*C_G*T*C_G*T*T*T*T*T_G*T*T_G*T*T (SEQ ID NO:50), T*C_G*T*C_G*T*T*T*T*T_7*T*C_7*T*T*T*T_G*T*C_G*T*T (SEQ ID NO:51), T*C_G*T*C_G*T*T*T*T*T_G*A*C_G*T*T (SEQ ID NO:52), T*C_G*T*C_G*T*T*T*T*T_G*A*C_G*T*T*T*T (SEQ ID NO:53), T*C_G*T*C_G*T*T*T*T*T_G*A*C_G*T*T*T*T*G*T*C*G*T*T (SEQ ID NO:54), T*C_G*T*C_G*T*T*T*T*T_G*A*C_G*T*T*T*T*G*T*C_G*T*T (SEQ ID NO:55), T*C_G*T*C_G*T*T*T*T*T_G*T*C_G*T*T (SEQ ID NO:56), T*C_G*T*C_G*T*T*T*T*T_G*T*C_G*T*T*T*T*G*T*C_G*T*T (SEQ ID NO:241), T*C_G*T*C_G*T*T*T*T*T_G*T*C_G*T*T*T*T*T_7*T*C_7*T*T (SEQ ID NO:58), T*C_G*T*C_G*T*T*T*T*T_G*T*C_G*T*T*T*T*T_G*T*C_G*T*T (SEQ ID NO:59), T*C_G*T*C_G*T*T*T*U_G*T*C_G*T*T*T (SEQ ID NO:60), T*C_G*T*C_G*T*T*T*U_G*T*C_G*T*T*T*T*T_G*T*C_G*T*T (SEQ ID NO:61), T*C_G*T*C_G*T*T*T_G*C_G*T*C_G*T (SEQ ID NO:62), T*C_G*T*C_G*T*T*T_G*C_G*T*C_G*T*T (SEQ ID NO:63), T*C_G*T*C_G*T*T*T_G*T*C_G*T (SEQ ID NO:64), T*C_G*T*C_G*T*T*T_G*T*C_G*T*T (SEQ ID NO:65), T*C_G*T*C_G*U*U*U*C_G*T*C_G*U*U*U*U_G*T*C_G*T*T (SEQ ID NO:66), T*C_G*T*T*T*T*T*G*T*C_G*T*T*T*T (SEQ ID NO:67), T*C_G*T*T*T*T*T*G*T*C_G*T*T*T*T*T*T*T (SEQ ID NO:68), T*C_G*T*T*T*T*T*T*T*T*C_G*T*C_G*T*T (SEQ ID NO:69), T*C_G*T*T_G*T*T*T*T*C_G*T*C_G*T*T (SEQ ID NO:70), T*C_G*T*T_G*T*T*T*T*C_G*T*T_G*T*T (SEQ ID NO:71), T*C_G*T*T_G*T*T*T*T*T_G*T*C_G*T*T (SEQ ID NO:72), T*C_G*T*T_G*T*T*T*T*T_G*T*T_G*T*T (SEQ ID NO:73), T*C_G*U*C_G*T*T*T*T_G*T*C_G*T*T*T*U_G*U*C_G*T*T (SEQ ID NO:74), T*G*T*C_G*T*T*G*T*C_G*T*T*G*T*C_G*T*T*G*T*C_G*T*T (SEQ ID NO:75), T*G*T*C_G*T*T*G*T*C_G*T*T_G*T*C_G*T*T_G*T*C_G*T*T (SEQ ID NO:76), T*G*T*C_G*T*T*T*C_G*T*C_G*T*T (SEQ ID NO:77), T*G*T*C_G*T*T*T*T_G*T*C_G*T*T (SEQ ID NO:78), T*T*A*G*T*T*C_G*T*A*G*T*T*C*T*T*C_G*T*T (SEQ ID NO:79), T*T*C_G*T*C_G*T*T*T*C_G*T*C_G*T*T (SEQ ID NO:80), T*T*C_G*T*C_G*T*T*T*C_G*T*C_G*T*T*T (SEQ ID NO:81), T*T*C_G*T*T*T*C_G*T*T*T_G*T*C_G*T*T (SEQ ID NO:82), T*T*C_G*T*T*T*C*T*T*A*G*T*T*C_G*T*A*G*T*T (SEQ ID NO:83), T*T*T*C_G*A*C_G*T*C_G*T*T*T (SEQ ID NO:84), T*T*T*T*T*C_G*T*C_G*T*T*T*T*T*G*T*C_G*T*C_G*T (SEQ ID NO:85), T*T*T*T*T*C_G*T*C_G*T*T*T*T*T*G*T*C_G*T*C_G*T*T*T*T (SEQ ID NO:86), T*T*T*T*T*C_G*T*C_G*T*T*T*T*T*T*T*T*T*C_G*T*C_G*T (SEQ ID NO:87), T*T*T*T*T*C_G*T*C_G*T*T*T*T*T*T*T*T*C_G*T*C_G*T*T*T*T (SEQ ID NO:88), T*T*T*T*T*C_G*T*C_G*T*T*T*T*T_G*T*C_G*T*C_G*T*T*T*T (SEQ ID NO:89), T*T*T*T*T*C_G*T*C_G*T*T*T*T*G*T*C_G*T (SEQ ID NO:90), T*T*T*T*T*C_G*T*T*T*T*G*T*C_G*T*T*T*T (SEQ ID NO:91), T*T*T*T*T*C_G*T*T*T*T*T*T*T*T*C_G*T (SEQ ID NO:92), T*T*T*T*T*C_G*T*T*T*T*T*T*T*T*C_G*T*T*T*T (SEQ ID NO:93), T*T*T*T*T*T*C_G_T*T*T*T_G*T*C_G*T*T*T*T (SEQ ID NO:94), T*T*T*T*T*T*T*T*T*C_G*T*T*T*T*G*T*C_G*T (SEQ ID NO:95), T*T_G*T*C_G*T*T*T*T*C_G*T*C_G*T*T (SEQ ID NO:96), T*T_G*T*C_G*T*T*T*T*C_G*T*T_G*T*T (SEQ ID NO:97), T*T_G*T*C_G*T*T*T*T*T_G*T*C_G*T*T (SEQ ID NO:98), and T*T_G*T*C_G*T*T*T*T*T_G*T*T_G*T*T (SEQ ID NO:99), wherein * represents phosphorothioate, _ represents phosphodiester, U represents 2'-deoxyuracil, and 7 represents 7-deazaguanine.

In one embodiment the immunostimulatory nucleic acid molecule is selected from the group consisting of:
T*C_G*T*C_G*T*T*T*T_G*T*C_G*T*T*T*G*T*C_G*T*T (SEQ ID NO:100), T*C_G*T*C_G*T*T*T*T_G*T*C_G*T*T (SEQ ID NO:101), T*C_G*T*C_G*T*T*T*C_G*T*C_G*T*T (SEQ ID NO:102), T*G*T*C_G*T*T*G*T*C_G*T*T_G*T*C_G*T*T_G*T*C_G*T*T (SEQ ID NO:103), and T*C_G*T*C_G*T*T*T*T*C*G*G*C*G*G*C*C*G*C*C*G (SEQ ID NO:104), wherein * represents phosphorothioate and _represents phosphodiester.

In another aspect the invention provides an immunostimulatory nucleic acid molecule comprising a chimeric backbone and at least one sequence $N_1YGN_2$, wherein independently for each sequence $N_1YGN_2$ YG is an internal pyrimidine-guanosine (YG) dinucleotide, $N_1$ and $N_2$ are each, independent of the other, any nucleotide, and wherein for the at least one sequence $N_1YGN_2$ and optionally for each additional sequence $N_1YGN_2$: the YG dinucleotide has a phosphodiester or phosphodiester-like internucleotide linkage, and $N_1$ and Y are linked by a phosphodiester or phosphodiester-like internucleotide linkage when $N_1$ is an internal nucleotide, G and $N_2$ are linked by a phosphodiester or phosphodiester-like internucleotide linkage when $N_2$ is an internal nucleotide, or $N_1$ and Y are linked by a phosphodiester or phosphodiester-like internucleotide linkage when $N_1$ is an internal nucleotide and G and $N_2$ are linked by a phosphodiester or phosphodiester-like internucleotide linkage when $N_2$ is an internal nucleotide, wherein all other internucleotide linkages are stabilized.

In one embodiment the immunostimulatory nucleic acid comprises a plurality of the sequence $N_1YGN_2$, wherein for each sequence $N_1YGN_2$: the YG dinucleotide has a phosphodiester or phosphodiester-like internucleotide linkage, and $N_1$ and Y are linked by a phosphodiester or phosphodiester-like internucleotide linkage when $N_1$ is an internal nucleotide, G and $N_2$ are linked by a phosphodiester or phosphodiester-like internucleotide linkage when $N_2$ is an internal nucleotide, or $N_1$ and Y are linked by a phosphodiester or phosphodiester-like internucleotide linkage when $N_1$ is an internal nucleotide and G and $N_2$ are linked by a phosphodiester or phosphodiester-like internucleotide linkage when $N_2$ is an internal nucleotide.

In one embodiment the immunostimulatory nucleic acid molecule is selected from the group consisting of:
T*C_G*T*C_G*T*T*T*T*G*T*C_G*T*T*T*T*G*T*C_G_T*T (SEQ ID NO:105),
T*C_G*T*C_G*T*T*T*T*G*T*C_G*T*T*T*T*G*T_C_G_T*T (SEQ ID NO:106),
T*C_G*T*C_G*T*T*T*T*G*T*C_G*T*T*T*T*G*T_C_G_T*T (SEQ ID NO:107),
T*C_G*T*C_G*T*T*T*T*G*T*C_G_T*T*T*T*G* T*C_G*T*T (SEQ ID NO:108),
T*C_G*T*C_G*T*T*T*T*G*T*C_G_T*T*T*T*G* T*C_G_T*T (SEQ ID NO:109),
T*C_G*T*C_G*T*T*T*T*G*T*C_G_T*T*T*T*G* T_C_G*T*T (SEQ ID NO:110),
T*C_G*T*C_G*T*T*T*T*G*T*C_G_T*T*T*T*G* T_C_G*T*T (SEQ ID NO:111),
T*C_G*T*C_G*T*T*T*T*G*T_C_G*T*T*T*T*G* T*C_G*T*T (SEQ ID NO:112),
T*C_G*T*C_G*T*T*T*T*G*T_C_G*T*T*T*T*G* T*C_G_T*T (SEQ ID NO:113),
T*C_G*T*C_G*T*T*T*T*G*T_C_G*T*T*T*T*G* T_C_G*T*T (SEQ ID NO:114),
T*C_G*T*C_G*T*T*T*T*G*T_C_G*T*T*T*T*G* T_C_G_T*T (SEQ ID NO:115),
T*C_G*T*C_G*T*T*T*T*G*T_C_G*T*T*T*T*G* T*C_G*T*T (SEQ ID NO:116),
T*C_G*T*C_G*T*T*T*T*G*T_C_G*T*T*T*T*G* T*C_G_T*T*T*G* (SEQ ID NO:117),
T*C_G*T*C_G*T*T*T*T*G*T*C_G*T*T*T*T*G* T_C_G*T*T (SEQ ID NO:118),
T*C_G*T*C_G*T*T*T*T*G*T*C_G*T*T*T*T*G* T_C_G_T*T (SEQ ID NO:119),
T*C_G*T*C_G_T*T*T*T*G*T*C_G*T*T*T*T*G* T*C_G*T*T (SEQ ID NO:120),
T*C_G*T*C_G_T*T*T*T*G*T*C_G*T*T*T*T*G* T*C_G_T*T (SEQ ID NO:121),
T*C_G*T*C_G_T*T*T*T*G*T*C_G*T*T*T*T*G* T_C_G*T*T (SEQ ID NO:122),
T*C_G*T*C_G_T*T*T*T*G*T*C_G*T*T*T*T*G* T_C_G_T*T (SEQ ID NO:123),
T*C_G*T*C_G_T*T*T*T*G*T*C_G*T*T*T*T*G* T*C_G*T*T (SEQ ID NO:124),
T*C_G*T*C_G_T*T*T*T*G*T*C_G*T*T*T*T*G* T*C_G_T*T (SEQ ID NO:125),
T*C_G*T*C_G_T*T*T*T*G*T*C_G*T*T*T*T*G* T_C_G*T*T (SEQ ID NO:126),
T*C_G*T*C_G_T*T*T*T*G*T*C_G*T*T*T*T*G* T_C_G_T*T (SEQ ID NO:127),
T*C_G*T*C_G_T*T*T*T*G*T*C_G*T*T*T*T*G* T*C_G*T*T (SEQ ID NO:128),
T*C_G*T*C_G_T*T*T*T*G*T*C_G*T*T*T*T*G* T*C_G_T*T (SEQ ID NO:129),
T*C_G*T*C_G_T*T*T*T*G*T*C_G*T*T*T*T*G* T_C_G*T*T (SEQ ID NO:130),
T*C_G*T*C_G_T*T*T*T*G*T*C_G*T*T*T*T*G* T_C_G_T*T (SEQ ID NO:131),
T*C_G*T*C_G_T*T*T*T*G*T*C_G*T*T*T*T*G* T*C_G*T*T (SEQ ID NO:132),
T*C_GGT*T (SEQ ID NO:133),
T*C_G*T*C_G_T*T*T*T*G*T_C_G*T*T*T*T*G* T_C_G*T*T (SEQ ID NO:134),
T_C_GT*T (SEQ ID NO:135),
T*C_G*T_C_G*T*T*T*T*G*T*C_G*T*T*T*T*G* T*C_G*T*T (SEQ ID NO:136),
T*C_G*T_C_G*T*T*T*T*G*T*C_G*T*T*T*T*G* T*C_G_T*T (SEQ ID NO:137),
T*C_G*T_C_G*T*T*T*T*G*T*C_G*T*T*T*T*G* T_C_G*T*T (SEQ ID NO:138),
T*C_G*T_C_G*T*T*T*T*G*T*C_G*T*T*T*T*G* T_C_GT*T (SEQ ID NO:139),
T*C_G*T_C_G*T*T*T*T*G*T*C_G*T*T*T*T*G* T*C_G*T*T (SEQ ID NO:140),
T*C_G*T_C_G*T*T*T*T*G*T*C_G*T*T*T*T*G* T*C_G_T*T (SEQ ID NO:141),
T*C_G*T_C_G*T*T*T*T*G*T*C_G*T*T*T*T*G* T_C_G*T*T (SEQ ID NO:142),
T*C_G*T_C_G*T*T*T*T*G*T*C_G_T*T*T*T*G*

T_C_G_T*T (SEQ ID NO:143),
T*C_G*T_C_G*T*T*T*T*G*T_C_G*T*T*T*T*G*
T*C_G*T*T (SEQ ID NO:144),
T*C_G*T_C_G*T*T*T*T*G*T_C_G*T*T*T*T*G*
T_C_G*T*T (SEQ ID NO:145),
T*C_G*T_C_G*T*T*T*T*G*T_C_G*T*T*T*T*G*
T*C_G*T*T (SEQ ID NO:146),
T*C_G*T_C_G*T*T*T*T*G*T_C_G*T*T*T*T*G*
T_C_G*T*T (SEQ ID NO:147),
T*C_G*T_C_G*T*T*T*T*G*T_C_G_T*T*T*T*G*
T*C_G*T*T (SEQ ID NO:148),
T*C_G*T_C_G*T*T*T*T*G*T_C_G_T*T*T*T*G*
T_C_G_T*T (SEQ ID NO:149),
T*C_G*T_C_G*T*T*T*T*G*T_C_G_T*T*T*T*G*
T*C_G*T*T (SEQ ID NO:150),
T*C_G*T_C_G*T*T*T*T*G*T_C_G_T*T*T*T*G*
T_C_G*T*T (SEQ ID NO:151),
T*C_G*T_C_G_T*T*T*T*G*T*C_G*T*T*T*T*G*
T*C_G*T*T (SEQ ID NO:152),
T*C_G*T_C_G_T*T*T*T*G*T*C_G*T*T*T*T*G*
T_C_G*T*T (SEQ ID NO:153),
T*C_G*T_C_G_T*T*T*T*G*T*C_G*T*T*T*T*G*
T_C_G*T*T (SEQ ID NO:154),
T*C_G*T_C_G_T*T*T*T*G*T*C_G*T*T*T*T*G*
T_C_G_T*T (SEQ ID NO:155),
T*C_G*T_C_G_T*T*T*T*G*T*C_G_T*T*T*T*G*
T*C_G*T*T (SEQ ID NO:156),
T*C_G*T_C_G_T*T*T*T*G*T_C_G*T*T*T*T*G*
T*C_G*T*T (SEQ ID NO:157),
T*C_G*T_C_G_T*T*T*T*G*T_C_G*T*T*T*T*G*
T*C_G*T*T (SEQ ID NO:158),
T*C_G*T_C_G_T*T*T*T*G*T_C_G_T*T*T*T*G*
T_C_G*T*T (SEQ ID NO:159),
T*C_G*T_C_G_T*T*T*T*G*T_C_G*T*T*T*T*G*
T*C_G*T*T (SEQ ID NO:160),
T*C_G*T_C_G_T*T*T*T*G*T_C_G*T*T*T*T*G*
T*C_G*T*T (SEQ ID NO:161),
T*C_G*T_C_G_T*T*T*T*G*T_C_G_T*T*T*T*G*
T_C_G*T*T (SEQ ID NO:162),
T*C_G*T_C_G_T*T*T*T*G*T_C_G_T*T*T*T*G*
T_C_G*T*T (SEQ ID NO:163),
T*C_G*T_C_G_T*T*T*T*G*T_C_G_T*T*T*T*G*
T*C_G*T*T (SEQ ID NO:164),
T*C_G*T_C_G_T*T*T*T*G*T_C_G_T*T*T*T*G*
T*C_G*T*T (SEQ ID NO:165),
T*C_G*T_C_G_T*T*T*T*G*T_C_G_T*T*T*T*G*
T_C_G*T*T (SEQ ID NO:166),
T*C_G*T_C_G_T*T*T*T*G*T_C_G_T*T*T*T*G*
T_C_G_T*T (SEQ ID NO:167), T*C_G.
T*C_G*T*T*T*T*G*T*C_G*T*T*T*T*G*T*C_G*
T*T (SEQ ID NO:168),
T*C_G*T_C_G*T*T*T*T*G*T*C_G*T*T*T*T*G*
T*C_G*T*T (SEQ ID NO:169),
T*C_G*T_C_G*T*T*T*T*G*T*C_G*T*T*T*T*G*
T_C_G*T*T (SEQ ID NO:170),
T*C_G*T_C_G*T*T*T*T*G*T*C_G*T*T*T*T*G*
T*C_G*T*T (SEQ ID NO:171),
T*C_G*T_C_G*T*T*T*T*G*T*C_G*T*T*T*T*G*
T*C_G*T*T (SEQ ID NO:172),
T*C_G*T_C_G*T*T*T*T*G*T*C_G*T*T*T*T*G*
T_C_G*T*T (SEQ ID NO:173),
T*C_G*T_C_G*T*T*T*T*G*T_C_G*T*T*T*T*G*
T_C_G*T*T (SEQ ID NO:174),
T*C_G*T_C_G*T*T*T*T*G*T_C_G*T*T*T*T*G*
T_C_GT*T (SEQ ID NO:175),
T*C_G*T_C_G*T*T*T*T*G*T_C_G*T*T*T*T*G*
T*C_G*T*T (SEQ ID NO:176),

T*C_G_T*C_G*T*T*T*T*G*T_C_G*T*T*T*T*G*
T*C_G_T*T (SEQ ID NO:177),
T*C_G_T*C_G*T*T*T*T*G*T_C_G*T*T*T*T*G*
T_C_G*T*T(SEQID NO:178),
T*C_G_T*C_G*T*T*T*T*G*T_C_G*T*T*T*T*G*
T*C_G*T*T (SEQ ID NO:179),
T*C_G_T*C_G*T*T*T*T*G*T_C_G_T*T*T*T*G*
T*C_G*T*T (SEQ ID NO:180),
T*C_G_T*C_G*T*T*T*T*G*T_C_G_T*T*T*T*G*
T_C_G*T*T (SEQ ID NO:181),
T*C_G_T*C_G*T*T*T*T*G*T_C_G_T*T*T*T*G*
T*C_G*T*T (SEQ ID NO:182),
T*C_G_T*C_G*T*T*T*T*G*T_C_G_T*T*T*T*G*
T_C_GT*T (SEQ ID NO:183),
T*C_G_T*C_G_T*T*T*T*G*T*C_G*T*T*T*T*G*
T*C_G*T*T (SEQ ID NO:184),
T*C_G_T*C_G_T*T*T*T*G*T*C_G*T*T*T*T*G*
T_C_GT*T (SEQ ID NO:185),
T*C_G_T*C_G_T*T*T*T*G*T*C_G*T*T*T*T*G*
T_C_G*T*T (SEQ ID NO:186),
T*C_G_T*C_G_T*T*T*T*G*T*C_G_T*T*T*T*G*
T_C_GT*T (SEQ ID NO:187),
T*C_G_T*C_G_T*T*T*T*G*T_C_G*T*T*T*T*G*
T*C_G*T*T (SEQ ID NO:188),
T*C_G_T*C_G_T*T*T*T*G*T_C_G*T*T*T*T*G*
T_C_G*T*T (SEQ ID NO:189),
T*C_G_T*C_G_T*T*T*T*G*T_C_G*T*T*T*T*G*
T_C_G*T*T (SEQ ID NO: 190),
T*C_G_T*C_G_T*T*T*T*G*T_C_G_T*T*T*T*G*
T_C_GT*T (SEQ ID NO:191),
T*C_G_T*C_G_T*T*T*T*G*T_C_G_T*T*T*T*G*
T*C_G*T*T (SEQ ID NO:192),
T*C_G_T*C_G_T*T*T*T*G*T_C_G_T*T*T*T*G*
T*C_GT*T (SEQ ID NO:193),
T*C_G_T*C_G_T*T*T*T*G*T_C_G_T*T*T*T*G*
T_C_G*T*T (SEQ ID NO:194),
T*C_G_T*C_G_T*T*T*T*G*T_C_G_T*T*T*T*G*
T_C_GT*T (SEQ ID NO: 195),
T*C_G_T*C_G_T*T*T*T*G*T_C_G*T*T*T*T*G*
T*C_G*T*T (SEQ ID NO:196),
T*C_G_T*C_G_T*T*T*T*G*T_C_G_T*T*T*T*G*
T_C_GT*T (SEQ ID NO:197),
T*C_G_T*C_G_T*T*T*T*G*T_C_G_T*T*T*T*G*
T*C_G*T*T (SEQ ID NO:198),
T*C_G_T*C_G_T*T*T*T*G*T_C_G_T*T*T*T*G*
T_C_GT*T (SEQ ID NO:199),
T*C_G_T_C_G*T*T*T*T*G*T_C_G*T*T*T*T*G*
T*C_G*T*T (SEQ ID NO:200),
T*C_G_T_C_G*T*T*T*T*G*T_C_G*T*T*T*T*G*
T_C_GT*T (SEQ ID NO:201),
T*C_G_T_C_G*T*T*T*T*G*T_C_G*T*T*T*T*G*
T_C_G*T*T (SEQ ID NO:202),
T*C_G_T_C_G*T*T*T*T*G*T_C_G_T*T*T*T*G*
T_C_GT*T (SEQ ID NO:203),
T*C_G_T_C_G*T*T*T*T*G*T_C_G_T*T*T*T*G*
T*C_G*T*T (SEQ ID NO:204),
T*C_G_T_C_G*T*T*T*T*G*T_C_G_T*T*T*T*G*
T_C_GT*T (SEQ ID NO:205),
T*C_G_T_C_G*T*T*T*T*G*T_C_G_T*T*T*T*G*
T_C_G*T*T (SEQ ID NO:206),
T*C_G_T_C_G*T*T*T*T*G*T_C_G_T*T*T*T*G*
T_C_GT*T (SEQ ID NO:207),
T*C_G_T_C_G*T*T*T*T*G*T_C_G*T*T*T*T*G*
T*C_G*T*T (SEQ ID NO:208),
T*C_G_T_C_G*T*T*T*T*G*T_C_G*T*T*T*T*G*
T_C_GT*T (SEQ ID NO:209),
T*C_G_T_C_G*T*T*T*T*G*T_C_G*T*T*T*T*G*

T_C_G*T*T (SEQ ID NO:210),
T*C_G_T_C_G*T*T*T*T*G*T_C_G*T*T*T*T*G*
T_C_GT*T (SEQ ID NO:211),
T*C_G_T_C_G*T*T*T*T*G*T_C_G_T*T*T*T*G*
T*C_G_T*T (SEQ ID NO:212),
T*C_G_T_C_G*T*T*T*T*G*T_C_G_T*T*T*T*G*
T*C_G_T*T (SEQ ID NO:213),
T*C_G_T_C_G*T*T*T*T*G*T_C_G_T*T*T*T*G*
T_C_G*T*T (SEQ ID NO:214),
T*C_G_T_C_G*T*T*T*T*G*T_C_G_T*T*T*T*G*
T_C_G_T*T (SEQ ID NO:215),
T*C_G_T_C_G_T*T*T*T*G*T*C_G*T*T*T*T*G*
T*C_G*T*T (SEQ ID NO:216),
T*C_G_T_C_G_T*T*T*T*G*T*C_G*T*T*T*T*G*
T*C_G_T*T (SEQ ID NO:217),
T*C_G_T_C_G_T*T*T*T*G*T*C_G*T*T*T*T*G*
T_C_G*T*T (SEQ ID NO:218),
T*C_G_T_C_G_T*T*T*T*G*T*C_G*T*T*T*T*G*
T_C_G_T*T (SEQ ID NO:219),
T*C_G_T_C_G_T*T*T*T*G*T*C_G_T*T*T*T*G*
T*C_G*T*T (SEQ ID NO:220),
T*C_G_T_C_G_T*T*T*T*G*T*C_G_T*T*T*T*G*
T*C_G_T*T (SEQ ID NO:221),
T*C_G_T_C_G_T*T*T*T*G*T*C_G_T*T*T*T*G*
T_C_G*T*T (SEQ ID NO:222),
T*C_G_T_C_G_T*T*T*T*G*T*C_G_T*T*T*T*G*
T_C_G_T*T (SEQ ID NO:223),
T*C_G_T_C_G_T*T*T*T*G*T_C_G*T*T*T*T*G*
T*C_G*T*T (SEQ ID NO:224),
T*C_G_T_C_G_T*T*T*T*G*T_C_G*T*T*T*T*G*
T*C_G_T*T (SEQ ID NO:225),
T*C_G_T_C_G_T*T*T*T*G*T_C_G*T*T*T*T*G*
T_C_G*T*T (SEQ ID NO:226),
T*C_G_T_C_G_T*T*T*T*G*T_C_G*T*T*T*T*G*
T_C_G_T*T (SEQ ID NO:227),
T*C_G_T_C_G_T*T*T*T*G*T_C_G_T*T*T*T*G*
T*C_G*T*T (SEQ ID NO:228),
T*C_G_T_C_G_T*T*T*T*G*T_C_G_T*T*T*T*G*
T*C_G_T*T (SEQ ID NO:229),
T*C_G_T_C_G_T*T*T*T*G*T_C_G_T*T*T*T*G*T_C_G*T*T (SEQ ID NO:230), and
T*C_G_T_C_G_T*T*T*T*G*T_C_G_T*T*T*T*G*T_C_G_T*T (SEQ ID NO:231), wherein * represents phosphorothioate and _ represents phosphodiester.

In one embodiment the immunostimulatory nucleic acid molecule is selected from the group consisting of:
T*C_G_T*C_G_T*T*T*T*G*T*C_G_T*T*T*T*G*T*C_G_T*T (SEQ ID NO:232),
T*C_G*T_C_G*T*T*T*T*G*T_C_G*T*T*T*T*G*T_C_G*T*T (SEQ ID NO:233), and
T*C_G_T_C_G_T*T*T*T*G*T_C_G_T*T*T*T*G*T_C_G_T*T (SEQ ID NO:234), wherein * represents phosphorothioate and _ represents phosphodiester.

In one embodiment the immunostimulatory nucleic acid molecule is selected from the group consisting of:
T*C*G*T*C*G*T*T*T_T_G*T*C*G*T*T*T_T_G*T*C*G*T*T (SEQ ID NO:235),
T*C*G*T*C*G*T*T*T*T_G_T*C*G*T*T*T*T_G_T*C*G*T*T (SEQ ID NO:236), and
T*C*G*T*C*G*T*T*T_T_G_T*C*G*T*T*T*T_T_G_T*C*G*T*T (SEQ ID NO:237), wherein * represents phosphorothioate and _ represents phosphodiester.

In one embodiment the immunostimulatory nucleic acid molecule is selected from the group consisting of:
T*C_G*T_C_G*T*T_T_G*T_C_G*T*T*T_T_G*T_C_G*T*T (SEQ ID NO:238),
T*C_G_T*C_G_T*T*T_G_T*C_G_T*T*T_G_T*C_G*T*T*T_G_T*C_G*T (SEQ ID NO:239), and
T*C_G_T_C_G_T*T*T_T_G_T_C_G_T*T*T_T_G_T_C_G_T*T (SEQ ID NO:240), wherein * represents phosphorothioate and _ represents phosphodiester.

In one embodiment the at least one internal YG dinucleotide having a phosphodiester or phosphodiester-like internucleotide linkage is CG. In one embodiment the at least one internal YG dinucleotide having a phosphodiester or phosphodiester-like internucleotide linkage is TG.

In one embodiment the phosphodiester or phosphodiester-like internucleotide linkage is phosphodiester. In one embodiment the phosphodiester-like linkage is boranophosphonate or diastereomerically pure Rp phosphorothioate.

In one embodiment the stabilized internucleotide linkages are selected from the group consisting of: phosphorothioate, phosphorodithioate, methylphosphonate, methylphosphorothioate, and any combination thereof. In one embodiment the stabilized internucleotide linkages are phosphorothioate.

In one embodiment the immunostimulatory nucleic acid molecule is a B-Class immunostimulatory nucleic acid molecule. In one embodiment the immunostimulatory nucleic acid molecule is a C-Class immunostimulatory nucleic acid molecule.

In one embodiment the immunostimulatory nucleic acid molecule is 4-100 nucleotides long. In one embodiment the immunostimulatory nucleic acid molecule is 6-40 nucleotides long. In one embodiment the immunostimulatory nucleic acid molecule is 6-19 nucleotides long.

In one embodiment the immunostimulatory nucleic acid molecule is not an antisense oligonucleotide, triple-helix-forming oligonucleotide, or ribozyme.

In another aspect the invention provides an oligonucleotide which comprises $$N_1—C\_G-N_2—C\_G-N_3$$

wherein $N_1$ and $N_3$ are each independently a nucleic acid sequence 1-20 nucleotides in length, wherein _ indicates an internal phosphodiester or phosphodiester-like internucleotide linkage, wherein $N_2$ is independently a nucleic acid sequence 0-20 nucleotides in length, and wherein G-$N_2$—C includes 1 or 2 stabilized linkages.

In another aspect the invention provides an oligonucleotide which comprises $$N_1—C\_G-N_2—C\_G-N_3$$

wherein $N_1$ and $N_3$ are each independently a nucleic acid sequence 1-20 nucleotides in length, wherein _ indicates an internal phosphodiester or phosphodiester-like internucleotide linkage,
wherein $N_2$ is independently a nucleic acid sequence 4-20 nucleotides in length, and
wherein G-$N_2$—C includes at least 5 stabilized linkages.

In another aspect the invention provides an oligonucleotide which comprises $$N_1—C\_G-N_2—C\_G-N_3$$

wherein $N_1$, $N_2$, and $N_3$ are each independently a nucleic acid sequence of 0-20 nucleotides in length and wherein _ indicates an internal phosphodiester or phosphodiester-like internucleotide linkage, wherein the oligonucleotide is not an antisense oligonucleotide, triple-helix-forming oligonucleotide, or ribozyme.

In another aspect the invention provides a an oligonucleotide which comprises $$X_1—N_1\text{-}(GTCGTT)_n—N_2—X_2 \text{ (SEQ ID NOS:18-20 and 57)}$$

wherein $N_1$ and $N_2$ are each independently a nucleic acid sequence of 0-20 nucleotides in length, wherein n=2 or n=4-6, wherein $X_1$ and $X_2$ are each independently a nucleic acid sequence having phosphorothioate internucleotide linkages of 3-10 nucleotides, wherein $N_1$-(GTCGTT)$_n$—$N_2$ includes at least one phosphodiester internucleotide linkage, and wherein 3' and 5' nucleotides of the oligonucleotide do not include a poly-G, poly-A, poly-T, or poly-C sequence.

In one embodiment the nucleic acid has a backbone comprising deoxyribose or ribose.

In one embodiment the oligonucleotide has a backbone comprising deoxyribose or ribose.

In one embodiment the oligonucleotide is in a pharmaceutical composition optionally comprising a pharmaceutically acceptable carrier.

In one embodiment the oligonucleotide further comprises an adjuvant or a cytokine.

In one embodiment the oligonucleotide further comprises an antigen, wherein the oligonucleotide is a vaccine adjuvant.

In one embodiment the antigen is selected from the group consisting of: a viral antigen, a bacterial antigen, a fingal antigen, a parasitic antigen, and a tumor antigen. In one embodiment the antigen is encoded by a nucleic acid vector. In one embodiment the antigen is a peptide antigen. In one embodiment the antigen is covalently linked to the oligonucleotide or immunostimulatory nucleic acid molecule. In another embodiment the antigen is not covalently linked to the oligonucleotide or immunostimulatory nucleic acid molecule.

In another aspect the invention provides a method for identifying a relative potency or toxicity of a test immunostimulatory nucleic acid molecule. The method involves selecting a reference immunostimulatory nucleic acid having a reference sequence, a stabilized backbone, and a reference immunostimulatory potency or toxicity; selecting a test immunostimulatory nucleic acid having the reference sequence, a phosphodiester or phosphodiester-like linkage in place of a stabilized linkage between Y and N of at least one internal YN dinucleotide in the reference sequence, wherein Y is a pyrimidine and N is any nucleotide, and having a test immunostimulatory potency or toxicity; and comparing the test immunostimulatory potency or toxicity to the reference immunostimulatory potency or toxicity to identify the relative potency or toxicity of a test immunostimulatory nucleic acid molecule.

In one embodiment the test immunostimulatory nucleic acid is a more potent inducer of TLR9 signaling activity than the reference immunostimulatory nucleic acid.

In one embodiment the test immunostimulatory nucleic acid is a more potent inducer of type 1 interferon than the reference immunostimulatory nucleic acid.

In one embodiment the test immunostimulatory nucleic acid is a more potent inducer of IP-10 than the reference immunostimulatory nucleic acid.

In one embodiment YN is YG. In one embodiment the at least one internal YG dinucleotide is CG. In one embodiment the at least one internal YG dinucleotide is TG.

In one embodiment the test immunostimulatory nucleic acid comprises a plurality of internal YG dinucleotides each having a phosphodiester or phosphodiester-like internucleotide linkage. In one embodiment the at least one internal YG dinucleotide is every internal YG dinucleotide.

In one embodiment the phosphodiester or phosphodiester-like linkage is phosphodiester. In one embodiment the phosphodiester-like linkage is boranophosphonate or diastereomerically pure Rp phosphorothioate.

In one embodiment the stabilized backbone comprises a plurality of internucleotide linkages selected from the group consisting of: phosphorothioate, phosphorodithioate, methylphosphonate, methylphosphorothioate, and any combination thereof. In one embodiment the stabilized backbone comprises a plurality of phosphorothioate internucleotide linkages.

In one embodiment the reference immunostimulatory nucleic acid molecule is a B-Class immunostimulatory nucleic acid molecule. In one embodiment the reference immunostimulatory nucleic acid molecule is a C-Class immunostimulatory nucleic acid molecule.

In one embodiment the reference immunostimulatory nucleic acid molecule is 4-100 nucleotides long. In one embodiment the reference immunostimulatory nucleic acid molecule is 6-40 nucleotides long. In one embodiment the reference immunostimulatory nucleic acid molecule is 6-19 nucleotides long.

In another aspect the invention provides a method for designing a stabilized immunostimulatory nucleic acid molecule less than 20 nucleotides long. The method involves selecting a sequence 6-19 nucleotides long, wherein the sequence includes at least one internal CG dinucleotide; selecting a phosphodiester or phosphodiester-like linkage between C and G of at least one internal CG dinucleotide; independently selecting a phosphodiester, phosphodiester-like, or stabilized linkage between C and G of each additional internal CG dinucleotide; and selecting a stabilized linkage for all other internucleotide linkages.

In another aspect, the invention is a method for treating or preventing allergy or asthma. The method is performed by administering to a subject an immunostimulatory CpG oligonucleotide described herein in an effective amount to treat or prevent allergy or asthma. In one embodiment the oligonucleotide is administered to a mucosal surface. In other embodiments the oligonucleotide is administered in an aerosol formulation. Optionally the oligonucleotide is administered intranasally.

A method for inducing cytokine production is provided according to another aspect of the invention. The method is performed by administering to a subject an immunostimulatory CpG oligonucleotide described herein in an effective amount to induce a cytokine selected from the group consisting of IL-6, IL-8, IL-12, IL-18, TNF, IFN-α, chemokines, and IFN-γ.

In another aspect the invention is a composition of the CpG immunostimulatory oligonucleotides described herein in combination with an antigen or other therapeutic compound, such as an anti-microbial agent. The anti-microbial agent may be, for instance, an anti-viral agent, an anti-parasitic agent, an anti-bacterial agent or an anti-fungal agent.

A composition of a sustained release device including the CpG immunostimulatory oligonucleotides described herein is provided according to another aspect of the invention.

The composition may optionally include a pharmaceutical carrier and/or be formulated in a delivery device. In some embodiments the delivery device is selected from the group consisting of cationic lipids, cell permeating proteins, and sustained release devices. In one embodiment the sustained release device is a biodegradable polymer or a microparticle.

According to another aspect of the invention a method of stimulating an immune response is provided. The method involves administering a CpG immunostimulatory oligonucleotide to a subject in an amount effective to induce an immune response in the subject. Preferably the CpG immunostimulatory oligonucleotide is administered orally, locally, in a sustained release device, mucosally, systemically, parenterally, or intramuscularly. When the CpG immunostimulatory oligonucleotide is administered to the mucosal surface it may be delivered in an amount effective for inducing a mucosal immune response or a systemic immune response. In preferred embodiments the mucosal surface is selected from the group consisting of an oral, nasal, rectal, vaginal, and ocular surface.

In some embodiments the method includes exposing the subject to an antigen wherein the immune response is an antigen-specific immune response. In some embodiments the antigen is selected from the group consisting of a tumor antigen, a viral antigen, a bacterial antigen, a parasitic antigen and a peptide antigen.

CpG immunostimulatory oligonucleotides are capable of provoking a broad spectrum of immune response. For instance these CpG immunostimulatory oligonucleotides can be used to redirect a Th2 to a Th1 immune response. CpG immunostimulatory oligonucleotides may also be used to activate an immune cell, such as a lymphocyte (e.g., B and T cells), a dendritic cell, and an NK cell. The activation can be performed in vivo, in vitro, or ex vivo, i.e., by isolating an immune cell from the subject, contacting the immune cell with an effective amount to activate the immune cell of the CpG immunostimulatory oligonucleotide and re-administering the activated immune cell to the subject. In some embodiments the dendritic cell presents a cancer antigen. The dendritic cell can be exposed to the cancer antigen ex vivo.

The immune response produced by CpG immunostimulatory oligonucleotides may also result in induction of cytokine production, e.g., production of IL-6, IL-8, IL-12, IL-18, TNF, IFN-$\alpha$, chemokines, and IFN-$\gamma$.

In still another embodiment, the CpG immunostimulatory oligonucleotides are useful for treating cancer. The CpG immunostimulatory oligonucleotides are also useful according to other aspects of the invention in preventing cancer (e.g., reducing a risk of developing cancer) in a subject at risk of developing a cancer. The cancer may be selected from the group consisting of biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreatic cancer, prostate cancer, rectal cancer, sarcomas, thyroid cancer, and renal cancer, as well as other carcinomas and sarcomas. In some important embodiments, the cancer is selected from the group consisting of bone cancer, brain and CNS cancer, connective tissue cancer, esophageal cancer, eye cancer, Hodgkin's lymphoma, larynx cancer, oral cavity cancer, skin cancer, and testicular cancer.

CpG immunostimulatory oligonucleotides may also be used for increasing the responsiveness of a cancer cell to a cancer therapy (e.g., an anti-cancer therapy), optionally when the CpG immunostimulatory oligonucleotide is administered in conjunction with an anti-cancer therapy. The anti-cancer therapy may be a chemotherapy, a vaccine (e.g., an in vitro primed dendritic cell vaccine or a cancer antigen vaccine) or an antibody based therapy. This latter therapy may also involve administering an antibody specific for a cell surface antigen of, for example, a cancer cell, wherein the immune response results in antibody dependent cellular cytotoxicity (ADCC). In one embodiment, the antibody may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Thus, according to some aspects of the invention, a subject having cancer or at risk of having a cancer is administered a CpG immunostimulatory oligonucleotide and an anti-cancer therapy. In some embodiments, the anti-cancer therapy is selected from the group consisting of a chemotherapeutic agent, an immunotherapeutic agent and a cancer vaccine.

In still another embodiment of the methods directed to preventing or treating cancer, the subject may be further administered interferon-$\alpha$.

The invention in other aspects relates to methods for preventing disease in a subject. The method involves administering to the subject a CpG immunostimulatory oligonucleotide on a regular basis to promote immune system responsiveness to prevent disease in the subject. Examples of diseases or conditions sought to be prevented using the prophylactic methods of the invention include microbial infections (e.g., sexually transmitted diseases) and anaphylactic shock from food allergies.

In other aspects, the invention is a method for inducing an innate immune response by administering to the subject a CpG immunostimulatory oligonucleotide in an amount effective for activating an innate immune response.

According to another aspect of the invention a method for treating or preventing a viral or retroviral infection is provided. The method involves administering to a subject having or at risk of having a viral or retroviral infection, an effective amount for treating or preventing the viral or retroviral infection of any of the compositions of the invention. In some embodiments the virus is caused by a hepatitis virus e.g., hepatitis B, hepatitis C, HIV, herpes virus, or papillomavirus.

A method for treating or preventing a bacterial infection is provided according to another aspect of the invention. The method involves administering to a subject having or at risk of having a bacterial infection, an effective amount for treating or preventing the bacterial infection of any of the compositions of the invention. In one embodiment the bacterial infection is due to an intracellular bacteria.

In another aspect the invention is a method for treating or preventing a parasite infection by administering to a subject having or at risk of having a parasite infection, an effective amount for treating or preventing the parasite infection of any of the compositions of the invention. In one embodiment the parasite infection is due to an intracellular parasite. In another embodiment the parasite infection is due to a non-helminthic parasite.

In some embodiments the subject is a human and in other embodiments the subject is a non-human vertebrate selected from the group consisting of a dog, cat, horse, cow, pig, turkey, goat, fish, monkey, chicken, rat, mouse, and sheep.

In another aspect the invention relates to a method for inducing a TH1 immune response by administering to a subject any of the compositions of the invention in an effective amount to produce a TH1 immune response.

In another aspect the invention relates to a method for inducing an immune response, by administering to a subject in need thereof an effective amount of an immunostimulatory oligonucleotide of 5'T*C*G*T*$X_1$*T*T3' wherein $X_1$ is 3-30 nucleotides, wherein * refers to the presence of a stabilized internucleotide linkage, and wherein the oligonucleotide includes at least 2 phosphodiester internucleotide linkages.

In another aspect, the invention relates to a method for treating autoimmune disease by administering to a subject having or at risk of having an autoimmune disease an effective amount for treating or preventing the autoimmune disease of any of the compositions of the invention.

In other embodiments the oligonucleotide is delivered to the subject in an effective amount to induce cytokine expression. Optionally the cytokine is selected from the group consisting of IL-6, TNFα, IFNα, IFNγ and IP-10. In other embodiments the oligonucleotide is delivered to the subject in an effective amount to shift the immune response to a Th1 biased response form a Th2 biased response.

The invention is some aspects is a method for treating airway remodeling, comprising: administering to a subject an oligonucleotide comprising a CG dinucleotide, in an effective amount to treat airway remodeling in the subject. In one embodiment the subject has asthma, chronic obstructive pulmonary disease, or is a smoker. In other embodiments the subject is free of symptoms of asthma.

Use of an oligonucleotide of the invention for stimulating an immune response is also provided as an aspect of the invention.

A method for manufacturing a medicament of an oligonucleotide of the invention for stimulating an immune response is also provided.

In another aspect the invention relates to a method for stimulating an immune response, by administering to a subject an oligonucleotide of at least 5 nucleotides in length in an effective amount to stimulate an immune response, wherein the oligonucleotide includes at least one immunostimulatory dinucleotide motif wherein the internucleotide linkage between the nucleotides of the dinucleotide has R chirality and wherein at least 70% of the other internucleotide linkages of the oligonucleotide have S chirality.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 3 is a set of graphs depicting levels of TNF-alpha (pg/ml) secreted from human PBMC following exposure of these cells to the oligonucleotides listed by number along the top X-axis of the graph and depicted by a ▲ versus a positive control oligonucleotide depicted by a ■. The test oligonucleotides shown in FIG. 3A include SEQ ID NO: 322, SEQ ID NO: 323, and SEQ ID NO: 324 and the positive control oligonucleotide is SEQ ID NO: 329. The test oligonucleotides shown in FIG. 3B include SEQ ID NO: 325, SEQ ID NO: 326, SEQ ID NO: 327, and SEQ ID NO: 328 and the positive control oligonucleotide is SEQ ID NO: 329. The concentration of oligonucleotide used to produce a particular data point is depicted along the X-axis (µM). The data shown represents the mean of three donors. Below the graphs the level of TNF-alpha (pg/ml) secreted by cells treated with a negative control (medium) and with LPS is listed for each experiment.

FIG. 6 is a set of graphs depicting levels of CD69 expression (MFI) on NK cells as an indicator of NK cell activation following exposure of these cells to the oligonucleotides listed by number along the top X-axis of the graph and depicted by a ▲ versus a positive control oligonucleotide depicted by a ■. The test oligonucleotides shown in FIG. 6A include SEQ ID NO: 322, SEQ ID NO: 323, and SEQ ID NO: 324 and the positive control oligonucleotide is SEQ ID NO: 329. The test oligonucleotides shown in FIG. 6B include SEQ ID NO: 325, SEQ ID NO: 326, SEQ ID NO: 327, and SEQ ID NO: 328 and the positive control oligonucleotide is SEQ ID NO: 329. The concentration of oligonucleotide used to produce a particular data point is depicted along the X-axis (μM). The data shown represents the mean of three donors. Below the graphs the level of CD69 expression on NK cells treated with a negative control (medium) and with LPS is listed for each experiment.

The renal exposure to SEQ ID No. 313 after IT administration in particular, is markedly reduced compared to exposure to SEQ ID No. 329 at the same dose level.

Figure 36:
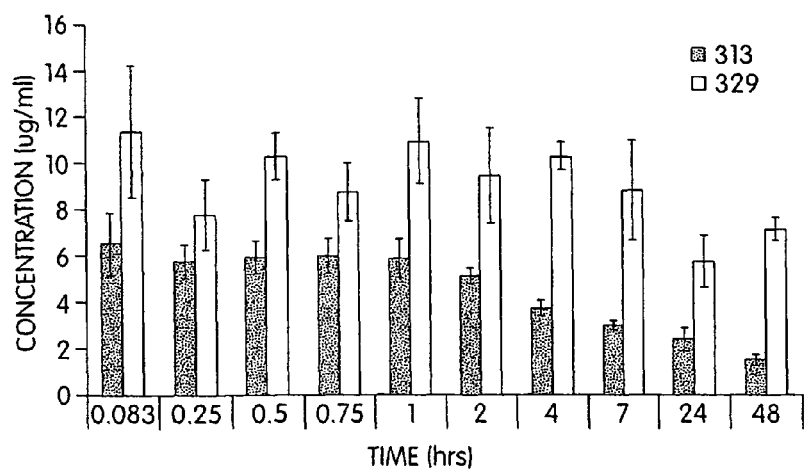

FIG. 36 shows ODN concentrations in rat kidneys following IV administration at 5 mg/kg.

Figure 37:
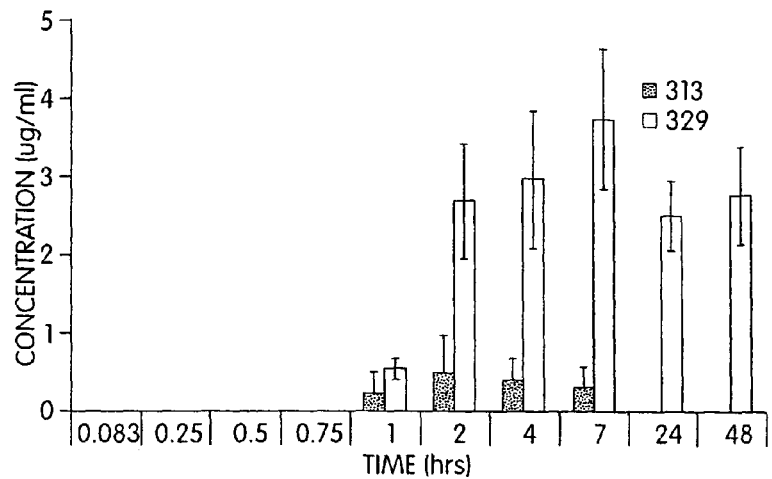

FIG. 37 shows ODN concentrations in rat kidneys following IT administration at 5 mg/kg.

Figure 38:
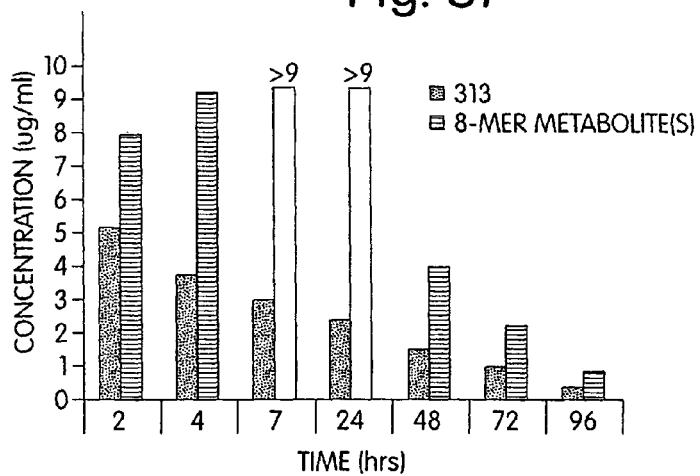

FIG. 38 shows concentrations of SEQ ID No. 313 and its 8-mer metabolite(s) in rat kidneys following IV administration of SEQ ID No. 313 at 5 mg/kg.

Figure 39:
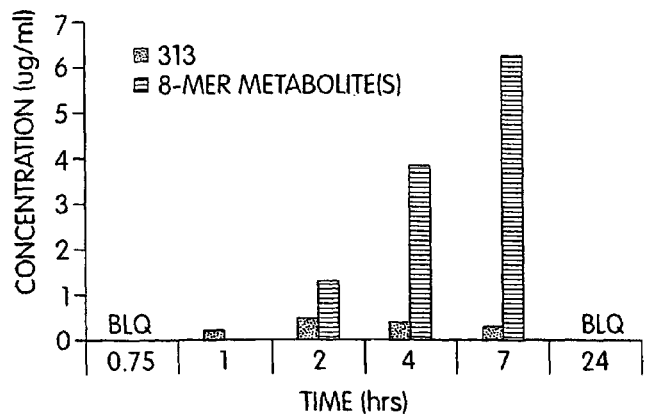

FIG. 39 shows concentrations of SEQ ID No.313 and its 8-mer metabolite(s) in rat kidneys following IT administration of SEQ ID No. 313 at 5 mg/kg.

Figure 40:
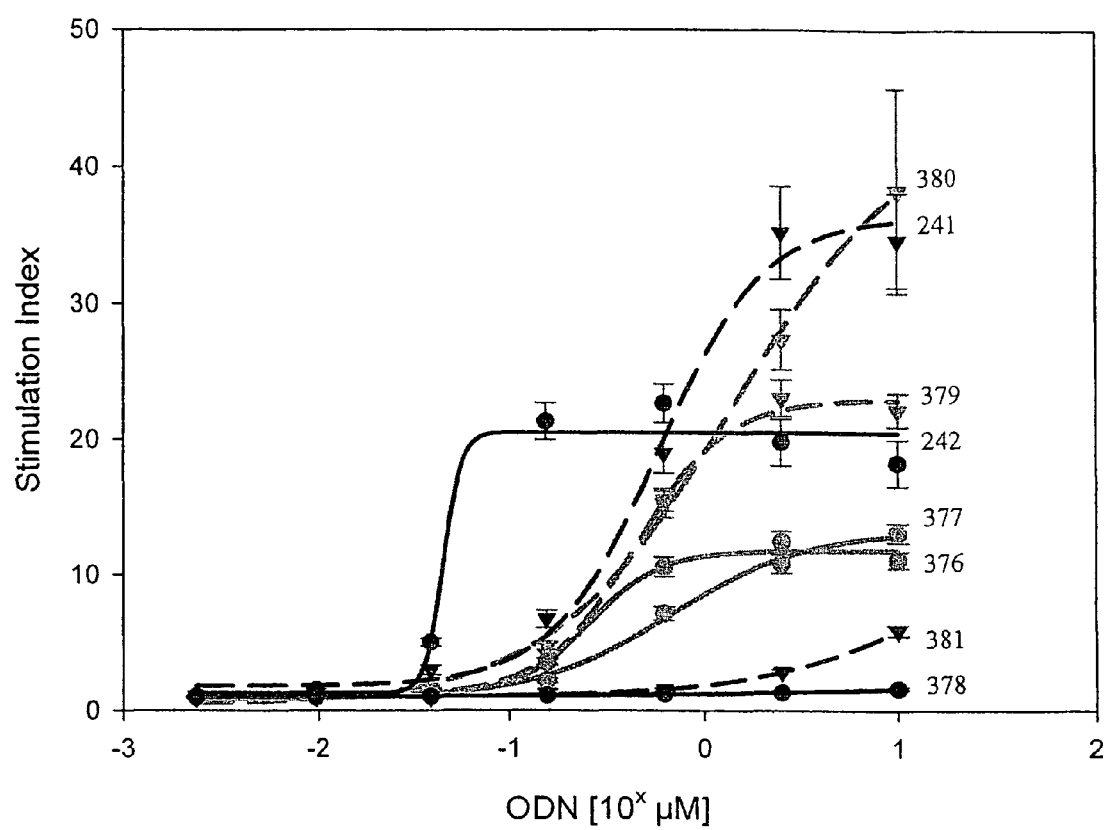

FIG. 40 is a graph depicting stimulation index of sets of Semi-soft ODN compared with fully phosphorothioate ODN having the same sequence.

FIG. 41 is a set of bar graphs depicting cytokine induction A & B (IP-10), C (IFN), and D & E (TNF) in response to the administration of soft (SEQ ID NO 294), semi-soft (SEQ ID NO 241), and fully phosphorothioate ODN (SEQ ID NO 242).

Figure 42A:
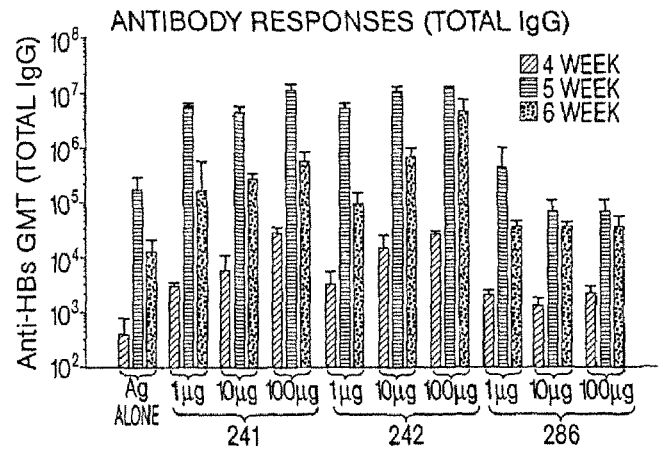
Figure 42B:
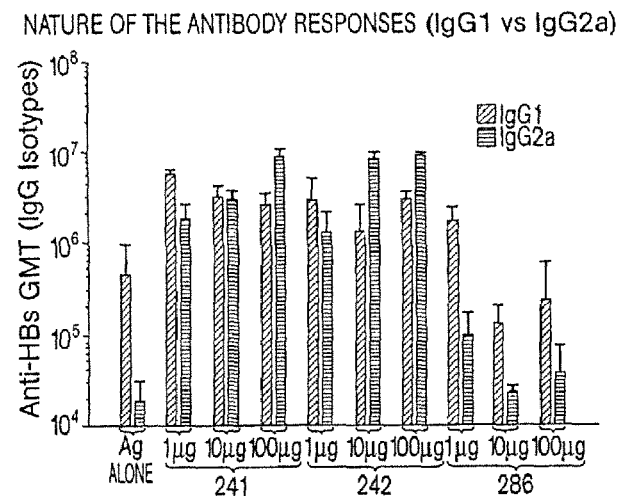

FIG. 42 is a set of graphs depicting antibody and cytotoxic T lymphocyte activity in response to the administration of soft (SEQ ID NO 294), semi-soft (SEQ ID NO 241), and fully phosphorothioate ODN (SEQ ID NO 242).

FIG. 43 is a set of graphs depicting antitumor therapy in mice using semi-soft (SEQ ID NO 241) or fully phosphorothioate ODN (SEQ ID NO 242). FIGS. 43 A and B depict the results in a renal cell carcinoma model. FIGS. 43C and D depict the results in a murine neuroblastoma model. FIGS. 43E and F depict the results in a murine non-small cell lung cancer model.

DETAILED DESCRIPTION

Soft and semi-soft immunostimulatory nucleic acids are provided according to the invention. The immunostimulatory oligonucleotides of the invention described herein, in some embodiments have improved properties including similar or enhanced potency, reduced systemic exposure to the kidney, liver and spleen, and may have reduced reactogenicity at injection sites. Although applicant is not bound by a mechanism, it is believed that these improved properties are associated with the strategic placement within the immunostimulatory oligonucleotides of phosphodiester or phosphodiester-like "internucleotide linkages". The term "internucleotide linkage" as used herein refers to the covalent backbone linkage joining two adjacent nucleotides in a nucleic acid molecule. The covalent backbone linkage will typically be a modified or unmodified phosphate linkage, but other modifications are possible. Thus a linear oligonucleotide that is n nucleotides long has a total of n–1 internucleotide linkages. These covalent backbone linkages can be modified or unmodified in the immunostimulatory oligonucleotides according to the teachings of the invention.

In particular, phosphodiester or phosphodiester-like internucleotide linkages involve "internal dinucleotides". An internal dinucleotide in general shall mean any pair of adjacent nucleotides connected by an internucleotide linkage, in which neither nucleotide in the pair of nucleotides is a terminal nucleotide, i.e., neither nucleotide in the pair of nucleotides is a nucleotide defining the 5' or 3' end of the oligonucleotide. Thus a linear oligonucleotide that is n nucleotides long has a total of n–1 dinucleotides and only n–3 internal dinucleotides. Each internucleotide linkage in an internal dinucleotide is an internal internucleotide linkage. Thus a linear oligonucleotide that is n nucleotides long has a total of n–1 internucleotide linkages and only n–3 internal internucleotide linkages. The strategically placed phosphodiester or phosphodiester-like internucleotide linkages, therefore, refer to phosphodiester or phosphodiester-like internucleotide linkages positioned between any pair of nucleotides in the nucleic acid sequence. In some embodiments the phosphodiester or phosphodiester-like internucleotide linkages are not positioned between either pair of nucleotides closest to the 5' or 3' end.

The invention is based at least in some aspects on the surprising discovery that the soft and semi-soft nucleic acids described herein have at least the same or in many cases possess greater immunostimulatory activity, in many instances, than corresponding fully stabilized immunostimulatory oligonucleotides having the same nucleotide sequence. This was unexpected because it is widely believed that phosphorothioate oligonucleotides are generally more immunostimulatory than unstabilized oligonucleotides. The results were surprising because it was expected that if the "softening" bond was placed between the critical immunostimulatory motif, i.e. CG that the nucleic acid might have reduced activity because the nucleic acid would easily be broken down into non-CG containing fragments in vivo. Contrary to the expectations many of these nucleic acids actually had equivalent or better activity in vitro and in vivo. It appears that the soft and semi-soft oligonucleotides are at least as potent as, if not more potent than, their fully stabilized counterparts; the net immunostimulatory effect of soft and semi-soft oligonucleotides represents a balance between activity and stability. At high concentrations, the balance appears to favor activity, i.e., potency dominates. At low concentrations, this balance appears to favor stability, i.e., the relative instability associated with nuclease susceptibility dominates.

The invention in one aspect relates to soft oligonucleotides. A soft oligonucleotide is an immunostimulatory oligonucleotide having a partially stabilized backbone, in which phosphodiester or phosphodiester-like internucleotide linkages occur only within and immediately adjacent to at least one internal pyrimidine -purine dinucleotide (YZ). Preferably YZ is YG, a pyrimidine-guanosine (YG) dinucleotide. The at least one internal YZ dinucleotide itself has a phosphodiester or phosphodiester-like internucleotide linkage. A phosphodiester or phosphodiester-like internucleotide linkage occurring immediately adjacent to the at least one internal YZ dinucleotide can be 5', 3', or both 5' and 3' to the at least one internal YZ dinucleotide. Preferably a phosphodiester or phosphodiester-like internucleotide linkage occurring immediately adjacent to the at least one internal YZ dinucleotide is itself an internal internucleotide linkage. Thus for a sequence $N_1$ YZ $N_2$, wherein $N_1$ and $N_2$ are each, independent of the other, any single nucleotide, the YZ dinucleotide has a phosphodiester or phosphodiester-like internucleotide linkage, and in addition (a) $N_1$ and Y are linked by a phosphodiester or phosphodiester-like internucleotide linkage when $N_1$ is an internal nucleotide, (b) Z and $N_2$ are linked by a phosphodiester or phosphodiester-like internucleotide linkage when $N_2$ is an internal nucleotide, or (c) $N_1$ and Y are linked by a phosphodiester or phosphodiester-like internucleotide linkage when $N_1$ is an internal nucleotide and Z and $N_2$ are linked by a phosphodiester or phosphodiester-like internucleotide linkage when $N_2$ is an internal nucleotide.

Nonlimiting examples of soft oligonucleotides include those described by SEQ ID NOs 105-231, SEQ ID NOs 232-234, SEQ ID Nos 235-237, and SEQ ID NOs 238-240.

Soft oligonucleotides according to the instant invention are believed to be relatively susceptible to nuclease cleavage compared to completely stabilized oligonucleotides. Without meaning to be bound to a particular theory or mechanism, it is believed that soft oligonucleotides of the invention are cleavable to fragments with reduced or no immunostimulatory activity relative to full-length soft oligonucleotides. Incorporation of at least one nuclease-sensitive internucleotide linkage, particularly near the middle of the oligonucleotide, is believed to provide an "off switch" which alters the pharnacokinetics of the oligonucleotide so as to reduce the duration of maximal immunostimulatory activity of the oligonucleotide. This can be of particular value in tissues and in clinical applications in which it is desirable to avoid injury related to chronic local inflammation or immunostimulation, e.g., the kidney.

The invention in another aspect relates to semi-soft oligonucleotides. A semi-soft oligonucleotide is an immunostimulatory oligonucleotide having a partially stabilized backbone, in which phosphodiester or phosphodiester-like internucleotide linkages occur only within at least one internal pyrimidine-purine (YZ) dinucleotide. Semi-soft oligonucleotides generally possess increased immunostimulatory potency relative to corresponding fully stabilized immunostimulatory oligonucleotides. For example, the immunostimulatory potency of semi-soft SEQ ID NO: 241 is 2-5 times that of all-phosphorothioate SEQ ID NO: 242, where the two oligonucleotides share the same nucleotide sequence and differ only as to internal YZ internucleotide linkages as follows, where * indicates phosphorothioate and _ indicates phosphodiester:

```
T*C_G*T*C_G*T*T*T*T_G*T*C_G*T*T*T*  (SEQ ID NO: 241)
T*G*T*C_G*T*T

T*C*G*T*C*G*T*T*T*T*G*T*C*G*T*T*T*  (SEQ ID NO: 242)
T*G*T*C*G*T*T
```

SEQ ID NO: 241 incorporates internal phophodiester internucleotide linkages involving both CG and TG (both YZ) dinucleotides. Due to the greater potency of semi-soft oligonucleotides, semi-soft oligonucleotides can be used at lower effective concentations and have lower effective doses than conventional fully stabilized immunostimulatory oligonucleotides in order to achieve a desired biological effect.

Whereas fully stabilized immunostimulatory oligonucleotides can exhibit dose-response maxima, semi-soft oligonucleotides of the instant invention appear to have monotonically increasing dose-response curves (as assayed by TLR9 stimulation) extending into higher concentrations beyond the optimal concentration for corresponding fully stabilized immunostimulatory oligonucleotides. Thus it is believed that semi-soft oligonuncleotides of the instant invention can induce greater immunostimulation than fully stabilized immunostimulatory oligonucleotides.

It has been discovered according to the instant invention that the immunostimulatory activity of weakly immunostimulatory fully stabilized oligonucleotides can be increased by incorporation of at least one internal YZ dinucleotide with a phosphodiester or phosphodiester-like internucleotide linkage. Thus it is possible to start with a weakly immunostimulatory oligonucleotide, having a fully stabilized backbone, and to improve its immunostimulatory activity by substituting a phosphodiester or phosphodiester-like internucleotide linkage for a stabilized internucleotide linkage of at least one internal YG dinucleotide. For example, SEQ ID NO: 243 was found to have more immunostimulatory activity than its fully stabilized counterpart SEQ ID NO: 244, where SEQ ID NO: 244 is a relatively weak immunostimulatory oligonucleotide compared to SEQ ID NO: 242:

```
T*G*T*C_G*T*T*G*T*C_G*T*T_G*T*C_G*  (SEQ ID NO: 243)
T*T_G*T*C_G*T*T

T*G*T*C*G*T*T*G*T*C*G*T*T*G*T*C*G*  (SEQ ID NO: 244)
T*T*G*T*C*G*T*T
```

Whereas fully stabilized immunostimulatory nucleic acids less than 20 nucleotides long can have modest immunostimulatory activity compared with longer (e.g., 24 nucleotides long) fully stabilized oligonucleotides, semi-soft oligonucleotides as short as 16 nucleotides long have been discovered to have immunostimulatory activity at least equal to immunostimulatory activity of fully stabilized oligonucleotides over 20 nucleotides long. For example, SEQ ID NO: 245 and 5602 (both 16-mers with partial sequence similarity to SEQ ID NO: 242) exhibit immunositmultory activity comparable to that of SEQ ID NO: 242 (24-mer).

```
T*C_G*T*C_G*T*T*T*C_G*T*C_G*T*T      (SEQ ID NO: 245)

5602 T*C_G*T*C_G*T*T*T*T_G*T*C_G*    (SEQ ID NO: 56)
T*T

T*C*G*T*C*G*T*T*T*T*G*T*C*G*T*T*T*   (SEQ ID NO: 242)
T*G*T*C*G*T*T
```

In some instances where a 6-mer phosphorothioate oligonucleotide appeared to lack immunostimulatory activity, substitution of even one phosphodiester internal YZ internucleotide linkage for a phosphorothioate linkage was found to yield a corresponding 6-mer with immunostimulatory activity.

It is also believed that the foregoing properties of semi-soft oligonucleotides generally increase with increasing "dose" of phosphodiester or phosphodiester-like internucleotide linkages involving internal YZ dinucleotides. Thus it is believed, for example, that generally for a given oligonucleotide sequence with five internal YZ dinucleotides, an oligonucleotide with five internal phosphodiester or phosphodiester-like YZ internucleotide linkages is more immunostimulatory than an oligonucleotide with four internal phosphodiester or phosphodiester-like YG internucleotide linkages, which in turn is more immunostimulatory than an oligonucleotide with three internal phosphodiester or phosphodiester-like YZ internucleotide linkages, which in turn is more immunostimulatory than an oligonucleotide with two internal phosphodiester or phosphodiester-like YZ internucleotide linkages, which in turn is more immunostimulatory than an oligonucleotide with one internal phosphodiester or phosphodiester-like YZ internucleotide linkage. Importantly, inclusion of even one internal phosphodiester or phosphodiester-like YZ internucleotide linkage is believed to be advantageous over no internal phosphodiester or phosphodiester-like YZ internucleotide linkage. In addition to the number of phosphodiester or phosphodiester-like internucleotide linkages, the position along the length of the nucleic acid can also affect potency.

Nonlimiting examples of semi-soft oligonucleotides include those described by SEQ ID NOs 1-99 and 241 and SEQ ID NOs 100-104.

The immunostimulatory oligonucleotides of the present invention are generally protected from rapid degradation in the serum. The immunostimulatory oligonucleotides of the present invention are also generally protected from rapid degradation in most tissues, with the exception of particular tissues with specific or excessive nuclease activity that are capable of degrading the immunostimulatory oligonucleotides. This results in the reduction of immunostimulatory oligonucleotides in those particular tissues, the accumulation of which could otherwise lead to undesirable effects from long-term therapy utilizing degradation-resistant oligonucleotides. The oligonucleotides of the instant invention will generally include, in addition to the phosphodiester or phosphodiester-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In a preferred embodiment, the at least one phosphate modification of the backbone at each end is independently a phosphorothioate, phosphorodithioate, methylphosphonate, or methylphosphorothioate internucleotide linkage. In another embodiment, the degradation-resistant end includes one or more nucleotide units connected by peptide or amide linkages at the 3' end. Yet other stabilized ends, including but not limited to those described further below, are meant to be encompassed by the invention.

As described above, the oligonucleotides of the instant invention include phosphodiester or phosphodiester-like linkages within and optionally adjacent to internal YG dinucleotides. Such YG dinucleotides are frequently part of immunostimulatory motifs. It is not necessary, however, that an oligonucleotide contain phosphodiester or phosphodiester-like linkages within every immunostimulatory motif. As an example, an oligonucleotide such as T*C*G*T*C*G*T*T*T*T*G*T*C*G*T*T*T*T*G*T* C*G*T*T (SEQ ID NO:242) with four CpG dinucleotides could have phosphodiester linkages between the C and G of the second, third, or fourth CpG dinucleotide, and any combination thereof. Additional phosphodiester or phosphodiester-like linkages may also be maintained for even more rapid renal digestion of these otherwise "stabilized oligonucleotides". For example, SEQ ID NO: 242 further contains two internal TG dinucleotides, either or both of which, alone or in combination with any one or combination of internal CG dinucleotides, can have phosphodiester or phosphodiester-like internucleotide linkages.

A phosphodiester internucleotide linkage is the type of linkage characteristic of nucleic acids found in nature. As shown in FIG. 20, the phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNAse H. Thus for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. Nos. 5,177,198; 5,859,231; 6,160,109; 6,207,819; Sergueev et al., (1998) J Am Chem Soc 120:9417-27. In another preferred embodiment the phosphodiester-like internucleotide linkage is diasteromerically pure Rp phosphorothioate. It is believed that diasteromerically pure Rp phosphorothioate is more susceptible to nuclease digestion and is better at activating RNAse H than mixed or diastereomerically pure Sp phosphorothioate. Stereoisomers of CpG oligonucleotides are the subject of co-pending U.S. patent application Ser. No. 09/361,575 filed Jul. 27, 1999, and published PCT application PCT/US99/17100 (WO 00/06588). It is to be noted that for purposes of the instant invention, the term "phosphodiester-like internucleotide linkage" specifically excludes phosphorodithioate and methylphosphonate internucleotide linkages.

The immunostimulatory nucleic acid molecules of the instant invention have chimeric backbone. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could in one embodiment include at least one phosphodiester (phosphodiester or phosphodiester-like) linkage and at least one boranophosphonate (stabilized) linkage. In another embodiment a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endonuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation: peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) *Chem Rev* 90:544; Goodchild J (1990) *Bioconjugate Chem* 1:165. Methods for preparing chimeric oligonucleotides are also known. For instance patents issued to Uhlmann et al have described such techniques.

Mixed backbone modified ODN may be synthesized using a commercially available DNA synthesizer and standard phosphoramidite chemistry. (F. E. Eckstein, "Oligonucleotides and Analogues—A Practical Approach" IRL Press Oxford, UK, 1991, and M. D. Matteucci and M. H. Caruthers, *Tetrahedron Lett.* 21, 719 (1980)) After coupling, PS linkages are introduced by sulfirization using the Beaucage reagent (R. P. Iyer, W. Egan, J. B. Regan and S. L. Beaucage, *J. Am. Chem. Soc.* 112, 1253 (1990)) (0.075 M in acetonitrile) or phenyl acetyl disulfide (PADS) followed by capping with acetic anhydride, 2,6-lutidine in tetrahydrofurane (1:1:8; v:v:v) and N-methylimidazole (16% in tetrahydrofurane). This capping step is performed after the sulfurization reaction to minimize formation of undesired phosphodiester (PO) linkages at positions where a phosphorothioate linkage should be located. In the case of the introduction of a phosphodiester linkage, e.g. at a CpG dinucleotide, the intermediate phosphorous-III is oxidized by treatment with a solution of iodine in water/pyridine. After cleavage from the solid support and final deprotection by treatment with concentrated ammonia (15 hrs at 50° C.), the ODN are analyzed by HPLC on a Gen-Pak Fax column (Millipore-Waters) using a NaCl-gradient (e.g. buffer A: 10 mM $NaH_2PO_4$ in acetonitrile/water=1:4/v:v pH 6.8; buffer B: 10 mM $NaH_2PO_4$, 1.5 M NaCl in acetonitrile/water=1:4/v:v; 5 to 60% B in 30 minutes at 1 ml/min) or by capillary gel electrophoresis. The ODN can be purified by HPLC or by FPLC on a Source High Performance column (Amersham Pharmacia). HPLC-homogeneous fractions are combined and desalted via a C18 column or by ultrafiltration. The ODN was analyzed by MALDI-TOF mass spectrometry to confirm the calculated mass.

The nucleic acids of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The size (i.e., the number of nucleotide residues along the length of the nucleic acid) of the immunostimulatory oligonucleotide may also contribute to the stimulatory activity of the oligonucleotide. For facilitating uptake into cells immunostimulatory oligonucleotides preferably have a minimum length of 6 nucleotide residues. Nucleic acids of any size greater than 6 nucleotides (even many kb long) are capable of inducing an immune response according to the invention if sufficient immunostimulatory motifs are present, since larger nucleic acids are degraded inside of cells. It is believed by the instant inventors that semi-soft oligonucleotides as short as 4 nucleotides can also be immunostimulatory if they can be delivered to the interior of the cell. In certain preferred embodiments according to the instant invention, the immunostimulatory oligonucleotides are between 4 and 100 nucleotides long. In typical embodiments the immunostimulatory oligonucleotides are between 6 and 40 nucleotides long. In certain preferred embodiments according to the instant invention, the immunostimulatory oligonucleotides are between 6 and 19 nucleotides long.

The oligonucleotides of the present invention are nucleic acids that contain specific sequences found to elicit an immune response. These specific sequences that elicit an immune response are referred to as "immunostimulatory motifs", and the oligonucleotides that contain immunostimulatory motifs are referred to as "immunostimulatory nucleic acid molecules" and, equivalently, "immunostimulatory nucleic acids" or "immunostimulatory oligonucleotides". The immunostimulatory oligonucleotides of the invention thus include at least one immunostimulatory motif. In a preferred embodiment the immunostimulatory motif is an "internal immunostimulatory motif". The term "internal immunostimulatory motif" refers to the position of the motif sequence within a longer nucleic acid sequence, which is longer in length than the motif sequence by at least one nucleotide linked to both the 5' and 3' ends of the immunostimulatory motif sequence.

In some embodiments of the invention the immunostimulatory oligonucleotides include immunostimulatory motifs which are "CpG dinucleotides". A CpG dinucleotide can be methylated or unmethylated. An immunostimulatory nucleic acid containing at least one unmethylated CpG dinucleotide is a nucleic acid molecule which contains an unmethylated cytosine-guanine dinucleotide sequence (i.e., an unmethylated 5' cytidine followed by 3' guanosine and linked by a phosphate bond) and which activates the immune system; such an immunostimulatory nucleic acid is a CpG nucleic acid. CpG nucleic acids have been described in a number of issued patents, published patent applications, and other publications, including U.S. Pat. Nos. 6,194,388; 6,207,646; 6,214,806; 6,218,371; 6,239,116; and 6,339,068. An immunostimulatory nucleic acid containing at least one methylated CpG dinucleotide is a nucleic acid which contains a methylated cytosine-guanine dinucleotide sequence (i.e., a methylated 5' cytidine followed by a 3' guanosine and linked by a phosphate bond) and which activates the immune system. In other embodiments the immunostimulatory oligonucleotides are free of CpG dinucleotides. These oligonucleotides which are free of CpG dinucleotides are referred to as non-CpG oligonucleotides, and they have non-CpG immunostimulatory motifs. The invention, therefore, also encompasses nucleic acids with other types of immunostimulatory motifs, which can be methylated or unmethylated. The immunostimulatory oligonucleotides of the invention, further, can include any combination of methylated and unmethylated CpG and non-CpG immunostimulatory motifs.

As to CpG nucleic acids, it has recently been described that there are different classes of CpG nucleic acids. One class is potent for activating B cells but is relatively weak in inducing IFN-α and NK cell activation; this class has been termed the B class. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the A class. The A class CpG nucleic acids typically have stabilized poly-G sequences at 5' and 3' ends and a palindromic phosphodiester CpG dinucleotide-containing sequence of at least 6 nucleotides. See, for example, published patent application PCT/US00/26527 (WO 01/22990). Yet another class of CpG nucleic acids activates B cells and NK cells and induces IFN-α; this class has been termed the C-class. The C-class CpG nucleic acids, as first characterized, typically are fully stabilized, include a B class-type sequence and a GC-rich palindrome or near-palindrome. This class has been described in co-pending U.S. provisional patent application 60/313,273, filed Aug. 17, 2001 and US10/224,523 filed on Aug. 19, 2002, the entire contents of which are incorporated herein by reference. Some non limiting examples of C-Class nucleic acids include:

| SEQ ID NO | Sequence |
|---|---|
| 275 | T*C_G*C_G*T*C_G*T*T*C_G*G*C*G*C_G*C*G*C*C*G |
| 369 | T*C_G*T*C_G*A*C_G*T*T*C_G*G*C*G*C_G*C*G*C*C*G |
| 370 | T*C_G*G*A*C_G*T*T*C_G*G*C*G*C_G*C*G*C*C*G |
| 371 | T*C_G*G*A*C_G*T*T*C_G*G*C*G*C*G*C*C*G |
| 372 | T*C_G*C_G*T*C_G*T*T*C_G*G*C*G*C*G*C*C*G |
| 373 | T*C_G*A*C_G*T*T*C_G*G*C*G*C_G*C*G*C*C*G |
| 374 | T*C_G*A*C_G*T*T*C_G*G*C*G*C*G*C*C*G |
| 375 | T*C_G*C_G*T*C_G*T*T*C_G*G*C*G*C*C*G |
| 316 | T*C_G*C_G*A*C_G*T*T*C_G*G*C*G*C_G*C*G*C*C*G |

Thus, the invention in one aspect involves the finding that specific sub-classes of CpG immunostimulatory oligonucleotides having chimeric backbones are highly effective in mediating immune stimulatory effects. These CpG nucleic acids are useful therapeutically and prophylactically for stimulating the immune system to treat cancer, infectious diseases, allergy, asthma, autoimmune disease, and other disorders and to help protect against opportunistic infections following cancer chemotherapy. The strong yet balanced, cellular and humoral immune responses that result from CpG stimulation reflect the body's own natural defense system against invading pathogens and cancerous cells.

The invention involves, in one aspect, the discovery that a subset of CpG immunostimulatory oligonucleotides have improved immune stimulatory properties and reduced renal inflammatory effect. In some instances, renal inflammation has been observed in subjects that have been administered a completely phosphorothioate oligonucleotide. It is believed that the chimeric nucleic acids described herein produce less renal inflammation than fully phosphorothioate oligonucleotides. Additionally these oligonucleotides are highly effective in stimulating an immune response. Thus, the phosphodiester region of the molecule did not reduce it's effectivity.

The preferred CpG immunostimulatory oligonucleotides fall within one of the following 6 general formulas:

(SEQ ID NO: 296)
5' T*C*G*T*CGTTTTGAN₁CGN₂*T*T 3', (SEQ ID NO: 301)
5' T*C*G*(T*/A*)TN₃CGTTTTN₄CGN₅*T*T 3', (SEQ ID NO: 307)
5' T*C*G*T*C*GNNNCGNCGNNNC*G*N*C*G*T*T 3', (SEQ ID NO: 311-312)
5' T*C_G(N₆C_GN₇)₂₋₃T*C_G*T*T 3', (SEQ ID NO: 331)
5' T*T*GX₁X₂TGX₃X₄T*T*T*T*N₁₀T*T*T*T*T*T*T 3'
and (SEQ ID NO: 332)
5' T*CGCGN₈CGCGC*GN₉ 3'.

In these formulas N is any nucleotide, $N_1$ is 0-6 nucleotides, $N_2$ is 0-7 nucleotides, $N_3$ is 0-4 nucleotides, $N_4$ is 1-5 nucleotides, $N_5$ is 0-7 nucleotides, $N_6$ and $N_7$ are independently between 1 and 5 nucleotides in length, $N_8$ is between 4 and 10 nucleotides in length, $N_9$ is between 0 and 3 nucleotides in length and wherein $N_{10}$ is between 4 and 8 nucleotides in length. $X_1$, $X_2$, $X_3$ and, $X_4$ are independently C or G. The formulas define subsets of the class of CpG oligonucleotides which demonstrated excellent immune stimulating properties and yet were more sensitive to degradation within the body than fully phosphorothioate containing oligonucleotides. In the formula 5' refers to the free 5' end of the oligonucleotide and 3' refers to the free 3' end of the oligonucleotide.

The symbol * used in the formulas refers to the presence of a stabilized internucleotide linkage. The internucleotide linkages not marked with an * may be stabilized or unstabilized, as long as the oligonucleotide includes at least 2-3 phosphodiester internucleotide linkages. In some embodiments it is preferred that the oligonucleotides include 3-6 phosphodiester linkages. In some cases the linkages between the CG motifs are phosphodiester and in other cases they are phosphorothioate or other stabilized linkages.

Other formulas include 5' TCGTCGTTTTGACGTTTTGTCGTT 3' (SEQ ID NO: 368), wherein at least one CG dinucleotide has a phosphodiester or phosphodiester-like internucleotide linkage, and the oligonucleotide includes at least one stabilized internucleotide linkage and 5'GNC 3', wherein N is a nucleic aid sequence of 4-10 nucleotides in length and is at least 50% T and does not include a CG dinucleotide, and the oligonucleotide includes at least one stabilized internucleotide linkage.

In some embodiment the oligonucleotide has one of the following structures:

(SEQ ID NO: 296)
5' T*C*G*T*C*G*TTTTGAN₁C*G*N₂*T*T 3', (SEQ ID NO: 296)
5' T*C*G*T*C*G*T_T_T_GAN₁C*G*N₂*T*T 3', (SEQ ID NO: 296)
5' T*C*G*T*C*G*T*T*T*GA_N₁C*G*N₂*T*T 3', (SEQ ID NO: 301)
5' T*C*G*(T*/A*)TN₃CGTTTTN₄C*G*N₅*T*T 3', (SEQ ID NO: 302)
5' T*C*G*A*T*N₃C*G*TTTTN₄C_G_*N₅*T*T 3', (SEQ ID NO: 303)
5' T*C*G*T*T*N₃C_G_TTTTN₄CGN₅*T*T 3', (SEQ ID NO: 307)
5' T*C*G*T*C*G*N*N*N*C_G_N_C_G_N*N*N*C*G*N*C*G*T*T 3',

-continued (SEQ ID NO: 308)
5' T*C*G*T*C*G*T*T*A*C_G_N_C_G_T*T*A*C*G*N*C*G*T*T 3',
or (SEQ ID NO: 309)
5' T*C*G*T*C*G*N*N*N*C_G_T_C_G_N*N*N*C*G*T*C*G*T*T 3'.

The symbol _ in these structures refers to the presence of a phosphodiester internucleotide linkage.

Some preferred examples of the structures include the following:

(SEQ ID NO: 327)
5' T*C*G*T*C*G*T*T*T*T*G*A_C_C_G_G_T*T*C*G*T*G*T*T 3', (SEQ ID NO: 328)
5' T*C*G*T*C*G*T*T*T*T*G_A_C*G*T*T*T*T*G*T*C*G*T*T 3', (SEQ ID NO: 324)
5' T*C*G*T*C*G*T*T_T_T_G*A*C*G*T*T*T*T 3', (SEQ ID NO: 325)
5' T*C*G*T*C*G*T*T_T_T_G*A*C*G*T*T 3', (SEQ ID NO: 323)
5' T*C*G*A*T*C*G*T*T*T*T_T_C_G*T*G*C*G*T*T*T*T*T 3', (SEQ ID NO: 326)
5' T*C*G*T*T*T*T*G*A_C_G_T*T*T*T*G*T*C*G*T*T 3', (SEQ ID NO: 322)
5' T*C*G*T*C*G*T*T*A*C_G_T_C_G_T*T*A*C*G*T*C*G*T*T 3', (SEQ ID NO: 313)
5' T*C_G*T*C_G*T*T*T*T*G*A*C_G*T*T*T*T*G*T*C_G*T*T 3', (SEQ ID NO: 314)
5' T*C_G*A*C_G*T*T*T*T*G*T*C_G*T*T*T*T*G*T*C_G*T*T 3', (SEQ ID NO: 319)
5, T*T*G*C_G*T*G*C_G*T*T*T*T*G*A*C_G*T*T*T*T*T*T 3', (SEQ ID NO: 316)
5' T*C_G*C_G*A*C_G*T*T*C_G*G*C*G*C_G*C*G*C*C*G 3', (SEQ ID NO: 317)
5' T*C*G*C*G*A*C_G*T*T*C*G*C*G*C_G*C*G*C*G 3', (SEQ ID NO: 320)
5' T*T*G*G_C*T*G*G_C*T*T*T*T*G*A*C_G*T*T*T*T*T*T 3', (SEQ ID NO: 321)
5' T*C*G*C_G*A*C*G*T*T*C_G*G*C*G*C_G*C*G*C*C*G 3',

T*C-G*T*C-G*T*T, C-G*T*C-G*T*T*T, G*T*C-G*T*T*T*T,
T*C-G*T*T*T*T*G, C-G*T*T*T*T*G*A, T*T*T*T*G*A*C-G,
T*T*T*G*A*C-G*T, T*T*G*A*C-G*T*T, T*G*A*C-G*T*T*T,
G*A*C-G*T*T*T*T, A*C-G*T*T*T*T*G, C-G*T*T*T*T*G*T,
T*T*T*T*G*T*C-G, T*T*T*G*T*C-G*T, G*T*T*T*T*G*T*C,
or T*T*G*T*C-G*T*T.

The immunostimulatory oligonucleotides generally have a length in the range of between 4 and 100 and in some embodiments 10 and 40. The length may be in the range of between 16 and 24 nucleotides.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases).

Nucleic acids also include substituted purines and pyrimidines such as C-5 propyne pyrimidine and 7-deaza-7-substituted purine modified bases. Wagner RW et al. (1996) Nat Biotechnol 14:840-4. Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

The immunostimulatory oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhlmann E et al. (1990) Chem Rev 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) Annu Rev Pharmacol Toxicol 36:107-129; and Hunziker J et al. (1995) Mod Synth Methods 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from:
a) the replacement of a phosphodiester internucleotide bridge located at the 3' and/or the 5' end of a nucleotide by a modified internucleotide bridge,
b) the replacement of phosphodiester bridge located at the 3' and/or the 5' end of a nucleotide by a dephospho bridge,
c) the replacement of a sugar phosphate unit from the sugar phosphate backbone by another unit,
d) the replacement of a β-D-ribose unit by a modified sugar unit, and
e) the replacement of a natural nucleotide base by a modified nucleotide base.

More detailed examples for the chemical modification of an oligonucleotide are as follows.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoramidate, boranophosphate, α-hydroxybenzyl phosphonate, phosphate-$(C_1$-$C_{21})$—O-alkyl ester, phosphate-$[(C_6$-$C_{12})$aryl-$(C_1$-$C_{21})$—O-alkyl]ester, $(C_1$ -$C_8)$alkylphosphonate and/or $(C_6$-$C_{12})$arylphosphonate bridges, $(C_7$-$C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethylhydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O—$(C_1-C_6)$alkyl-ribose, preferably 2'-O-$(C_1-C_6)$ alkyl-ribose is 2'-O-methylribose, 2'-O—$(C_2-C_6)$alkenyl-ribose, 2'-[O—$(C_1-C_6)$alkyl-O—$(C_1-C_6)$alkyl]-ribose, 2'-NH$_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some preferred embodiments the sugar is 2'-O-methyl-ribose, particularly for one or both nucleotides linked by a phosphodiester or phosphodiester-like internucleotide linkage.

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleotide base may be, for example, selected from hypoxanthine, uracil, dihydrouracil, pseudouracil, 2-thiouracil, 4-thiouracil, 5-aminouracil, 5-$(C_1-C_6)$-alkyluracil, 5-$(C_2-C_6)$-alkenyluracil, 5-$(C_2-C_6)$-alkynyluracil, 5-(hydroxymethyl)uracil, 5-chlorouracil, 5-fluorouracil, 5-bromouracil, 5-hydroxycytosine, 5-$(C_1-C_6)$-alkylcytosine, 5-$(C_2-C_6)$-alkenylcytosine, 5-$(C_2-C_6)$-alkynylcytosine, 5-chlorocytosine, 5-fluorocytosine, 5-bromocytosine, N2-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleotides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleotide bases. This list is meant to be exemplary and is not to be interpreted to be limiting.

In particular formulas described herein a set of modified bases is defined. For instance the letter Y is used to refer to a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer).

The letter Z is used to refer to guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6) alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

The oligonucleotides may have one or more accessible 5' ends. It is possible to create modified oligonucleotides having two such 5' ends. This may be achieved, for instance by attaching two oligonucleotides through a 3'-3' linkage to generate an oligonucleotide having one or two accessible 5' ends. The 3'3'-linkage may be a phosphodiester, phosphorothioate or any other modified internucleotide bridge. Methods for accomplishing such linkages are known in the art. For instance, such linkages have been described in Seliger, H.; et al., Oligonucleotide analogs with terminal 3'-3'- and 5'-5'-internucleotidic linkages as antisense inhibitors of viral gene expression, Nucleotides & Nucleotides (1991), 10(1-3), 469-77 and Jiang, et al., Pseudo-cyclic oligonucleotides: in vitro and in vivo properties, Bioorganic & Medicinal Chemistry (1999), 7(12), 2727-2735.

Additionally, 3'3'-linked nucleic acids where the linkage between the 3'-terminal nucleotides is not a phosphodiester, phosphorothioate or other modified bridge, can be prepared using-an additional spacer, such as tri- or tetra-ethylenglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. Nos. 5,658, 738, and 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

It recently has been reported that CpG oligonucleotides appear to exert their immunostimulatory effect through interaction with Toll-like receptor 9 (TLR9). Hemmi H et al. (2000) Nature 408:740-5. TLR9 signaling activity thus can be measured in response to CpG oligonucleotide or other immunostimulatory nucleic acid by measuring NF-κB, NF-κB-related signals, and suitable events and intermediates upstream of NF-κB.

For use in the instant invention, the oligonucleotides of the invention can be synthesized de novo using any of a number of procedures well known in the art. For example, the b-cyanoethyl phosphoramidite method (Beaucage, S. L., and Caruthers, M. H., *Tet. Let.* 22:1859, 1981); nucleotide H-phosphonate method (Garegg et al., *Tet. Let.* 27:4051-4054, 1986; Froehler et al., *Nucl. Acid. Res.* 14:5399-5407, 1986, ; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

The oligonucleotides are partially resistant to degradation (e.g., are stabilized). A "stabilized oligonucleotide molecule" shall mean an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases. Other modified oligonucleotides include phosphodiester modified nucleic acids, combinations of phosphodiester and phosphorothioate nucleic acid, methylphosphonate, methylphosphorothioate, phosphorodithioate, p-ethoxy, and combinations thereof.

Modified backbones such as phosphorothioates may be synthesized using automated techniques employing either phosphoramidate or H-phosphonate chemistries. Aryl-and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., *Chem. Rev.* 90:544, 1990; Goodchild, J., *Bioconjugate Chem.* 1:165, 1990).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

While CpG effects in mice are well characterized, information regarding the human system is limited. CpG phosphorothioate oligonucleotides with strong stimulatory activity in the mouse system show lower activity on human and other non-rodent immune cells. In the examples the development of a potent human CpG motif and the characterization of its effects and mechanisms of action on human PBMC, e.g., B-cells, and NK-cells is described. DNA containing these CpG motifs and partially modified backbones strongly stimulated human peripheral blood cells to produce IL-6, IL-10, IP-10, TNF-α, IFN-α, and IFN-γ. IFN-γ was increased over control levels. NK cells and T cells were also induced to express increased levels of CD69.

It has been discovered according to the invention that the subsets of CpG immunostimulatory oligonucleotides have dramatic immune stimulatory effects on human cells such as NK cells, suggesting that these CpG immunostimulatory oligonucleotides are effective therapeutic agents for human vaccination, cancer immunotherapy, asthma immunotherapy, general enhancement of immune function, enhancement of hematopoietic recovery following radiation or chemotherapy, autoimmune disease and other immune modulatory applications.

Thus the CpG immunostimulatory oligonucleotides are useful in some aspects of the invention as a vaccine for the treatment of a subject at risk of developing allergy or asthma, an infection with an infectious organism or a cancer in which a specific cancer antigen has been identified. The CpG immunostimulatory oligonucleotides can also be given without the antigen or allergen for protection against infection, allergy or cancer, and in this case repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing allergy or asthma includes those subjects that have been identified as having an allergy or asthma but that don't have the active disease during the CpG immunostimulatory oligonucleotide treatment as well as subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a CpG immunostimulatory oligonucleotide, the subject may be able to kill the cancer cells as they develop. If a tumor begins to form in the subject, the subject will develop a specific immune response against the tumor antigen.

In addition to the use of the CpG immunostimulatory oligonucleotides for prophylactic treatment, the invention also encompasses the use of the CpG immunostimulatory oligonucleotides for the treatment of a subject having an infection, an allergy, asthma, or a cancer.

A subject having an infection is a subject that has been exposed to an infectious pathogen and has acute or chronic detectable levels of the pathogen in the body. The CpG immunostimulatory oligonucleotides can be used with or without an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Allergies are generally caused by IgE antibody generation against harmless allergens. The cytokines that are induced by systemic or mucosal administration of CpG immunostimulatory oligonucleotides are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the CpG immunostimulatory oligonucleotides to shift the immune response in a subject from a predominant Th2 (which is associated with production of IgE antibodies and allergy) to a balanced Th2/Th1 response (which is protective against allergic reactions), an effective dose for inducing an immune response of a CpG immunostimulatory oligonucleotide can be administered to a subject to treat or prevent asthma and allergy.

Thus, the CpG immunostimulatory oligonucleotides have significant therapeutic utility in the treatment of allergic and non-allergic conditions such as asthma. Th2 cytokines, especially IL-4 and IL-5 are elevated in the airways of asthmatic subjects. These cytokines promote important aspects of the asthmatic inflammatory response, including IgE isotope switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms;. lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors, infections, and allergy/asthma in non human subjects. Cancer is one of the leading causes of death in companion animals (i.e., cats and dogs).

As used herein, the term treat, treated, or treating when used with respect to an disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

In the instances when the CpG oligonucleotide is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the CpG immunostimulatory oligonucleotide. For instance, in a subject at risk of developing a cancer or an infectious disease or an allergic or asthmatic response, the subject may be administered the CpG immunostimulatory oligonucleotide on a regular basis when that risk is greatest, i.e., during allergy season or after exposure to a cancer causing agent. Additionally the CpG immunostimulatory oligonucleotide may be administered to travelers before they travel to foreign lands where they are at risk of exposure to infectious agents. Likewise the CpG immunostimulatory oligonucleotide may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research*, 54:1055, by partially purifyng the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira, Rickettsia*, and *Actinomyces israelli*.

Examples of fungi include *Cryptococcus neoformans, Histoplasma capsulatum, Coccidioides immitis, Blastomyces dermatitidis, Chlamydia trachomatis, Candida albicans*.

Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*);

*Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The term substantially purified as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are included within the invention.

The oligonucleotides of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide flroate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconazole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

CpG immunostimulatory oligonucleotides can be combined with other therapeutic agents such as adjuvants to enhance immune responses. The CpG immunostimulatory oligonucleotide and other therapeutic agent may be administered simultaneously or sequentially. When the other therapeutic agents are administered simultaneously they can be administered in the same or separate formulations, but are administered at the same time. The other therapeutic agents are administered sequentially with one another and with CpG immunostimulatory oligonucleotide, when the administration of the other therapeutic agents and the CpG immunostimulatory oligonucleotide is temporally separated. The separation in time between the administration of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the CpG immunostimulatory oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The CpG immunostimulatory oligonucleotides are also useful as mucosal adjuvants. It has previously been discovered that both systemic and mucosal immunity are induced by mucosal delivery of CpG nucleic acids. Thus, the oligonucleotides may be administered in combination with other mucosal adjuvants.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with the CpG immunostimulatory oligonucleotides. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-1 5, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-γ and GM-CSF). The redirection or rebalance of the immune response from a Th2 to a Th1 response is particularly useful for the treatment or prevention of asthma. For instance, an effective amount for treating asthma can be that amount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The CpG immunostimulatory oligonucleotides of the invention cause an increase in Th1 cytokines which helps to rebalance the immune system, preventing or reducing the adverse effects associated with a predominately Th2 immune response.

The oligonucleotides of the invention may also be useful for treating airway remodeling. Airway remodeling results from smooth muscle cell proliferation and/or submucosal thickening in the airways, and ultimately causes narrowing of the airways leading to restricted airflow. The oligonucleotides of the invention may prevent further remodeling and possibly even reduce tissue build up resulting from the remodeling process.

The oligonucleotides are also useful for improving survival, differentiation, activation and maturation of dendritic cells. The CpG immunostimulatory oligonucleotides have the unique capability to promote cell survival, differentiation, activation and maturation of dendritic cells.

CpG immunostimulatory oligonucleotides also increase natural killer cell lytic activity and antibody dependent cellular cytotoxicity (ADCC). ADCC can be performed using a CpG immunostimulatory oligonucleotide in combination with an antibody specific for a cellular target, such as a cancer cell. When the CpG immunostimulatory oligonucleotide is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available.

The CpG immunostimulatory oligonucleotides may also be administered in conjunction with an anti-cancer therapy. Anti-cancer therapies include cancer medicaments, radiation and surgical procedures. As used herein, a "cancer medicament" refers to a agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the CpG immunostimulatory oligonucleotides. As an example, where appropriate, the CpG immunostimulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MM1270, BAY 12-9566, RAS farnesyl transferase inhibitor, farnesyl transferase inhibitor, MMP, MTA/LY231514, LY264618/Lometexol, Glamolec, $C_1$-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, IncelVVX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32Nalrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP 16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

The use of CpG immunostimulatory oligonucleotides in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The nucleic acids when used in combination with monoclonal antibodies serve to reduce the dose of the antibody required to achieve a biological result.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The CpG immunostimulatory oligonucleotides are also useful for treating and prevneting autoimmune disease. Autoimmune disease is a class of diseases in which an subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the CpG immunostimulatory nucleic acids be administered with self antigens, particularly those that are the targets of the autoimmune disorder.

In other instances, the the CpG immunostimulatory nucleic acids may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

The invention also includes a method for inducing antigen non-specific innate immune activation and broad spectrum resistance to infectious challenge using the CpG immunostimulatory oligonucleotides. The term antigen non-specific innate immune activation as used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The invention also relates to oligonucleotides having chiral internucleotide linkages. As described above the soft and semi-soft oligonucleotides of the invention may have phosphodiester like linkages between C and G. One example of a phosphodiester-like linkage is a phosphorothioate linkage in an Rp conformation.

At least one study has examined the effect of p-chirality upon the immune stimulatory effects of CpG oligonucleotides. Yu et al., compared stereo-enriched (not stereo-pure) phosphorothioate (PS)-oligonucleotides for their ability to induce spleen cell proliferation (Yu et al., 2000). In that study, a 19mer sequence containing a single CpG motif was found to induce high levels of mouse spleen cell proliferation if the oligonucleotide was synthesized with random p-chirality or was enriched for Sp internucleotide linkages, but the proliferation was markedly reduced if the oligonucleotide was enriched for Rp internucleotide linkages (Yu et al., 2000). However, that study did not examine the specific role of p-chirality at the CpG dinucleotide, nor did it determine whether the Rp CpG oligonucleotides would have activity in short term stimulation assays.

It has been discovered according to the invention that oligonucleotide p-chirality can have apparently opposite effects on the immune activity of a CpG oligonucleotide, depending upon the time point at which activity is measured. At an early time point of 40 minutes, the Rp but not the Sp stereoisomer of phosphorothioate CpG oligonucleotide induces JNK phosphorylation in mouse spleen cells (discussed in examples). In contrast, when assayed at a late time point of 44 hr, the Sp but not the Rp stereoisomer is active in stimulating spleen cell proliferation. We have demonstrated that this difference in the kinetics and bioactivity of the Rp and Sp stereoisomers does not result from any difference in cell uptake, but rather most likely is due to two opposing biologic roles of the p-chirality. First, the enhanced activity of the Rp stereoisomer compared to the Sp for stimulating immune cells at early time points indicates that the Rp may be more effective at interacting with the CpG receptor, TLR9, or inducing the downstream signaling pathways. On the other hand, the faster degradation of the Rp PS-oligonucleotides compared to the Sp results in a much shorter duration of signaling, so that the Sp PS-oligonucleotides appear to be more biologically active when tested at later time points.

The invention in some aspects is based on the novel finding that the previously reported relative lack of immune stimulation by Rp PS-Oligos is due only to their nuclease lability, not to an inherent inability to stimulate the CpG receptor and downstream pathways. When tested for their ability to stimulate JNK phosphorylation, which indicates activation of this mitogen activated protein kinase pathway, the Rp oligonucleotide appeared to be the most active, followed by the stereo-random oligo, but with no detectable activity of the Sp oligonucleotide. However, when these oligonucleotide were compared for their ability to activate the NF-κB pathway, as measured by the degradation of the inhibitory protein IκB-α, all of the CpG oligonucleotide were active, although the non-CpG control failed to induce IκB-α degradation. Thus, the Sp oligonucleotide is still biologically active. It's failure to induce the JNK pathway could be related to differences in the kinetics of activation of the JNK and NF-κB pathways, but due to limited amounts of the stereo-specific oligonucleotide that were available for testing, we were unable to confirm this hypothesis.

The experiments described in the Examples revealed a surprisingly strong effect of the p-chirality at the CpG dinucleotide itself. In comparison to a stereo-random CpG oligonucleotide the congener in which the single CpG dinucleotide was linked in Rp was slightly more active, while the congener containing an Sp linkage was nearly inactive for inducing spleen cell proliferation. The loss of activity of the Sp congener supports our hypothesis that the TLR9 receptor may not be indifferent to the chirality of the CpG dinucleotide in the DNA with which it interacts, but may actually be stimulated better by the Rp stereoisomer. Thus, the stimulatory effect of the stereo-random oligo is probably not only due to the presence of 50% Sp linkages that retard degradation, but also to the fact that half of the oligo molecules will have Rp chirality at the CpG dinucleotide, which appears to enhance the immune stimulatory effects.

The nuclease sensitivity of $R_p$ PS linkages has important implications for interpretation of pharmacokinetic (PK) and metabolism studies of PS-Oligos in humans or animals. The predominant serum nuclease activity is known to be a 3' exonuclease. In a typical stereo-random PS-oligo solution the last 3' internucleotide linkage will be expected to be of $R_p$ chirality in one half of the molecules. Therefore in these 50% of the PS-Oligo molecules, the terminal 3' base will be cleaved fairly rapidly after IV infusion. The second from the end 3' internucleotide linkage should be of $R_p$ chirality in one half of these molecules, and therefore in 25% of the starting PS-Oligo molecules the 3' end may be expected to be shortened by 2 bases relatively rapidly. This in vivo base-clipping process involving the 3' $R_p$ internucleotide linkages may be expected to continue until the 3' internucleotide linkage is of Sp configuration. Therefore, if the PS-Oligos were synthesized to have an Sp 3' terminal linkage, they should have much slower degradation and a different PK profile compared to stereo-random PS-Oligos. This should make it possible to use somewhat shorter oligonucleotide for in vivo applications. In designing optimized oligos for antisense applications, the enhanced RNA binding of the $R_p$ stereoisomer points to the desirability of having as much of the internal core of the oligonucleotide in $R_p$ configuration as possible. On the other hand, an optimized CpG oligonucleotide for immunostimulatory applications may be one in which all of the internucleotide linkages except the CpG would be of Sp chirality.

The CpG immunostimulatory oligonucleotides may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell. Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

Delivery vehicles or delivery devices for delivering antigen and oligonucleotides to surfaces have been described. The CpG immunostimulatory oligonucleotide and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., *Salmonella, Escherichia coli, Bacillus calmatte-guerin, Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art and some additional examples are provided below in the discussion of vectors.

The term effective amount of a CpG immunostimulatory oligonucleotide refers to the amount necessary or sufficient to realize a desired biologic effect. For example, an effective amount of a CpG immunostimulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular CpG immunostimulatory oligonucleotide being administered the size of the subject, or the severity of the disease or condition. One of ordinary skill in the art can empirically determine the effective amount of a particular CpG immunostimulatory oligonucleotide and/or antigen and/or other therapeutic agent without necessitating undue experimentation.

Subject doses of the compounds described herein for mucosal or local delivery typically range from about 0.1 μg to 10 mg per administration, which depending on the application could be given daily, weekly, or monthly and any other amount of time therebetween. More typically mucosal or local doses range from about 10 μg to 5 mg per administration, and most typically from about 100 μg to 1 mg, with 2-4 administrations being spaced days or weeks apart. More typically, immune stimulant doses range from 1 μg to 10 mg per administration, and most typically 10 μg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the CpG immunostimulatory oligonucleotides are administered in combination with other therapeutic agents or in specialized delivery vehicles typically range from about 0.1 μg to 10 mg per administration, which depending on the application could be given daily, weekly, or monthly and any other amount of time therebetween. More typically parenteral doses for these purposes range from about 10 μg to 5 mg per administration, and most typically from about 100 μg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG immunostimulatory oligonucleotide can be administered to a subject by any mode that delivers the oligonucleotide to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (i.e., CpG immunostimulatory oligonucleotides, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the oligonucleotide (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropyhnethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the oligonucleotide (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the oligonucleotide or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the oligonucleotides (or derivatives thereof). The oligonucleotide (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colorado; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide (or derivative) dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered-dose inhaler device will generally comprise a finely divided powder containing the oligonucleotide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide (or derivative) and may also include a bulking agent, such as lactose, sorbitol, sucrose, or mannitol in amounts which facilitate dispersal of the powder from the device, e.g., 50 to 90% by weight of the formulation. The oligonucleotide (or derivative) should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The CpG immunostimulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG immunostimulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods:
Oligodeoxynucleotides (ODNS)

All ODNs were purchased from biospring (Frankfurt, Germany) or Sigma-Ark (Darmstadt, Germany), and were controlled for identity and purity by Coley Pharmaceutical GmbH (Langenfeld, Germany). ODNs were diluted in phosphate-buffered saline (Sigma, Germany), and stored at −20° C. All dilutions were carried out using pyrogen-free reagents.

Cell Purification

Peripheral blood buffy coat preparations from healthy male and female human donors were obtained from the Blood Bank of the University of Dusseldorf (Germany) and from these, PBMC were purified by centrifugation over Ficoll-Hypaque (Sigma). The purified PBMC were either used freshly (for most assays) or were suspended in freezing medium and stored at −70° C. When required, aliquots of these cells were thawed, washed and resuspended in RPMI 1640 culture medium (BioWhittaker, Belgium) supplemented with 5% (v/v) heat inactivated human AB serum (BioWhittaker, Belgium) or 10% (v/v) heat inactivated FCS, 2 mM L-glutamine (BioWhittaker), 100 U/ml penicillin and 100 μg/ml streptomycin (Invitrogen (Karlsruhe, Germany)).

Cytokine Detection

Thawed or fresh PBMC were seeded on 48 well flat-bottom plates, or 96 well round-bottom plates, and incubated with ODN in the concentrations as indicated in a humidified incubator at 37° C. Culture supernatants were collected and if not used immediately, were frozen at −20° C. until required. Amounts of cytokines in the supernatants were assessed using commercially available ELISA Kits (Diaclone, USA) or in-house ELISAs developed using commercially available antibodies (from Becton Dickinson/Pharmingen or PBL).

Cultures for Flow Cytometric Analysis of NK Cell Activation

Fluorochrome conjugated monoclonal antibodies to CD3 (T cell marker), CD56 (NK cell marker) and CD69 (early activation marker on NK cells and T cells) were purchased from Becton Dickinson. PBMC were incubated for 24 hours with or without the addition of different concentrations of ODNs in 96 well round-bottom plates. NK cells were identified as CD56-positive and CD3-negative cells by flow cytometry. Flow cytometric data were acquired on a FACSCalibur (Becton Dickinson). Data were analyzed using the computer program CellQuest (Becton Dickinson).

Flow Cytometric Analysis of Cell Surface Activation Markers

For measurement of the expression of the co-stimulatory molecule CD86 as an activation marker on B cells, PBMCs were incubated for 48 h with ODN in the concentrations as indicated, and cells were stained with mAb for CD19 and CD86 (Pharmingen, Germany). CD86 expression on CD19 positive B cells was measured by flow cytometry.

For measurement of the expression of the co-stimulatory molecule CD80 as an activation marker on monocytes, PBMCs were incubated for 48 h with ODN in the concentrations as indicated, and cells were stained with mAb for CD14, CD19, and CD80 (Pharmingen, Germany). CD80 expression on CD14 positive CD19 negative monocytes was measured by flow cytometry. The results of both measurements are given as Mean Fluorescence Intensity (MFI).

Example 1

Levels of interferon-alpha (IFN-α), IFN-γ, IL-10, IL-6, and TNF-α secreted from human PBMC following exposure of these cells to the CpG oligonucleotides described herein is shown in the attached FIGS. 1-5. The test oligonucleotides examined are depicted in the figures by a ▲. An oligonucleotide that served as a positive control oligonucleotide was depicted by a ■. The test oligonucleotides shown in FIGS. 1A, 2A, 3A, 4A, and 5A include SEQ ID NO: 322, SEQ ID NO: 323, and SEQ ID NO: 324 The test oligonucleotides shown in FIGS. 1B, 2B, 3B, 4B, and 5B include SEQ ID NO: 325, SEQ ID NO: 326, SEQ ID NO: 327, and SEQ ID NO: 328. The concentration of oligonucleotide used to produce a particular data point is depicted along the X-axis (μM). Below the graphs the level of cytokine secreted by cells treated with a negative (medium) and in some cases LPS is listed for each experiment.

As demonstrated in FIGS. 1-5 the oligonucleotides tested in the assays were able to produce cytokine secretion at approximately equivalent or better levels than positive control oligonucleotides having a completely phosphorothioate backbone. Negative control caused the production of significantly less cytokines.

Example 2

Levels of CD69 expression (MFI) on NK cells in response to treatment with the test oligonucleotides versus control oligonucleotides was examined. CD69 expression is an indicator of T cell and NK cell activation. The cells were exposed to the test oligonucleotides depicted in FIG. 6 by a ▲ versus a positive control oligonucleotide depicted by a ■. The test oligonucleotides shown in FIG. 6A include SEQ ID NO: 322, SEQ ID NO: 323, and SEQ ID NO: 324. The test oligonucleotides shown in FIG. 6B include SEQ ID NO: 325, SEQ ID NO: 326, SEQ ID NO: 327, and SEQ ID NO: 328. The positive control oligonucleotide used in these studies is SEQ ID NO: 329. Below the graphs the level of CD69 expression on T and NK cells treated with a negative control (medium) and with LPS is listed for each experiment.

As demonstrated in FIG. 6 the oligonucleotides tested in the assays were able to induce CD69 expression at approximately equivalent or better levels than positive control oligonucleotides having a completely phosphorothioate backbone. The negative control caused the production of significantly less CD69.

Example 3

Levels of interferon-alpha (IFN-α) and IL-10 produced by human PBMC following exposure of these cells to the CpG oligonucleotides described herein is shown in the attached FIGS. 7-12 and 17. The test oligonucleotides examined are depicted in the figures by ■. An oligonucleotide that served as a positive control oligonucleotide SEQ ID NO: 242 was depicted by a ●. An oligonucleotide that served as a negative control oligonucleotide was depicted by a ◆ SEQ ID NO: 330. The test oligonucleotide shown in FIGS. 7A and 7B is SEQ ID NO: 313. The test oligonucleotide shown in FIGS. 8A and 8B is SEQ ID NO: 314. The test oligonucleotide shown in FIGS. 9A and 9B is SEQ ID NO: 319. The test oligonucleotide shown in FIGS. 10A and 10B is SEQ ID NO: 316. The test oligonucleotide shown in FIGS. 11A and 11B is SEQ ID NO: 317. The test oligonucleotide shown in FIGS. 12A and 12B is SEQ ID NO: 320. The test oligonucleotide shown in FIGS. 17A and 17B is SEQ ID NO: 321. The concentration of oligonucleotide used to produce a particular data point is depicted along the X-axis (μM).

As demonstrated in FIGS. 7-12 and 17 each of the oligonucleotides tested in the assays were able to produce different levels and patterns of cytokine secretion. For instance, at approximately equivalent or lower concentrations most of the tested ODN resulted in better induction of one or more cytokines than the positive control oligonucleotide having a completely phosphorothioate backbone. The negative control caused the production of significantly less cytokines.

Figure 17A:
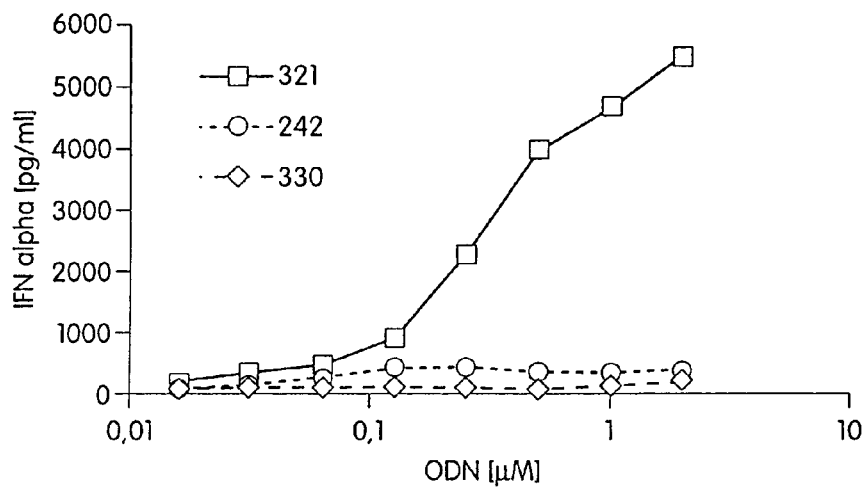
FIG. 17 is a set of graphs depicting levels of interferon-alpha (IFN-α) (17A) and IL-10 (17B) produced by human PBMC following exposure of these cells to the oligonucleotide SEQ ID NO: 321 in comparison to control oligonucleotide SEQ ID NO: 242 and to oligonucleotide SEQ ID NO: 330. The concentration of oligonucleotide used to produce a particular data point is depicted along the X-axis (μM).
Figure 17B:
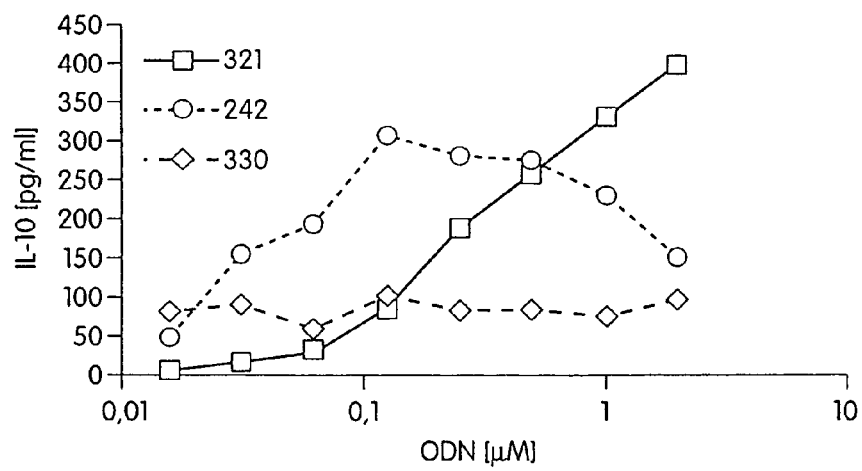

Upon incubation with SEQ ID NO: 313 PBMC secrete similar levels of Interferon-alpha (IFNα) and Interleukin-10 (IL-10) as after incubation with SEQ ID NO: 242. SEQ ID NO: 314 has similar effects on the amount of IL-10 secreted from human PBMC, as SEQ ID NO: 242, while the secretion of IFNα is strongly increased. In contrast to SEQ ID NO: 242, SEQ ID NO: 319 induces only low levels of IFNα secretion from human PBMC, while the amount of secreted IL-10 is comparable between the two oligonucleotides. SEQ ID NO: 316 was able to induce several times higher levels of IFNα from human PBMC than SEQ ID NO: 242. An increase in the total amount of secreted IL-10 was also observed. SEQ ID NO: 317 demonstrated similar properties to SEQ ID NO: 316, with strongly increased IFNα secretion from human PBMC compared to SEQ ID NO: 242. The levels of IL-10 secretion were slightly elevated. Although SEQ ID NO: 320 resulted in induction of IFNα and IL-10 from human PBMC the induction was less than that of SEQ ID NO: 242. SEQ ID NO: 321 is capable of inducing more than ten times higher levels of IFNU from human PBMC than SEQ ID NO: 242 (FIG. 17A). Compared to SEQ ID NO: 242, the IL-10 secretion from human PBMC induced by SEQ ID NO: 321 is slightly increased at higher concentrations of this oligonucleotide (FIG. 17B).

Example 4

Levels of B cell and monocyte activation following exposure of these cells to the CpG oligonucleotides described herein is shown in the attached FIGS. 13-15, 16 and 18-20. The test oligonucleotides examined are depicted in the Figures by a ■. An oligonucleotide that served as a positive control oligonucleotide SEQ ID NO: 242 was depicted by a ●. An oligonucleotide that served as a negative control oligonucleotide was depicted by a ♦ SEQ ID NO: 330. The test oligonucleotide shown in FIGS. 13A and 13B is SEQ ID NO: 313. The test oligonucleotide shown in FIGS. 14A and 14B is SEQ ID NO: 314. The test oligonucleotide shown in FIGS. 15A and 15B is SEQ ID NO: 319. The test oligonucleotide shown in FIGS. 16A and 16B is SEQ ID NO: 316. The test oligonucleotide shown in FIGS. 18A and 18B is SEQ ID NO: 321. The test oligonucleotide shown in FIGS. 19A and 19B is SEQ ID NO: 317. The test oligonucleotide shown in FIGS. 20A and 20B is SEQ ID NO: 320. The concentration of oligonucleotide used to produce a particular data point is depicted along the X-axis (μM).

As demonstrated in FIGS. 13-15, 16 and 18-20 each of the oligonucleotides tested in the assays were able to produce different levels and patterns of cell surface marker expression. For instance, at approximately equivalent or lower concentrations most of the tested ODN resulted in better induction of the cell surface markers than the positive control oligonucleotide having a completely phosphorothioate backbone.

Figure 1A:
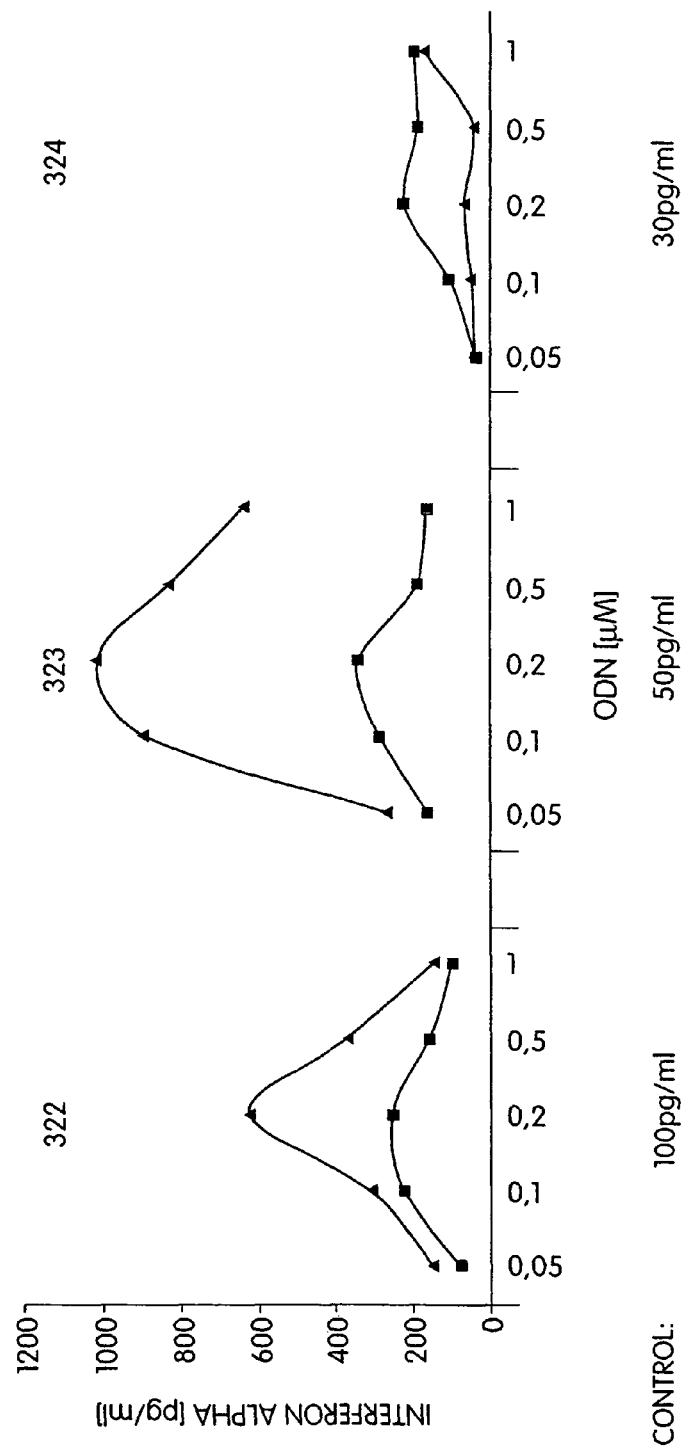
FIG. 1 is a set of graphs depicting levels of interferon-alpha (pg/ml) secreted from human PBMC following exposure of these cells to the oligonucleotides listed by number along the top X-axis of the graph and depicted by a ▲ versus a positive control oligonucleotide depicted by a ■. The test oligonucleotides shown in FIG. 1A include SEQ ID NO: 322, SEQ ID NO: 323, and SEQ ID NO: 324 and the positive control oligonucleotide is SEQ ID NO: 242. The test oligonucleotides shown in FIG. 1B include SEQ ID NO: 325, SEQ ID NO: 326, SEQ ID NO: 327, and SEQ ID NO: 328) and the positive control oligonucleotide is 5' TCG TCG TTT TGA CGT TTT GTC GTT 3' (SEQ ID NO: 329). The concentration of oligonucleotide used to produce a particular data point is depicted along the X-axis (µM). The data shown represents the mean of six donors. Below the graphs the level of Interferon-alpha (pg/ml) secreted by cells treated with a negative control (medium) is listed for each experiment.
Figure 1B:
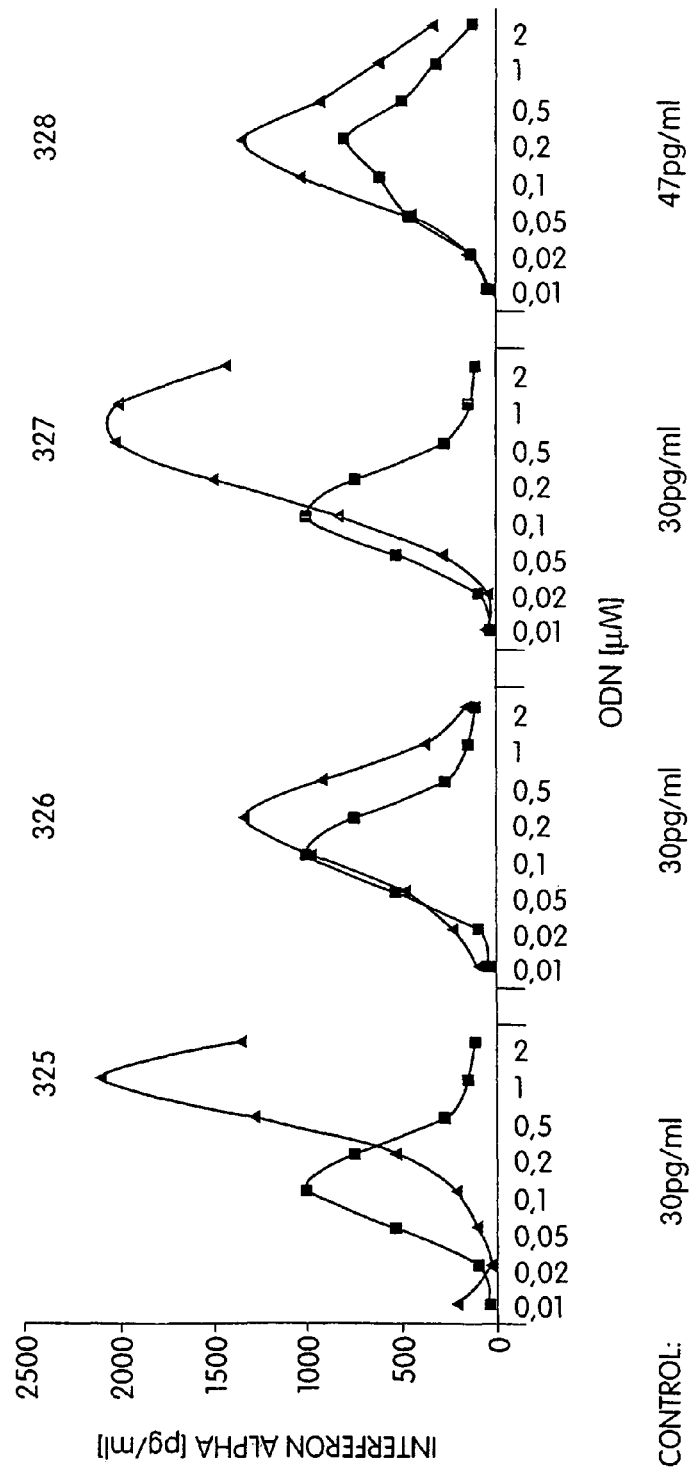
Figure 2A:
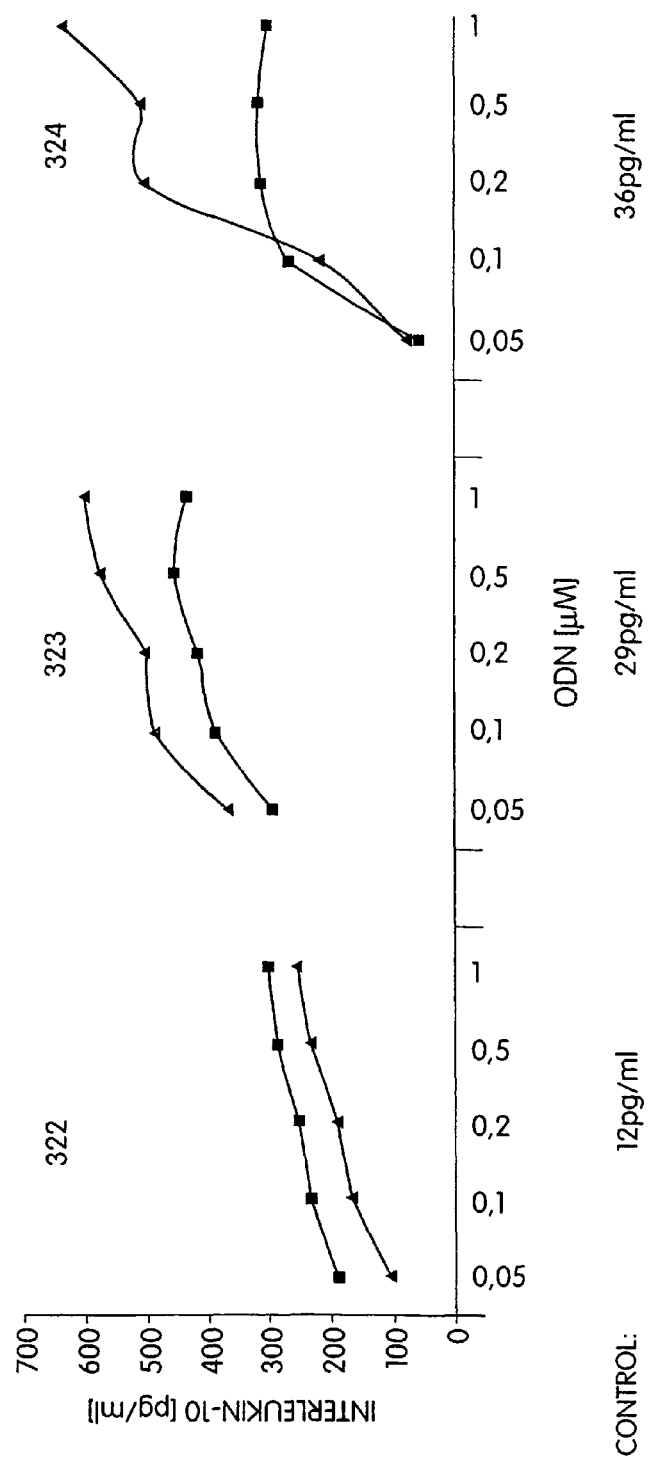
FIG. 2 is a set of graphs depicting levels of IL-10 (pg/ml) secreted from human PBMC following exposure of these cells to the oligonucleotides listed by number along the top X-axis of the graph and depicted by a ▲ versus a positive control oligonucleotide depicted by a ■. The test oligonucleotides shown in FIG. 2A include (SEQ ID NO: 322), SEQ ID NO: 323, and SEQ ID NO: 324 and the positive control oligonucleotide is SEQ ID NO: 242. The test oligonucleotides shown in FIG. 2B include SEQ ID NO: 325, SEQ ID NO: 326, SEQ ID NO: 327, and SEQ ID NO: 328 and the positive control oligonucleotide is SEQ ID NO: 329. The concentration of oligonucleotide used to produce a particular data point is depicted along the X-axis (µM). The data shown represents the mean of six donors. Below the graphs the level of IL-10 (pg/ml) secreted by cells treated with a negative control (medium) is listed for each experiment.
Figure 2B:
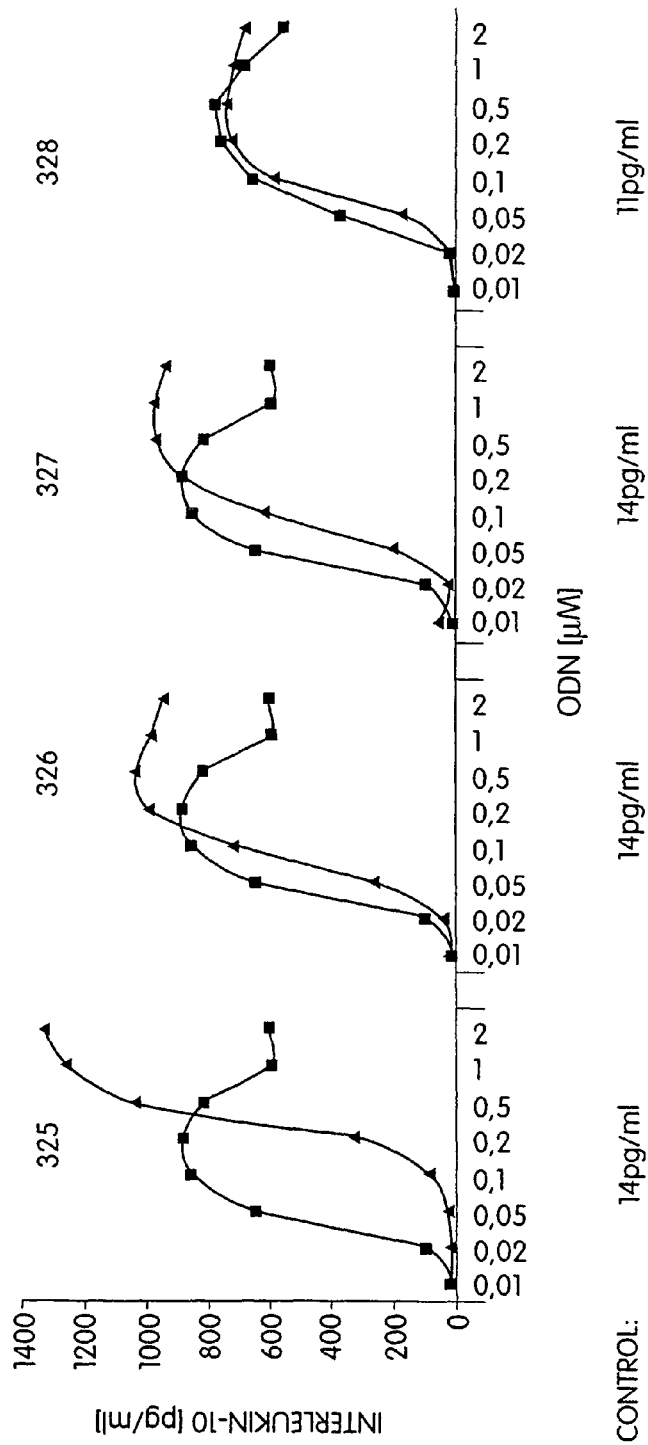
Figure 4B:
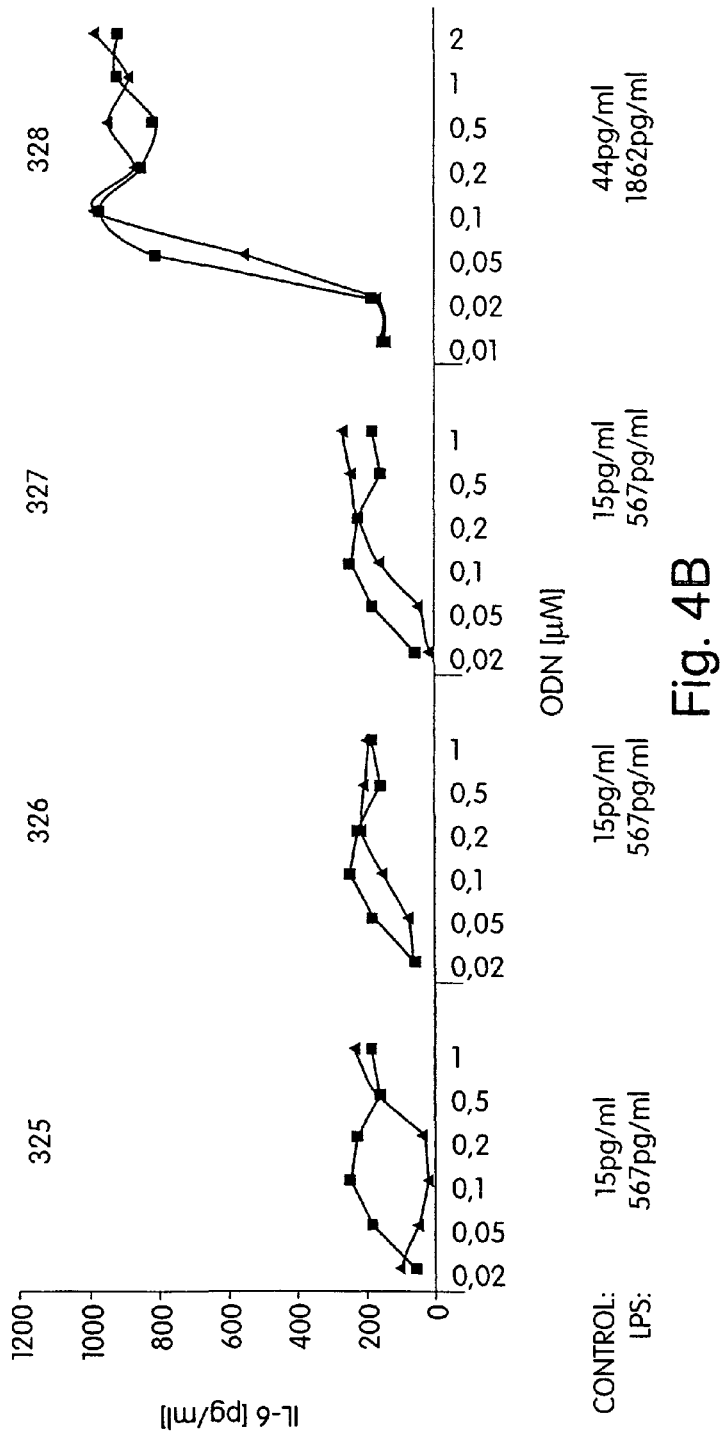
FIG. 4 is a set of graphs depicting levels of IL-6 (pg/ml) secreted from human PBMC following exposure of these cells to the oligonucleotides listed by number along the top X-axis of the graph and depicted by a ▲ versus a positive control oligonucleotide depicted by a ■. The test oligonucleotides shown in FIG. 4A include SEQ ID NO: 322, SEQ ID NO: 323, and SEQ ID NO: 324 and the positive control oligonucleotide is SEQ ID NO: 329 (with a complete phosphorothioate modified backbone). The test oligonucleotides shown in FIG. 4B include SEQ ID NO: 325, SEQ ID NO: 326, SEQ ID NO: 327, and SEQ ID NO: 328 and the positive control oligonucleotide is SEQ ID NO: 329. The concentration of oligonucleotide used to produce a particular data point is depicted along the X-axis (µM). The data shown represents the mean of three donors. Below the graphs the level of IL-6 (pg/ml) secreted by cells treated with a negative control (medium) and with LPS is listed for each experiment.
Figure 5B:
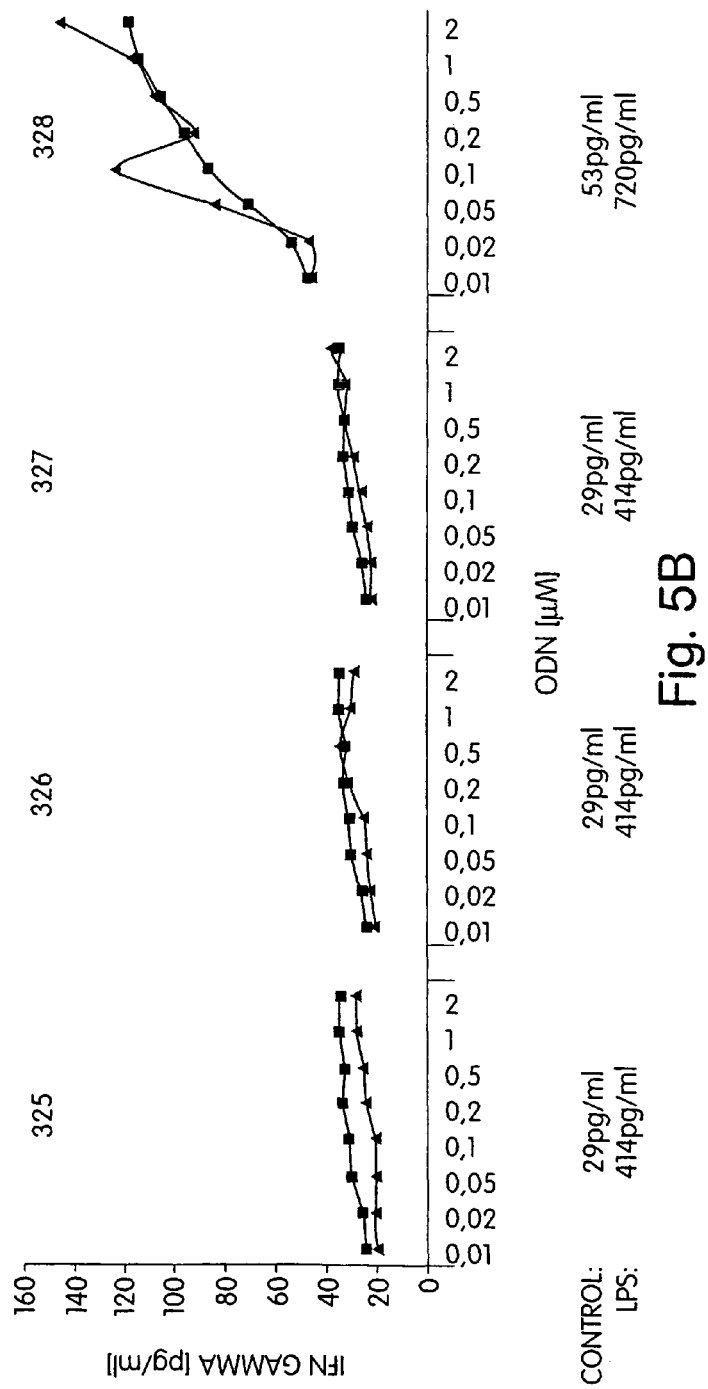
FIG. 5 is a set of graphs depicting levels of interferon-gamma (pg/ml) secreted from human PBMC following exposure of these cells to the oligonucleotides listed by number along the top X-axis of the graph and depicted by a ▲ versus a positive control oligonucleotide depicted by a ■. The test oligonucleotides shown in FIG. 5A include SEQ ID NO: 322, SEQ ID NO: 323, and SEQ ID NO: 324 and the positive control oligonucleotide is SEQ ID NO: 329. The test oligonucleotides shown in FIG. 5B include SEQ ID NO: 325, SEQ ID NO: 326, SEQ ID NO: 327, and SEQ ID NO: 328 and the positive control oligonucleotide is SEQ ID NO: 329. The concentration of oligonucleotide used to produce a particular data point is depicted along the X-axis (µM). The data shown represents the mean of three donors. Below the graphs the level of interferon-gamma (pg/ml) secreted by cells treated with a negative (medium) and with LPS is listed for each experiment.
Figure 7A:
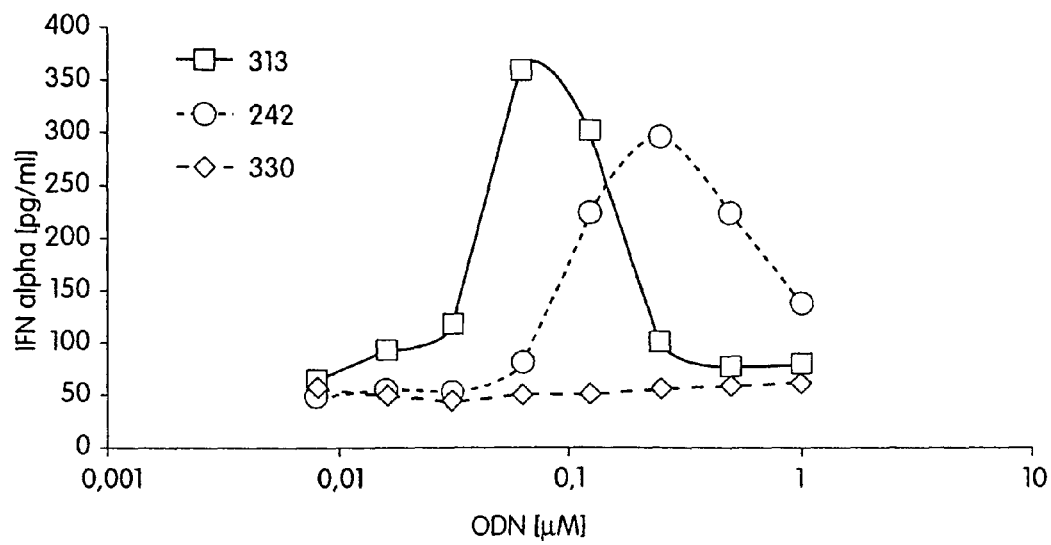
FIG. 7 is a set of graphs depicting levels of interferon-alpha (IFN-α) (7A) and IL-10 (7B) produced by human PBMC following exposure of these cells to the oligonucleotide SEQ ID NO: 313 and depicted by a ■ versus a positive control oligonucleotide SEQ ID NO: 242 depicted by a ●. The concentration of oligonucleotide used to produce a particular data point is depicted along the X-axis (μM).
Figure 7B:
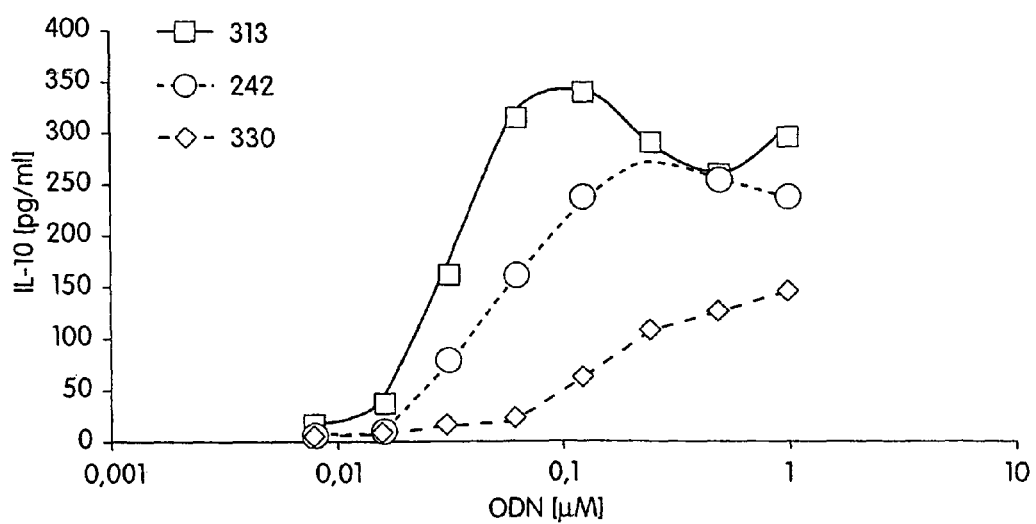
Figure 8A:
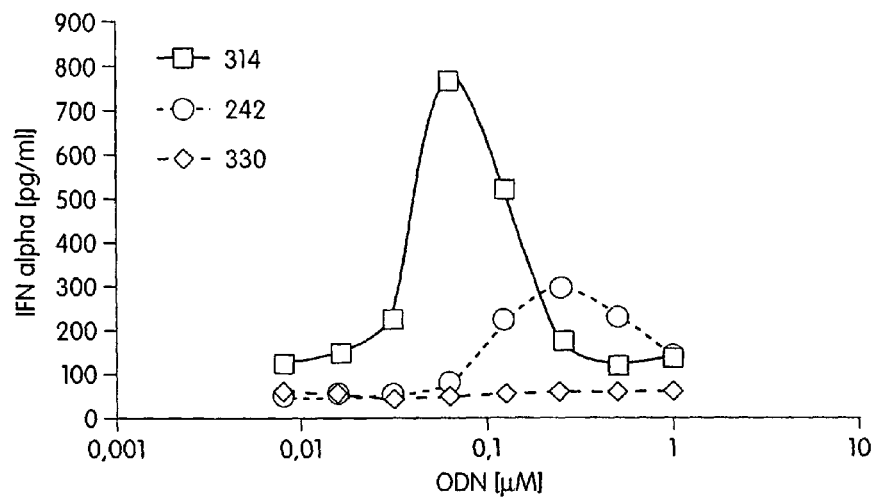
FIG. 8 is a set of graphs depicting levels of interferon-alpha (IFN-α) (8A) and IL-10 (8B) produced by human PBMC following exposure of these cells to the oligonucleotide SEQ ID NO: 314 and depicted by a ■ versus a positive control oligonucleotide SEQ ID NO: 242 depicted by a ●. The negative control ODN is SEQ ID No 330: tccaggacttctctcaggtt. The concentration of oligonucleotide used to produce a particular data point is depicted along the X-axis (μM).
Figure 8B:
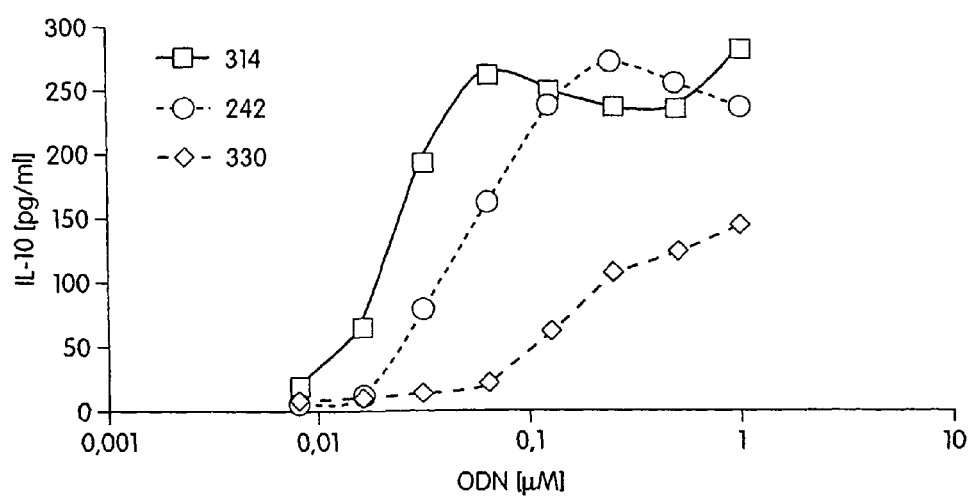
Figure 9A:
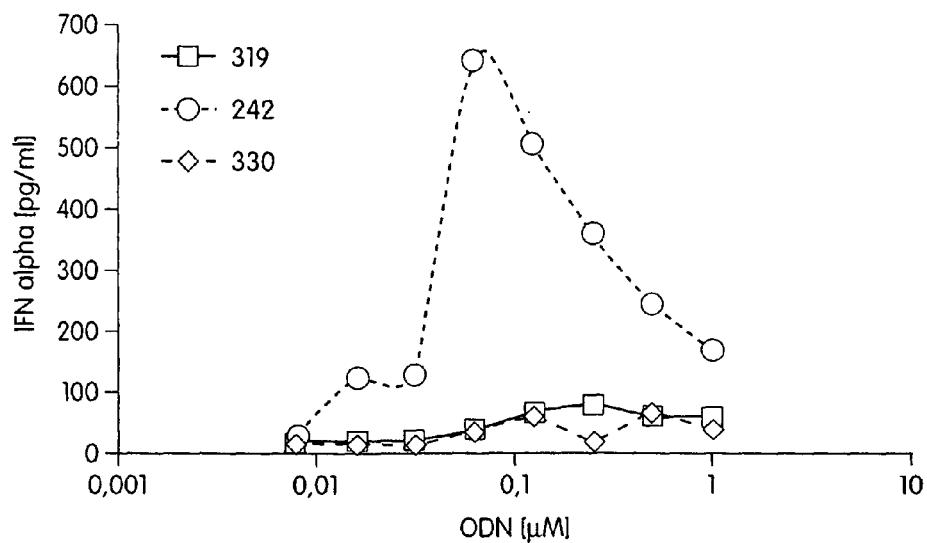
FIG. 9 is a set of graphs depicting levels of interferon-alpha (IFN-α) (9A) and IL-10 (9B) produced by human PBMC following exposure of these cells to the oligonucleotide SEQ ID NO: 319 and depicted by a ■ versus a positive control oligonucleotide SEQ ID NO: 242 depicted by a ●. The concentration of oligonucleotide used to produce a particular data point is depicted along the X-axis (μM).
Figure 9B:
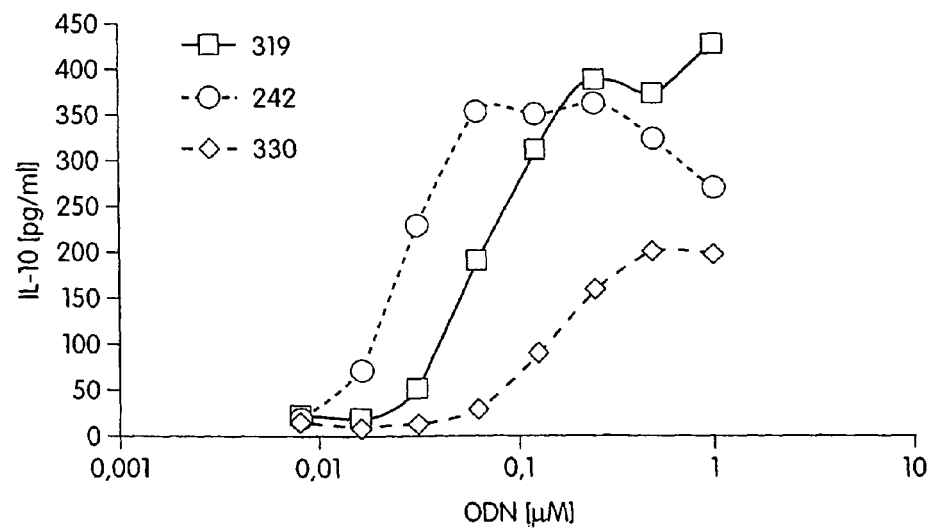
Figure 10A:
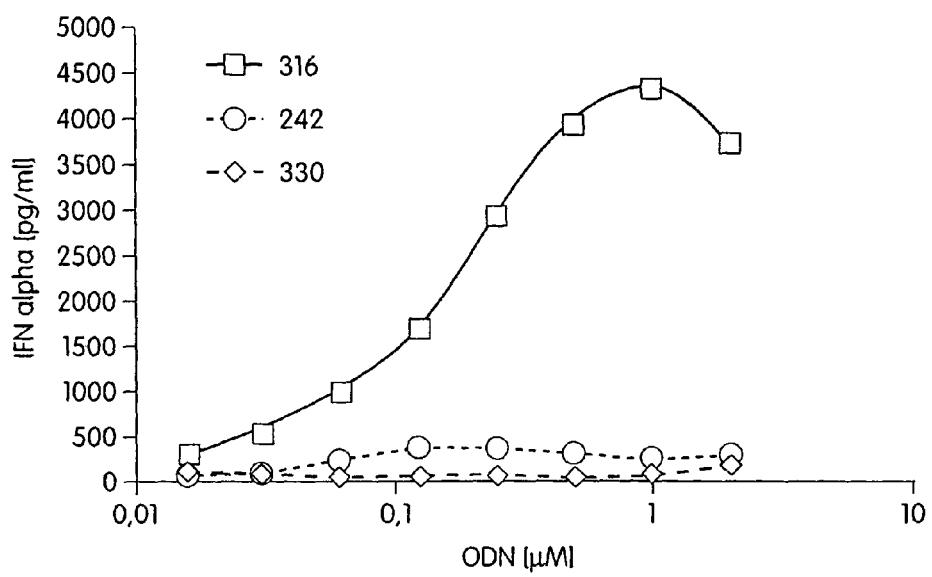
FIG. 10 is a set of graphs depicting levels of interferon-alpha (IFN-α) (10A) and IL-10 (10B) produced by human PBMC following exposure of these cells to the oligonucleotide SEQ ID NO: 316 and depicted by a ■ versus a positive control oligonucleotide SEQ ID NO: 242 depicted by a ●. The concentration of oligonucleotide used to produce a particular data point is depicted along the X-axis (μM).
Figure 10B:
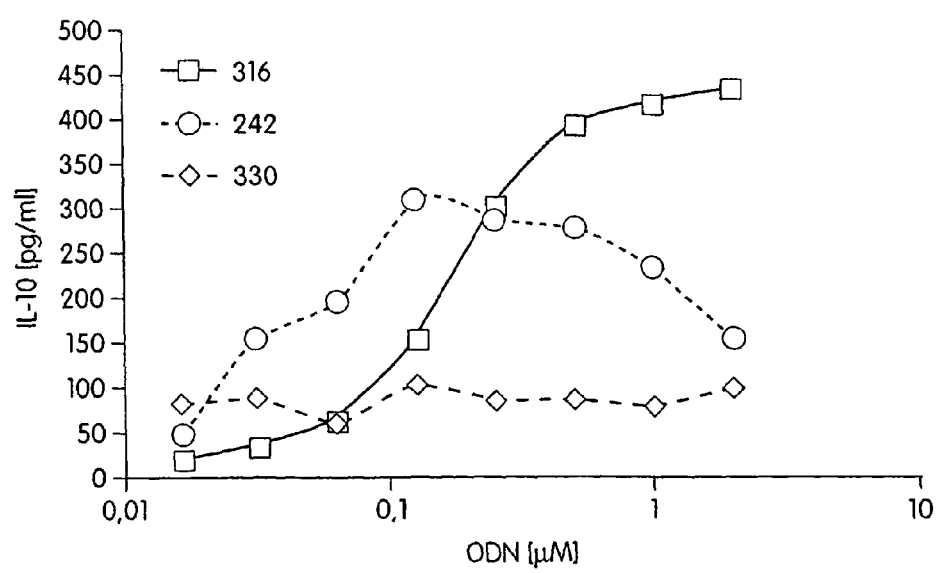
Figure 11A:
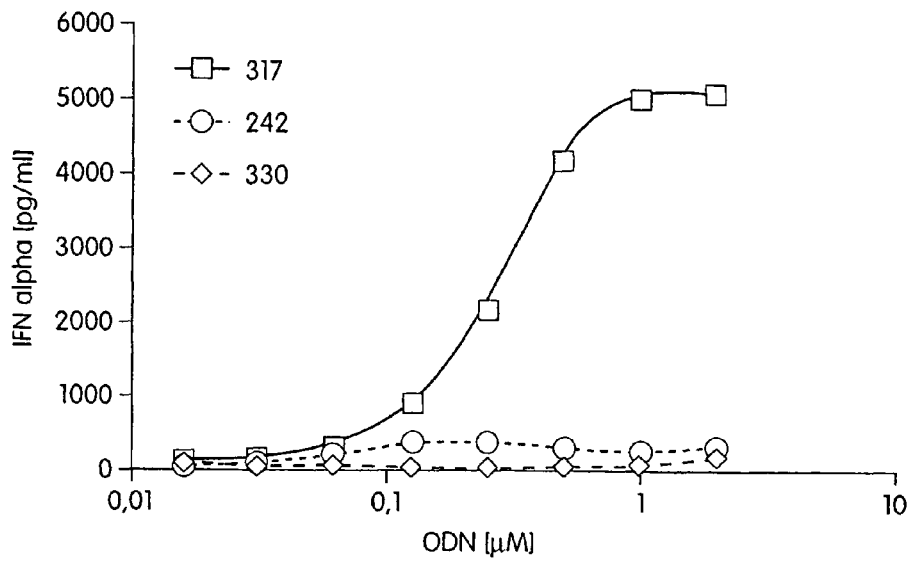
FIG. 11 is a set of graphs depicting levels of interferon-alpha (IFN-α) (11A) and IL-10 (11B) produced by human PBMC following exposure of these cells to the oligonucleotide SEQ ID NO: 317 and depicted by a ■ versus a positive control oligonucleotide SEQ ID NO: 242 depicted by a ●. The concentration of oligonucleotide used to produce a particular data point is depicted along the X-axis (μM).
Figure 11B:
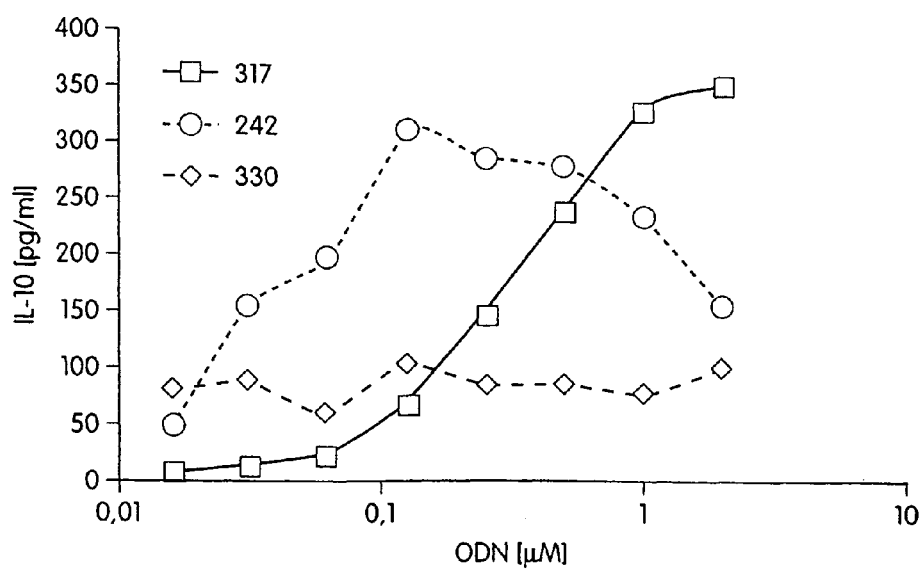
Figure 12A:
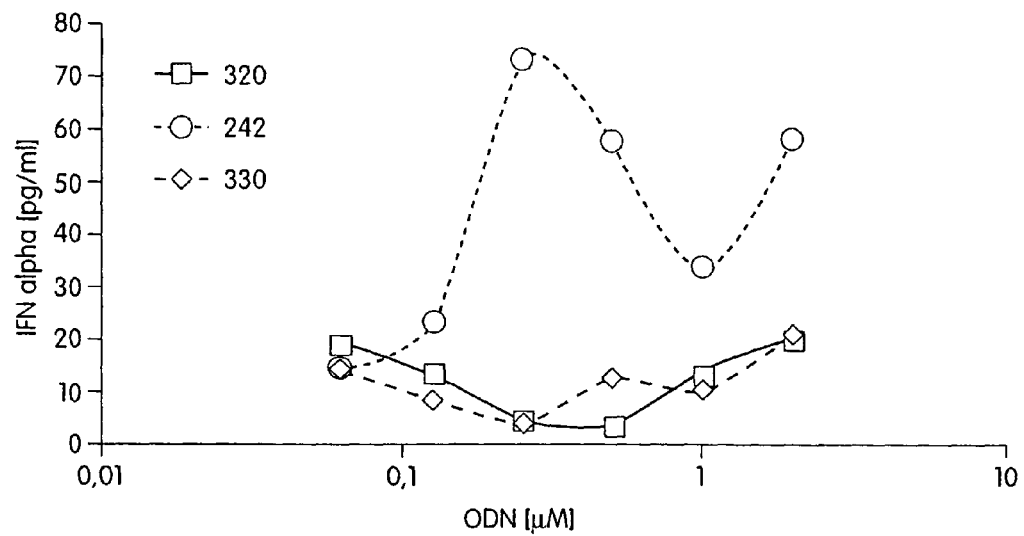
FIG. 12 is a set of graphs depicting levels of interferon-alpha (IFN-α) (12A) and IL-10 (12B) produced by human PBMC following exposure of these cells to the oligonucleotide SEQ ID NO: 320 and depicted by a ■ versus a positive control oligonucleotide SEQ ID NO: 242 depicted by a ●. The concentration of oligonucleotide used to produce a particular data point is depicted along the X-axis (μM).
Figure 12B:
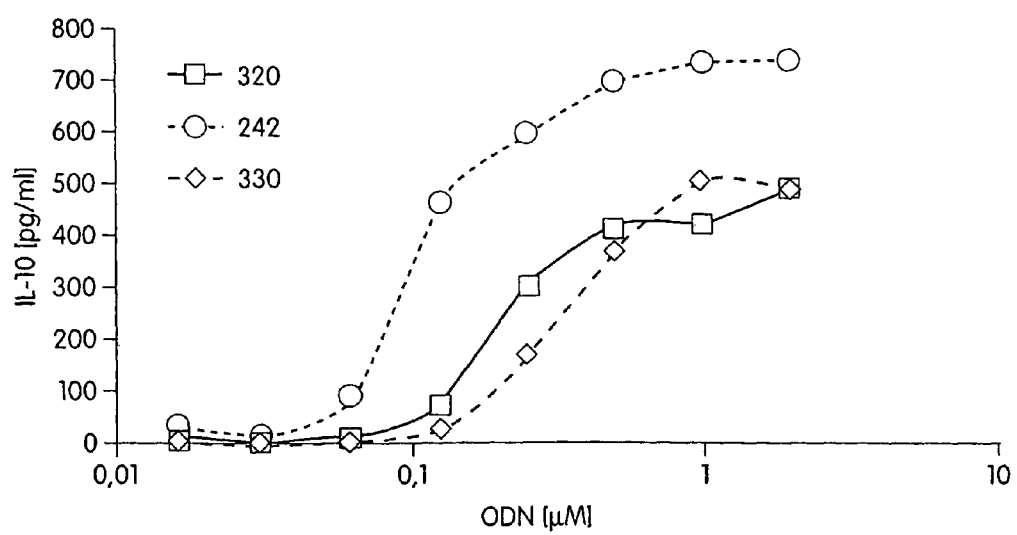
Figure 13A:
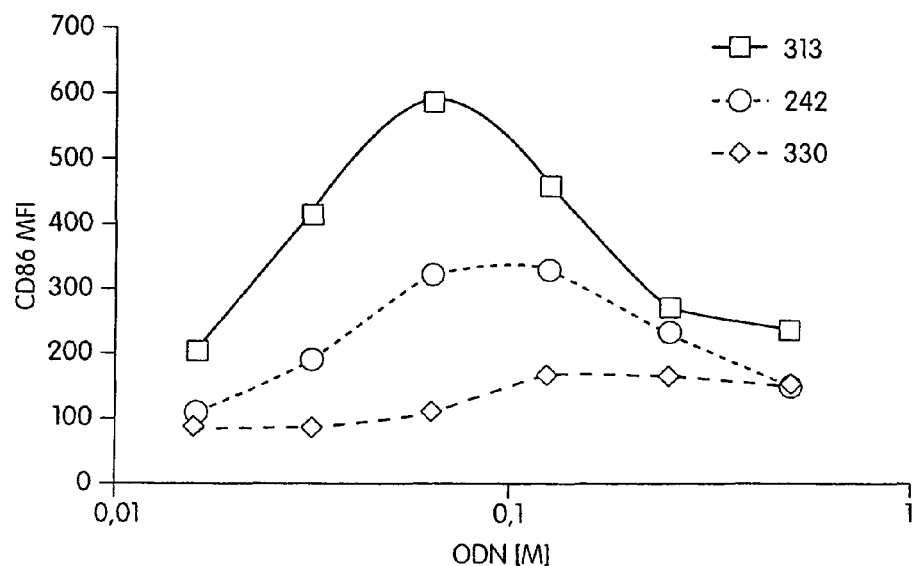
FIG. 13 is a set of graphs depicting levels of CD86 expression on B cells (13A) and CD80 expression on monocytes (13B) following exposure of these cells to the oligonucleotide SEQ ID NO: 313 and depicted by a ■ versus a positive control oligonucleotide SEQ ID NO: 242 depicted by a ●. The concentration of oligonucleotide used to produce a particular data point is depicted along the X-axis (μM).
Figure 13B:
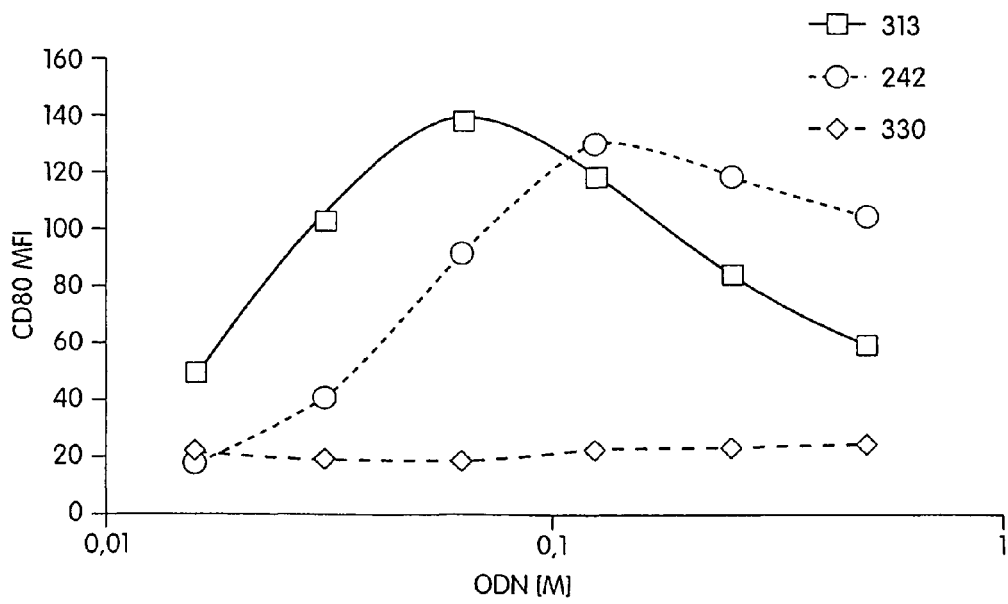
Figure 14A:
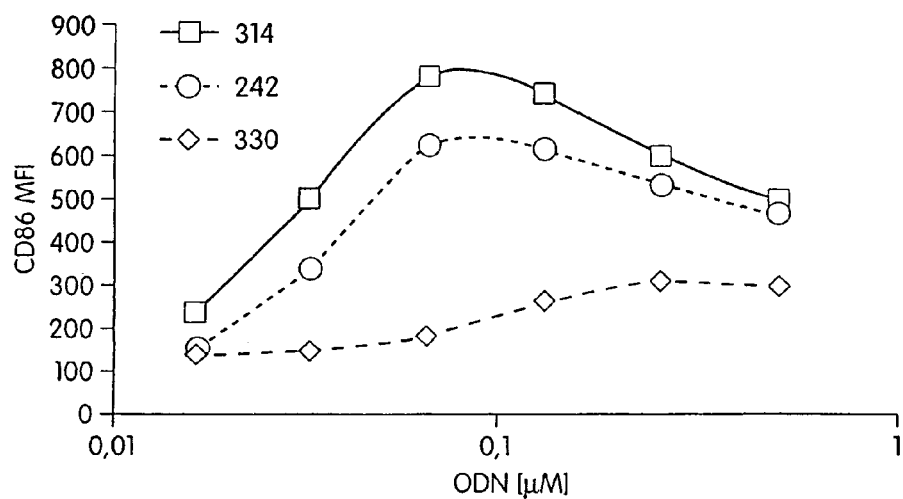
FIG. 14 is a set of graphs depicting levels of CD86 expression on B cells (14A) and CD80 expression on monocytes (14B) following exposure of these cells to the oligonucleotide SEQ ID NO: 314 and depicted by a ■ versus a positive control oligonucleotide SEQ ID NO: 242 depicted by a ●. The concentration of oligonucleotide used to produce a particular data point is depicted along the X-axis (μM).
Figure 14B:
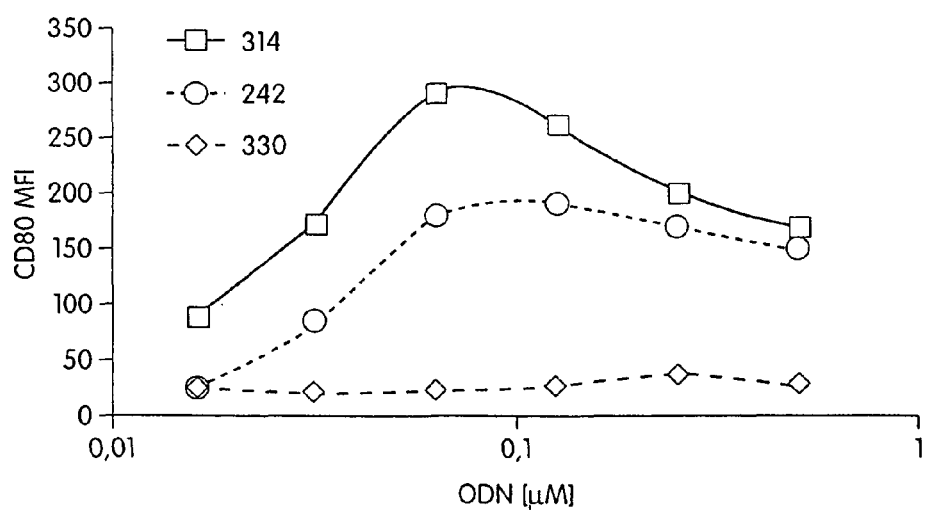
Figure 15A:
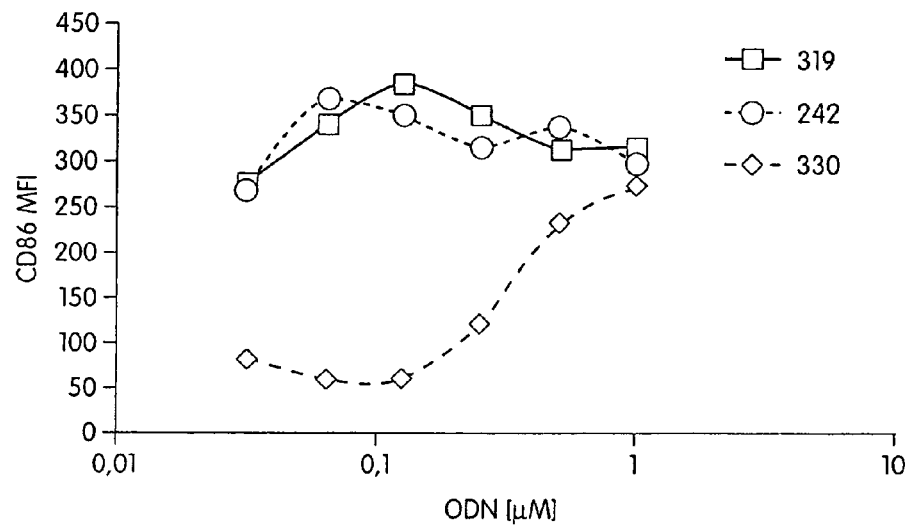
FIG. 15 is a set of graphs depicting levels of CD86 expression on B cells (15A) and CD80 expression on monocytes (15B) following exposure of these cells to the oligonucleotide SEQ ID NO: 319 and depicted by a ■ versus a positive control oligonucleotide SEQ ID NO: 242 depicted by a ●. The concentration of oligonucleotide used to produce a particular data point is depicted along the X-axis (μM).
Figure 15B:
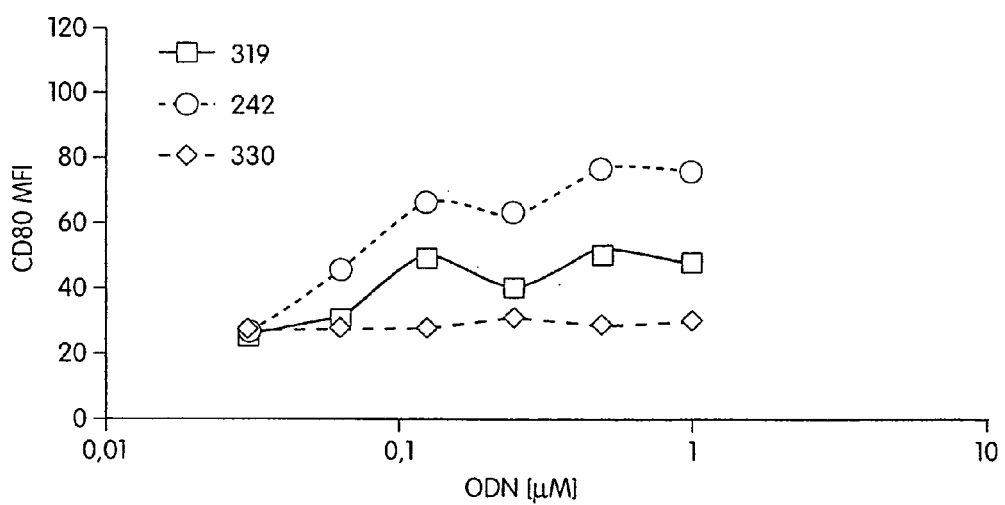
Figure 16A:
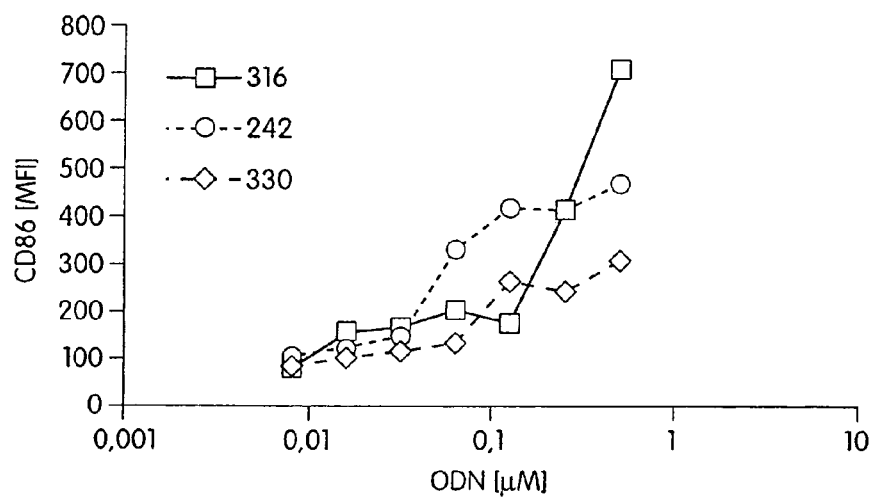
FIG. 16 is a set of graphs depicting CD86 expression on B cells (16A) and CD80 expression on monocytes (16B) following exposure of these cells to the oligonucleotide SEQ ID NO: 316 and compared with a positive control oligonucleotide SEQ ID NO: 242, and oligonucleotide 5' TCC AGG ACT TCT CTC AGG TT 3') SEQ ID NO: 330. The concentration of oligonucleotide used to produce a particular data point is depicted along the X-axis (μM).
Figure 16B:
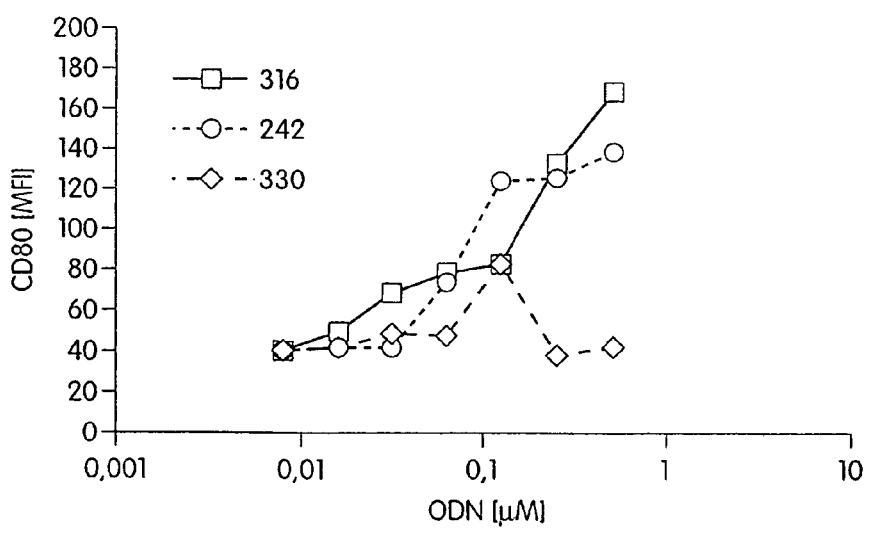
Figure 18A:
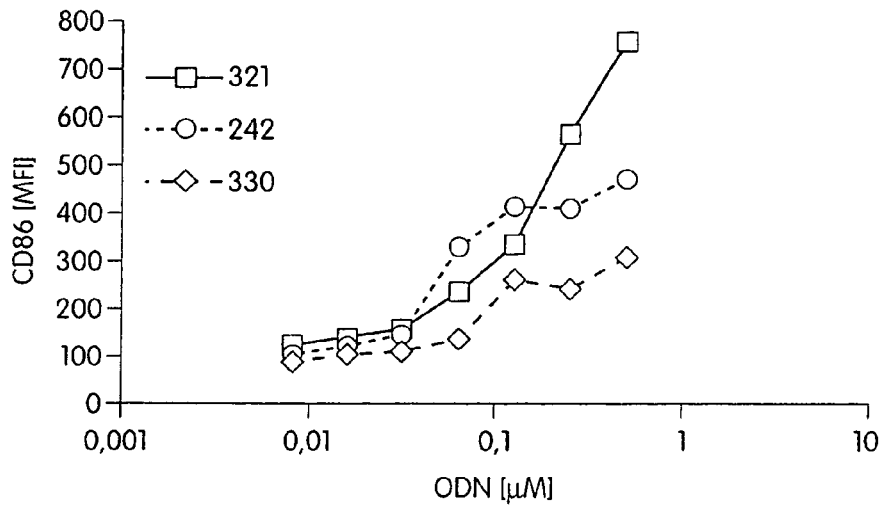
FIG. 18 is a set of graphs depicting CD86 expression on B cells (18A) and CD80 expression on monocytes (18B) following exposure of these cells to the oligonucleotide SEQ ID NO: 321 and compared with a positive control oligonucleotide SEQ ID NO: 242, and oligonucleotide SEQ ID NO: 330. The concentration of oligonucleotide used to produce a particular data point is depicted along the X-axis (μM).
Figure 18B:
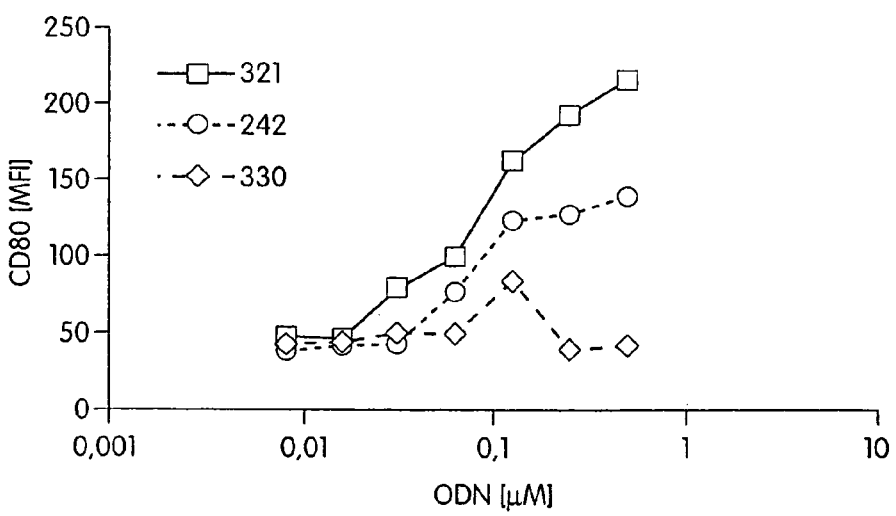
Figure 19A:
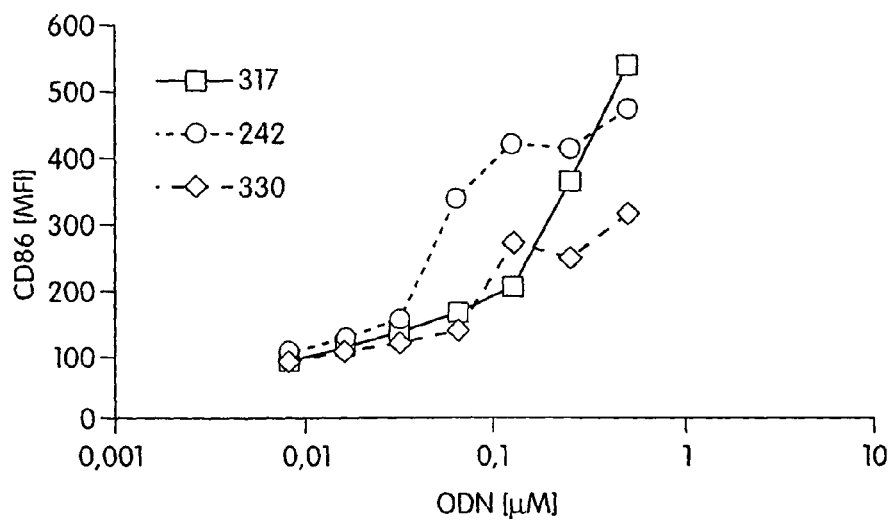
FIG. 19 is a set of graphs depicting CD86 expression on B cells (19A) and CD80 expression on monocytes (19B) following exposure of these cells to the oligonucleotide SEQ ID NO: 317 and compared with a positive control oligonucleotide SEQ ID NO: 242, and oligonucleotide SEQ ID NO: 330. The concentration of oligonucleotide used to produce a particular data point is depicted along the X-axis (μM).
Figure 19B:
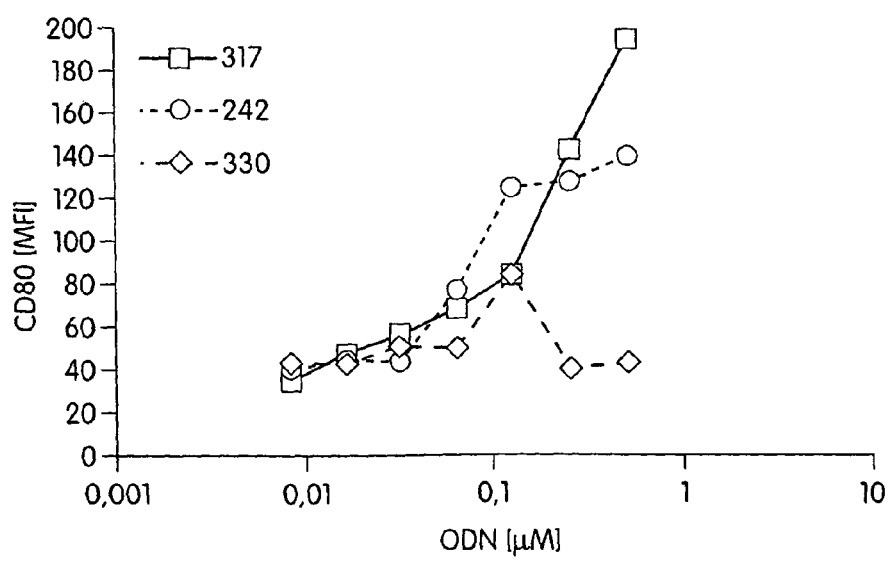
Figure 20A:
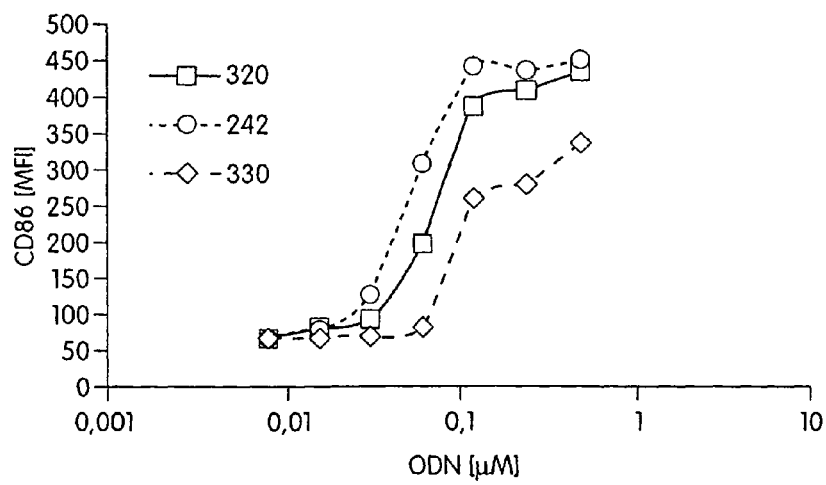
FIG. 20 is a set of graphs depicting CD86 expression on B cells (20A) and CD80 expression on monocytes (20B) following exposure of these cells to the oligonucleotide SEQ ID NO: 320 and compared with a positive control oligonucleotide SEQ ID NO: 242, and oligonucleotide SEQ ID NO: 330. The concentration of oligonucleotide used to produce a particular data point is depicted along the X-axis (μM).
Figure 20B:
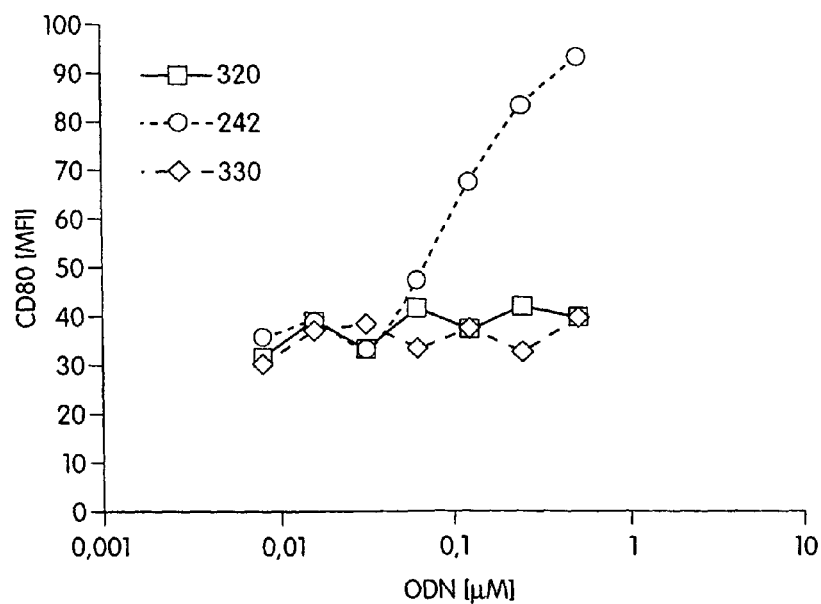
Figure 21:
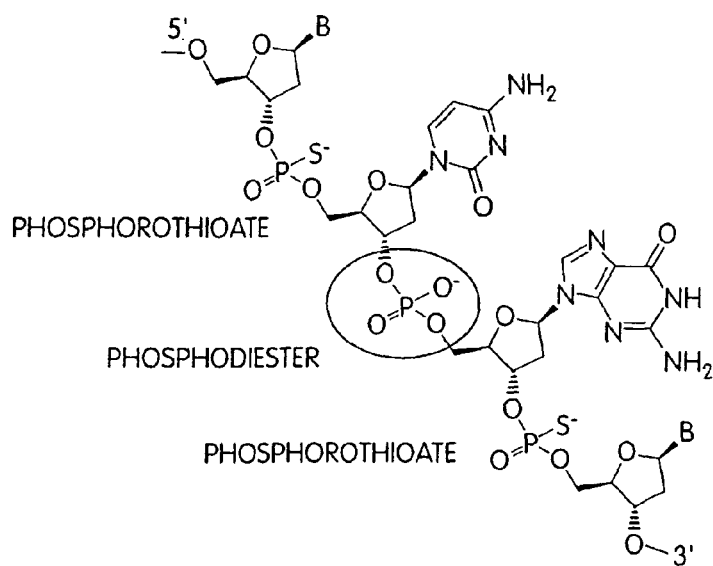
FIG. 21 is a graphic representation of a portion of a nucleic acid molecule, depicting structural features including bases (B), sugars, and backbone with a phosphodiester linkage (shown circled) between 5' cytidine and 3' guanosine and adjacent phosphorothioate linkages.
Figure 22:
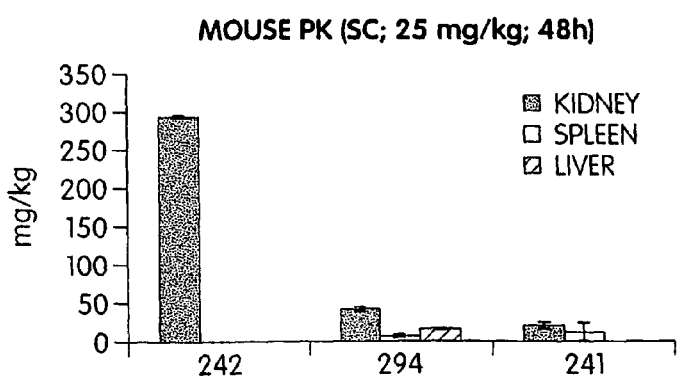
FIG. 22 is bar graph depicting relative tissue amounts of phosphorothioate (SEQ ID NO: 242), soft (SEQ ID NO: 294), and semi-soft (SEQ ID NO: 241) oligonucleotides in kidney, spleen, and liver 48 hours after subcutaneous injection into mice. Oligonucleotides SEQ ID NO: 242 and SEQ ID NO: 241 have identical base sequences and differ in their backbone composition.

The level of CD86 expression on B cells and CD80 expression on monocytes induced by SEQ ID NO: 313 is comparable to SEQ ID NO: 242. In contrast to SEQ ID NO: 242, SEQ ID NO: 313 stimulates the cells at lower concentrations compared to SEQ ID NO: 242 suggesting increased potency. The levels of CD86 expression on B cells and CD80 expression on monocytes induced by SEQ ID NO: 314 are comparable. The effects of SEQ ID NO: 314 are observed using a lower concentrations of SEQ ID NO: 314 compared to SEQ ID NO: 242, demonstrating increased potency of SEQ ID NO: 314. On B cells, surface expression of CD86 is strongly upregulated with SEQ ID NO: 319, with a signal strength comparable to SEQ ID NO: 242. On monocytes, only weakly elevated levels of CD80 expression can be detected with SEQ ID NO: 319. The potency of SEQ ID NO: 319 to induce CD86 upregulation on B cells is slightly reduced compared to SEQ ID NO: 242. Compared to SEQ ID NO: 242, SEQ ID NO: 316 induces higher levels of the activation marker CD86 on B cells (FIG. 16A), and of the activation marker CD80 on monocytes (FIG. 16B). B cells become strongly activated upon incubation of human PBMC with SEQ ID NO: 321 as shown by CD86 expression (FIG. 18A). The level of CD86 is higher than that induced by SEQ ID NO: 242. Also the activation of monocytes as determined by CD80 expression is stronger with SEQ ID NO: 321 than with SEQ ID NO: 242 (FIG. 18B). SEQ ID NO: 317 induces CD86 expression on B cells at comparable levels as SEQ ID NO: 242 (FIG. 19A), while expression of the activation marker CD80 on monocytes is increased compared to SEQ ID NO: 242 (FIG. 19B). SEQ ID NO: 320 induces CD86 expression on B cells to a similar extent as SEQ ID NO: 2426 (FIG. 20A).

Example 5

Semi-soft Oligonucleotides are Immunostimulatory for Human PBMC in Vitro

In this example semi-soft oligonucleotides were assessed for their ability to induce cytokines and chemokines in vitro. Peripheral blood mononuclear cells (PBMC) were obtained from three healthy human donors and cultured in the presence of various concentrations (0.05, 0.1, 0.2, 0.5, 1.0, and 5.0 μM) of fully stabilized CpG SEQ ID NO: 242 or semi-soft SEQ ID NO:241. After 6, 16, or 48 hours, culture supernatants were collected and various cytokines (IFN-α, TNF-α, IL-10) and the chemokine IP-10 in the supernatants were measured by ELISA. At low concentration of oligonucleotide, the semi-soft and fully stabilized oligonucleotides induced IFN-α to a similar extent after 16 or 48 hours in culture. However, maximum induction of IFN-α with ODN 5476 was reached at about half the oligonucleotide concentration needed for SEQ ID NO: 242. At intermediate concentrations, SEQ ID NO: 242 induced more IFN-α than SEQ ID NO: 241, and at high concentrations, neither SEQ ID NO: 242 nor SEQ ID NO: 241 induced much IFN-α. The chemokine IP-10 was stimulated to a similar extent and with a similar concentration dependence by the semi-soft and fully stabilized oligonucleotides. In both cases, ca. 700 μg/mL of IP-10 was observed at lower concentrations of oligonucleotide, and less IP-10 was induced at higher concentrations of oligonucleotide. A similar pattern to that of IP-10 was observed for the cytokine IL-10, except that the semi-soft oligonucleotide at 0.05 μM induced a significant amount of IL-10, whereas the fully stabilized oligonucleotide at 0.05 μM induced little to no IL-10. Semi-soft and fully stabilized oligonucleotides were similar in their ability to induce TNF-α, i.e., both types of oligonucleotide strongly induced TNF-α, particularly at high concentration.

TABLE 1

| | | Cytokines and chemokine (pg/mL)[1] induced by oligonucleotides (μM) | | | | | |
|---|---|---|---|---|---|---|---|
| | ODN | 0.05 | 0.1 | 0.2 | 0.5 | 1.0 | 5.0 |
| IFN-α | SEQ ID NO: 241 | 534.8 (3.5) | 466.0 (7.5) | 251.6 (22.9) | 25.4 (21.4) | 22.9 (26.3) | 26.7 (22.1) |
| | SEQ ID NO: 242 | 444.0 (23.9) | 573.6 (41.7) | 892.4 (58.0) | 583.6 (51.5) | 115.6 (2.5) | 51.5 (12.8) |
| IP-10 | SEQ ID NO: 241 | 5677.8 (18.9) | 6221.5 (22.4) | 4936.6 (11.8) | 1493.6 (5.5) | 121.9 (0.4) | 0.0 (0.0) |
| | SEQ ID NO: 242 | 7287.4 (5.5) | 6685.8 (12.8) | 6967.4 (15.9) | 4422.7 (11.0) | 361.7 (2.6) | 0.0 (0.0) |
| IL-10 | SEQ ID NO: 241 | 447.6 (3.7) | 385.3. (4.9) | 257.3 (3.1) | 92.9 (1.6) | 46.5 (0.2) | 17.3 (1.5) |
| | SEQ ID NO: 242 | 73.4 (1.0) | 399.8 (3.0) | 367.7 (9.8) | 237.8 (2.6) | 52.3 (1.3) | 10.5 (0.3) |
| TNF-α | SEQ ID NO: 241 | 179.0 (18.3) | 186.4 (15.9) | 229.9 (23.4) | 178.8 (9.0) | 368.2 (22.3) | 886.3 (31.7) |
| | SEQ ID NO: 242 | 196.8 (25.9) | 211.5 (8.7) | 242.7 (5.5) | 262.1 (6.3) | 479.8 (33.5) | 939.6 (69.7) |

[1]Values reported as mean (standard deviation).

Example 6

Stimulation of Murine Macrophages In Vitro by Semi-soft SEQ ID NO: 241 v. Fully Stabilized ODN A murine macrophage cell line (RAW264) was incubated for 16 hours with semi-soft oligonucleotide SEQ ID NO: 241, fully stabilized oligonucleotide SEQ ID NO: 242, fully stabilized ODN 1826, lipopolysaccharide (LPS) or PBS. Semi-soft and fully stabilized ODN were examined at concentrations of 0.02, 0.05, and 0.1 μM. Supernatants were collected and the p40 subunit of IL-12 (IL-12p40, pg/mL) measured by ELISA. Results are shown in Table 2. Semi-soft oligonucleotide SEQ ID NO: 241 was significantly more potent at inducing macrophages to secrete IL-12p40 than either fully stabilized ODN.

TABLE 2

IL-12p40 secretion by murine macrophages stimulated by semi-soft oligonucleotide SEQ ID NO: 241

| ODN | ODN concentration (μM) | IL-12 p40, pg/mL mean (S.D.) |
|---|---|---|
| SEQ ID NO: 241 | 0.02 | 148.8 (37.5) |
| | 0.05 | 149.8 (28.7) |
| | 0.1 | 162.3 (8.4) |
| SEQ ID NO: 242 | 0.02 | 41.4 (18.6) |
| | 0.05 | 42.0 (26.2) |
| | 0.1 | 23.0 (10.7) |
| SEQ ID NO: 386 | 0.02 | 43.5 (23.0) |
| | 0.05 | 38.3 (19.2) |
| | 0.1 | 54.4 (4.1) |
| LPS | — | 346.5 (20.5) |
| PBS | — | 32.0 (12.1) |

Example 7

Semi-soft B Class Oligonucleotides with Sequence Optimized for Stimulation of Human Immune Cells are Potent Immunostimulators of Murine Immune Cells It has been reported that human and murine immune cells respond to different CpG ODN. Fully stabilized CpG SEQ ID NO: 242 has been considered "optimal" for stimulating human immune cells, but has not been considered "optimal" for stimulating murine immune cells. Conversely, fully stabilized CpG ODN 5890 (5' T*C*A*A*C*G*T*T 3') has been considered "optimal" for stimulating murine immune cells, but has not been considered "optimal" for stimulating human immune cells. Both human and murine B cells are reported to express TLR9. TLR9-expressing HEK293 murine splenocytes were cultured in the presence of various concentrations of fully stabilized CpG SEQ ID NO:242, fully stabilized CpG ODN 5890, or semi-soft SEQ ID NO:241, and TLR9 activation was measured as follows. Cells used for this assay were expressed murine TLR9 and contained a reporter gene construct. Cells were incubated with ODNs for 16 h at 37° C. in a humidified incubator. Each data point was performed in triplicate. Cells were lysed and assayed for reporter gene activity. Stimulation indices were calculated in reference to reporter gene activity of medium without addition of ODN. Semi-soft oligonucleotide SEQ ID NO: 241 and fully stabilized oligonucleotide SEQ ID NO: 242 have the identical base sequence. Results are shown in Table 3. At the lowest concentrations, SEQ ID NO: 241 and SEQ ID NO: 242 had minimal immunostimulatory effect. However, as concentration increased to 14 nM and above, SEQ ID NO: 241 was clearly more immunostimulatory than SEQ ID NO: 242. At the highest concentration studied in this experiment, SEQ ID NO: 241 was at least as stimulatory as the murine-optimized fully stabilized oligonucleotide ODN 5890.

TABLE 3

Stimulation index of murine TLR9 expressing HEK293 cells by
semi-soft ODN with sequence optimized for human cells

| Conc. | ODN | | |
|---|---|---|---|
| | 5890 | SEQ ID NO: 241 | SEQ ID NO: 242 |
| 0.9 nM | 1.4 | 0.7 | 0.9 |
| 3.5 nM | 2.4 | 1.1 | 1.2 |
| 14 nM | 12.5 | 1.9 | 1.1 |
| 58 nM | 21.4 | 4.3 | 2.0 |
| 0.23 µM | 25.2 | 12.0 | 6.2 |
| 0.94 µM | 28.6 | 18.3 | 8.0 |
| 3.75 µM | 29.3 | 32.1 | 10.3 |

Example 8-9

Semi-soft Oligonucleotides Induce NK Cell Activation

Semi-soft and fully stabilized oligonucleotides were also compared in terms of their ability to stimulate NK cell activation. Using a standard chromium release assay, $10 \times 10^6$ BALB/c spleen cells were cultured in 2 mL RPMI supplemented with 10% FBS (heat inactivated to 65° C. for 30 min.), 50 µM 2-mercaptoethanol, 100 U/mL penicillin, 100 µg/mL streptomycin, and 2 mM L-glutamate, with or without either semi-soft SEQ ID NO: 241 or fully stabilized SEQ ID NO: 242, each ODN added to a final concentration of 1, 3, or 10 µg/mL, for 48 hours. Cells were washed and then used as effector cells in a short-term $^{51}$Cr release assay with YAC-1 and 2C11, two NK-sensitive target cell lines (Ballas Z K et al. (1993) *J Immunol* 150:17-30). Effector cells were added at various concentrations to $10^4$ $^{51}$Cr-labeled target cells in V-bottom microtiter plates in 0.2 mL, and incubated in 5% CO$_2$ for 4 hr at 37° C. Effector cell:target cell (E:T) ratios studied were 6.25:1, 25:1, 50:1, and 100:1. Plates were then centrifuiged and an aliquot of the supernatant counted for radioactivity. Percent specific lysis was determined by calculating the ratio of the $^{51}$Cr released in the presence of effector cells minus the $^{51}$Cr released when the target cells are cultured alone, over the total counts released after cell lysis in 2% acetic acid (100 percent lysis) minus the $^{51}$Cr cpm released when the cells are cultured alone. Results are shown in Table 5 below. In summary, semi-soft oligonucleotide SEQ ID NO: 241 and fully stabilized SEQ ID NO: 242 induced essentially comparable levels of NK cell activation over all ODN concentrations and E:T ratios examined.

TABLE 5

NK cell-mediated specific lysis

| ODN | µg/mL | E:T Ratio | | | |
|---|---|---|---|---|---|
| | | 6.25:1 | 25:1 | 50:1 | 100:1 |
| SEQ ID NO: 241 | 1 | 8 | 17 | 17.5 | 27.5 |
| | 3 | 2.5 | 5 | 8 | 15 |
| | 10 | 4 | 12.5 | 20 | 28 |
| SEQ ID NO: 242 | 1 | 7 | 8 | 12.5 | 22 |
| | 3 | 3.5 | 4 | 11 | 18 |
| | 10 | 5 | 12.5 | 23 | 32.5 |

Example 10

Semi-soft Oligonucleotides are Generally More Immunostimulatory Than All-phosphorothioate Oligonucleotides of the Same or Similar Sequence All tested semi-soft versions were more active in the human TLR9 assay than the corresponding uniformly phosphorothioate molecule (Table 6). The average stimulation index was calculated from data points of four concentrations (0.1 µM, 0.5 µM, 2 µM, and 8 µM). In the Table, U represents 2'-deoxyuracil.

TABLE 6

Relative average stimulation indices of semi-soft
oligonucleotides versus all-phosphorothioate
oligonucleotides of the same or similar sequence

| Sequence | Relative Average Stimulation Index |
|---|---|
| T*C*G*T*C*G*T*T*T*T*C*G*G*C*G*G*C*C*G*C*C*G (SEQ ID NO: 247) | 1.00 |
| T*C*G*C*C*G*T*T*T*T*C_G*G*C_G*G*C*C_G*C*C*G (SEQ ID NO: 248) | 0.74 |
| T*C*G*C*C*G*T*T*T*T*C_G*G*C_G*G*C*C_G*C*C*G (SEQ ID NO: 249) | 0.72 |
| T*C*G*T*C*G*T*T*T*T*C_G*G*C_G*G*C*C_G*C*C*G (SEQ ID NO: 250) | 1.37 |
| T*C*G*T*C*G*T*T*T*T*C_G*G*C_G*G*C*C_G*C*C*G (SEQ ID NO: 251) | 1.25 |
| T*C_G*C*C_G*T*T*T*T*C_G*G*C_G*G*C*C_G*C*C*G (SEQ ID NO: 252) | 2.99 |
| T*C_G*C*C_G*T*T*T*T*C_G*G*C_G*G*C*C_G*C*C*G (SEQ ID NO: 253) | 2.22 |
| T*C_G*T*C_G*T*T*T*T*C*G*G*C*G*G*C*C*G*C*C*G (SEQ ID NO: 254) | 3.46 |

TABLE 6-continued

Relative average stimulation indices of semi-soft
oligonucleotides versus all-phosphorothioate
oligonucleotides of the same or similar sequence

| Sequence | Relative Average Stimulation Index |
|---|---|
| T*C_G*T*C_G*T*T*T*T*C*G*G*C*G*G*C*C*G*C*C*G (SEQ ID NO: 255) | 4.08 |
| T*C_G*T*C_G*T*T*T*T*C_G*G*C_G*G*C*C_G*C*C*G (SEQ ID NO: 256) | 5.69 |
| T*C_G*T*C_G*T*T*T*T*C_G*C_G*G*C*C_G*C*C*G (SEQ ID NO: 257) | 4.49 |
| **T*G*T*C*G*T*T*G*T*C*G*T*T*G*T*C*G*T*T*G*T*C*G*T*T** (SEQ ID NO: 244) | 1.00 |
| T*G*T*C_G*T*T*G*T*C_G*T*T*G*T*C_G*T*T*G*T*C_G*T*T (SEQ ID NO: 258) | 4.23 |
| T*G*T*C_G*T*T*G*T*C_G*T*T_G*T*C_G*T*T_G*T*C_G*T*T (SEQ ID NO: 243) | 4.74 |
| **T*C*G*T*C*G*T*T*T*C*G*T*C*G*T*T*T*T*G*T*C*G*T*T** (SEQ ID NO: 259) | 1.00 |
| T*C_G*T*C_G*T*T*T*C_G*T*C_G*T*T*T*T*G*T*C_G*T*T (SEQ ID NO: 260) | 1.80 |
| **T*C*G*T*C*G*T*T*T*T*G*A*C*G*T*T*T*T*G*T*C*G*T*T** (SEQ ID NO: 261) | 1.00 |
| T*C_G*T*C_G*T*T*T*C_G*A*C_G*T*T*T*T*G*T*C_G*T*T (SEQ ID NO: 262) | 2.71 |
| T*C_G*T*C_G*T*T*T*T_G*A*C_G*T*T*T*T*G*T*C_G*T*T (SEQ ID NO: 263) | 3.01 |
| T*C_G*T*C_G*T*T*T*T_G*A*C_G*T*T*T*T*G*T*C_G*T*T (SEQ ID NO: 264) | 3.06 |
| T*C_G*T*C_G*T*T*T*T_G*A*C_G*T*T*T*T (SEQ ID NO: 265) | 2.06 |
| T*C_G*T*C_G*T*T*T*T_G*A*C_G*T*T (SEQ ID NO: 266) | 1.43 |
| T*C_G*T*C_G*T*T*T*T*C_G*A*C*G*T*T (SEQ ID NO: 267) | 0.91 |
| **G*T*T*C*T*C*G*C*T*G*G*T*G*A*G*T*T*T*C*A** (SEQ ID NO: 268) | 1.00 |
| G*T*T*C*T*C_G*C*T_G*G*T_G*A*G*T*T*T*C*A (SEQ ID NO: 269) | 3.45 |
| **T*C*G*T*C*G*T*T*T*C*G*T*C*G*T*T*T*T*C*G*T*C*G*T*T** (SEQ ID NO: 270) | 1.00 |
| T*C_G*T*C_G*T*T*T*C_G*T*C_G*T*T*T*C_G*T*C_G*T*T (SEQ ID NO: 271) | 2.49 |
| T*C_G*T*C_G*T*T*T*U_G*T*C_G*T*T*T*T_G*T*C_G*T*T (SEQ ID NO: 272) | 2.51 |
| **T*C*G*T*C*G*T*T*T*U*G*T*C*G*T*T*T*T*G*T*C*G*T*T** (SEQ ID NO: 273) | 1.00 |
| T*C_G*T*C_G*T*T*T*U_G*T*C_G*T*T*T*T_G*T*C_G*T*T (SEQ ID NO: 274) | 2.62 |
| **T*C*G*T*C*G*T*T*T*T*G*T*C*G*T*T*T*T*G*T*C*G*T*T** (SEQ ID NO: 242) | 1.00 |

TABLE 6-continued

Relative average stimulation indices of semi-soft oligonucleotides versus all-phosphorothioate oligonucleotides of the same or similar sequence

| Sequence | Relative Average Stimulation Index |
|---|---|
| T*C_G*T*C_G*T*T*T*T_G*T*C_G*T*T*T_G*T*C_G*T*T (SEQ ID NO: 276) | 1.95 |
| **T*C*G*U*C*G*T*T*T*T*G*T*C*G*T*T*T*U*G*U*C*G*T*T** (SEQ ID NO: 277) | 1.00 |
| T*C_G*U*C_G*T*T*T*T_G*T*C_G*T*T*T*U_G*U*C_G*T*T (SEQ ID NO: 278) | 1.39 |
| **T*C*G*T*C*G*U*U*U*T*G*T*C*G*U*U*U*U*G*T*C*G*T*T** (SEQ ID NO: 279) | 1.00 |
| T*C_G*T*C_G*U*U*U*C_G*T*C_G*U*U*U*U_G*T*C_G*T*T (SEQ ID NO: 280) | 2.05 |
| *A\*A\*C\*G\*T\*C\*G\*T\*T\*T\*T\*C\*G\*T\*C\*G\*T\*T* (SEQ ID NO: 281) | 1.00 |
| A*A*C_G*T*C_G*T*T*T*T*C_G*T*C_G*T*T (SEQ ID NO: 282) | 1.58 |

Example 11

Improved In Vitro Potency of Semi-soft Versions of Weakly Immunostimulatory Fully Stabilized Oligonucleotides (T*G*T*C*G*T*T*G*T*C*G*T*T*G*T*C*G*T*T*G*T*C*G*T*T, SEQ ID NO:244) is a fully stabilized, all-phosphorothioate CpG oligonucleotide with low immunostimulatory potency compared to SEQ ID NO: 242. Related semi-soft oligonucleotides (T*G*T*C_G*T*T*G*T*C_G*T*T*G*T*C_G*T*T*G*T*C_G*T*T, SEQ ID NO:258) and (T*G*T*C_G*T*T*G*T*C_G*T*T_G*T*C_G*T*T_G*T*C_G*T*T, SEQ ID NO:243) were many-fold more potent than SEQ ID NO: 244 and even more potent than SEQ ID NO: 242.

(SEQ ID NO: 258)
T*G*T*C_G*T*T*G*T*C_G*T*T*G*T*C_G*T*T*G*T*C_G*T*T (SEQ ID NO: 243)
T*G*T*C_G*T*T*G*T*C_G*T*T_G*T*C_G*T*T_G*T*C_G*T*T (SEQ ID NO: 244)
T*G*T*C*G*T*T*G*T*C*G*T*T*G*T*C*G*T*T*G*T*C*G*T*T

TABLE 7

Improved immune stimulation by semi-soft variants of a fully stabilized but weakly immunostimulatory oligonucleotide

| ODN | ODN concentration, μM | | | |
|---|---|---|---|---|
| | 0.1 | 0.5 | 2 | 8 |
| SEQ ID NO: 244 | 16.0 | 47.5 | 71.4 | 68.5 |
| SEQ ID NO: 243 | 19.3 | 40.5 | 78.2 | 77.9 |
| SEQ ID NO: 241 | 2.6 | 9.5 | 12.9 | 14.0 |
| SEQ ID NO: 242 | 10.6 | 34.2 | 38.3 | 40.8 |

Example 12

Semi-soft Oligonucleotides of Reduced Length are Immunostimulatory In Vitro

Semi-soft 16-mer, SEQ ID NO:283, 16-mer, SEQ ID NO:245, 17-mer, SEQ ID NO:284, and 24-mer, SEQ ID NO:241 were compared with fully stabilized ODNs 24-mer, SEQ ID NO:242 and 18-mer, SEQ ID NO:285 in terms of their ability to stimulate TLR9 signaling. Each oligonucleotide was added to HEK293 cells transfected with human TLR9 and a reporter gene construct at a concentration of 1, 6, 12, or 24 μg/mL, and TLR9 activation was measured as described above.

(SEQ ID NO: 283)
(16-mer) T*C_G*T*C_G*T*T*T*T*C_G*T*C_G*T (SEQ ID NO: 245)
(16-mer) T*C_G*T*C_G*T*T*T*T*C_G*T*C_G*T*T (SEQ ID NO: 284)
(17-mer) T*C_G*T*C_G*T*T*T*T*C_G*T*C_G*T*T (SEQ ID NO: 285)
(18-mer) A*A*C*G*T*C*G*T*T*T*T*C*G*T*C*G*T*T -continued (SEQ ID NO: 241)
(24-mer) T*C_G*T*C_G*T*T*T*T_G*T*C_G*T*T*T*T*G*T*C_
        G*T*T (SEQ ID NO: 242)
(24-mer) T*C*G*T*C*G*T*T*T*T*G*T*C*G*T*T*T*T*G*T*C*
        G*T*T While the 18-mer fully stabilized oligonucleotide ODN SEQ ID NO: 285 was less immunostimulatory than the 24-mer fully stabilized oligonucleotide SEQ ID NO: 242 at all concentrations examined, the 16-mer and 17-mer semi-soft oligonucleotides were at least as stimulatory as 24-mer SEQ ID NO: 242 at concentrations of 6 μg/mL and above. In addition, the 16-mer and 17-mer semi-soft oligonucleotides were nearly as immunostimulatory as 24-mer semi-soft oligonucleotide SEQ ID NO: 241.

TABLE 8

Immunostimulatory activity of short semi-soft oligonucleotides compared with short and long fully stabilized and semi-soft oligonucleotides

| ODN | ODN concentration, μg/mL | | | |
|---|---|---|---|---|
| | 1 | 6 | 12 | 24 |
| SEQ ID NO: 283 | 1.2 | 17.1 | 29.0 | 39.5 |
| SEQ ID NO: 245 | 1.1 | 8.4 | 31.3 | 48.9 |
| SEQ ID NO: 284 | 3.4 | 23.9 | 35.9 | 45.6 |
| SEQ ID NO: 285 | 4.6 | 12.9 | 15.9 | 18.0 |
| SEQ ID NO: 241 | 6.4 | 33.0 | 50.8 | 58.6 |
| SEQ ID NO: 242 | 11.0 | 24.6 | 26.2 | 21.9 |

Example 13

Semi-soft Oligonucleotides are Immunostimulatory In Vivo

BALB/c mice were divided into groups and administered subcutaneously 400 μg semi-soft oligonucleotide SEQ ID NO: 241, fully stabilized immunostimulatory oligonucleotide SEQ ID NO: 242, fully stabilized negative control oligonucleotide (TGCTGCTTTTGTGCTTTTGTGCTT, SEQ ID NO:286), or an equivalent volume of phosphate-buffered saline (PBS). Animals were bled 3 hours after injection and serum levels of IP-10, IFN-γ, and TNF-α determined using appropriate cytokine-specific ELISA. Serum IP-10 was about two times higher in animals receiving semi-soft SEQ ID NO: 241 (8,000-12,000 pg/mL) than fully stabilized immunostimulatory oligonucleotide SEQ ID NO: 242 (3,500-8,000 pg/mL). Serum 1P-10 in animals receiving control SEQ ID NO: 286 had the same low level of IP-10 as animals receiving PBS. Semi-soft oligonucleotide SEQ ID NO: 241 and fully stabilized immunostimulatory oligonucleotide SEQ ID NO: 242 induced similar amounts of IFN-γ, ca. 150 pg/mL. Semi-soft oligonucleotide SEQ ID NO: 241 induced 30-45 percent more TNF-α than fully stabilized immunostimulatory oligonucleotide SEQ ID NO: 242 (ca. 1,550 pg/mL versus ca. 1,175 pg/mL in one experiment and ca. 710 pg/mL versus 490 pg/mL in another experiment.

In another set of in vivo experiments, semi-soft and fully stabilized oligonucleotides were examined for their ability to treat tumors in BALB/c mice. Three groups of BALB/c mice were injected i.p. with murine renal adenocarcinoma of spontaneous origin (Renca) cells, using an established tumor model. Salup R R et al. (1985) *J Immunopharmacol* 7:417-36. Each group of mice also received either 100 mg semi-soft oligonucleotide SEQ ID NO: 241, 100 mg fully stabilized immunostimulatory oligonucleotide SEQ ID NO: 242, or an equivalent volume of PBS. Mice were followed for survival and for tumor size at death. Mice receiving sham treatment with PBS had a median survival of 44 days and 20 percent survival at 50 days. In contrast, mice receiving semi-soft oligonucleotide SEQ ID NO: 241 had 80 percent survival at 50 days, and mice receiving fully stabilized immunostimulatory oligonucleotide SEQ ID NO: 242 had 70 percent survival at 50 days. In terms of tumor size (cubic millimeters), after 52 days mice receiving PBS had tumor volumes of nearly 1200 $mm^3$, while mice receiving semi-soft oligonucleotide SEQ ID NO: 241 or fully stabilized immunostimulatory oligonucleotide SEQ ID NO: 242 had tumors of ca. 250 $mm^3$ and 180 $mm^3$, respectively. Thus the semi-soft oligonucleotide and the fully stabilized oligonucleotide were both highly effective in reducing tumor burden and extending survival in this model experiment.

Example 14

Soft or Semi-soft Oligonucleotides Have Reduced Nephrotoxicity

It has been observed that administration of fully stabilized immunostimulatory oligonucleotides to monkeys can be associated with development of glomerulonephritis, i.e., kidney inflammation. Glomerulonephritis can be diagnosed and monitored by the presence of red blood cells and protein in the urine, often accompanied by reduced glomerular filtration rate (with azotemia), water and salt retention, hypertension, and edema. Normally urine is essentially free of blood cells and plasma proteins. Diagnosis can also be made by renal tissue histologic examination. Kidney tissue is reported to be rich in nucleases, which are expected to be more active on soft oligonucleotides than on fully stabilized immunostimulatory oligonucleotides.

Monkeys are divided into two groups, one administered soft oligonucleotides, and the other administered fully stabilized immunostimulatory oligonucleotides. The soft oligonucleotides and the fully stabilized immunostimulatory oligonucleotides are identical in sequence and differ in their internucleotide linkages only. Both groups of monkeys receive the same dose of immunostimulatory oligonucleotide. Pretreatment (baseline) and periodic on-treatment measurements are made of at least one parameter useful for assessing for the presence of glomerulonephritis, including, for example, dipstick urinalysis for the presence of proteinuria and/or hematuria, microscopic urine analysis for the presence of red blood cells and/or red blood cell casts, urine protein concentration, blood urea nitrogen (BUN), serum creatinine, blood pressure, body weight, and kidney biopsy with light and/or electron microscopic tissue analysis. Clinical findings are correlated with the type of immunostimulatory oligonucleotide administered to each monkey, and results are compared between groups for statistical significance.

Optionally, additional paired groups of monkeys, administered either soft or semisoft oligonucleotides or fully stabilized immunostimulatory oligonucleotides as above but using higher or lower oligonucleotide dose(s), are included to evaluate results further as a function of oligonucleotide dose.

Monkeys receiving soft oligonucleotides are significantly less prone to develop glomerulonephritis than monkeys receiving fully stabilized immunostimulatory oligonucleotides.

Example 15

Soft Oligonucleotides Have Increased Immunostimulatory Potency at High Concentration Soft oligonucleotides were compared with SEQ ID NO: 242 for their ability to induce TLR9 activity. Soft ODN and control SEQ ID NO: 242 were compared at each of four concentrations, 1 µg/ml, 6 µg/ml, 12 µg/ml, and 24 µg/ml. The ratios at each concentration of activation by each soft oligonucleotide compared to activation by SEQ ID NO: 242 are shown in Table 9 below. These results indicate that soft oligonucleotides are more immunostimulatory than SEQ ID NO: 242 at the higher concentrations examined.

SEQ ID NO: 287
T*G*T*C_G_T*T*G*T*C_G_T*T*G*T*C_G_T*T*G_T*C_G*T*T

SEQ ID NO: 288
T*C_G_T*T*T*T*T*T*C_G_T*T*T*T*T*T*T*C_G_T*T*T

SEQ ID NO: 289
T*C_G*T*C_G*T*T*T*T*T*C_G_G*T*C_G_T*T*T*T

SEQ ID NO: 290
T*C_G_T*C_G_T*T*T*T*T*C_G_T*G*C_G_T*T*T*T*T

SEQ ID NO: 291
T*C_G_T*C_G_T*T*T*T*C_G_T*T*T*T*T*T*C_G*T*T*T

SEQ ID NO: 292
T*C_G_T*T*T*T*G*T*C_G_T*T*T*T*T*T*T*C_G*A

SEQ ID NO: 293
T*C_G_T*C_G_T*T*T*T_G_T*C_G_T*T*T*T_G*T_C_G*T*T

TABLE 9

Relative potency of soft oligonucleotides compared to SEQ ID NO: 242 at each concentration

| ID | ODN concentration, µg/mL | | | |
|---|---|---|---|---|
| | 1 | 6 | 12 | 24 |
| SEQ ID NO: 287 | 0.11 | 0.12 | 1.00 | 1.68 |
| SEQ ID NO: 288 | 0.30 | 0.62 | 1.67 | 1.81 |
| SEQ ID NO: 289 | 0.13 | 0.52 | 1.67 | 1.97 |
| SEQ ID NO: 290 | 0.18 | 0.41 | 1.69 | 2.27 |
| SEQ ID NO: 291 | 0.16 | 0.35 | 1.56 | 1.81 |
| SEQ ID NO: 292 | 0.25 | 0.48 | 1.38 | 1.84 |
| SEQ ID NO: 293 | 0.10 | 0.11 | 1.20 | 2.05 |

Example 16

Oligonucleotide Stability in Serum and in Tissues

Mice were injected subcutaneously with 25 mg/kg of semi-soft oligonucleotide SEQ ID NO: 241, soft oligonucleotide (T*C*G*T*C*G*T*T*T*T*T_G_T_C_G_T*T*T*T*G*T*C*G*T*T; SEQ ID NO:294), or fully stabilized oligonucleotide SEQ ID NO: 242. Tissue and serum samples were obtained after selected number of hours and analyzed for intact oligonucleotide and fragments thereof.

Tissue or serum samples were spiked with a known amount of internal standard ODN (1.25 µg polyT) and ODN were isolated from tissue and plasma samples by solid phase extraction (SPE) methods described below. The resulting solutions containing the analyte, metabolites, and internal standard were analysed by capillary gel electrophoresis (CGE) and MALDI-TOF methods also described below. Total amounts of the recovered ODN (i.e., analyte plus metabolites) from kidney, liver, spleen, and serum samples analysed by CGE were defined. A standard deviation was calculated. The relative amount in percent of the total peak area was assigned to each metabolite.

SPE. For isolation of ODN from serum, 100 µg of the sample was spiked with 1.25 µg internal standard ODN, mixed and dissolved in 5 ml SAX-buffer. This solution was applied on an anion exchange column (SAX, Agilent), the column was washed and ODN eluted with a buffer of increased ionic strength. The resulting eluate was desalted using a reversed phase (RP) column (Glen Research) or a comparable column (HLB, Waters). The eluates from the RP column, containing only water and acetonitrile were dried and solubilized in the same tube in 60 µl deionized water. For further desalting of the samples a membrane dialysis was performed. Samples were analysed directly by capillary gel electrophoresis. For MALDI-TOF MS, samples were used either undiluted or concentrated, i.e., 50 µl of the ODN sample were dried in a vacuum and dissolved in deionized water and assayed as described below.

ODN from tissues were isolated according to a similar SPE protocol. 100 mg of tissue was homogenised using a FastPrep device. Proteinase K was added and proteins hydrolysed for 2 h. A phenol extraction was performed before proceeding with the water soluble fraction in the SPE method described above.

CGE. The desalted samples containing analyte, its metabolites, and a defined amount of internal standard ODN were electrokinetically injected into a gel-filled capillary (neutral, 30 cm, eCAP DNA capillary, Beckman #477477) at the sample side with water pre-injection. A voltage of 300 V/cm was applied while detection was monitored at 260 nm. Separation was carried out at 25° C. in Tris/boric acid/EDTA buffer containing 7M urea. The analyte was identified by its relative migration time ($MT_{Oligo}/MT_{Int\ Std.}$) compared to that of a standard which is similarly prepared and concomitantly analysed. The relative migration time and relative area percent of any electrophoretic peak that is >3× signal: noise (S:N) ratio was recorded. Peak heights of between 3× and 10× signal: noise were recorded as not quantifiable.

% Oligo=(peak area/total peak area>3×S:N)×100%

MALDI-TOF. The desalted samples containing the analyte and its metabolites were analysed on an Applied Biosystems MALDI-TOF mass spectrometer with a delayed extraction source, a nitrogen laser at 337 nm wavelength, and a 1.2 meter flight tube. Instrument settings were as follows: voltage 25 kV; grid voltage 95.4%; guide wire 0.1%; delay time 1200 nsec. As matrix 3-hydroxypicolinic acid containing diammonium citrate was used. The spectra of the ODN samples were calibrated externally on the same plate under identical conditions using a set of standard ODN of known molecular weights.

Results obtained at 48 hours are shown in FIG. 20. FIG. 20 shows that in the kidney semi-soft SEQ ID NO: 241 and soft ODN SEQ ID NO: 294 were reduced dramatically (by 93 percent and by 87 percent, respectively) compared with all-phophorothioate SEQ ID NO: 242.

Example 17

C Oligonucleotides are Immunostimulatory in vitro

Semi-soft C-Class oligonucleotides were prepared with phophodiester linkages within the 5' non-palindromic portion (ODN SEQ ID NO: 255), the 3' palindromic portion (ODN SEQ ID NO: 251), and within both the 5' non-palindromic portion and the 3' palindromic portion (ODN SEQ ID NO: 295). In addition, ODN SEQ ID NO: 252 was prepared with linkages like ODN SEQ ID NO: 295 but with 2'-O-Me ribose sugars in the nucleotides making up the 3' palindromic portion (shown underlined below). These oligonucleotides were then evaluated using a TLR9 assay described above.

```
                                                  (SEQ ID NO: 255)
T*C_G*T*C_G*T*T*T*T*C*G*G*C*G*G*C*C*G*C*C*G (SEQ ID NO: 251)
T*C*G*T*C*G*T*T*T*T*C_G*G*C_G*G*C*C_G*C*C*G (SEQ ID NO: 295)
T*C_G*T*C_G*T*T*T*T*C_G*G*C_G*G*C*C_G*C*C*G (SEQ ID NO: 252)
T*C_G*C*C_G*T*T*T*T*C_G*G*C_G*G*C*C_G*C*C*G
```

C-Class oligonucleotides with fully stabilized backbones generally exhibit relatively low TLR9 activity compared with B-Class oligonucleotides. As shown in Table 10 below, incorporation of semi-soft sequence in just the 5' non-palindromic portion (ODN SEQ ID NO: 255) significantly enhanced TLR9 activity compared to incorporation of semi-soft sequence in just the 3' palindromic portion (ODN SEQ ID NO: 251). Incorporation of semi-soft sequence in both the 5' non-palindromic portion and the 3' palindromic portion (ODN SEQ ID NO: 295) resulted in enhanced TLR9 activity compared to incorporation of semi-soft sequence in just the 3' palindromic portion (ODN SEQ ID NO: 251).

TABLE 10

TLR9 stimulation by semi-soft C-Class oligonucleotides

| ODN | ODN concentration, μg/mL | | | |
|---|---|---|---|---|
|  | 0.1 | 0.5 | 2.0 | 8.0 |
| SEQ ID NO: 255 | 2.3 | 16.9 | 36.4 | 35.7 |
| SEQ ID NO: 251 | 1.2 | 2.5 | 8.4 | 16.8 |
| SEQ ID NO: 295 | 2.0 | 11.6 | 29.8 | 37.3 |
| SEQ ID NO: 252 | 1.1 | 3.9 | 22.1 | 47.0 |

Semi-soft C-Class oligonucleotides not only retain their ability to induce IFN-α by human PBMC, but they also are significantly more potent at low concentrations. The enhanced potency was most pronounced in those C-Class oligonucleotides that included semi-soft sequence in the 5' non-palindromic portion (ODN SEQ ID NO: 255 and ODN SEQ ID NO: 295). ODN SEQ ID NO: 255, SEQ ID NO: 251, and SEQ ID NO: 295 were evaluated by ELISA and compared with SEQ ID NO: 242, the fully stabilized form of these three semi-soft oligonucleotides and a potent C-Class oligonucleotide inducer of IFN-α. Results are presented in Table 11.

TABLE 11

IFN-α induction (pg/mL) by semi-soft versions of C-Class oligonucleotide

| ODN | ODN concentration, μM | | | | |
|---|---|---|---|---|---|
|  | 0.1 | 0.2 | 0.5 | 1.0 | 2.0 |
| SEQ ID NO: 255 | 3202 | 7429 | 937 | 64 | 3 |
| SEQ ID NO: 251 |  | 688 | 3033 | 3083 |  |
| SEQ ID NO: 295 | 2560 | 3363 | 3246 | 930 | 41 |
| — | 50 | 504 | 3247 | 2114 | 1789 |

Example 18

Physicochemical Characteristics of SEQ ID NO. 313

Methods:

The powder X-ray diffractometric pattern of SEQ ID NO. 313 showed a halo which is characteristic of an amorphous-phase. Water vapor sorption analysis has shown SEQ ID NO. 313 to be highly hygroscopic. The tendency of the drug to exchange moisture may result in varying amount of moisture depending on the humidity of the environment. The compound exhibits high water solubility (>100 mg/mL) and thus has adequate solubility throughout the useable pH range. Analysis of aqueous solutions of the drug at elevated temperature show that it degrades rapidly in mildly acidic to acidic environments, but. solutions buffered above pH six appear to have adequate solution stability.

Results:

SEQ ID NO. 313 was found to be amorphous in nature and highly hygroscopic. The compound exhibits high water solubility (>100 mg/mL) and thus has adequate solubility throughout the useable pH range. The ODN degrades rapidly in mildly acidic to acidic environments. Solutions buffered above pH six appear to have adequate solution stability.

Example 19

Stimulation of TLR9-transfected Cells in vitro

Methods:

HEK 293 cells transfected with human TLR9 were incubated with SEQ. ID No. 313 or SEQ ID No. 329 for 16 hours. The signal was determined by a luciferase readout.

Results

Compared with SEQ ID No. 329, SEQ ID No. 313 was a more potent stimulator of the target receptor TLR9.

Example 20

Stimulation of Human Immune Cells in vitro

Methods:

Human peripheral blood mononuclear cells from 6 donors were incubated with SEQ ID No. 313 or SEQ ID.No. 329 for 24 or 48 hours. Secretion of cytokines were measured.

Results

Figure 23:
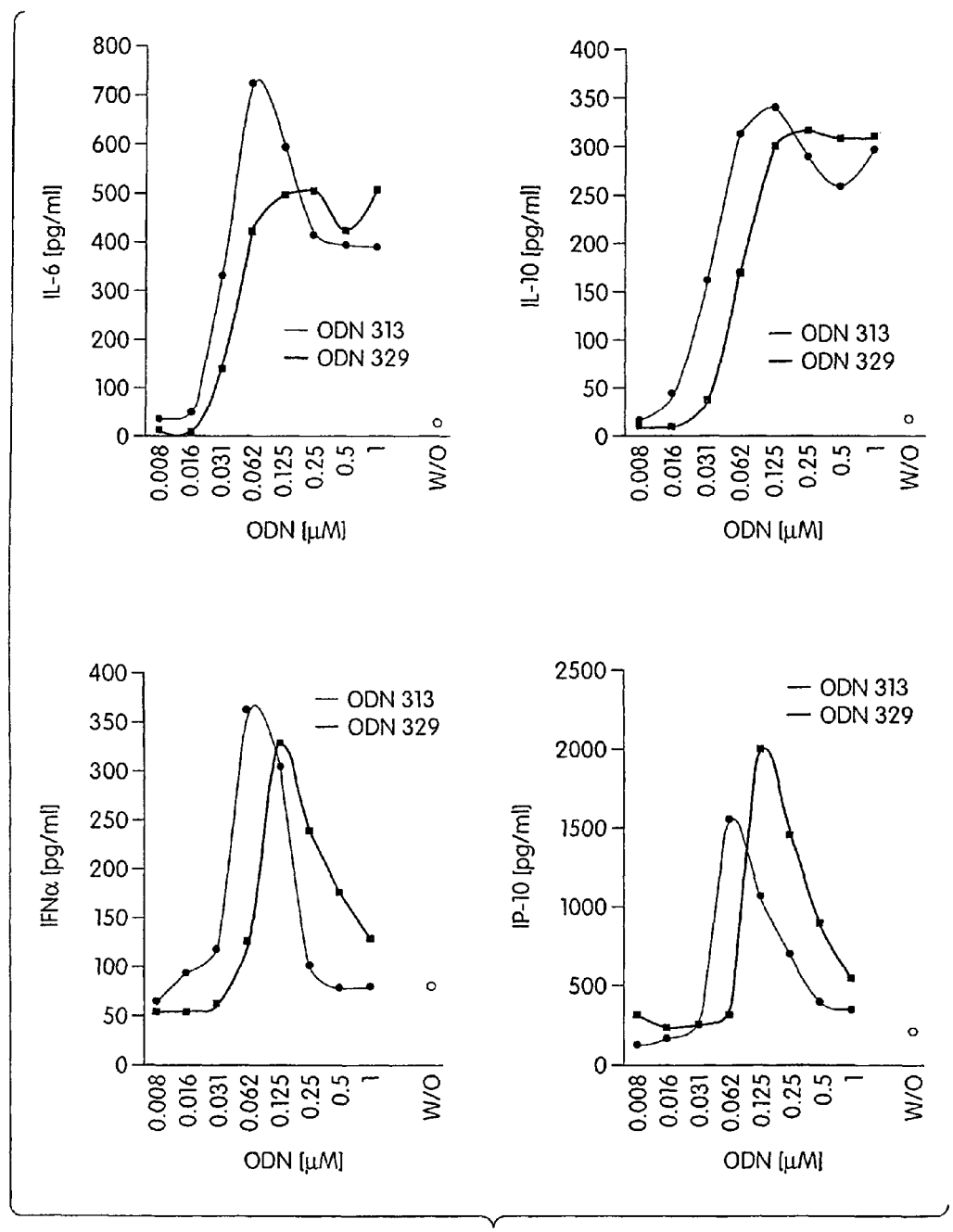
FIG. 23 shows Stimulation of human immune cells in vitro by induction of cytokines IL-6, IL-10, IFNα and IP-10

The results are shown in FIG. 23. Compared with SEQ ID No.329, SEQ ID No. 313 showed increased or at least simillar efficacy and/or potency as an inducer of TLR9-associated cytokines IL-6, IL-10, IFNα and IP-10.

Example 21

Stimulation of Murine Splenocytes in vitro

Methods:

Murine (BALB/c) splenocytes were incubated with SEQ ID No. 313 or SEQ ID No. 329 for 48 hours. Secretion of cytokines and IP-10 were measured.

Results

Figure 24:
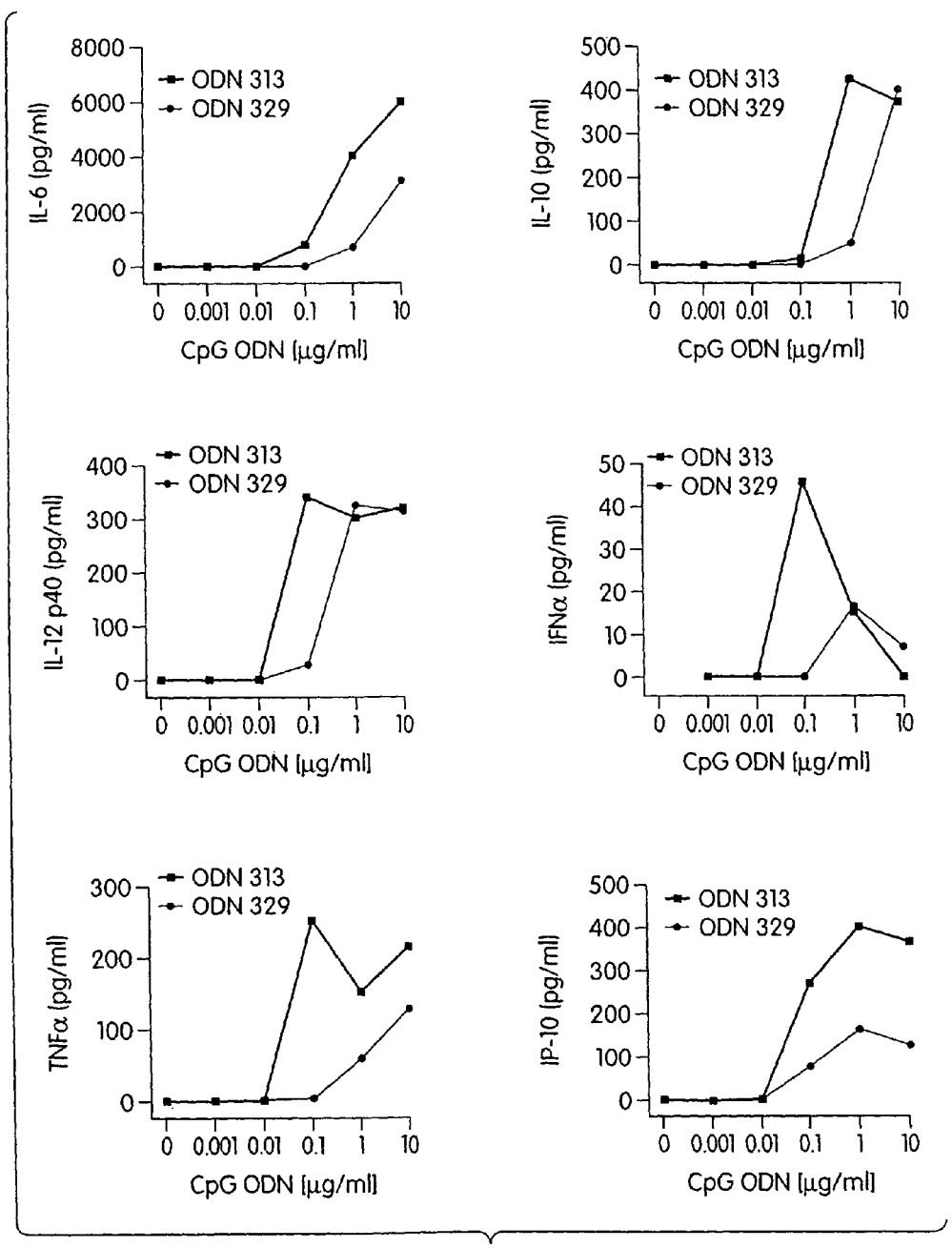
FIG. 24 shows Stimulation of murine splenocytes in vitro by increased efficacy and/or potency as an inducer of TLR9-associated cytokines IL-6, IL-10, IL-12p40, IFNα, TNFα and IP-10, without detectable secretion of IL-1β, IL-2, IL-4, IL-5 or GM-CSF.

Compared with SEQ ID No. 329, SEQ ID No.313 showed increased or at least simillar efficacy and/or potency as an inducer of cytokines IL-6, IL-10, IL-12p40, IFNα, TNFα and IP-10. The data is shown in FIG. 24. This data demonstrates that the activity of SEQ ID No. 313 on murine immune cells is comparable to that on human cells (above) and is similarly consistent with activation via TLR9.

Example 22

Cytokine Gene Induction in Mice in vivo

Methods:

This study assessed expression of cytokines in mouse lungs after SEQ ID No. 313 was dosed into the airways. To investigate kidney exposure, induction of the same cytokines (as described in Examples 10 and 21) in this organ was also assessed. Mice (male, BALB/c) were dosed with SEQ ID No.313 or SEQ ID No. 329 (each 1 mg/kg) either by intranasal instillation or by bolus intravenous injection. Lungs and kidney were removed 8 or 15 hours after dosing. RNA was extracted and reverse transcribed to cDNA. Target fragments of cDNA were amplified and detected by real-time PCR (Roche LightCycler using SYBR Green detection method). The primers for GAPDH, IFN gamma, IL-6, IP-10, and TNF-alpha were designed using the LC PROBE DESIGN software from Roche(Version 1.0 Roche catalog No 3 139 174. The primers for IFNalpha were designed using PRIMER 3 software. Product yield was normalized as the ratio of control gene (GAPDH) expression.

Results

Figure 25A:
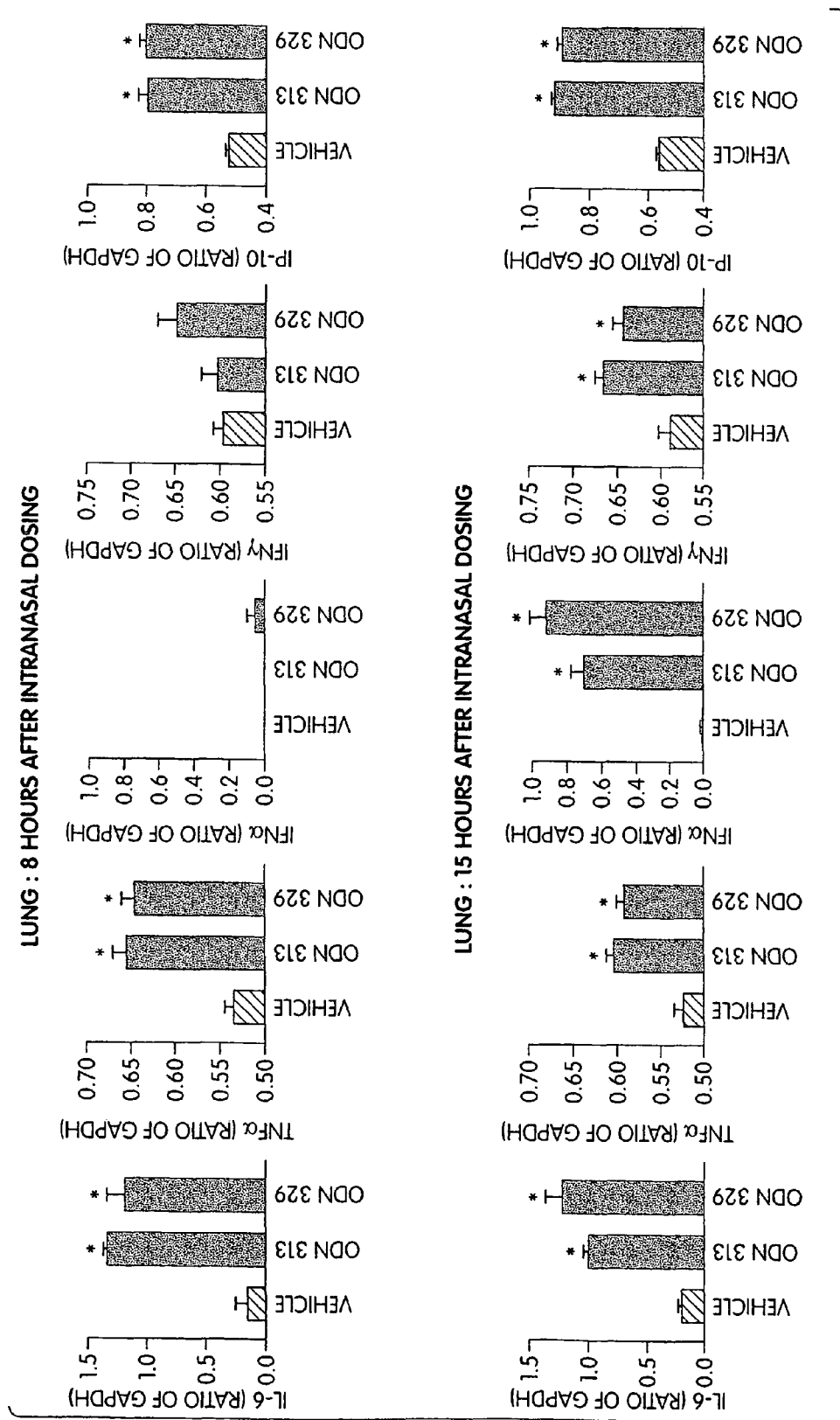
FIG. 25 shows induced expression of TLR9-associated genes (IL-6, TNFα, IFNα, IFNγ and IP-10) in the lung by an ODN of the invention (SEQ ID No.313).
Figures 1, 25B:
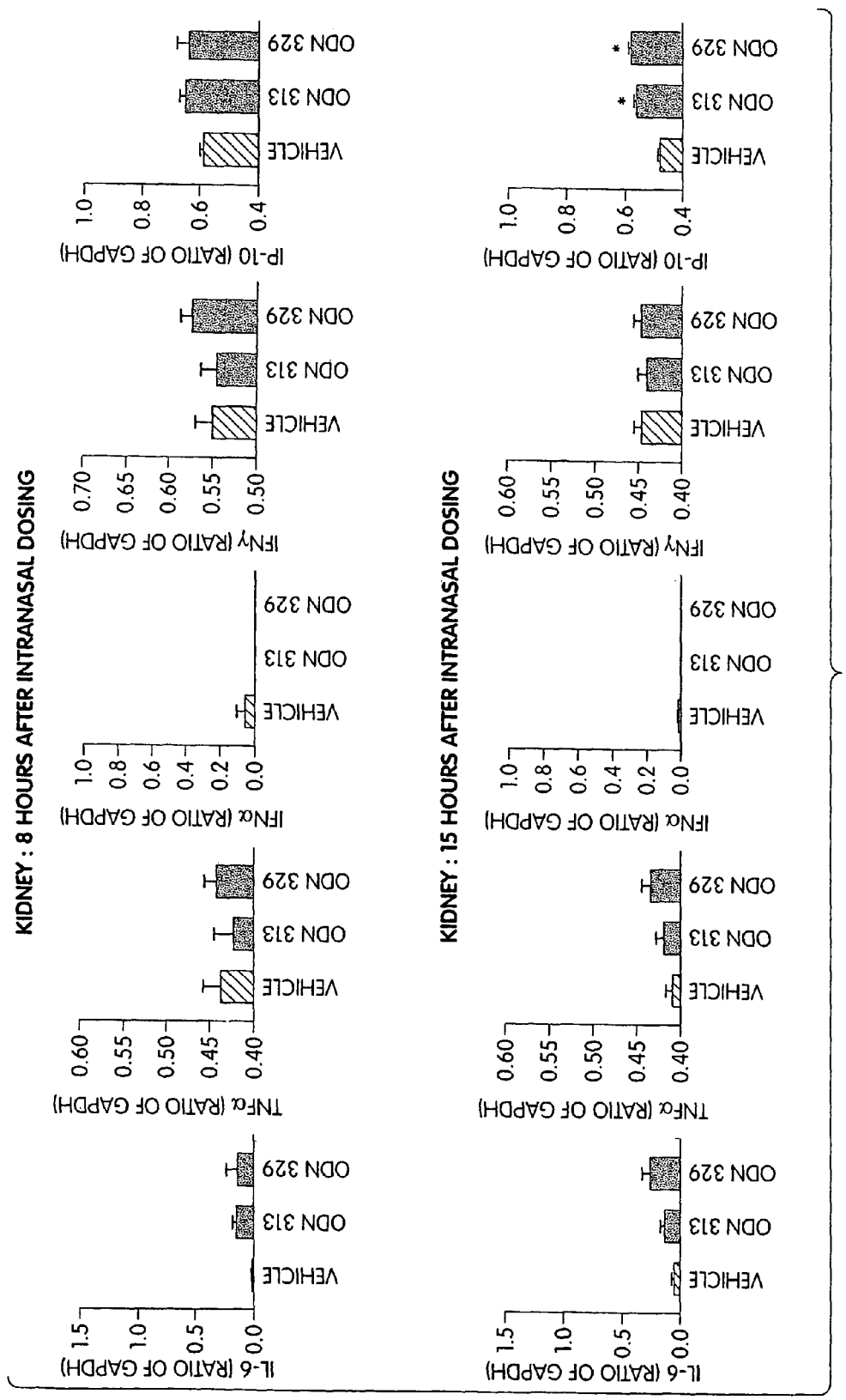
Figures 2, 25B:
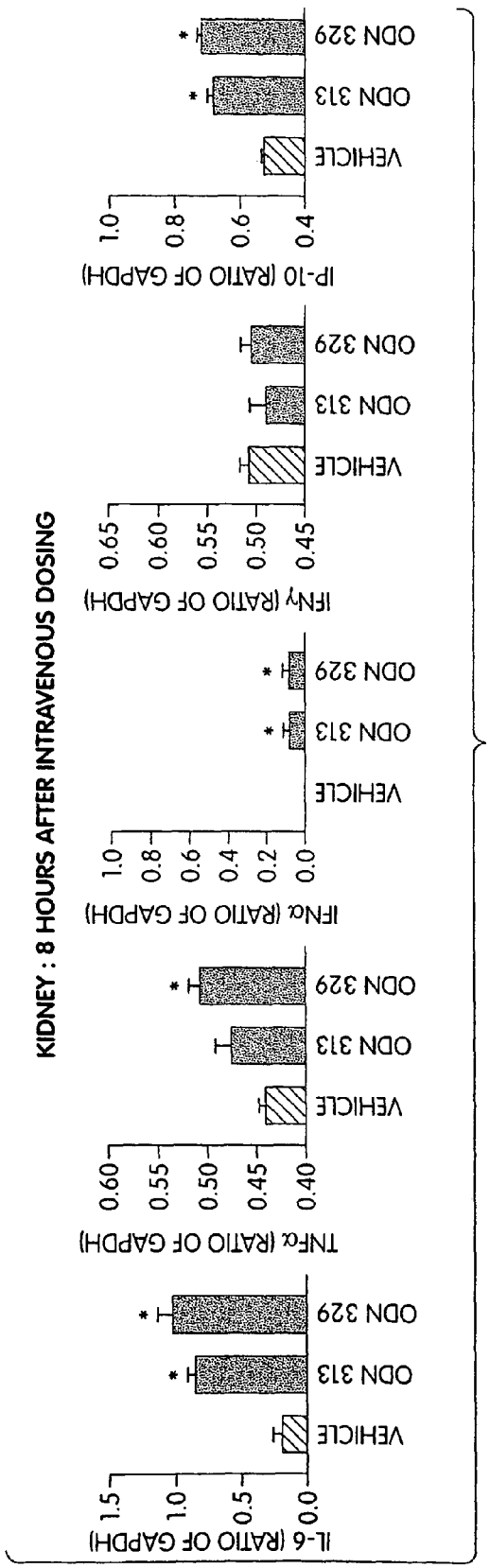

When dosed into the airways, SEQ ID No. 313 induced expression of TLR9-associated genes (IL-6, TNFα, IFNα, IFNγ and EP-10) in the lung. The results are shown in FIG. 25. However, with the exception of EP-10, these genes were not expressed in kidneys of mice dosed by this route. Since IP-10 is typically induced by interferons, expression of this chemokine could have occurred indirectly as a result of interferons secreted into the systemic circulation from the lung. When SEQ ID No. 313 was administered intravenously, each of these genes except IFNγ was induced in kidney. Therefore, the lack of renal impact of the SEQ ID No. 313 after dosing into the airways was likely due to low systemic exposure.

CpG ODNs may cause renal effects through a number of mechanisms. An acute renal granulomatous inflammation caused by a TLR9-dependent mechanism has been observed after systemic exposure to some CpG ODNs. Our results suggest that systemic exposure to SEQ ID No. 313 administered into the airways is not sufficient to directly induce TLR9-associated genes in the kidney.

Example 23

Effects on Antigen-induced Lymph Node Development in Mice in vivo

Methods:

This study investigated the ability of SEQ ID No.313 to induce immune deviation away from a Th2-type response in draining lymph nodes of mice. Mice (male, BALB/c) were sensitized by injection into the right rear footpad with antigen (ovalbumin, 100 µg) in complete Freund's adjuvant. Mice were simultaneously injected into the same footpad with SEQ ID No. 313 or SEQ ID No. 329 (1.5 mg/kg) or vehicle (saline). Six days after footpad injection, the draining popliteal lymph node was removed. T cells (CD3$^+$) and B cells (B220$^+$) were counted by flow cytometry. An ex vivo antigen recall assay was performed as follows 1×10$^6$ cells (from the draining popliteal lymph node) were incubated in 220 ul medium RPMI 1640+10% fetal bovine serum containing either ovalbumin (100 ug/ml) or diluent. After 36 hoursculture medium was removed and the concentrations of IL-1beta, IL-2, IL-4, IL-5, IL-6, IL-10, IL-12p70, GM-CSF, IFN gamma, and TNF alpha were measured using a kit from LINCO research, Inc. 14 research Park Drive, st charles, Mo. 63304 and analysed on the Luminex multiplex system (Luminex Corporation, 12212 Technology Boulevard, Austin, Tex. 78727-6115).

Results

Figure 26:
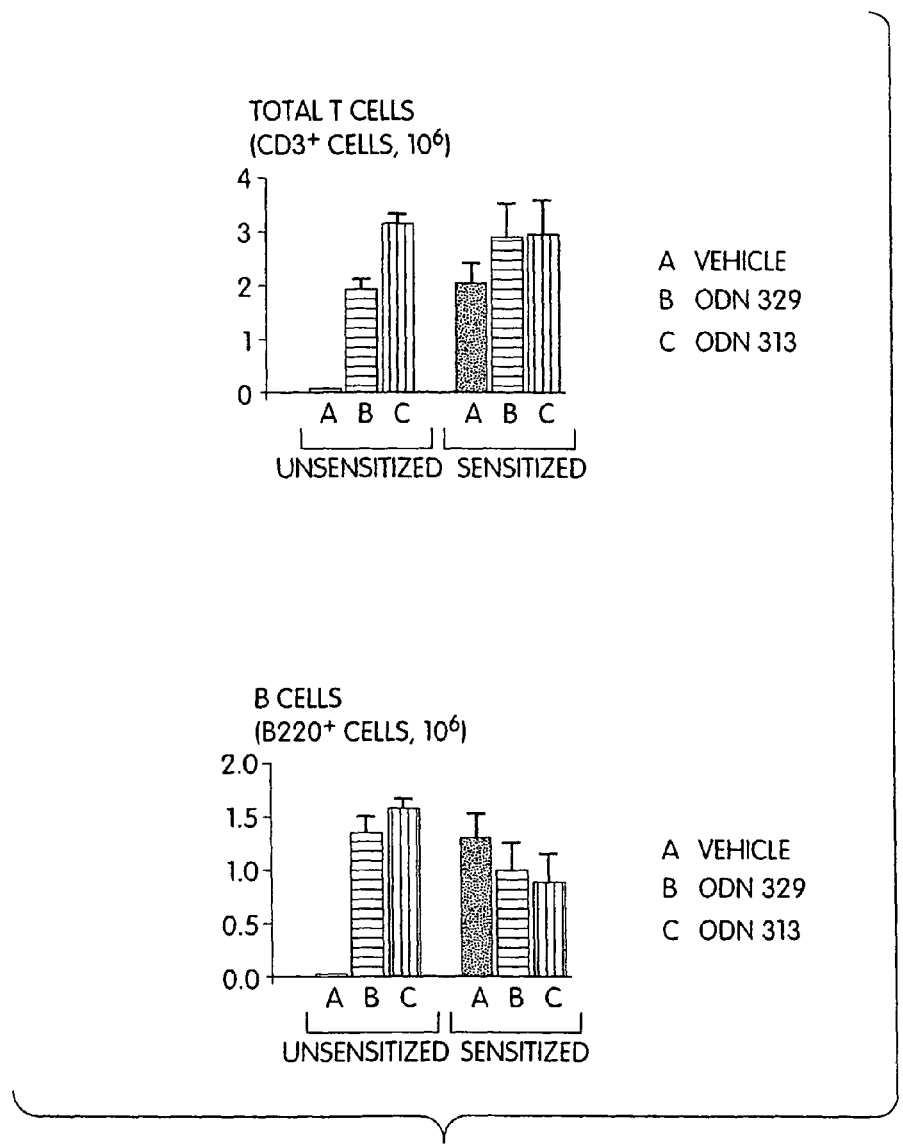
FIG. 26. shows the effects of CpG ODN on antigen-induced lymph node development in mice in vivo.

Cell numbers in popliteal lymph nodes Sensitization caused accumulations of T cells and B cells in draining popliteal lymph nodes. These antigen-induced accumulations were not significantly increased further in mice that also received a CpG ODN. However, each CpG ODN injected alone to unsensitized mice did cause both T cell and B cell accumulations. The data is shown in FIG. 26.

Figure 27:
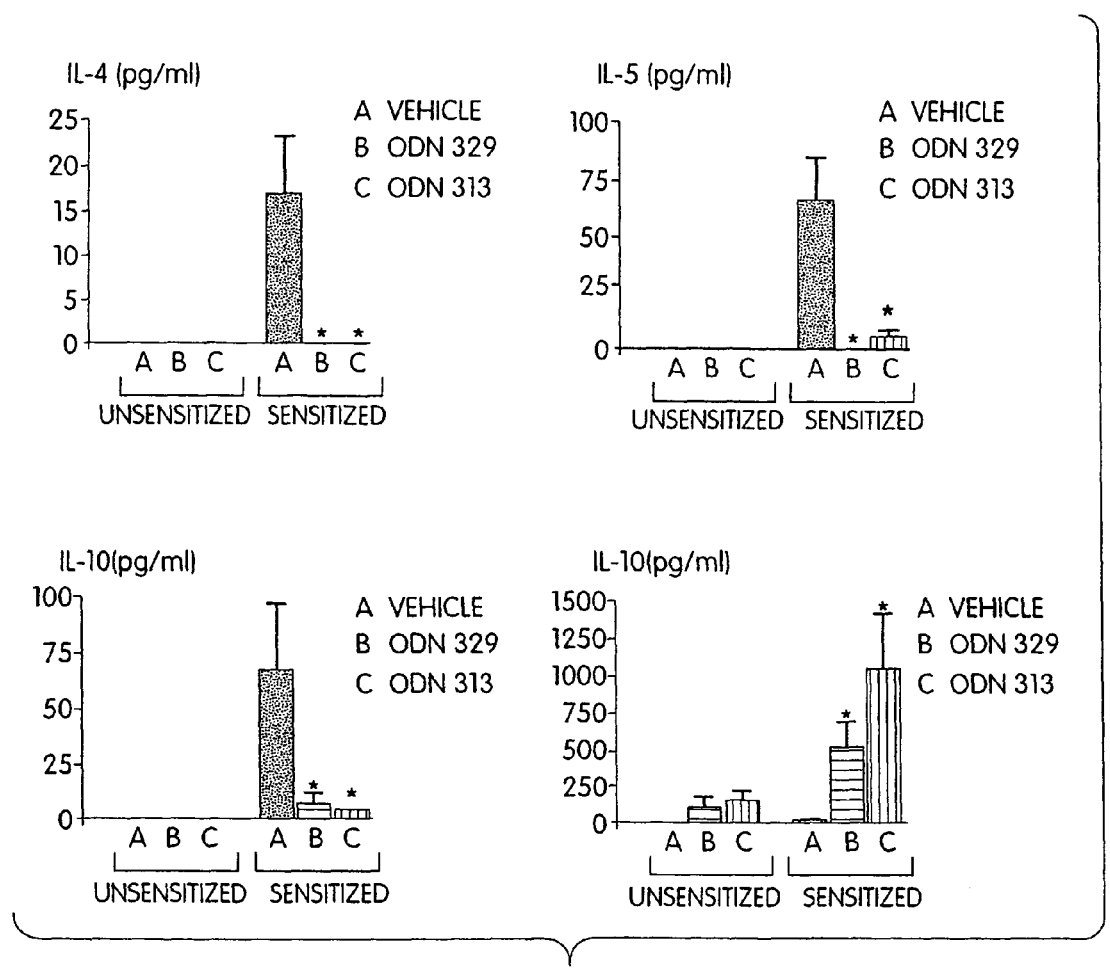
FIG. 27 demonstrates that CpG ODN suppress a Th2 response to antigen sensitization.

Antigen recall assay Draining lymph node cells taken from antigen-sensitized mice secreted IL-4, IL-5, IL-10 and IFNγ when restimulated with antigen ex vivo. In sensitized mice that also received a CpG ODN, secretions of Th2-type cytokines IL-4, IL-5 and IL-10 were reduced, whereas secretion of the Th1-type cytokine IFNγ was increased. Our data, shown in FIG. 27, supports the hypothesis that SEQ ID No. 313, like SEQ ID No. 329, suppresses a Th2 response to antigen sensitization. Results are mean±s.e.m. (n=9-10). *P<0.05 compared with sensitized, vehicle-treated group (Kruskal-Wallis multiple comparison test).

Example 24

Effects on Antigen-induced IgE Production in Mice in vivo

Methods:

Mice (male BALB/c) were sensitized on study days 0 and 7 with antigen (ovalbumin, 100 µg, i.p.) with aluminum hydroxide adjuvant. Mice received SEQ ID No. 313 (0.15 or 1.5 mg/kg, i.p.) or SEQ ID No. 17 (1.5 mg/kg, i.p.) two days before each sensitization and on the day of each sensitization. Serum was collected on study day 18. Titers of antigen (ovalbumin)-specific IgE and IgG2a were measured by ELISA. A summary of the protocol is shown in Table 12.

TABLE 12

| Summary of study protocol | | | | | |
|---|---|---|---|---|---|
| | | | Sensitize ↓ | | Sensitize ↓ |
| | ODN ↓ | ODN ↓ | ODN ↓ | ODN ↓ | |
| Day: | −2 | 0 | 5 | 7 | 18 ↓ Endpoint |

Results

Figure 28:
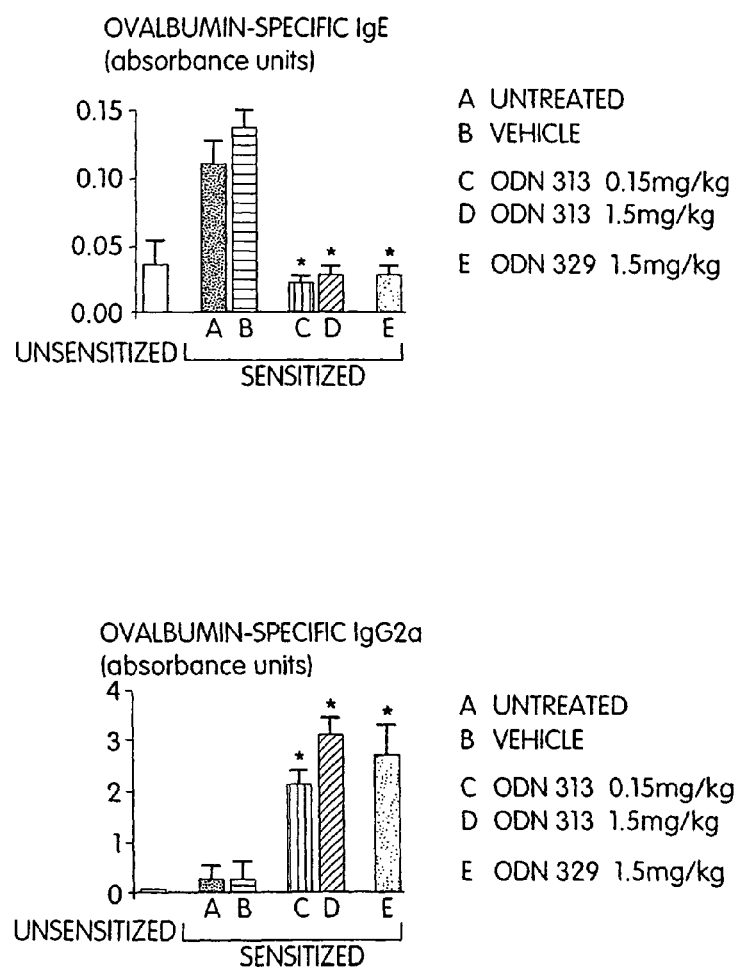
FIG. 28 shows the effects on antigen-induced IgE production in mice in vivo.

In mice treated with SEQ ID No. 313 or SEQ ID No. 329, production of antigen-specific IgE was completely prevented. In contrast, production of IgG2a was increased. Since IgE and IgG2a production are characteristic of Th2-type and Th1-type responses respectively, this effect is further evidence that SEQ ID No. 313 can suppress Th2-type responses to antigen sensitization. Alternatively CpG ODNs may directly induce T-beta expression and class switching from IgE in B cells. The data are shown in FIG. 28. Results are mean±s.e.m. (n=10-12, except 5 for the SEQ ID NO: 329 group). *P<0.05 compared with sensitized, vehicle-treated group (Kruskal-Wallis multiple comparison test).

Example 25

Effects Against Antigen-induced Airways Inflammation in Mice in vivo

Methods:
Mice (male BALB/c) were sensitized on study days 0 and 7 with antigen (ovalbumin, 100 µg, i.p.) with aluminum hydroxide adjuvant. Mice were antigen challenged by exposure to inhaled ovalbumin aerosol, twice each week for two consecutive weeks. The first challenge was on study day 21. SEQ ID No. 313 (0.1-1000 µg/kg), SEQ ID No. 329 (1-1000 µg/kg) or vehicle (saline, 20 µl) were administered into the airways by intranasal instillation once each week, two days before the first antigen challenge of the week. Endpoints were assessed 48 hours after the last antigen challenge. Cells in airways were recovered by bronchoalveolar lavage and differential cell counts were made. Eosinophil numbers (eosinophil volume density) and mucus secretion (PAS staining) in lung tissue were determined by histopathological assessment. The protocol is outlined in Table 13.

TABLE 13

Summary of study protocol

| | Sensitize | | | Challenge | | | Challenge | | |
|---|---|---|---|---|---|---|---|---|---|
| | ↓ | ↓ | ODN ↓ | ↓ | ↓ | ODN ↓ | ↓ | ↓ | |
| Day: | 0 | 7 | 19 | 21 | 24 | 26 | 28 | 31 | 33 ↓ Endpoints |

Figure 29:
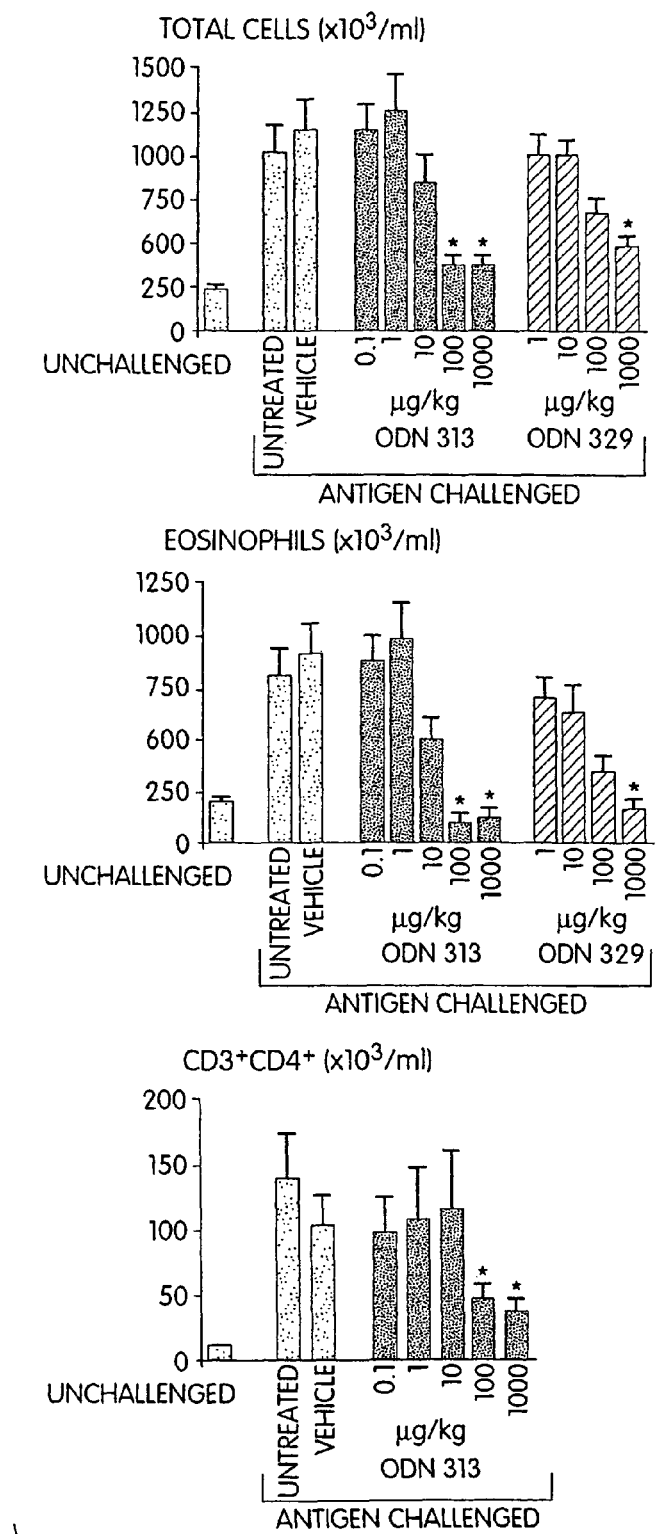
FIG. 29 demonstrates that antigen challenge caused an increase in the total number of leukocytes, predominantly eosinophils, in the airway lumen.
Figure 30:
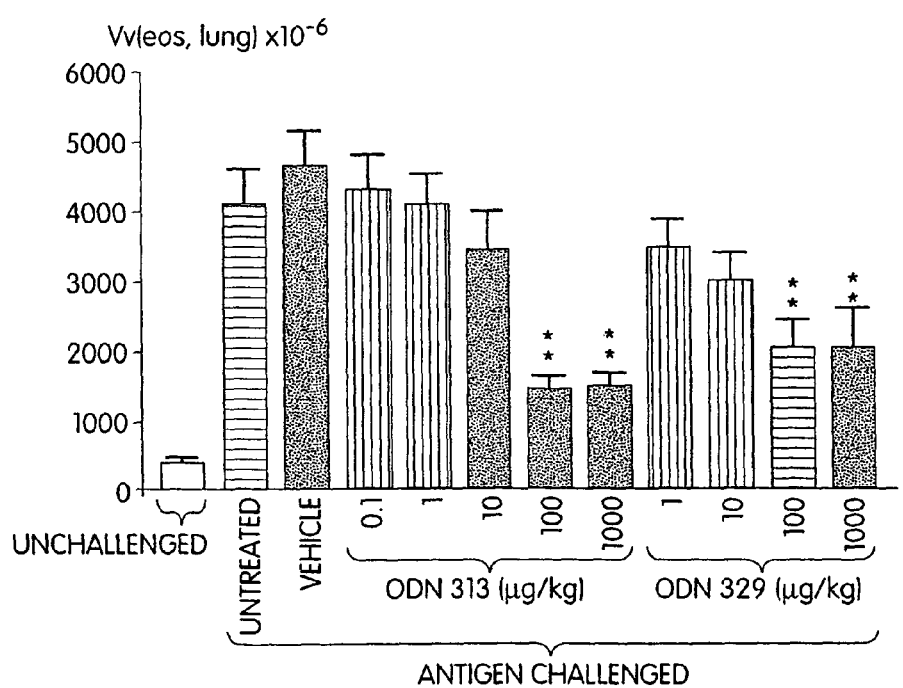
FIG. 30 shows that antigen challenge caused an increase in the total number of leukocytes, predominantly eosinophils, in the airway lumen and that this was suppressed by an ODN of the invention (SEQ ID No. 313) in a dose-related manner.

Results
Antigen challenge caused an increase in the total number of leukocytes, predominantly eosinophils, in the airway lumen. The data are shown in FIG. 29. The eosinophilia was suppressed significantly in a dose-related manner by SEQ ID No. 313 or SEQ ID No.329. $ED_{50}$ values against eosinophilia were: SEQ ID No.313: 23 µg/kg; SEQ ID No. 329: 47 µg/kg. Challenge also caused an accumulation of $CD4^+$ T cells ($CD3^+CD4^+$ cells) that was significantly suppressed by SEQ ID No.313. SEQ ID No. 313 also significantly suppressed antigen-induced eosinophil accumulation in lung tissue and epithelial mucus secretion. Results in FIG. 29 are mean±s.e.m. (n=15). *P<0.05 compared with antigen challenged, vehicle-treated group (Kruskal-Wallis multiple comparison test). Results in FIG. 30 are mean±s.e.m. (n=6). *P<0.05, **P<0.001 compared with antigen challenged, vehicle-treated group (ANOVA, Dunnett's multiple comparison test).

Example 26

Effects Against Antigen-induced airways Hyperreactivity in Mice in vivo

Methods:
Mice (male BALB/c) were sensitized on study days 0 and 7 with antigen (ovalbumin, 100 µg, i.p.) with aluminum hydroxide adjuvant. Mice were antigen challenged by exposure to inhaled ovalbumin aerosol, twice each week for two consecutive weeks. The first challenge was on study day 19. SEQ ID No. 313 (10-1000 µg/kg) or vehicle (saline, 20 µl) were administered intranasally once each week, two days before the first antigen challenge of the week. Airways hyperreactivity was assessed 24 hours after the last antigen challenge by measuring bronchoconstriction (increase in airway resistance) to intravenous methacholine. For each animal, a dose-response curve to methacholine was obtained, and airway reactivity was quantified as the area under the curve. The protocol is shown in Table 14.

TABLE 14

Summary of study protocol

| | Sensitize | | | Challenge | | | Challenge | | |
|---|---|---|---|---|---|---|---|---|---|
| | ↓ | ↓ | ODN ↓ | ↓ | ↓ | ODN ↓ | ↓ | ↓ | |
| Day: | 0 | 7 | 17 | 19 | 22 | 24 | 26 | 29 | 30 ↓ Endpoints |

Figure 31:
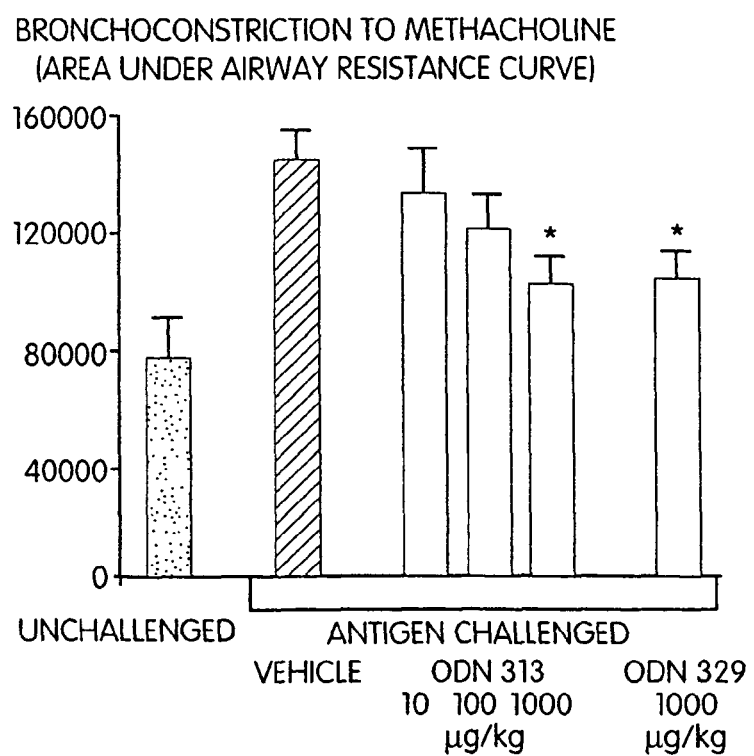
FIGS. 31 and 32 show that antigen challenge caused airway hyperreactivity and that this was suppressed by an ODN of the invention (SEQ ID No. 313) in a dose-related manner.
Figure 32:
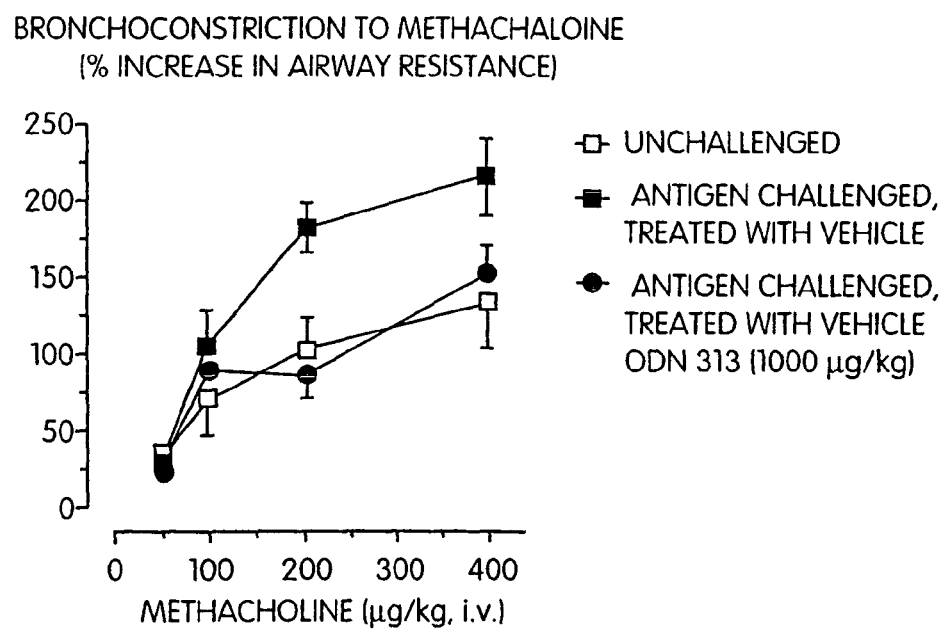

Results
Antigen challenge caused airway hyperreactivity. SEQ ID No. 313 suppressed the development of antigen-induced airway hyperreactivity in a dose-related manner. The data is shown in FIGS. 31 and 32 as sample dose-response curves to methacholine to show effect of SEQ ID No. 313 (1000 µg/kg). Dose-response curves to methacholine are quantified as area under the curve. Results are mean±s.e.m. (n=6-8). *P<0.05 compared with antigen challenged, vehicle-treated group (Kruskal-Wallis multiple comparison test).

An analysis of the full dose-response (RL) curves between the mice that were antigen challenged, treated with vehicle and each of the respective mice that were antigen challenged, treated with SEQ ID No. 313 was carried out using a repeated measures MANOVA. While there was a significant difference (P<0.05) between the dose-response curves with the 100 and 1000 ug/kg SEQ ID No. 313 treatment groups, there was no significant difference between the mice that were antigen challenged, treated with vehicle and the similarly treated animals dosed with 10 ug/kg SEQ ID No. 313.

Example 27

In vivo Pharmacokinetics (PK) Study in the Rat

A PK study was carried out in rats to determine whether SEQ ID No. 313, a 'semi-soft' ODN, is cleared from plasma & tissues, particularly from the kidneys, at a faster rate than SEQ ID No. 329, a fully phosphothioate ODN, which is identical in base sequence to SEQ ID No. 313.

Methods
56 rats were administered by Intravenous (IV) & Intratratcheal (IT) routes 5 mg/kg (for both IV & IT) of SEQ ID No. 313 and SEQ ID No. 329. Plasma, Lungs, Kidneys were collected. The study lasted 5 days, with 14 time points per dose group. 3 rats/time point for IV group (Total=42 rats) and 4 rats/time point for IT group were used.

Figure 33:
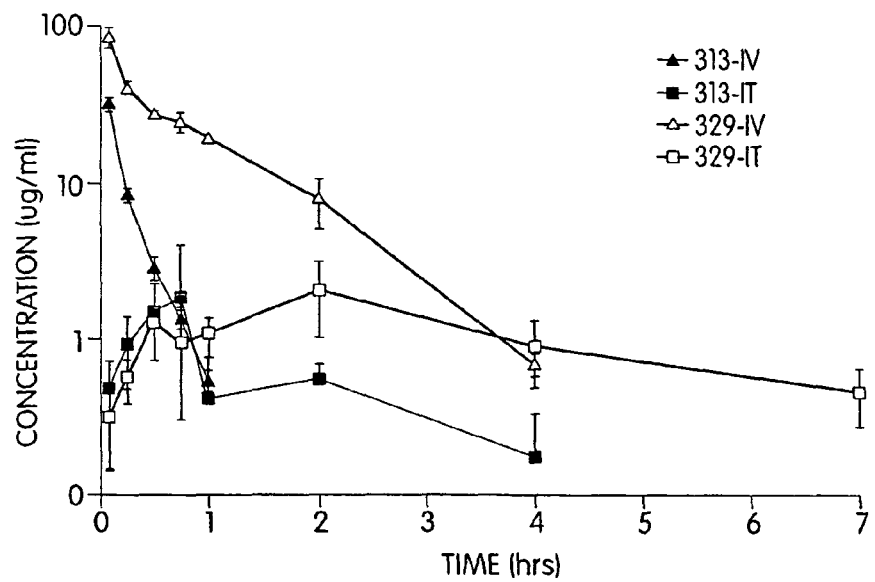
FIG. 33 shows ODN concentrations in rat plasma following IV & IT administration at 5 mg/kg. The plasma data shows that SEQ ID No. 313 is cleared more rapidly from plasma compared to SEQ ID No. 329 following both IV & IT administration.

Results
FIG. 33 shows ODN concentrations in rat plasma following IV & IT administration at 5 mg/kg. The plasma data shows that SEQ ID No. 313 is cleared more rapidly from plasma compared to SEQ ID No. 329 following both IV & IT administration.

Figure 34:
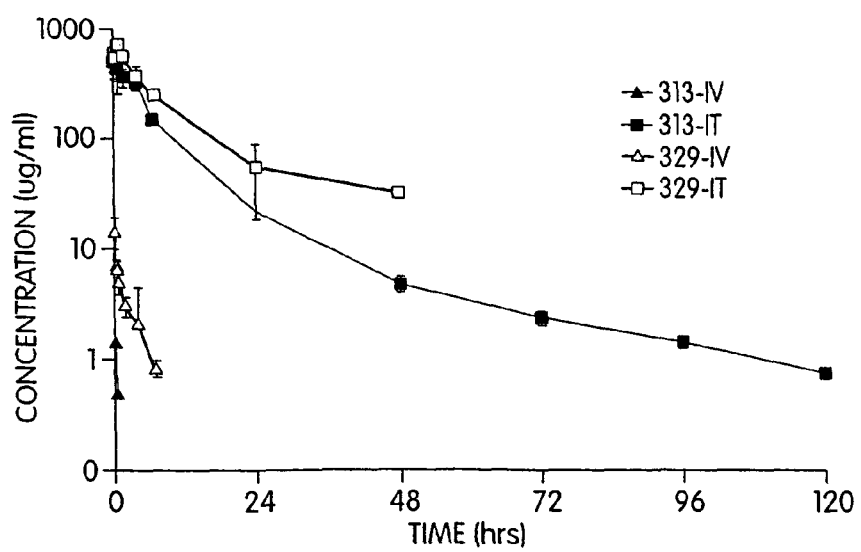
FIG. 34 shows ODN concentrations in rat lungs following IV & IT administration at 5 mg/kg. Following IV administration at the same dose level, lung concentrations of SEQ ID No. 313 are lower than SEQ ID No. 329 concentrations. After IT administration the difference is less marked. Lung data for SEQ ID No. 329 is only available for up to 48 hrs post-dose.

FIG. 34 shows ODN concentrations in rat lungs following IV & IT administration at 5 mg/kg. Following IV administration at the same dose level, lung concentrations of SEQ ID No. 313 are lower than SEQ ID No. 329 concentrations. After IT administration the difference is less marked. Lung data for SEQ ID No.329 is only available for up to 48 hrs post-dose.

Figure 35:
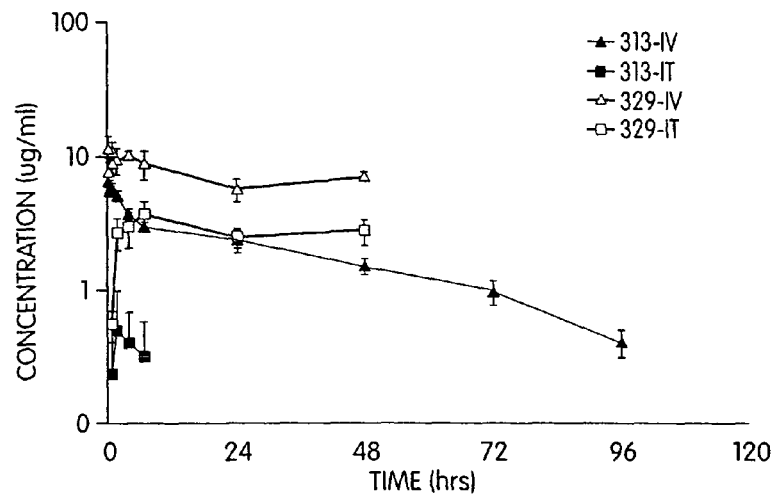
FIG. 35 shows ODN concentrations in rat kidneys following IV & IT administration at 5 mg/kg. The kidney data indicates that absolute levels of SEQ ID No. 313 in the kidneys are lower than corresponding SEQ ID No.329 concentrations following both IV and IT administration.

FIG. 35 shows ODN concentrations in rat kidneys following TV & IT administration at 5 mg/kg. The kidney data indicates that absolute levels of SEQ ID No. 313 in the kidneys are lower than corresponding SEQ ID No. 329 concentrations following both IV and IT administration. The renal exposure to SEQ ID No.313 after IT administration in particular, is markedly reduced compared to exposure to SEQ ID No. 329 at the same dose level. This can be seen more clearly in FIGS. 36 & 37.

FIG. 36 shows ODN concentrations in rat kidneys following IV administration at 5 mg/kg. FIG. 37 shows ODN concentrations in rat kidneys following IT administration at 5 mg/kg. Following IT administration both SEQ ID No. 313 & SEQ ID No. 329 are below the lower limit of quantitation (0.4-0.6 µg/g) in the kidneys for up to 1 hr post-dose. After 1 hr, SEQ ID No. 329 can be detected in all kidney samples collected during the study period (48 hrs). SEQ ID No. 313, on the other hand, is only present in measurable levels for up to 7 hrs post-dose.

TABLE 15

Summary of mean PK parameters for SEQ ID No. 313 & SEQ ID No. 329 following IV & IT administration to rats at a dose level of 5 mg/kg.

| Dose Group | Tissue | ODN | Cmax (ug/ml) | Tmax (hrs) | $T_{1/2}$ (hrs) | $AUC_{0-INF}$ (hr · ug/ml) | $AUC_{0-48 h}$* (hr · ug/ml) |
|---|---|---|---|---|---|---|---|
| IV | Plasma | 10 | na | na | 0.20 | 9.5 | 9.3 |
| (5 mg/kg) |  | 17 | na | na | 0.62 | 62.8 | 62.2 |
|  | Lungs | 10 | 1.4 | 0.25 | 0.17 | 0.47 | 0.35 |
|  |  | 17 | 14.4 | 0.083 | 2.5 | 23.7 | 20.8 |
|  | Kidneys | 10 | 6.6 | 0.083 | 24.9 | 184 | 123 |
|  |  | 17 | 11.4 | 0.083 | nc | nc | 346 |
| IT | Plasma | 10 | 1.9 | 0.75 | 1.20 | 2.68 | 2.35 |
| (5 mg/kg) |  | 17 | 2.1 | 2 | 2.3 | 9.01 | 7.46 |
|  | Lungs | 10 | 632 | 0.25 | 28.1 | 5540 | 5350 |
|  |  | 17 | 692 | 1 | (31)** | (7908)** | 6505 |
|  | Kidneys | 10 | 0.49 | 2 | 7.8 | 5.81 | 2.34 |
|  |  | 17 | 3.8 | 7 | nc | nc | 134 | na—Not applicable
nc—Not calculable. Could not be estimated accurately due to insufficient data points in terminal phase or terminal elimination phase not reached during the study period.
*$AUC_{0-48 h}$ or $AUC_{0-LAST}$ when last measurable conc. before 48 h.
**Very approximate estimate (based on 2 data points only in terminal phase).
10 - SEQ ID No. 313
17 - SEQ ID No. 329

TABLES 16(a)-(c)

Systemic and tissue exposure to SEQ ID No. 313 & SEQ ID No. 329 following IT & IV administration to rats at a dose level of 5 mg/kg.

| ODN | Dose Route | $AUC_{0-48 hr}$ (hr · ug/ml) | SEQ ID NO: 313:SEQ ID NO: 329 Ratio |
|---|---|---|---|
| (a) - Plasma data ||||
| SEQ ID | IT | 2.35 | 0.32 (IT) |
| No. 313 | IV | 9.30 | 0.15 (IV) |
|  | IT:IV Ratio | 0.25 |  |
| SEQ ID | IT | 7.46 |  |
| No. 329 | IV | 62.2 |  |
|  | IT:IVRatio | 0.12 |  |
| (b) - Lung data ||||
| SEQ ID | IT | 5350 | 0.82 (IT) |
| No. 313 | IV | 0.35 | 0.017 (IV) |
|  | IT:IV Ratio | 15286 |  |
| SEQ ID | IT | 6505 |  |
| No. 329 | IV | 21 |  |
|  | IT:IV Ratio | 313 |  |
| (c) - Kidney data ||||
| SEQ ID | IT | 2.34 | 0.017 (IT) |
| No. 313 | IV | 123 | 0.36 (IV) |
|  | IT:IV Ratio | 0.019 |  |
| SEQ ID | IT | 134 |  |
| No. 329 | IV | 346 |  |
|  | IT:IV Ratio | 0.39 |  |

Systemic and renal exposure of SEQ ID No. 313 was found to be markedly lower than exposure to SEQ ID No. 329 following administration of the 2 ODNs by either the intravenous (IV) or intratracheal (IT) routes.

The plasma AUC for SEQ ID No. 313 after IT administration at 5 mg/kg was 2.7 hr.µg/ml. The corresponding value for SEQ ID No. 329 was 9.0 hr.µg/ml. Thus, the systemic exposure to SEQ ID No. 313 is a third of that seen with SEQ ID No. 329.

The kidney AUC for SEQ ID No. 313 after IT administration at 5 mg/kg was 2.35 hr.µg/ml. The corresponding value for SEQ ID No. 329 was 134 hr.µg/ml. Thus, for the same dose level, renal exposure to SEQ ID No. 313 is only about 2% of the exposure seen with SEQ ID No. 329.

Unlike the case with plasma and kidneys, the lung exposure to SEQ ID No. 313 following IT administration was not reduced to such a large extent when compared to the exposure to SEQ ID No. 329. The lung AUC for SEQ ID No. 313 was approximately 70-80% of the lung AUC for SEQ ID No. 329 at the same dose level. Since the lung is the target tissue, it is advantageous that the clearance of the ODN from the lung is not increased to the same extent as from plasma and kidneys.

FIG. 38 shows concentrations of SEQ ID No. 313 and its 8-mer metabolite(s) in rat kidneys following IV administration of SEQ ID No. 313 at 5 mg/kg.

FIG. 39 shows concentrations of SEQ ID No. 313 and its 8-mer metabolite(s) in rat kidneys following IT administration of SEQ ID No. 313 at 5 mg/kg. Due to methodological issues the data for the 8-mer metabolite of SEQ ID No. 313 in plasma & tissues is incomplete. However, 8-mer data is available for some of the IV and all of the IT kidney samples. This data shows that in most of those kidney samples where 8-mer concentrations have been successfully measured, the levels of the metabolite exceed the levels of SEQ ID No. 313, indicating that endonuclease activity is an important route of metabolism for SEQ ID No. 313.

The introduction of a number of phosphodiester linkages (SEQ ID No. 313) into a fully phosphothioate backbone (SEQ ID No. 329) appears to have increased the degradation rate of the ODN, resulting in more rapid clearance, particularly from the kidneys.

Example 28

Activation of TLR9 Using Semi-Soft ODN Compared with Fully Phosphorothioate ODN

Methods

Stably transfected HEK293 cells expressing the human TLR9 were described before [Bauer et al.; PNAS; 2001]. Briefly, HEK293 cells were transfected by electroporation with vectors expressing the human TLR9 and a 6×NFκB-luciferase reporter plasmid. Stable transfectants ($3 \times 10^4$ cells/well) were incubated with ODN for 16 h at 37° C. in a humidified incubator. Each data point was done in triplicate. Cells were lysed and assayed for luciferase gene activity (using the Brightlite kit from Perkin-Elmer, Ueberlingen, Germany). Stimulation indices were calculated in reference to reporter gene activity of medium without addition of ODN.

Results

TLR9, is readily activated by ODNs containing optimal immunostimulatory CpG sequences. We incubated a cell line stably expressing the human TLR9 with a panel of semi-soft ODN and a panel of fully phosphorothioate ODN having the same ODN sequence as the semi-soft ODN. The results are shown in FIG. 40.

The results demonstrate that each of the semi-soft ODN shown in the table below, SEQ ID NOs. 376, 378, 380, 382, 384, 241 activated higher levels of TLR9 than the same sequence ODN having a fully phosphorothioate backbone, SEQ ID NOs. 377, 379, 381, 383, 385, and 242 respectively.

Example 29

Rp Internucleotide Linkages as Phosphodiester Like linkages in Semi-Soft Oligonucleotides Methods Cell Culture Conditions and Reagents For B cell proliferation assays, spleen cells from BALB/c mice (4-18 weeks old) were cultured at $2-5 \times 10^5$-$10^6$ cells/ml in RPMI for 44 hr. in 96-well microtiter plates, and then pulsed with 1 µCi of $^3$H thymidine for 4-6 hr, before being harvested and cpm determined by scintillation counting as previously described(Krieg et al., 1995). For Western blots, WEHI-231 cells (American Type Culture Collection, Rockville, Md.) were cultured at 37° C. in a 5% $CO_2$ humidified incubator and maintained in RPMI 1640 (Life Technologies, Gaithersburg, Md.) supplemented with 10% heat-inactivated FCS (Life Technologies, Gaithersburg, Md.), 1.5 mM L-glutamine, 50 µM 2-ME, 100 U/ml penicillin, and 100 µg/ml streptomycin.

Oligonucleotides.

Oligodeoxynucleotides (PO-Oligos) and stereo-random oligo(deoxynucleoside phosphorothioate)s [Mix-PS]-Oligos were purchased from Operon Technologies (Alameda, Calif.) or prepared by the standard phosphoramidite method(Caruthers, 1985)(Stec et al., 1984). The oligonucleotide [Mix-PS]-d(TCCATGACGTTCCTGACGTT) ([Mix-PS]-SEQ ID NO:386) was used as a positive control since it had previously been found to have strong immune stimulatory effects on mouse cells(Yi et al., 1996). For a CpG PS-Oligo with a minimal stimulatory motif, the sequence PS-d(TCAACGTT)-2066 was chosen for study as a typical CpG motif with broad immune stimulatory effects representative of the broad family of CpG DNA. This sequence was called [Mix-PS]-2066 when made with a stereo-random backbone. When this octamer sequence was made with a complete or partially stereo-defined backbone, the PS-Oligo was referred to as either [All-Rp-PS]-2066 or [All-Sp-PS]-2066 when the entire backbone was stereo-defined, or as [CG-Rp-PS]-2066 or [CG-Sp-PS]-2066 when only the CpG dinucleotide was stereo-defined. Other PS-Oligos used included CpG PS-d(TCAACGTTGA) ([Mix-PS]—SEQ ID NO:387) and its All-Rp- and All-Sp-stereo-defined counterparts, and the control non-CpG PS-d(TCAAGCTTGA) [Mix-PS]—SEQ ID NO:388.

```
SEQ ID No. 376   T*G*T*C_G*T*T*T*T*T*T*T*T*T*T*T*T*T*T*T
SEQ ID No. 377   T*G*T*C*G*T*T*T*T*T*T*T*T*T*T*T*T*T*T*T
SEQ ID No. 378   U*G*T*C_G*T*T*U*U*U*U*U*U*U*U*U*U*U*U*U
SEQ ID No. 379   U*G*T*C*G*T*T*U*U*U*U*U*U*U*U*U*U*U*U*U
SEQ ID No. 380   D*G*T*C_G*T*T*D*D*D*D*D*D*D*D*D*D*D*D*T
SEQ ID No. 381   D*G*T*C*G*T*T*D*D*D*D*D*D*D*D*D*D*D*D*T
SEQ ID No. 382   U*G*T*C_G*T*T*U*U*U*U_G_G_G_A_G_G*G*G
SEQ ID No. 383   U*G*T*C*G*T*T*U*U*U*U*G*G*G*A*G*G*G*G
SEQ ID No. 384   U*G*T*C_G*T*T*C*C*U*U_G_G_G_A_G_G*G*G
SEQ ID No. 385   U*G*T*C*G*T*T*C*C*U*U*G*G*G*A*G*G*G*G
SEQ ID No. 241   T*C_G*T*C_G*T*T*T*T_G*T*C_G*T*T*T*T*G*T*C_G*T*T
SEQ ID No. 242   T*C*G*T*C*G*T*T*T*T*G*T*C*G*T*T*T*T*G*T*C*G*T*T
```

Stereo-defined phosphorothioate oligodeoxynucleotides were prepared by the oxathiaphospholane method as described(Stec et al., 1995)(Stec et al., 1998). The syntheses were performed manually. The first nucleoside units from the 3'-end were anchored to the solid support by a DBU-resistant sarcosinyl linker(Brown et al., 1989). Appropriately protected deoxynucleosidyl monomers possessing 3'-O-(2-thio-"spiro"-4,4-pentamethylene-1  ,3,2-oxathiaphospholane) moiety were synthesized and separated chromatographically into pure P-diastereomers. For synthesis of [CG-Rp-PS]-2066 and [CG-Sp-PS]-2066, unresolved mixtures of both P-diastereomers (in Rp:Sp ratio ca. 1:1)(Stec et al., 1998) were used for assembling of internucleotide linkages of randomal configuration of P atoms. All synthesized oligomers were purified by two-step RP-HPLC: DMT-on (retention times in the range 23-24 minutes) and DMT-off (retention times 14-16 minutes); chromatographic system: an ODS Hypersil column, 5 µm, 240×4.6mm, 0-40% $CH_3CN$ in 0.1 M triethylammonium bicarbonate, pH 7.5, gradient 1%/min. Their purity was assessed by polyacrylamide gel electrophoresis.

For studies of PS-Oligo uptake, fluorescein conjugated stereoregular PS-Oligos were prepared by solid phase elongation of manually synthesized stereo-defined PS-oligomers. After detritylation step, fluorescein phosphoramidite (Chem-Genes Corporation, Ashland, Mass.; working concentration 125 mg/mL) and 1-H-tetrazole were routinely added (coupling time 120 s), followed by sulfirization with S-Tetra reagent(Stec et al., 1993). Cleavage from the support and deprotection were performed with conc. ammonium hydroxide for 1 h at room temperature and 4 h at 55° C., respectively. The resulting oligomers were purified by one step RP-HPLC (vide supra). Because of remarkable hydrophobicity of fluoresceine moiety, the Rp- and Sp-oligomer was eluted at retention times 14.5, 14.8 and 14.7, 15.0 min, respectively, i.e. at the end of failed sequences. In both cases two P-diastereomers were eluted due to non-stereospecificity of the phosphoramidite/sulfurization method of elongation with the fluorescein monomer.

Western Blot Analysis

Cells were harvested and resuspended in fresh medium at a concentration of $2*10^6$ cells/ml. Cells were allowed to rest for four hours prior to a 40-minute stimulation. Cells were harvested and washed three times with cold PBS. Cells were lysed in 0.05M Tris (pH 7.4), 0.14M NaCl, 1% NP-40, 0.001M $Na_3VO_4$, 0.01M NaF, 4.3 mg/ml β-glycerophosphate, 0.002M DTT, 50 µg/ml PMSF, 12.5 µg/ml antipain, 12.5 µg/ml aprotinin, 12.5 µg/ml leupeptin, 1.25 µg/ml pepstatin, 19 µg/ml bestatin, 10 µg/ml phosphoramidon, 12.5 µg/ml trypsin inhibitor by freezing and thawing followed by a 30 minute incubation on ice. The samples were then centrifuged at 10,000×g for 10 min at 4° C. The supernatants were saved as whole cell lysates for further analysis. Equal amounts of whole cell lysates (20 µg) were boiled in SDS sample buffer for 5 minutes before being subjected to electrophoresis on an 11% denaturing polyacrylamide gel. After electrophoresis, proteins were transferred to nitrocellulose membranes using a semi-dry blotter (Bio-Rad Laboratories, Hercules, Calif.). Blots were blocked with 5% non-fat milk before hybridization with phospho-SAPKJJNK (Cell Signaling Technology, Beverly, Mass.), IκB-α and JNK1 (Santa Cruz Biotechnology, Inc., Santa Cruz, Calif.). Blots were visualized using enhanced chemiluminescence reagents (ECL, Amersham International) according to the manufacturer's protocol.

Results

Induction of spleen cell $^3H$ thymidine incorporation by the Sp stereoisomer of CpG PS-Oligos. In order to determine the stereo-specificity of the immune stimulatory effects of CpG DNA, BALB/c spleen cells were cultured with stereo-defined octanucleotides PS-d(TCAACGTT)-2066 in which all of the internucleotide linkages are either $R_P$ or $S_P$ configuration at the concentrations indicated in Table 17. The cells were cultured for 48 hr, which allows sufficient time for B cells to be induced to proliferate by the CpG motifs(Krieg et al., 1995). The stereo-random [Mix-PS]-2066, possessing a CpG motif, induced strong dose-dependent spleen cell proliferation (Table 17). The Sp isomer also induced proliferation, and appeared to be marginally more potent than [Mix-PS]-2066. In contrast, the Rp stereoisomer did not induce any detectable proliferation, which was consistent with the findings of Yu et al.,(Yu et al., 2000).

TABLE 17

Induction of spleen cell proliferation by the Sp stereoisomer of CpG octamers.

| Oligo | Concentration | cpm | SI |
|---|---|---|---|
| None (medium) | | 2170 | 1 |
| 2066 (stereo-random CpG) | 0.4 µM | 3154 | 1.5 |
| " | 2.4 µM | 16,525 | 7.6 |
| " | 4.8 µM | 30,811 | 14.2 |
| Rp (2066) | 0.4 µM | 1207 | 0.6 |
| " | 2.4 µM | 985 | 0.5 |
| " | 4.8 µM | 640 | 0.3 |
| Sp (2066) | 0.4 µM | 9567 | 4.4 |
| " | 2.4 µM | 35,372 | 16.3 |
| " | 4.8 µM | 43,591 | 20.1 |
| Rp (2066) + 2066[1] | 0.4 µM | 1,597 | 0.7 |
| " | 2.4 µM | 10,255 | 4.7 |
| " | 4.8 µM | 15,841 | 7.3 |

SI = stimulation index compared to medium control
[1]each of the two PS-Oligos were added to the indicated concentration at the start of culture Our previous studies had demonstrated that decamer CpG PS-Oligos have improved immune stimulatory effects compared to the octamers used in the first experiments. Therefore, these experiments were repeated using the construct PS-SEQ ID NO:387, which was synthesized either as a stereo-random [Mix-PS]—SEQ ID NO:387, or in the All-Rp- or All-Sp-form. Again, both the [Mix-PS]—SEQ ID NO:387 and the [All-Sp-PS]—SEQ ID NO:387 induced strong $^3H$ thymidine incorporation in a dose dependent manner. However, in this case, the [All-Rp-PS]—SEQ ID NO:387 was also able to induce a substantial increase in cell proliferation at the highest concentrations, indicating that it retained at least partial stimulatory activity.

Preference for Rp chirality at the CpG dinucleotide in octamer PS-Oligos. It remained unclear whether the apparent preference for the Sp stereoisomer in the initial experiments resulted from an effect within the CG dinucleotide itself, or whether this effect may be outside the CG. In order to determine this, two octamers PS-2066 were synthesized in which the backbone was stereo-random except for the linkage between the central CG, which was defined as either Sp or Rp. Surprisingly, this experiment appeared to give the opposite result from those using PS-Oligos in which the entire backbone was stereoregular since [CG-Rp-PS]-2066 caused as strong an increase in spleen cell $^3H$ thymidine incorporation as the control stereorandom PS-Oligo In contrast, PS-Oligo [CG-Sp-PS]-2066 was essentially inactive.

Inhibition of spleen cell $^3H$ thymidine incorporation by the R stereoisomer of CpG PS-Oligo. The level of $^3H$ thymidine incorporation in the wells treated with the Rp stereoisomer was lower than the control wells, suggesting possible inhibitory activity, although no cytotoxicity was apparent on microscopic examination of the cells. Indeed, when cells were cultured with an equimolar mixture of the [Mix-PS]-2066 and the All-Rp stereoisomer, there was an approximate 50% reduction in the level of $^3$H thymidine incorporation compared to cells cultured with only the [Mix-PS]-2066 (Table 17).

Preferential immune stimulation by [Rp-PS]-Oligos at early timepoints. The $^3$H thymidine incorporation assays performed in the preceding experiments are vulnerable to an artifact resulting from PS-Oligo degradation, with release of cold thymidine that competes with the labeled material, artificially suppressing its incorporation(Matson et al., 1992). Previous studies have demonstrated that [Rp-PS]-Oligos are far more susceptible to nuclease degradation than Sp counterparts. Thus, it was possible that the apparent lack of stimulatory effect of the [Rp-PS]-Oligo in our $^3$H thymidine incorporation assays may have been a misleading artifact that did not reflect the true effects of the [Rp-PS]-Oligo. In order to detect the stimulatory effects of the [Rp-PS]-Oligo at an early timepoint, before the PS-Oligo can be degraded, and as an independent biologic assay for CpG-induced stimulation, we tested the ability of these PS-Oligos to induce rapid phosphorylation of the regulatory mitogen activated protein kinase, JNK. Surprisingly, we found that upon treatment with CpG sequences PS- SEQ ID NO:386 and PS-SEQ ID NO:387, within forty minutes JNK phosphorylation was induced strongly not by the [Sp-PS]-isomers but only by the stereo-random [Mix-PS]—and by [Rp-PS]-isomers. A control non-CpG [Mix-PS]—SEQ ID NO:388 did not induce detectable JNK phosphorylation. All samples contained comparable amounts of total JNK protein.

Although no effect of the CpG [Sp-PS]-Oligo could be detected in the JNK phosphorylation assay, the oligo was biologically active in this experiment, because the level of the inhibitory protein IκB-a was reduced by all of the CpG PS-Oligos, regardless of stereoisomer, but not by the control non-CpG PS-SEQ ID NO:388.

Stereo-independence ofPS-Oligo cell surface binding and uptake. One potential explanation that could contribute to the observed differences in bioactivity of the PS-Oligo stereoisomers is that cell binding or uptake of the PS-Oligos may be stereo-dependent. To test this possibility, P-stereo-defined PS-Oligos were synthesized with fluorescent tags and incubated with cells. Consistent with the results of past studies, the PS-Oligos showed a concentration-dependent and temperature-dependent pattern of cell uptake. Notably, there was no detectable difference in the binding or uptake of the Rp or Sp PS-Oligos.

Example 30

Semi-soft C Class Oligonucleotide ODN 316 and Semi-soft B Class Oligonucleotide ODN 313 Reduce Antigen-induced Airways Inflammation in vivo This study assessed the in vivo effect of ODN 316 in a murine model of antigen-induced airways inflammation. The B class ODN 313 was included in the study for comparison.

Methods. Mice (male BALB/c) were sensitized on study days 0 and 7 with antigen (ovalbumin, 10 μg, i.p.) with aluminum hydroxide adjuvant (Pierce Alum).

Mice were antigen challenged by exposure to inhaled ovalbumin aerosol, twice each week for two consecutive weeks. The first challenge was administered on study day 21. The aerosol was generated for 1 hour from a 1% solution of ovalbumin in PBS using a DeVilbiss Ultraneb nebulizer. Separate mice acted as unchallenged controls.

ODN 316 or ODN 313 (1-100 μg/kg) or vehicle (saline, 20 μl) were administered intranasally once each week, two days before the first antigen challenge of the week.

Endpoints were assessed on study day 33 (i.e., 48 hours after the last antigen challenge). Cells in airways were recovered by bronchoalveolar lavage. Differential cell counts were made by an Advia automated cell counter with random samples checked by visually counting cells on cytocentrifuge preparations stained with Wright-Giemsa stain. Numbers of CD4$^+$ T cells (CD3$^+$CD4$^+$ cells) were counted by flow cytometry. Results were expressed in terms of mean±SEM for each group. Significance was measured using the Kruskall-Wallis multiple comparison test.

Results. Antigen challenge caused an increase in the total number of leukocytes in the airway lumen. This increase was predominantly due to an accumulation of eosinophils (e.g., $3 \times 10^5$ eosinophils/ml in antigen-challenged, vehicle-treated mice versus $<1 \times 10^4$ eosinophils/ml in unchallenged mice). The eosinophilia was suppressed significantly by ODN 316 or ODN 313 (e.g., ca. $5 \times 10^4$ eosinophils/ml (P<0.05) in antigen-challenged mice treated with 100 μg/ml of either ODN).

Antigen challenge also caused an accumulation of CD4$^+$ T cells that was significantly suppressed by either ODN (e.g., ca. $2 \times 10^4$ CD4$^+$ T cells/ml in antigen-challenged mice treated with 100 μg/ml of either ODN, versus ca. $1.3 \times 10^5$ CD4$^+$ T cells/ml (P<0.05) in antigen-challenged, vehicle-treated mice).

Conclusions. Each of semi-soft C class ODN 316 and semi-soft B class oligonucleotide ODN 313 suppressed antigen-induced airways eosinophilia and the accumulation of CD4$^+$ T cells in vivo.

Example 31

Comparison of Semi-soft B, C, and T Class ODN: Induction of Cytokine Secretion from Murine Splenocytes in vitro This study investigated the ability of semi-soft B, C, and T class ODNs to induce cytokine secretion from murine splenocytes in vitro.

Methods. Splenocytes from BALB/c mice were harvested and pooled. Splenocytes were incubated in 48-well culture plates at $1 \times 10^7$ cells/1 ml in RPMI 1640+10% fetal bovine serum containing individual ODN (0, 0.001, 0.01, 0.1, 1 or 10 μg/ml). Tested ODN included semi-soft B class ODN 20674, semi-soft C class ODN 316 and ODN 317, and semi-soft T class ODN 319 and ODN 320.

After 48 hours incubation (37° C., 5% CO$_2$), culture medium was removed and concentrations of IL-1β, IL-2, IL-4, IL-5, IL-6, IL-10, GM-CSF, IFN-γ and TNF-α were measured using the Luminex cytokine multiplex system. IL-12p40, IFN-α and IP-10 concentrations were measured by ELISA. Lower limits of accurate detectability were 3.2-10 μg/ml. Activation status of cells was assessed by measuring CD40, CD69 and CD86 expression on CD3+ and B220+ cells by flow cytometry.

Results. Each of the ODNs induced activation of B cells (B220+ cells) as measured by increased expression of CD40, CD69 and CD86, and activation of T cells (CD3+ cells) as measured by increased expression of CD69.

The ODNs induced secretion of IL-6, IL-10, IL-12p40, IFN-α, TNF-α and IP-10. Titers of the other cytokines measured were not increased. For example, at an ODN concentration of 1 μg/ml, cytokine secretion levels were found to be as follows (all expressed in pg/ml):

TABLE 18

In Vitro Cytokine Secretion in Response to Semi-Soft B, C, and T Class ODN

| ODN | IL-6 | IL-10 | IL-12p40 | IFN-α | TNF-α | IP-10 |
|---|---|---|---|---|---|---|
| 313 | 4000 | 410 | 300 | 12 | 150 | 400 |
| 316 | 3600 | 820 | 820 | 90 | 400 | 780 |
| 317 | 2200 | 410 | 790 | 140 | 340 | 760 |
| 319 | 1200 | 200 | 300 | nd | 50 | 30 |
| 320 | 150 | nd | 160 | nd | 15 | 25 | nd—not detected

When compared with the semi-soft B class ODN 313, the two semi-soft C class ODNs induced higher titers of IL-10, IL-12p40, IFN-α, TNF-α and IP-10, but did not cause more marked B cell activation. The two semi-soft T class ODNs appeared to be less effective than the semi-soft B and C class ODNs as cytokine inducers.

Conclusions. Each B class and C class ODN induced a profile of cytokine induction that was consistent with activation of TLR9, and each caused activation of B cells. The T class ODNs were less effective cytokine inducers.

When compared with the semi-soft B class ODN 313, the semi-soft C class ODNs 316 and 317 each induced higher concentrations of immune-modifying cytokines, but without inducing more B cell activation. This data suggests a therapeutic benefit of the C class ODNs.

Example 32

Cytokine, Antibody, and CTL Induction in vivo in Response to CpG ODN

Cytokine measurements: BALB/c mice were administrated 400 mg ODN (SEQ ID NO.s 294 (soft), 241 (semi-soft), 242, and 286) by SC injection. Animals were bled at 3 hours post injection and IP-10, IFN-gamma and TNF-alpha levels in plasma was measured by ELISA. The Results are shown in The results are shown in FIG. 41 A & B (IP-10), C (IFN), and D & E (TNF)

Antibody Response: BALB/c mice were immunized with 1 mg HBsAg alone or in combination with CpG ODN by IM injection. Animals were boosted at 4 weeks post primary immunization. Antibody titers were measured by end point ELISA. IgG isotype titers were measured at 2 weeks post boost by end point ELISA. The results are shown in FIG. 42A and B.

Figure 42C:
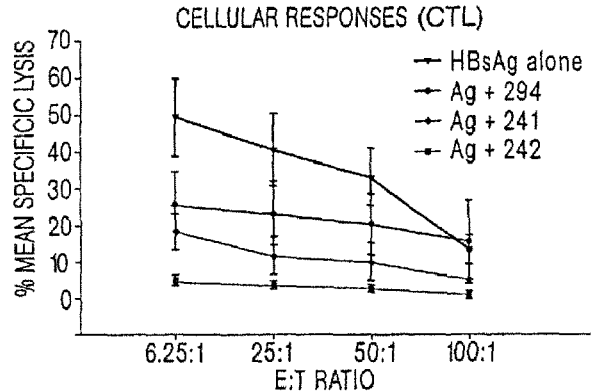

Cytotoxic T lymphocyte Response: BALB/c mice were immunized with 1 mg HBsAg alone or in combination with CpG ODN by IM injection. Animals were boosted at 4 weeks post primary immunization. CTL activity was measured at 4 wk post boost by 51 Cr release assay. The results are shown in FIG. 42C.

Thus, soft and semi-soft ODN have similar or are better in activating murine immune system as seen by both in vitro and in vivo studies and can augment antigen specific immune responses.

Example 33

Use of CpG ODN in in vivo Anti-cancer Therapy

Figure 43A:
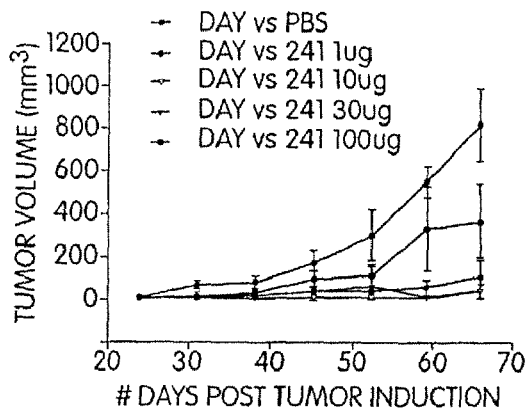
Figure 43B:
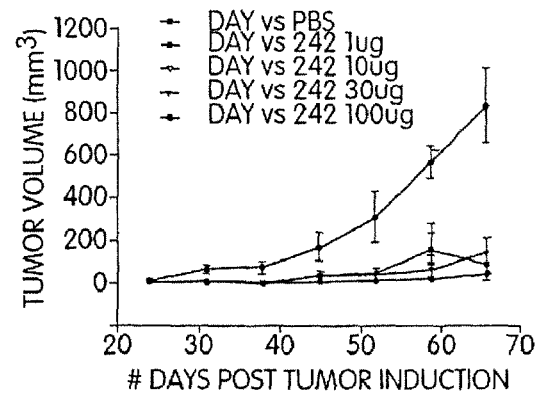

The ODN of the invention were tested for efficacy in three cancer models as mono-therapies. Initially the ODN were administered to mice having renal cell carcinoma (renca). The methods were performed as follows: Tumors were induced by injecting 2×105 renca cells SC in the left flank of mice on Day 0. Treatment followed and involved SC injections of PBS, CpG ODN 241 or 242 weekly for 5 weeks starting on day 10 post tumor cell injection. The results are shown in FIG. 43A and B.

Figure 43C:
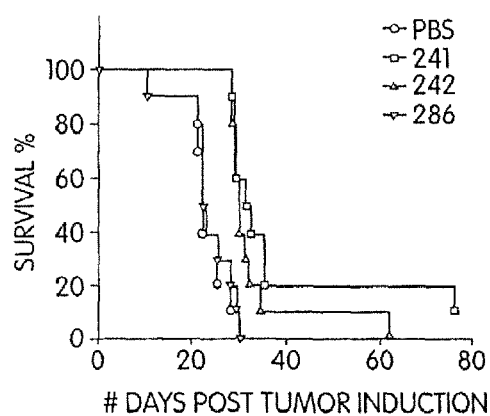
Figure 43D:
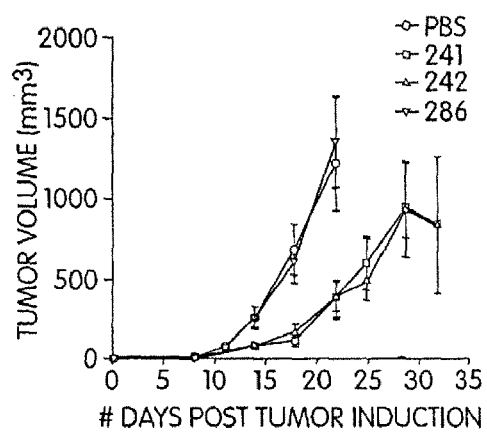
Figure 43E:
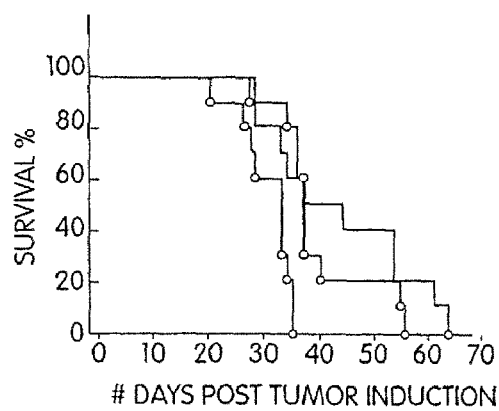
Figure 43F:
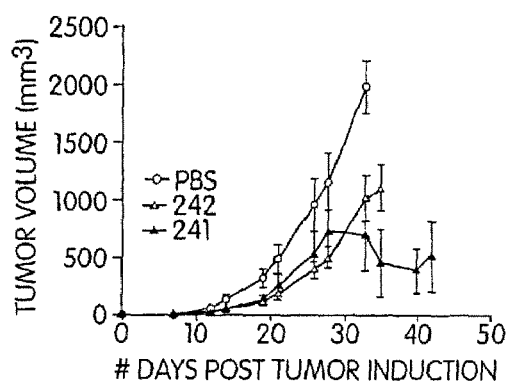

The second model tested was murine non-small cell lung cancer (Lewis lung carcinoma). Tumors were induced by injecting 2×106 Lewis Lung Carcinoma cells SC in the left flank of mice on day 0. Treatment followed and involved SC injections of PBS, 100 mg CpG ODN 241 or 242 on days 1, 3, 7 & weekly for 2 months. The results are shown in FIG. 43E and F.

A third model tested was murine neuroblastoma. 1×106 Neuro2a cells were injected SC in the left flank on day 0. SC injections of PBS, 100mg CpG ODN 241 or 242 were performed daily from day 10 to day 15. The results are shown in FIG. 43C and D.

Thus, semi-soft ODN can control growth of cancer (murine renca, LLC, neuroblastoma) and enhance survival of mice bearing these cancers.

Example 34

Peri-renal Inflammation Resulting from Administration of Soft, Semi-soft and Hard ODN in BALB/c Mice in TLR-9 Knockout Mice Peri-renal inflammation was assessed in BALB/c mice in TLR-9 knockout mice. The results are shown in Table 19 and 20 respectively. Semi soft ODN (241) induced less inflammation at the site of injection, induced no (100 mg dose) or little (250 mg dose) peri-renal inflammation, and were better tolerated following multiple administrations of ODN

TABLE 19

| Group | Kidney parenchyma inflammation | Renal capsule granulomatous inflammation | Adipose tissue granulomatous inflammation |
|---|---|---|---|
| PBS | Normal 5/5 | Normal 5/5 | Normal 5/5 |
| 242 100 mg | Mild 2/5 | Mild to moderate 5/5 | Mild to moderate 4/5 |
| 242 250 mg | Mild 1/4 | Mild to moderate 4/4 | Marked 4/4 |
| 241 100 mg | Normal 5/5 | Normal 5/5 | Normal 5/5 |
| 241 250 mg | Mild 2/5 | Mild 2/5 | Mild to moderate 3/5 |

TABLE 20

| Group | Kidney parenchyma inflammation | Renal capsule granulomatous inflammation | Adipose tissue granulomatous inflammation |
|---|---|---|---|
| PBS | Normal 5/5 | Normal 5/5 | Normal 5/5 |
| 242 100 mg | Normal 5/5 | Normal 5/5 | Normal 5/5 |
| 242 250 mg | Normal 5/5 | Normal 5/5 | Normal 5/5 |
| 241 100 | Normal 5/5 | Normal 5/5 | Normal 5/5 |
| 241 250 mg | Normal 5/5 | Normal 5/5 | Normal 5/5 |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

SEQUENCE LISTING

```
<160> NUMBER OF SEQ ID NOS: 391

<210> SEQ ID NO 1
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 1
acgtcgtttt cgtcgtt                                                  17

<210> SEQ ID NO 2
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 2
gcgtcgacgt cgacgc                                                   16

<210> SEQ ID NO 3
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 3
gcgtcgtttt cgtcgc                                                   16

<210> SEQ ID NO 4
<211> LENGTH: 19
<212> TYPE: DNA
<213> ORGANISM: Artificial sequence
<220> FEATURE:
<223> OTHER INFORMATION: Synthetic oligodeoxynucleotide

<400> SEQUENCE: 4
tccatgacgt tcctgatgc                                                19

<210> SEQ ID NO 5
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 5
tcgtcgtttt cgtcgtt                                                  17

<210> SEQ ID NO 6
<211> LENGTH: 22
<212> TYPE: DNA
<213> ORGANISM: Artificial sequence
<220> FEATURE:
<223> OTHER INFORMATION: Synthetic oligodeoxynucleotide
```

```
<400> SEQUENCE: 6
tcgtcgtttt cggcggccgc cg                                        22

<210> SEQ ID NO 7
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 7
tcgtcgtttt cgtcgtt                                              17

<210> SEQ ID NO 8
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 8
tcgtcgtttc gtcgtt                                               16

<210> SEQ ID NO 9
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 9
tcgtcgtttt cgtcgtt                                              17

<210> SEQ ID NO 10
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 10
tcgtcgtttt cgtcgtt                                              17

<210> SEQ ID NO 11
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 11
tcgtcgtttt cgtcgtt                                              17

<210> SEQ ID NO 12
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (3)..(3)
<223> OTHER INFORMATION: deazaguanine
<220> FEATURE:
<221> NAME/KEY: misc_feature
<222> LOCATION: (6)..(6)
<223> OTHER INFORMATION: deazaguanine
```

```
<400> SEQUENCE: 12
tcntcntttt gtcgttttgt cgtt                                              24

<210> SEQ ID NO 13
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (3)..(3)
<223> OTHER INFORMATION: deazaguanine
<220> FEATURE:
<221> NAME/KEY: misc_feature
<222> LOCATION: (22)..(22)
<223> OTHER INFORMATION: deazaguanine

<400> SEQUENCE: 13
tcntcgtttt gtcgttttgt cntt                                              24

<210> SEQ ID NO 14
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 14
tcgccgtttt cggcggccgc cg                                                22

<210> SEQ ID NO 15
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 15
tcgtcgtttt acgacgtcgc g                                                 21

<210> SEQ ID NO 16
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 16
tcgtcgtttt acgacgtcgt g                                                 21

<210> SEQ ID NO 17
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 17
tcgtcgtttt acggcgccgc gccg                                              24

<210> SEQ ID NO 18
<211> LENGTH: 72
<212> TYPE: DNA
<213> ORGANISM: Artificial sequence
<220> FEATURE:
<223> OTHER INFORMATION: Synthetic oligodeoxynucleotide
<220> FEATURE:
```

```
<221> NAME/KEY: misc_feature
<222> LOCATION: (1)..(10)
<223> OTHER INFORMATION: n is a, c, g, or t with a phosphorothioate
      link, and any 1-7 may be absent
<220> FEATURE:
<221> NAME/KEY: misc_feature
<222> LOCATION: (11)..(30)
<223> OTHER INFORMATION: n is a, c, g, or t, and any 1-20 may be absent
<220> FEATURE:
<221> NAME/KEY: misc_feature
<222> LOCATION: (43)..(62)
<223> OTHER INFORMATION: n is a, c, g, or t, and any 1-20 may be absent
<220> FEATURE:
<221> NAME/KEY: misc_feature
<222> LOCATION: (63)..(72)
<223> OTHER INFORMATION: n is a, c, g, or t with a phosphorothioate
      link, and any 1-7 may be absent

<400> SEQUENCE: 18
nnnnnnnnnn nnnnnnnnnn nnnnnnnnnn gtcgttgtcg ttnnnnnnnn nnnnnnnnnn      60
nnnnnnnnnn nn                                                          72

<210> SEQ ID NO 19
<211> LENGTH: 84
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(10)
<223> OTHER INFORMATION: n is a, c, g, or t, with a phosphorothioate
      link, and any 1-7 may be absent
<220> FEATURE:
<221> NAME/KEY: misc_feature
<222> LOCATION: (11)..(30)
<223> OTHER INFORMATION: n is a, c, g, or t, and any 1-20 may be absent
<220> FEATURE:
<221> NAME/KEY: misc_feature
<222> LOCATION: (55)..(74)
<223> OTHER INFORMATION: n is a, c, g, or t, and any 1-20 may be absent
<220> FEATURE:
<221> NAME/KEY: misc_feature
<222> LOCATION: (75)..(84)
<223> OTHER INFORMATION: n is a, c, g, or t, with a phosphorothioate
      link, and any 1-7 may be absent

<400> SEQUENCE: 19
nnnnnnnnnn nnnnnnnnnn nnnnnnnnnn gtcgttgtcg ttgtcgttgt cgttnnnnnn      60
nnnnnnnnnn nnnnnnnnnn nnnn                                             84

<210> SEQ ID NO 20
<211> LENGTH: 90
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(10)
<223> OTHER INFORMATION: n is a, c, g, or t, with a phosphorothioate
      link, and any 1-7 may be absent
<220> FEATURE:
<221> NAME/KEY: misc_feature
<222> LOCATION: (11)..(30)
<223> OTHER INFORMATION: n is a, c, g, or t, and any 1-20 may be absent
<220> FEATURE:
<221> NAME/KEY: misc_feature
<222> LOCATION: (61)..(80)
<223> OTHER INFORMATION: n is a, c, g, or t, and any 1-20 may be absent
<220> FEATURE:
<221> NAME/KEY: misc_feature
<222> LOCATION: (81)..(90)
<223> OTHER INFORMATION: n is a, c, g, or t, with a phosphorothioate
``` link, and any 1-7 may be absent

<400> SEQUENCE: 20
nnnnnnnnnn nnnnnnnnnn nnnnnnnnnn gtcgttgtcg ttgtcgttgt cgttgtcgtt    60
nnnnnnnnnn nnnnnnnnnn nnnnnnnnnn    90

<210> SEQ ID NO 21
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 21
tcgtcgtttt cggcgcgcgc cg    22

<210> SEQ ID NO 22
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 22
tcgtcgtttt cgtcgtt    17

<210> SEQ ID NO 23
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 23
tcgtcgtttt cgtcgtt    17

<210> SEQ ID NO 24
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 24
tcgtcgtttt cgtcgtt    17

<210> SEQ ID NO 25
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 25
tcgtcgtttt gcgacgtcgc g    21

<210> SEQ ID NO 26
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 26
tcgtcgtttt tcgacgtcga g    21

<210> SEQ ID NO 27
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 27
tcgtcgtttt tcgacgtcgc g    21

<210> SEQ ID NO 28
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (6)..(6)
<223> OTHER INFORMATION: deazaguanine
<220> FEATURE:
<221> NAME/KEY: misc_feature
<222> LOCATION: (19)..(19)
<223> OTHER INFORMATION: deazaguanine

<400> SEQUENCE: 28
tcgtcntttt gtcgttttnt cgtt    24

<210> SEQ ID NO 29
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 29
tcgtcgtttc gacgtt    16

<210> SEQ ID NO 30
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 30
tcgtcgtttc gacgttttgt cgtt    24

<210> SEQ ID NO 31
<211> LENGTH: 28
<212> TYPE: DNA
<213> ORGANISM: Artificial sequence
<220> FEATURE:
<223> OTHER INFORMATION: Synthetic oligodeoxynucleotide

<400> SEQUENCE: 31
tcgtcgtttc gtcgacgtcg tttcgtcg    28

<210> SEQ ID NO 32
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 32
tcgtcgtttc gtcgat    16

```
<210> SEQ ID NO 33
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 33
tcgtcgtttc gtcgatt                                                    17

<210> SEQ ID NO 34
<211> LENGTH: 15
<212> TYPE: DNA
<213> ORGANISM: Artificial sequence
<220> FEATURE:
<223> OTHER INFORMATION: Synthetic oligodeoxynucleotide

<400> SEQUENCE: 34
tcgtcgtttc gtcgt                                                      15

<210> SEQ ID NO 35
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 35
tcgtcgtttc gtcgtt                                                     16

<210> SEQ ID NO 36
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 36
tcgtcgtttc gtcgtttcgt cgtt                                            24

<210> SEQ ID NO 37
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 37
tcgtcgtttc gtcgttttgt cgtt                                            24

<210> SEQ ID NO 38
<211> LENGTH: 26
<212> TYPE: DNA
<213> ORGANISM: Artificial sequence
<220> FEATURE:
<223> OTHER INFORMATION: Synthetic oligodeoxynucleotide

<400> SEQUENCE: 38
tcgtcgtttg tcgtcggcgg ccgccg                                          26

<210> SEQ ID NO 39
<211> LENGTH: 22
<212> TYPE: DNA
<213> ORGANISM: Artificial sequence
<220> FEATURE:
<223> OTHER INFORMATION: Synthetic oligodeoxynucleotide
```

```
<400> SEQUENCE: 39
tcgtcgtttt cggcgcgcgc cg                                          22

<210> SEQ ID NO 40
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 40
tcgtcgtttt cggcggccgc cg                                          22

<210> SEQ ID NO 41
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 41
tcgtcgtttt cgtcgtt                                                17

<210> SEQ ID NO 42
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 42
tcgtcgtttt cggcgcgcgc cg                                          22

<210> SEQ ID NO 43
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 43
tcgtcgtttt cggcggccgc cg                                          22

<210> SEQ ID NO 44
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 44
tcgtcgtttt cgtcgt                                                 16

<210> SEQ ID NO 45
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 45
tcgtcgtttt cgtcgtt                                                17

<210> SEQ ID NO 46
<211> LENGTH: 17
<212> TYPE: DNA
```

```
<213> ORGANISM: Artificial sequence
<220> FEATURE:
<223> OTHER INFORMATION: Synthetic oligodeoxynucleotide

<400> SEQUENCE: 46
tcgtcgtttt cgttgtt                                                   17

<210> SEQ ID NO 47
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 47
tcgtcgtttt gtcgtcgttt t                                              21

<210> SEQ ID NO 48
<211> LENGTH: 23
<212> TYPE: DNA
<213> ORGANISM: Artificial sequence
<220> FEATURE:
<223> OTHER INFORMATION: Synthetic oligodeoxynucleotide

<400> SEQUENCE: 48
tcgtcgtttt ttttcgtcgt ttt                                            23

<210> SEQ ID NO 49
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 49
tcgtcgtttt tgtcgtt                                                   17

<210> SEQ ID NO 50
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 50
tcgtcgtttt tgttgtt                                                   17

<210> SEQ ID NO 51
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (11)..(11)
<223> OTHER INFORMATION: deazaguanine
<220> FEATURE:
<221> NAME/KEY: misc_feature
<222> LOCATION: (14)..(14)
<223> OTHER INFORMATION: deazaguanine

<400> SEQUENCE: 51
tcgtcgtttt ntcnttttgt cgtt                                           24

<210> SEQ ID NO 52
<211> LENGTH: 16
<212> TYPE: DNA
```

```
<213> ORGANISM: Artificial sequence
<220> FEATURE:
<223> OTHER INFORMATION: Synthetic oligodeoxynucleotide

<400> SEQUENCE: 52
tcgtcgtttt gacgtt                                               16

<210> SEQ ID NO 53
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 53
tcgtcgtttt gacgtttt                                             18

<210> SEQ ID NO 54
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 54
tcgtcgtttt gacgttttgt cgtt                                      24

<210> SEQ ID NO 55
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 55
tcgtcgtttt gacgttttgt cgtt                                      24

<210> SEQ ID NO 56
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 56
tcgtcgtttt gtcgtt                                               16

<210> SEQ ID NO 57
<211> LENGTH: 96
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(10)
<223> OTHER INFORMATION: n is a, c, g, or t, with a phosphorothioate
      link, wherein any of one to seven n may be absent.
<220> FEATURE:
<221> NAME/KEY: misc_feature
<222> LOCATION: (11)..(30)
<223> OTHER INFORMATION: n is a, c, g, or t, wherein any of one to
      twenty n may be absent.
<220> FEATURE:
<221> NAME/KEY: misc_feature
<222> LOCATION: (67)..(86)
<223> OTHER INFORMATION: n is a, c, g, or t, wherein any of one to
      twenty n may be absent.
<220> FEATURE:
<221> NAME/KEY: misc_feature
```

<222> LOCATION: (87)..(96)
<223> OTHER INFORMATION: n is a, c, g, or t, with a phosphorothioate
      link, wherein any of one to seven n may be absent.

<400> SEQUENCE: 57 nnnnnnnnn nnnnnnnnnn nnnnnnnnnn gtcgttgtcg ttgtcgttgt cgttgtcgtt    60
gtcgttnnnn nnnnnnnnnn nnnnnnnnnn nnnnnn                             96

<210> SEQ ID NO 58
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (19)..(19)
<223> OTHER INFORMATION: deazaguanine
<220> FEATURE:
<221> NAME/KEY: misc_feature
<222> LOCATION: (22)..(22)
<223> OTHER INFORMATION: deazaguanine

<400> SEQUENCE: 58
tcgtcgtttt gtcgttttnt cntt                                          24

<210> SEQ ID NO 59
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 59
tcgtcgtttt gtcgttttgt cgtt                                          24

<210> SEQ ID NO 60
<211> LENGTH: 17
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (10)..(10)
<223> OTHER INFORMATION: 2'-deoxyuracil

<400> SEQUENCE: 60
tcgtcgtttn gtcgttt                                                  17

<210> SEQ ID NO 61
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (10)..(10)
<223> OTHER INFORMATION: 2'-deoxyuracil

<400> SEQUENCE: 61
tcgtcgtttn gtcgttttgt cgtt                                          24

<210> SEQ ID NO 62
<211> LENGTH: 16
<212> TYPE: DNA
<213> ORGANISM: Artificial sequence
<220> FEATURE:

```
<223> OTHER INFORMATION: Synthetic oligodeoxynucleotide

<400> SEQUENCE: 62
tcgtcgtttg cgtcgt                                                   16

<210> SEQ ID NO 63
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 63
tcgtcgtttg cgtcgtt                                                  17

<210> SEQ ID NO 64
<211> LENGTH: 14
<212> TYPE: DNA
<213> ORGANISM: Artificial sequence
<220> FEATURE:
<223> OTHER INFORMATION: Synthetic oligodeoxynucleotide

<400> SEQUENCE: 64
tcgtcgtttg tcgt                                                     14

<210> SEQ ID NO 65
<211> LENGTH: 15
<212> TYPE: DNA
<213> ORGANISM: Artificial sequence
<220> FEATURE:
<223> OTHER INFORMATION: Synthetic oligodeoxynucleotide

<400> SEQUENCE: 65
tcgtcgtttg tcgtt                                                    15

<210> SEQ ID NO 66
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (7)..(9)
<223> OTHER INFORMATION: 2'-deoxyuracil
<220> FEATURE:
<221> NAME/KEY: misc_feature
<222> LOCATION: (15)..(18)
<223> OTHER INFORMATION: 2'-deoxyuracil

<400> SEQUENCE: 66
tcgtcgnnnc gtcgnnnngt cgtt                                          24

<210> SEQ ID NO 67
<211> LENGTH: 15
<212> TYPE: DNA
<213> ORGANISM: Artificial sequence
<220> FEATURE:
<223> OTHER INFORMATION: Synthetic oligodeoxynucleotide

<400> SEQUENCE: 67
tcgttttgtc gtttt                                                    15

<210> SEQ ID NO 68
<211> LENGTH: 19
<212> TYPE: DNA
<213> ORGANISM: Artificial sequence
<220> FEATURE:
```

```
<223> OTHER INFORMATION: Synthetic oligodeoxynucleotide

<400> SEQUENCE: 68
tcgttttgtc gttttttt                                              19

<210> SEQ ID NO 69
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 69 tcgtttttt tcgtttt                                                17

<210> SEQ ID NO 70
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 70
tcgttgtttt cgtcgtt                                               17

<210> SEQ ID NO 71
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 71
tcgttgtttt cgttgtt                                               17

<210> SEQ ID NO 72
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 72
tcgttgtttt tgtcgtt                                               17

<210> SEQ ID NO 73
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 73
tcgttgtttt tgttgtt                                               17

<210> SEQ ID NO 74
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (4)..(4)
<223> OTHER INFORMATION: 2'-deoxyuracil
<220> FEATURE:
<221> NAME/KEY: misc_feature
<222> LOCATION: (18)..(18)
```

```
<223> OTHER INFORMATION: 2'-deoxyuracil
<220> FEATURE:
<221> NAME/KEY: misc_feature
<222> LOCATION: (20)..(20)
<223> OTHER INFORMATION: 2'-deoxyuracil

<400> SEQUENCE: 74
tcgncgtttt gtcgtttngn cgtt                                          24

<210> SEQ ID NO 75
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 75
tgtcgttgtc gttgtcgttg tcgtt                                         25

<210> SEQ ID NO 76
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 76
tgtcgttgtc gttgtcgttg tcgtt                                         25

<210> SEQ ID NO 77
<211> LENGTH: 15
<212> TYPE: DNA
<213> ORGANISM: Artificial sequence
<220> FEATURE:
<223> OTHER INFORMATION: Synthetic oligodeoxynucleotide

<400> SEQUENCE: 77
tgtcgtttcg tcgtt                                                    15

<210> SEQ ID NO 78
<211> LENGTH: 15
<212> TYPE: DNA
<213> ORGANISM: Artificial sequence
<220> FEATURE:
<223> OTHER INFORMATION: Synthetic oligodeoxynucleotide

<400> SEQUENCE: 78
tgtcgttttg tcgtt                                                    15

<210> SEQ ID NO 79
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 79
ttagttcgta gttcttcgtt                                               20

<210> SEQ ID NO 80
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 80
```

```
ttcgtcgttt cgtcgtt                                              17

<210> SEQ ID NO 81
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 81
ttcgtcgttt cgtcgttt                                             18

<210> SEQ ID NO 82
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 82
ttcgtcgttt tgtcgtt                                              17

<210> SEQ ID NO 83
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 83
ttcgttctta gttcgtagtt                                           20

<210> SEQ ID NO 84
<211> LENGTH: 14
<212> TYPE: DNA
<213> ORGANISM: Artificial sequence
<220> FEATURE:
<223> OTHER INFORMATION: Synthetic oligodeoxynucleotide

<400> SEQUENCE: 84
tttcgacgtc gttt                                                 14

<210> SEQ ID NO 85
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 85
ttttcgtcgt tttgtcgtcg t                                         21

<210> SEQ ID NO 86
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 86
ttttcgtcgt tttgtcgtcg tttt                                      24

<210> SEQ ID NO 87
<211> LENGTH: 23
<212> TYPE: DNA
<213> ORGANISM: Artificial sequence
<220> FEATURE:
```

<223> OTHER INFORMATION: Synthetic oligodeoxynucleotide

<400> SEQUENCE: 87
ttttcgtcgt ttttttcgt cgt                                        23

<210> SEQ ID NO 88
<211> LENGTH: 26
<212> TYPE: DNA
<213> ORGANISM: Artificial sequence
<220> FEATURE:
<223> OTHER INFORMATION: Synthetic oligodeoxynucleotide

<400> SEQUENCE: 88
ttttcgtcgt ttttttcgt cgtttt                                     26

<210> SEQ ID NO 89
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 89
ttttcgtcgt tttgtcgtcg tttt                                      24

<210> SEQ ID NO 90
<211> LENGTH: 15
<212> TYPE: DNA
<213> ORGANISM: Artificial sequence
<220> FEATURE:
<223> OTHER INFORMATION: Synthetic oligodeoxynucleotide

<400> SEQUENCE: 90
ttttcgtttt gtcgt                                                15

<210> SEQ ID NO 91
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 91
ttttcgtttt gtcgtttt                                             18

<210> SEQ ID NO 92
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 92
ttttcgtttt ttttcgt                                              17

<210> SEQ ID NO 93
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 93
ttttcgtttt ttttcgtttt                                           20

<210> SEQ ID NO 94

```
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 94
ttttcgtttt gtcgtttt                                                 18

<210> SEQ ID NO 95
<211> LENGTH: 19
<212> TYPE: DNA
<213> ORGANISM: Artificial sequence
<220> FEATURE:
<223> OTHER INFORMATION: Synthetic oligodeoxynucleotide

<400> SEQUENCE: 95 tttttttcg ttttgtcgt                                                 19

<210> SEQ ID NO 96
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 96
ttgtcgtttt cgtcgtt                                                  17

<210> SEQ ID NO 97
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 97
ttgtcgtttt cgttgtt                                                  17

<210> SEQ ID NO 98
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 98
ttgtcgtttt tgtcgtt                                                  17

<210> SEQ ID NO 99
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 99
ttgtcgtttt tgttgtt                                                  17

<210> SEQ ID NO 100
<211> LENGTH: 23
<212> TYPE: DNA
<213> ORGANISM: Artificial sequence
<220> FEATURE:
<223> OTHER INFORMATION: Synthetic oligodeoxynucleotide

<400> SEQUENCE: 100
```
tcgtcgtttt gtcgtttgtc gtt                           23

<210> SEQ ID NO 101
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 101
tcgtcgtttt gtcgtt                                   16

<210> SEQ ID NO 102
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 102
tcgtcgtttc gtcgtt                                   16

<210> SEQ ID NO 103
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 103
tgtcgttgtc gttgtcgttg tcgtt                         25

<210> SEQ ID NO 104
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 104
tcgtcgtttt cggcggccgc cg                            22

<210> SEQ ID NO 105
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 105
tcgtcgtttt gtcgttttgt cgtt                          24

<210> SEQ ID NO 106
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 106
tcgtcgtttt gtcgttttgt cgtt                          24

<210> SEQ ID NO 107
<211> LENGTH: 24
<212> TYPE: DNA
<213> ORGANISM: Artificial sequence
<220> FEATURE:

-continued

<223> OTHER INFORMATION: Synthetic oligodeoxynucleotide

<400> SEQUENCE: 107
tcgtcgtttt gtcgttttgt cgtt                                  24

<210> SEQ ID NO 108
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 108
tcgtcgtttt gtcgttttgt cgtt                                  24

<210> SEQ ID NO 109
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 109
tcgtcgtttt gtcgttttgt cgtt                                  24

<210> SEQ ID NO 110
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 110
tcgtcgtttt gtcgttttgt cgtt                                  24

<210> SEQ ID NO 111
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 111
tcgtcgtttt gtcgttttgt cgtt                                  24

<210> SEQ ID NO 112
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 112
tcgtcgtttt gtcgttttgt cgtt                                  24

<210> SEQ ID NO 113
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 113
tcgtcgtttt gtcgttttgt cgtt                                  24

<210> SEQ ID NO 114

```
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 114
tcgtcgtttt gtcgttttgt cgtt                                              24

<210> SEQ ID NO 115
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 115
tcgtcgtttt gtcgttttgt cgtt                                              24

<210> SEQ ID NO 116
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 116
tcgtcgtttt gtcgttttgt cgtt                                              24

<210> SEQ ID NO 117
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 117
tcgtcgtttt gtcgttttgt cgtt                                              24

<210> SEQ ID NO 118
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 118
tcgtcgtttt gtcgttttgt cgtt                                              24

<210> SEQ ID NO 119
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 119
tcgtcgtttt gtcgttttgt cgtt                                              24

<210> SEQ ID NO 120
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 120
```

```
tcgtcgtttt gtcgttttgt cgtt                                              24

<210> SEQ ID NO 121
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 121
tcgtcgtttt gtcgttttgt cgtt                                              24

<210> SEQ ID NO 122
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 122
tcgtcgtttt gtcgttttgt cgtt                                              24

<210> SEQ ID NO 123
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 123
tcgtcgtttt gtcgttttgt cgtt                                              24

<210> SEQ ID NO 124
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 124
tcgtcgtttt gtcgttttgt cgtt                                              24

<210> SEQ ID NO 125
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 125
tcgtcgtttt gtcgttttgt cgtt                                              24

<210> SEQ ID NO 126
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 126
tcgtcgtttt gtcgttttgt cgtt                                              24

<210> SEQ ID NO 127
<211> LENGTH: 24
<212> TYPE: DNA
<213> ORGANISM: Artificial sequence
<220> FEATURE:
```

<223> OTHER INFORMATION: Synthetic oligodeoxynucleotide

<400> SEQUENCE: 127
tcgtcgtttt gtcgttttgt cgtt                                              24

<210> SEQ ID NO 128
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 128
tcgtcgtttt gtcgttttgt cgtt                                              24

<210> SEQ ID NO 129
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 129
tcgtcgtttt gtcgttttgt cgtt                                              24

<210> SEQ ID NO 130
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 130
tcgtcgtttt gtcgttttgt cgtt                                              24

<210> SEQ ID NO 131
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 131
tcgtcgtttt gtcgttttgt cgtt                                              24

<210> SEQ ID NO 132
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 132
tcgtcgtttt gtcgttttgt cgtt                                              24

<210> SEQ ID NO 133
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 133
tcgtcgtttt gtcgttttgt cgtt                                              24

<210> SEQ ID NO 134

```
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 134
tcgtcgtttt gtcgttttgt cgtt                                              24

<210> SEQ ID NO 135
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 135
tcgtcgtttt gtcgttttgt cgtt                                              24

<210> SEQ ID NO 136
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 136
tcgtcgtttt gtcgttttgt cgtt                                              24

<210> SEQ ID NO 137
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 137
tcgtcgtttt gtcgttttgt cgtt                                              24

<210> SEQ ID NO 138
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 138
tcgtcgtttt gtcgttttgt cgtt                                              24

<210> SEQ ID NO 139
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 139
tcgtcgtttt gtcgttttgt cgtt                                              24

<210> SEQ ID NO 140
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 140
```

-continued

```
tcgtcgtttt gtcgttttgt cgtt                                              24

<210> SEQ ID NO 141
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 141
tcgtcgtttt gtcgttttgt cgtt                                              24

<210> SEQ ID NO 142
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 142
tcgtcgtttt gtcgttttgt cgtt                                              24

<210> SEQ ID NO 143
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 143
tcgtcgtttt gtcgttttgt cgtt                                              24

<210> SEQ ID NO 144
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 144
tcgtcgtttt gtcgttttgt cgtt                                              24

<210> SEQ ID NO 145
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 145
tcgtcgtttt gtcgttttgt cgtt                                              24

<210> SEQ ID NO 146
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 146
tcgtcgtttt gtcgttttgt cgtt                                              24

<210> SEQ ID NO 147
<211> LENGTH: 24
<212> TYPE: DNA
<213> ORGANISM: Artificial sequence
<220> FEATURE:
```

<223> OTHER INFORMATION: Synthetic oligodeoxynucleotide

<400> SEQUENCE: 147
tcgtcgtttt gtcgttttgt cgtt                                          24

<210> SEQ ID NO 148
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 148
tcgtcgtttt gtcgttttgt cgtt                                          24

<210> SEQ ID NO 149
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 149
tcgtcgtttt gtcgttttgt cgtt                                          24

<210> SEQ ID NO 150
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 150
tcgtcgtttt gtcgttttgt cgtt                                          24

<210> SEQ ID NO 151
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 151
tcgtcgtttt gtcgttttgt cgtt                                          24

<210> SEQ ID NO 152
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 152
tcgtcgtttt gtcgttttgt cgtt                                          24

<210> SEQ ID NO 153
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 153
tcgtcgtttt gtcgttttgt cgtt                                          24

<210> SEQ ID NO 154

```
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 154
tcgtcgtttt gtcgttttgt cgtt                                              24

<210> SEQ ID NO 155
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 155
tcgtcgtttt gtcgttttgt cgtt                                              24

<210> SEQ ID NO 156
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 156
tcgtcgtttt gtcgttttgt cgtt                                              24

<210> SEQ ID NO 157
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 157
tcgtcgtttt gtcgttttgt cgtt                                              24

<210> SEQ ID NO 158
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 158
tcgtcgtttt gtcgttttgt cgtt                                              24

<210> SEQ ID NO 159
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 159
tcgtcgtttt gtcgttttgt cgtt                                              24

<210> SEQ ID NO 160
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 160
```

-continued

```
tcgtcgtttt gtcgttttgt cgtt                                              24

<210> SEQ ID NO 161
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 161
tcgtcgtttt gtcgttttgt cgtt                                              24

<210> SEQ ID NO 162
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 162
tcgtcgtttt gtcgttttgt cgtt                                              24

<210> SEQ ID NO 163
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 163
tcgtcgtttt gtcgttttgt cgtt                                              24

<210> SEQ ID NO 164
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 164
tcgtcgtttt gtcgttttgt cgtt                                              24

<210> SEQ ID NO 165
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 165
tcgtcgtttt gtcgttttgt cgtt                                              24

<210> SEQ ID NO 166
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 166
tcgtcgtttt gtcgttttgt cgtt                                              24

<210> SEQ ID NO 167
<211> LENGTH: 24
<212> TYPE: DNA
<213> ORGANISM: Artificial sequence
<220> FEATURE:
```

```
<223> OTHER INFORMATION: Synthetic oligodeoxynucleotide

<400> SEQUENCE: 167
tcgtcgtttt gtcgttttgt cgtt                                              24

<210> SEQ ID NO 168
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 168
tcgtcgtttt gtcgttttgt cgtt                                              24

<210> SEQ ID NO 169
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 169
tcgtcgtttt gtcgttttgt cgtt                                              24

<210> SEQ ID NO 170
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 170
tcgtcgtttt gtcgttttgt cgtt                                              24

<210> SEQ ID NO 171
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 171
tcgtcgtttt gtcgttttgt cgtt                                              24

<210> SEQ ID NO 172
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 172
tcgtcgtttt gtcgttttgt cgtt                                              24

<210> SEQ ID NO 173
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 173
tcgtcgtttt gtcgttttgt cgtt                                              24

<210> SEQ ID NO 174
```

```
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 174
tcgtcgtttt gtcgttttgt cgtt                                              24

<210> SEQ ID NO 175
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 175
tcgtcgtttt gtcgttttgt cgtt                                              24

<210> SEQ ID NO 176
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 176
tcgtcgtttt gtcgttttgt cgtt                                              24

<210> SEQ ID NO 177
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 177
tcgtcgtttt gtcgttttgt cgtt                                              24

<210> SEQ ID NO 178
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 178
tcgtcgtttt gtcgttttgt cgtt                                              24

<210> SEQ ID NO 179
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 179
tcgtcgtttt gtcgttttgt cgtt                                              24

<210> SEQ ID NO 180
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 180
```
tcgtcgtttt gtcgttttgt cgtt                                          24

<210> SEQ ID NO 181
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 181
tcgtcgtttt gtcgttttgt cgtt                                          24

<210> SEQ ID NO 182
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 182
tcgtcgtttt gtcgttttgt cgtt                                          24

<210> SEQ ID NO 183
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 183
tcgtcgtttt gtcgttttgt cgtt                                          24

<210> SEQ ID NO 184
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 184
tcgtcgtttt gtcgttttgt cgtt                                          24

<210> SEQ ID NO 185
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 185
tcgtcgtttt gtcgttttgt cgtt                                          24

<210> SEQ ID NO 186
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 186
tcgtcgtttt gtcgttttgt cgtt                                          24

<210> SEQ ID NO 187
<211> LENGTH: 24
<212> TYPE: DNA
<213> ORGANISM: Artificial sequence
<220> FEATURE:

-continued

<223> OTHER INFORMATION: Synthetic oligodeoxynucleotide

<400> SEQUENCE: 187
tcgtcgtttt gtcgttttgt cgtt    24

<210> SEQ ID NO 188
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 188
tcgtcgtttt gtcgttttgt cgtt    24

<210> SEQ ID NO 189
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 189
tcgtcgtttt gtcgttttgt cgtt    24

<210> SEQ ID NO 190
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 190
tcgtcgtttt gtcgttttgt cgtt    24

<210> SEQ ID NO 191
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 191
tcgtcgtttt gtcgttttgt cgtt    24

<210> SEQ ID NO 192
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 192
tcgtcgtttt gtcgttttgt cgtt    24

<210> SEQ ID NO 193
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 193
tcgtcgtttt gtcgttttgt cgtt    24

<210> SEQ ID NO 194

```
<210> SEQ ID NO 194
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 194
tcgtcgtttt gtcgttttgt cgtt                                              24

<210> SEQ ID NO 195
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 195
tcgtcgtttt gtcgttttgt cgtt                                              24

<210> SEQ ID NO 196
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 196
tcgtcgtttt gtcgttttgt cgtt                                              24

<210> SEQ ID NO 197
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 197
tcgtcgtttt gtcgttttgt cgtt                                              24

<210> SEQ ID NO 198
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 198
tcgtcgtttt gtcgttttgt cgtt                                              24

<210> SEQ ID NO 199
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 199
tcgtcgtttt gtcgttttgt cgtt                                              24

<210> SEQ ID NO 200
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 200
```
tcgtcgtttt gtcgttttgt cgtt                                          24

<210> SEQ ID NO 201
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 201
tcgtcgtttt gtcgttttgt cgtt                                          24

<210> SEQ ID NO 202
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 202
tcgtcgtttt gtcgttttgt cgtt                                          24

<210> SEQ ID NO 203
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 203
tcgtcgtttt gtcgttttgt cgtt                                          24

<210> SEQ ID NO 204
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 204
tcgtcgtttt gtcgttttgt cgtt                                          24

<210> SEQ ID NO 205
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 205
tcgtcgtttt gtcgttttgt cgtt                                          24

<210> SEQ ID NO 206
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 206
tcgtcgtttt gtcgttttgt cgtt                                          24

<210> SEQ ID NO 207
<211> LENGTH: 24
<212> TYPE: DNA
<213> ORGANISM: Artificial sequence
<220> FEATURE:

<223> OTHER INFORMATION: Synthetic oligodeoxynucleotide

<400> SEQUENCE: 207
tcgtcgtttt gtcgttttgt cgtt          24

<210> SEQ ID NO 208
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 208
tcgtcgtttt gtcgttttgt cgtt          24

<210> SEQ ID NO 209
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 209
tcgtcgtttt gtcgttttgt cgtt          24

<210> SEQ ID NO 210
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 210
tcgtcgtttt gtcgttttgt cgtt          24

<210> SEQ ID NO 211
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 211
tcgtcgtttt gtcgttttgt cgtt          24

<210> SEQ ID NO 212
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 212
tcgtcgtttt gtcgttttgt cgtt          24

<210> SEQ ID NO 213
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 213
tcgtcgtttt gtcgttttgt cgtt          24

<210> SEQ ID NO 214

```
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 214
tcgtcgtttt gtcgttttgt cgtt                                              24

<210> SEQ ID NO 215
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 215
tcgtcgtttt gtcgttttgt cgtt                                              24

<210> SEQ ID NO 216
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 216
tcgtcgtttt gtcgttttgt cgtt                                              24

<210> SEQ ID NO 217
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 217
tcgtcgtttt gtcgttttgt cgtt                                              24

<210> SEQ ID NO 218
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 218
tcgtcgtttt gtcgttttgt cgtt                                              24

<210> SEQ ID NO 219
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 219
tcgtcgtttt gtcgttttgt cgtt                                              24

<210> SEQ ID NO 220
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 220
```

```
tcgtcgtttt gtcgttttgt cgtt                                              24

<210> SEQ ID NO 221
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 221
tcgtcgtttt gtcgttttgt cgtt                                              24

<210> SEQ ID NO 222
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 222
tcgtcgtttt gtcgttttgt cgtt                                              24

<210> SEQ ID NO 223
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 223
tcgtcgtttt gtcgttttgt cgtt                                              24

<210> SEQ ID NO 224
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 224
tcgtcgtttt gtcgttttgt cgtt                                              24

<210> SEQ ID NO 225
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 225
tcgtcgtttt gtcgttttgt cgtt                                              24

<210> SEQ ID NO 226
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 226
tcgtcgtttt gtcgttttgt cgtt                                              24

<210> SEQ ID NO 227
<211> LENGTH: 24
<212> TYPE: DNA
<213> ORGANISM: Artificial sequence
<220> FEATURE:
```

<223> OTHER INFORMATION: Synthetic oligodeoxynucleotide

<400> SEQUENCE: 227
tcgtcgtttt gtcgttttgt cgtt                                   24

<210> SEQ ID NO 228
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 228
tcgtcgtttt gtcgttttgt cgtt                                   24

<210> SEQ ID NO 229
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 229
tcgtcgtttt gtcgttttgt cgtt                                   24

<210> SEQ ID NO 230
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 230
tcgtcgtttt gtcgttttgt cgtt                                   24

<210> SEQ ID NO 231
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 231
tcgtcgtttt gtcgttttgt cgtt                                   24

<210> SEQ ID NO 232
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 232
tcgtcgtttt gtcgttttgt cgtt                                   24

<210> SEQ ID NO 233
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 233
tcgtcgtttt gtcgttttgt cgtt                                   24

<210> SEQ ID NO 234

```
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 234
tcgtcgtttt gtcgttttgt cgtt                                              24

<210> SEQ ID NO 235
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 235
tcgtcgtttt gtcgttttgt cgtt                                              24

<210> SEQ ID NO 236
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 236
tcgtcgtttt gtcgttttgt cgtt                                              24

<210> SEQ ID NO 237
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 237
tcgtcgtttt gtcgttttgt cgtt                                              24

<210> SEQ ID NO 238
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 238
tcgtcgtttt gtcgttttgt cgtt                                              24

<210> SEQ ID NO 239
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 239
tcgtcgtttt gtcgttttgt cgtt                                              24

<210> SEQ ID NO 240
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 240
```

-continued

```
tcgtcgtttt gtcgttttgt cgtt                                        24

<210> SEQ ID NO 241
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 241
tcgtcgtttt gtcgttttgt cgtt                                        24

<210> SEQ ID NO 242
<211> LENGTH: 23
<212> TYPE: DNA
<213> ORGANISM: Artificial sequence
<220> FEATURE:
<223> OTHER INFORMATION: Synthetic oligodeoxynucleotide

<400> SEQUENCE: 242
tcgtcgtttt gtcgttttgt cgt                                         23

<210> SEQ ID NO 243
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 243
tgtcgttgtc gttgtcgttg tcgtt                                       25

<210> SEQ ID NO 244
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 244
tgtcgttgtc gttgtcgttg tcgtt                                       25

<210> SEQ ID NO 245
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 245
tcgtcgtttc gtcgtt                                                 16

<210> SEQ ID NO 246
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 246
tcgtcgtttt gtcgtt                                                 16

<210> SEQ ID NO 247
<211> LENGTH: 22
<212> TYPE: DNA
<213> ORGANISM: Artificial sequence
<220> FEATURE:
```

-continued

<223> OTHER INFORMATION: Synthetic oligodeoxynucleotide

<400> SEQUENCE: 247
tcgtcgtttt cggcggccgc cg    22

<210> SEQ ID NO 248
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 248
tcgccgtttt cggcggccgc cg    22

<210> SEQ ID NO 249
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 249
tcgccgtttt cggcggccgc cg    22

<210> SEQ ID NO 250
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 250
tcgtcgtttt cggcggccgc cg    22

<210> SEQ ID NO 251
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 251
tcgtcgtttt cggcggccgc cg    22

<210> SEQ ID NO 252
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 252
tcgccgtttt cggcggccgc cg    22

<210> SEQ ID NO 253
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 253
tcgccgtttt cggcggccgc cg    22

<210> SEQ ID NO 254

```
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 254
tcgtcgtttt cggcggccgc cg                                                  22

<210> SEQ ID NO 255
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 255
tcgtcgtttt cggcggccgc cg                                                  22

<210> SEQ ID NO 256
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 256
tcgtcgtttt cggcggccgc cg                                                  22

<210> SEQ ID NO 257
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 257
tcgtcgtttt cggcggccgc cg                                                  22

<210> SEQ ID NO 258
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 258
tgtcgttgtc gttgtcgttg tcgtt                                               25

<210> SEQ ID NO 259
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 259
tcgtcgtttc gtcgttttgt cgtt                                                24

<210> SEQ ID NO 260
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 260
```

-continued tcgtcgtttc gtcgttttgt cgtt                                              24

<210> SEQ ID NO 261
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 261
tcgtcgtttt gacgttttgt cgtt                                              24

<210> SEQ ID NO 262
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 262
tcgtcgtttc gacgttttgt cgtt                                              24

<210> SEQ ID NO 263
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 263
tcgtcgtttt gacgttttgt cgtt                                              24

<210> SEQ ID NO 264
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 264
tcgtcgtttt gacgttttgt cgtt                                              24

<210> SEQ ID NO 265
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 265
tcgtcgtttt gacgtttt                                                     18

<210> SEQ ID NO 266
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 266
tcgtcgtttt gacgtt                                                       16

<210> SEQ ID NO 267
<211> LENGTH: 16
<212> TYPE: DNA
<213> ORGANISM: Artificial sequence
<220> FEATURE:

```
<223> OTHER INFORMATION: Synthetic oligodeoxynucleotide

<400> SEQUENCE: 267
tcgtcgtttc gacgtt                                                    16

<210> SEQ ID NO 268
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 268
gttctcgctg gtgagtttca                                                20

<210> SEQ ID NO 269
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 269
gttctcgctg gtgagtttca                                                20

<210> SEQ ID NO 270
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 270
tcgtcgtttc gtcgtttcgt cgtt                                           24

<210> SEQ ID NO 271
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 271
tcgtcgtttc gtcgtttcgt cgtt                                           24

<210> SEQ ID NO 272
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (10)..(10)
<223> OTHER INFORMATION: 2'-deoxyuracil

<400> SEQUENCE: 272
tcgtcgtttn gtcgttttgt cgtt                                           24

<210> SEQ ID NO 273
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (10)..(10)
```

```
<223> OTHER INFORMATION: 2'-deoxyuracil

<400> SEQUENCE: 273
tcgtcgtttn gtcgttttgt cgtt                                              24

<210> SEQ ID NO 274
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (10)..(10)
<223> OTHER INFORMATION: 2'-deoxyuracil

<400> SEQUENCE: 274
tcgtcgtttn gtcgttttgt cgtt                                              24

<210> SEQ ID NO 275
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 275
tcgcgtcgtt cggcgcgcgc cg                                                22

<210> SEQ ID NO 276
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 276
tcgtcgtttt gtcgttttgt cgtt                                              24

<210> SEQ ID NO 277
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (4)..(4)
<223> OTHER INFORMATION: 2'-deoxyuracil
<220> FEATURE:
<221> NAME/KEY: misc_feature
<222> LOCATION: (18)..(18)
<223> OTHER INFORMATION: 2'-deoxyuracil
<220> FEATURE:
<221> NAME/KEY: misc_feature
<222> LOCATION: (20)..(20)
<223> OTHER INFORMATION: 2'-deoxyuracil

<400> SEQUENCE: 277
tcgncgtttt gtcgtttngn cgtt                                              24

<210> SEQ ID NO 278
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (4)..(4)
```

```
<223> OTHER INFORMATION: 2'-deoxyuracil
<220> FEATURE:
<221> NAME/KEY: misc_feature
<222> LOCATION: (18)..(18)
<223> OTHER INFORMATION: 2'-deoxyuracil
<220> FEATURE:
<221> NAME/KEY: misc_feature
<222> LOCATION: (20)..(20)
<223> OTHER INFORMATION: 2'-deoxyuracil

<400> SEQUENCE: 278
tcgncgtttt gtcgtttngn cgtt                                              24

<210> SEQ ID NO 279
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (7)..(9)
<223> OTHER INFORMATION: 2'-deoxyuracil
<220> FEATURE:
<221> NAME/KEY: misc_feature
<222> LOCATION: (15)..(18)
<223> OTHER INFORMATION: 2'-deoxyuracil

<400> SEQUENCE: 279
tcgtcgnnnt gtcgnnnngt cgtt                                              24

<210> SEQ ID NO 280
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (7)..(9)
<223> OTHER INFORMATION: 2'-deoxyuracil
<220> FEATURE:
<221> NAME/KEY: misc_feature
<222> LOCATION: (15)..(18)
<223> OTHER INFORMATION: 2'-deoxyuracil

<400> SEQUENCE: 280
tcgtcgnnnc gtcgnnnngt cgtt                                              24

<210> SEQ ID NO 281
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 281
aacgtcgttt tcgtcgtt                                                     18

<210> SEQ ID NO 282
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 282
aacgtcgttt tcgtcgtt                                                     18

<210> SEQ ID NO 283
```

```
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 283
tcgtcgtttt cgtcgt                                                       16

<210> SEQ ID NO 284
<211> LENGTH: 17
<212> TYPE: DNA
<213> ORGANISM: Artificial sequence
<220> FEATURE:
<223> OTHER INFORMATION: Synthetic oligodeoxynucleotide

<400> SEQUENCE: 284
tcgtcgtttt cgtcgtt                                                      17

<210> SEQ ID NO 285
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 285
aacgtcgttt tcgtcgtt                                                     18

<210> SEQ ID NO 286
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 286
tgctgctttt gtgcttttgt gctt                                              24

<210> SEQ ID NO 287
<211> LENGTH: 25
<212> TYPE: DNA
<213> ORGANISM: Artificial sequence
<220> FEATURE:
<223> OTHER INFORMATION: Synthetic oligodeoxynucleotide

<400> SEQUENCE: 287
tgtcgttgtc gttgtcgttg tcgtt                                             25

<210> SEQ ID NO 288
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 288 tcgtttttt cgttttttc gttt                                                24

<210> SEQ ID NO 289
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 289
```

```
tcgtcgtttt tcggtcgttt t                                          21
```

<210> SEQ ID NO 290
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 290

```
tcgtcgtttt tcgtgcgttt tt                                         22
```

<210> SEQ ID NO 291
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 291

```
tcgtcgtttt cgttttttc gttt                                        24
```

<210> SEQ ID NO 292
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 292

```
tcgttttgtc gttttttcg a                                           21
```

<210> SEQ ID NO 293
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 293

```
tcgtcgtttt gtcgttttgt cgtt                                       24
```

<210> SEQ ID NO 294
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 294

```
tcgtcgtttt gtcgttttgt cgtt                                       24
```

<210> SEQ ID NO 295
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 295

```
tcgtcgtttt cggcggccgc cg                                         22
```

<210> SEQ ID NO 296
<211> LENGTH: 29
<212> TYPE: DNA
<213> ORGANISM: Artificial sequence
<220> FEATURE:

```
<223> OTHER INFORMATION: Synthetic oligodeoxynucleotide
<220> FEATURE:
<221> NAME/KEY: misc_feature
<222> LOCATION: (13)..(18)
<223> OTHER INFORMATION: n is a, c, g, or t, and any 1-6 may be absent
<220> FEATURE:
<221> NAME/KEY: misc_feature
<222> LOCATION: (21)..(27)
<223> OTHER INFORMATION: n is a, c, g, or t, and any 1-7 may be absent

<400> SEQUENCE: 296
tcgtcgtttt gannnnnncg nnnnnnntt                              29

<210> SEQ ID NO 297
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 297
tcgtcgtttt gaccggttcg tgtt                                   24

<210> SEQ ID NO 298
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 298
tcgtcgtttt gacgttttgt cgtt                                   24

<210> SEQ ID NO 299
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 299
tcgtcgtttt gacgtttt                                          18

<210> SEQ ID NO 300
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 300
tcgtcgtttt gacgtt                                            16

<210> SEQ ID NO 301
<211> LENGTH: 31
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (6)..(9)
<223> OTHER INFORMATION: n is a, c, g, or t, and any 1-4 may be absent
<220> FEATURE:
<221> NAME/KEY: misc_feature
<222> LOCATION: (16)..(20)
<223> OTHER INFORMATION: n is a, c, g, or t, and any 1-4 may be absent
<220> FEATURE:
<221> NAME/KEY: misc_feature
<222> LOCATION: (23)..(29)
```

```
<223> OTHER INFORMATION: n is a, c, g, or t, and any 1-7 may be absent

<400> SEQUENCE: 301
tcgwtnnnnc gttttnnnnn cgnnnnnnnt t                                    31

<210> SEQ ID NO 302
<211> LENGTH: 18
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 302
tcgatncgtt ttncgntt                                                   18

<210> SEQ ID NO 303
<211> LENGTH: 18
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 303
tcgttncgtt ttncgntt                                                   18

<210> SEQ ID NO 304
<211> LENGTH: 23
<212> TYPE: DNA
<213> ORGANISM: Artificial sequence
<220> FEATURE:
<223> OTHER INFORMATION: Synthetic oligodeoxynucleotide

<400> SEQUENCE: 304
tcgatcgttt ttcgtgcgtt ttt                                             23

<210> SEQ ID NO 305
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 305
tcgttttgac gttttgtcgt t                                               21

<210> SEQ ID NO 306
```

```
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 306
tcgtcgnnnc gncgnnncgn cgtt                                          24

<210> SEQ ID NO 307
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 307
tcgtcgnnnc gncgnnncgn cgtt                                          24

<210> SEQ ID NO 308
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 308
tcgtcgttac gncgttacgn cgtt                                          24

<210> SEQ ID NO 309
<211> LENGTH: 24
<212> TYPE: DNA
<213> ORGANISM: Artificial sequence
<220> FEATURE:
```

```
<223> OTHER INFORMATION: Synthetic oligodeoxynucleotide
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t

<400> SEQUENCE: 309
tcgtcgnnnc gtcgnnncgt cgtt                                           24

<210> SEQ ID NO 310
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 310
tcgtcgttac gtcgttacgt cgtt                                           24

<210> SEQ ID NO 311
<211> LENGTH: 32
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (4)..(8)
<223> OTHER INFORMATION: n is a, c, g, or t, and any 1-4 may be absent
<220> FEATURE:
<221> NAME/KEY: misc_feature
<222> LOCATION: (11)..(15)
<223> OTHER INFORMATION: n is a, c, g, or t, and any 1-4 may be absent
<220> FEATURE:
<221> NAME/KEY: misc_feature
<222> LOCATION: (16)..(20)
<223> OTHER INFORMATION: n is a, c, g, or t, and any 1-4 may be absent
<220> FEATURE:
<221> NAME/KEY: misc_feature
<222> LOCATION: (23)..(27)
<223> OTHER INFORMATION: n is a, c, g, or t, and any 1-4 may be absent

<400> SEQUENCE: 311 tcgnnnncg nnnnnnnnnn cgnnnntcg tt                                    32

<210> SEQ ID NO 312
<211> LENGTH: 44
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (4)..(8)
<223> OTHER INFORMATION: n is a, c, g, or t, and any 1-4 may be absent
<220> FEATURE:
<221> NAME/KEY: misc_feature
<222> LOCATION: (11)..(15)
<223> OTHER INFORMATION: n is a, c, g, or t, and any 1-4 may be absent
<220> FEATURE:
<221> NAME/KEY: misc_feature
<222> LOCATION: (16)..(20)
<223> OTHER INFORMATION: n is a, c, g, or t, and any 1-4 may be absent
<220> FEATURE:
<221> NAME/KEY: misc_feature
<222> LOCATION: (23)..(27)
<223> OTHER INFORMATION: n is a, c, g, or t, and any 1-4 may be absent
<220> FEATURE:
<221> NAME/KEY: misc_feature
<222> LOCATION: (28)..(32)
```

```
<223> OTHER INFORMATION: n is a, c, g, or t, and any 1-4 may be absent
<220> FEATURE:
<221> NAME/KEY: misc_feature
<222> LOCATION: (35)..(39)
<223> OTHER INFORMATION: n is a, c, g, or t, and any 1-4 may be absent

<400> SEQUENCE: 312 tcgnnnncg nnnnnnnnnn cgnnnnnnnn nncgnnnnt cgtt                           44

<210> SEQ ID NO 313
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 313
tcgtcgtttt gacgttttgt cgtt                                               24

<210> SEQ ID NO 314
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 314
tcgacgtttt gtcgttttgt cgtt                                               24

<210> SEQ ID NO 315
<211> LENGTH: 24
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (6)..(15)
<223> OTHER INFORMATION: n is a, c, g, or t, any 1-6 may be absent,
      and at least one phosphodiester-linked cg dinucleotide is present.
<220> FEATURE:
<221> NAME/KEY: misc_feature
<222> LOCATION: (22)..(24)
<223> OTHER INFORMATION: n is a, c, g, or t, and any 1-3 may be absent

<400> SEQUENCE: 315
tcgcgnnnnn nnnncgcgc gnnn                                                24

<210> SEQ ID NO 316
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 316
tcgcgacgtt cggcgcgcgc cg                                                 22

<210> SEQ ID NO 317
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 317
tcgcgacgtt cgcgcgcgcg                                                    20
```

```
<210> SEQ ID NO 318
<211> LENGTH: 28
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (14)..(21)
<223> OTHER INFORMATION: n is a, c, g, or t, any 1-4 may be absent,
      and at least one phosphodiester-linked cg dinucleotide is present.

<400> SEQUENCE: 318
ttgsstgsst tttnnnnnnn nttttttt                                       28

<210> SEQ ID NO 319
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 319
ttgcgtgcgt tttgacgttt tttt                                           24

<210> SEQ ID NO 320
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 320
ttggctggct tttgacgttt tttt                                           24

<210> SEQ ID NO 321
<211> LENGTH: 22
<212> TYPE: DNA
<213> ORGANISM: Artificial sequence
<220> FEATURE:
<223> OTHER INFORMATION: Synthetic oligodeoxynucleotide

<400> SEQUENCE: 321
tcgcgacgtt cggcgcgcgc cg                                             22

<210> SEQ ID NO 322
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 322
tcgtcgttac gtcgttacgt cgtt                                           24

<210> SEQ ID NO 323
<211> LENGTH: 23
<212> TYPE: DNA
<213> ORGANISM: Artificial sequence
<220> FEATURE:
<223> OTHER INFORMATION: Synthetic oligodeoxynucleotide

<400> SEQUENCE: 323
tcgatcgttt ttcgtgcgtt ttt                                            23

<210> SEQ ID NO 324
<211> LENGTH: 18
<212> TYPE: DNA
```

```
<213> ORGANISM: Artificial sequence
<220> FEATURE:
<223> OTHER INFORMATION: Synthetic oligodeoxynucleotide

<400> SEQUENCE: 324
tcgtcgtttt gacgtttt                                                    18

<210> SEQ ID NO 325
<211> LENGTH: 16
<212> TYPE: DNA
<213> ORGANISM: Artificial sequence
<220> FEATURE:
<223> OTHER INFORMATION: Synthetic oligodeoxynucleotide

<400> SEQUENCE: 325
tcgtcgtttt gacgtt                                                      16

<210> SEQ ID NO 326
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 326
tcgttttgac gttttgtcgt t                                                21

<210> SEQ ID NO 327
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 327
tcgtcgtttt gaccggttcg tgtt                                             24

<210> SEQ ID NO 328
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 328
tcgtcgtttt gacgttttgt cgtt                                             24

<210> SEQ ID NO 329
<211> LENGTH: 24
<212> TYPE: DNA
<213> ORGANISM: Artificial sequence
<220> FEATURE:
<223> OTHER INFORMATION: Synthetic oligodeoxynucleotide

<400> SEQUENCE: 329
tcgtcgtttt gacgttttgt cgtt                                             24

<210> SEQ ID NO 330
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 330
tccaggactt ctctcaggtt                                                  20
```

```
<210> SEQ ID NO 331
<211> LENGTH: 21
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 331
ttgnntgnnt tttnttttt t                                      21

<210> SEQ ID NO 332
<211> LENGTH: 13
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 332
tcgcgncgcg cgn                                              13

<210> SEQ ID NO 333
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 333
cgtcgttttg acgttttgtc gtt                                   23

<210> SEQ ID NO 334
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 334
gtcgttttga cgttttgtcg tt                                    22

<210> SEQ ID NO 335
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 335
tcgttttgac gttttgtcgt t                                     21
```

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
cgttttgacg ttttgtcgtt                                           20

<210> SEQ ID NO 337
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 337
gttttgacgt tttgtcgtt                                            19

<210> SEQ ID NO 338
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 338
ttttgacgtt ttgtcgtt                                             18

<210> SEQ ID NO 339
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 339
tttgacgttt tgtcgtt                                              17

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
ttgacgtttt gtcgtt                                               16

<210> SEQ ID NO 341
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 341
tgacgttttg tcgtt                                                15

<210> SEQ ID NO 342
<211> LENGTH: 14
<212> TYPE: DNA
<213> ORGANISM: Artificial sequence
<220> FEATURE:
<223> OTHER INFORMATION: Synthetic oligonucleotide -continued

<400> SEQUENCE: 342
gacgttttgt cgtt                                                         14

<210> SEQ ID NO 343
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 343
acgttttgtc gtt                                                          13

<210> SEQ ID NO 344
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 344
gttttgtcgt t                                                            11

<210> SEQ ID NO 345
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 345
gttttgtcgt t                                                            11

<210> SEQ ID NO 346
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 346
ttttgtcgtt                                                              10

<210> SEQ ID NO 347
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 347
tcgtcgtttt gacgttttgt cgt                                               23

<210> SEQ ID NO 348
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 348
tcgtcgtttt gacgttttgt cg                                                22

<210> SEQ ID NO 349
<211> LENGTH: 21
<212> TYPE: DNA

```
<213> ORGANISM: Artificial sequence
<220> FEATURE:
<223> OTHER INFORMATION: Synthetic oligonucleotide

<400> SEQUENCE: 349
tcgtcgtttt gacgttttgt c                                              21

<210> SEQ ID NO 350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 350
tcgtcgtttt gacgttttgt                                                20

<210> SEQ ID NO 351
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 351
tcgtcgtttt gacgttttg                                                 19

<210> SEQ ID NO 352
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 352
tcgtcgtttt gacgtttt                                                  18

<210> SEQ ID NO 353
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 353
tcgtcgtttt gacgttt                                                   17

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
tcgtcgtttt gacgtt                                                    16

<210> SEQ ID NO 355
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 355
tcgtcgtttt gacgt                                                     15
```

```
<210> SEQ ID NO 356
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 356
tcgtcgtttt gacg                                                        14

<210> SEQ ID NO 357
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 357
tcgtcgtttt gac                                                         13

<210> SEQ ID NO 358
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 358
tcgtcgtttt ga                                                          12

<210> SEQ ID NO 359
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 359
tcgtcgtttt g                                                           11

<210> SEQ ID NO 360
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 360
tcgtcgtttt                                                             10

<210> SEQ ID NO 361
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 361
cgtcgttttg acgttttgtc gt                                               22

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide
```

-continued

<400> SEQUENCE: 362
gtcgttttga cgttttgtcg                                           20

<210> SEQ ID NO 363
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 363
tcgttttgac gttttgtc                                             18

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
cgttttgacg ttttgt                                               16

<210> SEQ ID NO 365
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 365
gttttgacgt tttg                                                 14

<210> SEQ ID NO 366
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 366
ttttgacgtt tt                                                   12

<210> SEQ ID NO 367
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 367
tttgacgttt                                                      10

<210> SEQ ID NO 368
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 368
tcgtcgtttt gacgttttgt cgtt                                      24

<210> SEQ ID NO 369
<211> LENGTH: 23
<212> TYPE: DNA

```
<213> ORGANISM: Artificial sequence
<220> FEATURE:
<223> OTHER INFORMATION: Synthetic oligodeoxynucleotide

<400> SEQUENCE: 369
tcgtcgacgt tcggcgcgcg ccg                                    23

<210> SEQ ID NO 370
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 370
tcggacgttc ggcgcgcgcc g                                      21

<210> SEQ ID NO 371
<211> LENGTH: 19
<212> TYPE: DNA
<213> ORGANISM: Artificial sequence
<220> FEATURE:
<223> OTHER INFORMATION: Synthetic oligodeoxynucleotide

<400> SEQUENCE: 371
tcggacgttc ggcgcgccg                                         19

<210> SEQ ID NO 372
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 372
tcgcgtcgtt cggcgcgccg                                        20

<210> SEQ ID NO 373
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 373
tcgacgttcg gcgcgcgccg                                        20

<210> SEQ ID NO 374
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 374
tcgacgttcg gcgcgccg                                          18

<210> SEQ ID NO 375
<211> LENGTH: 18
<212> TYPE: DNA
<213> ORGANISM: Artificial sequence
<220> FEATURE:
<223> OTHER INFORMATION: Synthetic oligodeoxynucleotide

<400> SEQUENCE: 375
tcgcgtcgtt cggcgccg                                          18
```

<210> SEQ ID NO 376
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 376
tgtcgttttt tttttttttt                                               20

<210> SEQ ID NO 377
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 377
tgtcgttttt tttttttttt                                               20

<210> SEQ ID NO 378
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n = uracil
<220> FEATURE:
<221> NAME/KEY: misc_feature
<222> LOCATION: (8)..(20)
<223> OTHER INFORMATION: n = uracil

<400> SEQUENCE: 378
ngtcgttnnn nnnnnnnnnn                                               20

<210> SEQ ID NO 379
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n = uracil
<220> FEATURE:
<221> NAME/KEY: misc_feature
<222> LOCATION: (8)..(20)
<223> OTHER INFORMATION: n = uracil

<400> SEQUENCE: 379
ngtcgttnnn nnnnnnnnnn                                               20

<210> SEQ ID NO 380
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n is 2'-deoxyuracil
<220> FEATURE:
<221> NAME/KEY: misc_feature
<222> LOCATION: (8)..(19)
<223> OTHER INFORMATION: n is 2'-deoxyuracil -continued

```
<400> SEQUENCE: 380
ngtcgttnnn nnnnnnnnnt                                                20

<210> SEQ ID NO 381
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n is 2'-deoxyuracil
<220> FEATURE:
<221> NAME/KEY: misc_feature
<222> LOCATION: (8)..(19)
<223> OTHER INFORMATION: n is 2'-deoxyuracil

<400> SEQUENCE: 381
ngtcgttnnn nnnnnnnnnt                                                20

<210> SEQ ID NO 382
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (8)..(12)
<223> OTHER INFORMATION: n is uracil

<400> SEQUENCE: 382
ngtcgttnnn nngggagggg                                                20

<210> SEQ ID NO 383
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (8)..(12)
<223> OTHER INFORMATION: n is uracil

<400> SEQUENCE: 383
ngtcgttnnn nngggagggg                                                20

<210> SEQ ID NO 384
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (10)..(12)
<223> OTHER INFORMATION: n is uracil
```

<400> SEQUENCE: 384
ngtcgttccn nngggagggg                                            20

<210> SEQ ID NO 385
<211> LENGTH: 20
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (10)..(12)
<223> OTHER INFORMATION: n is uracil

<400> SEQUENCE: 385
ngtcgttccn nngggagggg                                            20

<210> SEQ ID NO 386
<211> LENGTH: 20
<212> TYPE: DNA
<213> ORGANISM: Artificial sequence
<220> FEATURE:
<223> OTHER INFORMATION: Synthetic oligodeoxynucleotide

<400> SEQUENCE: 386
tccatgacgt tcctgacgtt                                            20

<210> SEQ ID NO 387
<211> LENGTH: 10
<212> TYPE: DNA
<213> ORGANISM: Artificial sequence
<220> FEATURE:
<223> OTHER INFORMATION: Synthetic oligodeoxynucleotide

<400> SEQUENCE: 387
tcaacgttga                                                       10

<210> SEQ ID NO 388
<211> LENGTH: 10
<212> TYPE: DNA
<213> ORGANISM: Artificial sequence
<220> FEATURE:
<223> OTHER INFORMATION: Synthetic oligodeoxynucleotide

<400> SEQUENCE: 388
tcaagcttga                                                       10

<210> SEQ ID NO 389
<211> LENGTH: 64
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: n is a, c, g, or t, and any 1-19 may be absent
<220> FEATURE:
<221> NAME/KEY: misc_feature
<222> LOCATION: (23)..(42)
<223> OTHER INFORMATION: n is a, c, g, or t, and any 1-20 may be absent
<220> FEATURE:
<221> NAME/KEY: misc_feature
<222> LOCATION: (45)..(64)
<223> OTHER INFORMATION: n is a, c, g, or t, and any 1-19 may be absent

```
<400> SEQUENCE: 389
nnnnnnnnnn nnnnnnnnnn cgnnnnnnnn nnnnnnnnnn nncgnnnnnn nnnnnnnnnn    60 nnnn                                                                 64

<210> SEQ ID NO 390
<211> LENGTH: 64
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: n is a, c, g, or t, and any 1-19 may be absent
<220> FEATURE:
<221> NAME/KEY: misc_feature
<222> LOCATION: (23)..(42)
<223> OTHER INFORMATION: n is a, c, g, or t, and any 1-16 may be absent
<220> FEATURE:
<221> NAME/KEY: misc_feature
<222> LOCATION: (45)..(64)
<223> OTHER INFORMATION: n is a, c, g, or t, and any 1-19 may be absent

<400> SEQUENCE: 390
nnnnnnnnnn nnnnnnnnnn cgnnnnnnnn nnnnnnnnnn nncgnnnnnn nnnnnnnnnn    60 nnnn                                                                 64

<210> SEQ ID NO 391
<211> LENGTH: 64
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: n is a, c, g, or t, and any 1-20 may be absent
<220> FEATURE:
<221> NAME/KEY: misc_feature
<222> LOCATION: (23)..(42)
<223> OTHER INFORMATION: n is a, c, g, or t, and any 1-20 may be absent
<220> FEATURE:
<221> NAME/KEY: misc_feature
<222> LOCATION: (45)..(64)
<223> OTHER INFORMATION: n is a, c, g, or t, and any 1-20 may be absent

<400> SEQUENCE: 391
nnnnnnnnnn nnnnnnnnnn cgnnnnnnnn nnnnnnnnnn nncgnnnnnn nnnnnnnnnn    60 nnnn                                                                 64

??

??

??

??

- 1 -

- 1 -
```

We claim:

1. A method for treating a vertebrate having renal cell carcinoma, lung cancer, or neuroblastoma, the method comprising administering a modified oligonucleotide having at least two CpG immunostimulatory motifs, wherein C is unmethylated cytidine, and G is guanosine, wherein each CpG has a phosphodiester or phosphodiester-like internucleotide linkage, and wherein all other internucleotide linkages are stabilized, to a mucosal surface of the vertebrate, wherein the stabilized internucleotide linkage is a phosphorothioate linkage, and wherein the administration results in the treatment of the vertebrate having renal cell carcinoma, lung cancer, or neuroblastoma.

2. The method according to claim 1, wherein the modified oligonucleotide is administered orally.

3. The method according to claim 1, wherein the route of administration is selected from the group consisting of intranasal, intratracheal, rectal, and vaginal administration.

4. The method according to claim 1, wherein the vertebrate is selected from the group consisting of fish, chicken, turkey, human and non-human vertebrate.

5. The method according to claim 4, wherein the non-human vertebrate is selected from the group consisting of rats, mice, cats, dogs, horses, cows, pigs, and primates.

6. The method according to claim 1, wherein the modified oligonucleotide comprises two oligonucleotides linked by a non-nucleotidic linker and having two 5' ends, wherein at least one of the oligonucleotides is an immunostimulatory oligonucleotide having an accessible 5' end and comprises an immunostimulatory motif.

7. The method according to claim 1, further comprising administering an agent selected from the group consisting of vaccines, allergens, antigens, antibodies, immunotherapeutics, chemotherapeutic drugs, antibiotics, lipids, and other adjuvants.

8. The method according to claim 7, further comprising administering a microbial antigen, cancer antigen or allergen.

9. The method according to claim 1, further comprising administering an adjuvant.

* * * * *